(12) United States Patent
Chiosis et al.

(10) Patent No.: US 10,758,538 B2
(45) Date of Patent: *Sep. 1, 2020

(54) HEAT SHOCK PROTEIN BINDING COMPOUNDS, COMPOSITIONS, AND METHODS FOR MAKING AND USING SAME

(71) Applicant: Memorial Sloan-Kettering Cancer Center, New York, NY (US)

(72) Inventors: Gabriela Chiosis, New York, NY (US); Tony Taldone, Forest Hills, NY (US); Anna Rodina, New York, NY (US); Pallav Patel, Fresh Meadows, NY (US); Yanlong Kang, Plainsboro, NJ (US)

(73) Assignee: Memorial Sloan-Kettering Cancer Center, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/037,160

(22) Filed: Jul. 17, 2018

(65) Prior Publication Data
US 2019/0038626 A1 Feb. 7, 2019

Related U.S. Application Data

(60) Continuation of application No. 15/230,700, filed on Aug. 8, 2016, now Pat. No. 10,052,325, which is a division of application No. 13/391,148, filed as application No. PCT/US2010/045817 on Aug. 17, 2010, now Pat. No. 9,567,318.

(60) Provisional application No. 61/272,101, filed on Aug. 17, 2009.

(51) Int. Cl.
| | | |
|---|---|---|
| *A61K 31/513* | (2006.01) | |
| *A61K 31/506* | (2006.01) | |
| *A61K 31/496* | (2006.01) | |
| *C07D 239/60* | (2006.01) | |
| *C07D 239/56* | (2006.01) | |
| *C07D 495/04* | (2006.01) | |
| *C07D 239/47* | (2006.01) | |
| *C07D 403/12* | (2006.01) | |
| *C07D 239/38* | (2006.01) | |

(52) U.S. Cl.
CPC .......... *A61K 31/513* (2013.01); *A61K 31/496* (2013.01); *A61K 31/506* (2013.01); *C07D 239/38* (2013.01); *C07D 239/47* (2013.01); *C07D 239/56* (2013.01); *C07D 239/60* (2013.01); *C07D 403/12* (2013.01); *C07D 495/04* (2013.01); *A61K 2121/00* (2013.01)

(58) Field of Classification Search
CPC .. C07D 239/56; C07D 495/04; C07D 239/47; C07D 239/38; C07D 403/12; C07D 239/60; A61K 31/506; A61K 31/496; A61K 31/513; A61K 2121/00
See application file for complete search history.

(56) References Cited

U.S. PATENT DOCUMENTS

| | | |
|---|---|---|
| 3,154,551 A | 10/1964 | Hitchings et al. |
| 3,248,393 A | 4/1966 | Roth et al. |
| 4,096,264 A | 6/1978 | Bochis et al. |
| 4,251,454 A | 2/1981 | Kompis et al. |
| 4,552,900 A * | 11/1985 | Sirrenberg ........... C07D 239/34 514/269 |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,707,930 A | 1/1998 | Felix et al. |
| 5,848,551 A | 12/1998 | Ohmi et al. |
| 5,948,551 A | 9/1999 | Gompper et al. |
| 6,107,301 A | 8/2000 | Aldrich et al. |
| 7,517,886 B2 | 4/2009 | Singh et al. |

(Continued)

FOREIGN PATENT DOCUMENTS

| | | |
|---|---|---|
| CN | 1930135 A | 3/2007 |
| EP | 2343282 A1 | 7/2011 |

(Continued)

OTHER PUBLICATIONS

Caldwell, W.T. and Sayin, A.N., The Preparation of a Pyrimidine Analog (Isostere) of Promizole and Other Substituted Pyrimidines, J. Am. Chem. Soc., 74(17):4314-4317 (1952).

(Continued)

*Primary Examiner* — Alexander R Pagano
*Assistant Examiner* — Ebenezer O Sackey
(74) *Attorney, Agent, or Firm* — Choate, Hall & Stewart LLP; John P. Rearick; Erica M. D'Amato

(57) ABSTRACT

The present subject matter relates to a compound represented by the general formula (I) or (I') or a pharmacologically acceptable salt thereof; pharmaceutical compositions containing at least one of these compounds; methods of making at least one of these compounds; methods of using at least one of these compounds for treating and/or preventing various cancers and/or proliferation disorders; methods of using at least one of these compounds for monitoring the effectiveness of an anticancer therapy against various cancers. In one embodiment, the subject matter relates to compounds that bind with a level of specificity to heat shock protein 70 (Hsp70). In another embodiment, the subject matter relates to compounds that bind with a level of specificity to inhibit both heat shock protein 70 (Hsp70) and heat shock cognate protein 70 (Hsc70).

18 Claims, 21 Drawing Sheets
Specification includes a Sequence Listing.

(56) References Cited

U.S. PATENT DOCUMENTS

| | | | |
|---|---|---|---|
| 9,567,318 B2* | 2/2017 | Chiosis | C07D 239/47 |
| 9,878,987 B2 | 1/2018 | Chiosis et al. | |
| 10,052,325 B2* | 8/2018 | Chiosis | C07D 239/47 |
| 10,160,729 B2 | 12/2018 | Chiosis et al. | |
| 2003/0153584 A1 | 8/2003 | Weaver et al. | |
| 2005/0070712 A1 | 3/2005 | Kosogof et al. | |
| 2005/0277654 A1 | 12/2005 | Maynard et al. | |
| 2008/0124407 A1 | 5/2008 | Eaton et al. | |
| 2012/0252818 A1 | 10/2012 | Chiosis et al. | |
| 2013/0085156 A1 | 4/2013 | Mitsuya et al. | |
| 2015/0291565 A1 | 10/2015 | Djaballah et al. | |
| 2017/0165265 A1 | 6/2017 | Chiosis et al. | |
| 2017/0233352 A1 | 8/2017 | Chiosis et al. | |
| 2018/0170883 A1 | 6/2018 | Chiosis et al. | |
| 2018/0251471 A1 | 9/2018 | Chen et al. | |
| 2018/0256558 A1 | 9/2018 | Min et al. | |
| 2019/0241526 A1 | 8/2019 | Chiosis et al. | |

FOREIGN PATENT DOCUMENTS

| | | |
|---|---|---|
| GB | 1014881 A | 12/1965 |
| GB | 1015784 A | 1/1966 |
| JP | S51-091273 A | 8/1976 |
| JP | 52-73896 A | 6/1977 |
| JP | 59-184167 | 10/1984 |
| JP | 2004-523474 A | 8/2004 |
| JP | 2004-528293 A | 9/2004 |
| JP | 2005-517675 A | 6/2005 |
| JP | 2007-526268 A | 9/2007 |
| JP | 2008-533166 A | 8/2008 |
| JP | 2009-506999 A | 2/2009 |
| WO | WO-96/05309 A2 | 2/1996 |
| WO | WO-00/059893 A1 | 10/2000 |
| WO | WO-02/024681 A2 | 3/2002 |
| WO | WO-02/053557 A1 | 7/2002 |
| WO | WO-02/060450 A1 | 8/2002 |
| WO | WO-03/055860 A1 | 7/2003 |
| WO | WO-2004/081001 A1 | 9/2004 |
| WO | WO-2005/021552 A1 | 3/2005 |
| WO | WO-2005/095359 A1 | 10/2005 |
| WO | WO-2006/101977 A2 | 9/2006 |
| WO | WO-2007/025901 A1 | 3/2007 |
| WO | WO-2007/131034 A1 | 11/2007 |
| WO | WO-2008/026768 A1 | 3/2008 |
| WO | WO-2008/073687 A2 | 6/2008 |
| WO | WO-2008/092199 A1 | 8/2008 |
| WO | WO-2008/153042 A1 | 12/2008 |
| WO | WO-2009/023846 A2 | 2/2009 |
| WO | WO-2009/061345 A2 | 5/2009 |
| WO | WO-2009/067081 A1 | 5/2009 |
| WO | WO-2010/144345 A1 | 12/2010 |
| WO | WO-2011/022440 A2 | 2/2011 |

OTHER PUBLICATIONS

Cerchietti, L.C. et al, A purine scaffold Hsp90 inhibitor destabilizes BCL-6 and has specific antitumor activity in BCL-6-dependent B cell lymphomas. Nat Med., 15(12):1369-76 (2009).
Cerchietti, L.C. et al, BCL6 repression of EP300 in human diffuse large B cell lymphoma cells provides a basis for rational combinatorial therapy, J. Clin Invest., 120(12): 4569-4582 (2010).
Chothia, C. and Lesk, A.M., The relation between the divergence of sequence and structure in proteins, The EMBO Journal, 5(4):823-6 (1986).
Database Registry [Online]: Chemical Abstracts Service, Columbus, Ohio, USA. Retrieved from STN, Registry No. 412341-81-2 (Entered STN: May 8, 2002).
Extended European Search Report for EP 10810519.8, 2 pages (dated Feb. 5, 2013).
Gompper, R. et al, Reactions of α, β-unsaturated β-amino-and β-hydroxycarbonyl compounds with sulfur monochloride and related compounds, Justus Liebigs Annalen der Chemie, 675: 151-174 (1964).
Halgren, T.A., Identifying and characterizing binding sites and assessing; druggability, Journal of Chemical Information and Modeling, 49(2):377-89 (2009).
Hanahan, D. and Weinberg, R.A., Hallmarks of cancer: the next generation, Cell, 144(5):646-74 (2011).
Hanahan, D. and Weinberg, R.A., The hallmarks of cancer, Cell, 100(1):57-70 (2000).
Håvik, B. and Bramham, C.R., Additive viability-loss following hsp70/hsc70 double interference and Hsp90 inhibition in two breast cancer cell lines, Oncology Reports, 17(6):1501-10 (2007).
International Search Report for PCT/US2010/045817, 5 pages (dated Jun. 21, 2011).
International Search Report of PCT/US2015/030641, 5 pages (dated Jul. 29, 2015).
Kang, Y. et al., Heat shock protein 70 inhibitors. 1. 2,5'-thiodipyrimidine and 5-(phenylthio)pyrimidine acrylamides as irreversible binders to an allosteric site on heat shock protein 70, Journal of Medicinal Chemistry, 57(4):1188-1207 (2014).
Koos, M. et al., Synthesis of some sulfur bridged pyrimidines, pyrazoles and imidazoles Proceedings of ECSOC-1: The First International Electronic Conference on Synthetic Organic Chemistry, and Proceedings of ECSOC-2: The Second International Electronic Conference on Synthetic Organic Chemistry, Sep. 1-30, 1997, 315-318 (1997).
Kundu, N. G. and Nandi, B., Depropargylation under palladium-copper catalysis: synthesis of diaryl sulfides, Tetrahedron, 57(27): 5885-5895 (2001).
Liebscher, M. and Roujeinikova, A., Allosteric coupling between the lid and interdomain linker in DnaK revealed by inhibitor binding studies, Journal of Bacteriology, 191(5):1456-62 (2009).
Nylandsted, J. et al., Eradication of glioblastoma, and breast and colon carcinoma xenografts by Hsp70 depletion, Cancer Research, 62(24):7139-42 (2002).
Rodina, A. et al., Affinity Purification Probes of Potential Use To Investigate the Endogenous Hsp70 Interactome in Cancer, ACS Chemical Biology, 8 pages (2014).
Rodina, A. et al., Identification of an allosteric pocket on human hsp70 reveals a mode of inhibition of this therapeutically important protein, Chemistry & Biology, 20(12):1469-80 (2013).
Roth, B. And Bunnett, J.F., 5-Arylthiopyrimidines. IV. Spectrophotometric Determination of Successive Acid Dissociation Constants Differing by Less Than Two pK Units, J. Am. Chem. Soc., 87(2):334-339 (1965).
Roth, B. and Schloemer, L.A., 5-Arylthiopyrimidines. III. Cyclization of 4-Hydroxy Derivatives to 10H-Pyrimido[5,4-b][1,4]benzothiazines (1,3-Diazaphenothiazines), J. Org. Chem., 28(10):2659-2672 (1963).
Roth, H. and Bunnett, J.F., 5-Arylthiopyrimidines. V. Kinetics of the Cyclization of 4-Oxo Derivatives to 10H- and 10-Alkylpyrimido[5,4-b][1,4]benzothiazines (1,3-Diazaphenothiazines), J. Am. Chem. Soc. 87(2):340-349 (1965).
Sugiyama, K. et al., Studies on 1,4-Benzothiazines. IV. Reactions of 2-Acyl-4H-1,4-benzothiazines with Hydroxylamine, Hydrazine, Guanidine and Acetamidine, Chem. Pharm. Bull., 32(4):1593-1596 (1984).
Taldone, T. et al., Heat shock protein 70 inhibitors. 2. 2,5'-thiodipyrimidines, 5-(phenylthio)pyrimidines, 2-(pyridin-3-ylthio)pyrimidines, and 3-(phenylthio)pyridines as reversible binders to an allosteric site on heat shock protein 70, Journal of Medicinal Chemistry, 57(4):1208-1224 (2014).
Taldone, T. et al., Protein chaperones: a composition of matter review (2008-2013), Expert Opin. Ther. Pat., 24(5):501-18 (2014).
Thomas, A.A. et al., Non-charged thiamine analogs as inhibitors of enzyme transketolase, Bioorg. Med. Chem. Lett., 18(2):509-12 (2008).
Wallner, B. and Elofsson, A., All are not equal: a benchmark of different homology modeling programs, Protein Science, 14(5):1315-27 (2005).
Weinstein, I.B., Cancer. Addiction to oncogenes—the Achilles heal of cancer, Science, 297(5578):63-4 (2002).
Written Opinion for PCT/US2010/045817, 7 pages (dated Jun. 21, 2011).

(56) References Cited

OTHER PUBLICATIONS

Yanagita, M. and Futaki, R., Pyrimidine Derivatives. II. Synthesis of p-Aminophenyl 2-amino-5-pyrimidyl Sulfone, Yakugaku Zasshi, 72(2): 236-238 (1952).
Yoshikawa, T. and Zasshi, Y., Syntheses of pyrimidine derivatives, II. Syntheses of dipyrimidyl sulfone derivatives and diazotization of 6-(5-amino-2-pyrimidylamino acid, Kumamoto University, 76:776-8 (1956).
Falco, 5-Arylthiopyrimidines. I. 2- and 4-Alkylamino and 4-Diamino Derivatives, Journal of Organic Chemistry, 26: 1143-6 (1961).
Zhao, W.Z. et al, [Synthesis and antibacterial activity of 2,4-diamino-5-(substituted anilino) pyrimidines], Yaoxue Xuebao, 22(7): 541-4 (1987). [Chinese].

* cited by examiner

SEQUENCE LISTING

```
<160> NUMBER OF SEQ ID NOS: 12

<210> SEQ ID NO 1
<211> LENGTH: 641
<212> TYPE: PRT
<213> ORGANISM: Homo sapiens

<400> SEQUENCE: 1

Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240
```

Phe Val Glu Glu Phe Lys Arg Lys His Lys Lys Asp Ile Ser Gln Asn
            245                 250                 255

Lys Arg Ala Val Arg Arg Leu Arg Thr Ala Cys Glu Arg Ala Lys Arg
        260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
        290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
        370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
        450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
        530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
        610                 615                 620

Gln Gly Pro Lys Gly Gly Ser Gly Ser Gly Pro Thr Ile Glu Glu Val
625                 630                 635                 640

Asp

<210> SEQ ID NO 2

<211> LENGTH: 382
<212> TYPE: PRT
<213> ORGANISM: Homo sapiens

<400> SEQUENCE: 2

```
Met Ala Lys Ala Ala Ile Gly Ile Asp Leu Gly Thr Thr Tyr Ser
1               5                   10                  15

Cys Ile Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
                100                 105                 110

Ala Phe Tyr Pro Glu Glu Ile Ser Ser Met Val Leu Thr Lys Met Lys
            115                 120                 125

Glu Ile Ala Glu Ala Tyr Leu Gly Tyr Pro Val Thr Asn Ala Val Ile
130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
            195                 200                 205

Ile Leu Thr Ile Asp Asp Gly Ile Phe Glu Val Lys Ala Thr Ala Gly
210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
            275                 280                 285

Glu Gly Ile Asp Phe Tyr Thr Ser Ile Thr Arg Ala Arg Phe Glu Glu
290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
            355                 360                 365

Val Ala Tyr Gly Ala Ala Val Gln Ala Ala Ile Leu Met Gly
370                 375                 380
```

<210> SEQ ID NO 3
<211> LENGTH: 605
<212> TYPE: PRT
<213> ORGANISM: Escherichia coli

<400> SEQUENCE: 3

```
Met Gly Lys Ile Ile Gly Ile Asp Leu Gly Thr Thr Asn Ser Cys Val
1               5                   10                  15

Ala Ile Met Asp Gly Thr Thr Pro Arg Val Leu Glu Asn Ala Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
    50                  55                  60

Thr Leu Phe Ala Ile Lys Arg Leu Ile Gly Arg Arg Phe Gln Asp Glu
65                  70                  75                  80

Glu Val Gln Arg Asp Val Ser Ile Met Pro Phe Lys Ile Ile Ala Ala
                85                  90                  95

Asp Asn Gly Asp Ala Trp Val Glu Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Leu Asp Lys Gly Thr Gly Asn Arg Thr Ile Ala Val
            180                 185                 190

Tyr Asp Leu Gly Gly Gly Thr Phe Asp Ile Ser Ile Ile Glu Ile Asp
        195                 200                 205

Glu Val Asp Gly Glu Lys Thr Phe Glu Val Leu Ala Thr Asn Gly Asp
    210                 215                 220

Thr His Leu Gly Gly Glu Asp Phe Asp Ser Arg Leu Ile Asn Tyr Leu
225                 230                 235                 240

Val Glu Glu Phe Lys Lys Asp Gln Gly Ile Asp Leu Arg Asn Asp Pro
                245                 250                 255

Leu Ala Met Gln Arg Leu Lys Glu Ala Ala Glu Lys Ala Lys Ile Glu
            260                 265                 270

Leu Ser Ser Ala Gln Gln Thr Asp Val Asn Leu Pro Tyr Ile Thr Ala
        275                 280                 285

Asp Ala Thr Gly Pro Lys His Met Asn Ile Lys Val Thr Arg Ala Lys
    290                 295                 300

Leu Glu Ser Leu Val Glu Asp Leu Val Asn Arg Ser Ile Glu Pro Leu
305                 310                 315                 320

Lys Val Ala Leu Gln Asp Ala Gly Leu Ser Val Ser Asp Ile Asp Asp
                325                 330                 335

Val Ile Leu Val Gly Gly Gln Thr Arg Met Pro Met Val Gln Lys Lys
            340                 345                 350

Val Ala Glu Phe Phe Gly Lys Glu Pro Arg Lys Asp Val Asn Pro Asp
        355                 360                 365

Glu Ala Val Ala Ile Gly Ala Ala Val Gln Gly Gly Val Leu Thr Gly
    370                 375                 380
```

```
Asp Val Lys Asp Val Leu Leu Asp Val Thr Pro Leu Ser Leu Gly
385                 390                 395                 400

Ile Glu Thr Met Gly Gly Val Met Thr Thr Leu Ile Ala Lys Asn Thr
                405                 410                 415

Thr Ile Pro Thr Lys His Ser Gln Val Phe Ser Thr Ala Glu Asp Asn
            420                 425                 430

Gln Ser Ala Val Thr Ile His Val Leu Gln Gly Glu Arg Lys Arg Ala
            435                 440                 445

Ala Asp Asn Lys Ser Leu Gly Gln Phe Asn Leu Asp Gly Ile Asn Pro
450                 455                 460

Ala Pro Arg Gly Met Pro Gln Ile Glu Val Thr Phe Asp Ile Asp Ala
465                 470                 475                 480

Asp Gly Ile Leu His Val Ser Ala Lys Asp Lys Asn Ser Gly Lys Glu
                485                 490                 495

Gln Lys Ile Thr Ile Lys Ala Ser Ser Gly Leu Asn Glu Asp Glu Ile
            500                 505                 510

Gln Lys Met Val Arg Asp Ala Glu Ala Asn Ala Glu Ala Asp Arg Lys
            515                 520                 525

Phe Asp Glu Leu Val Gln Thr Arg Asn Gln Gly Asp His Leu Leu His
530                 535                 540

Ser Thr Arg Lys Gln Val Glu Glu Ala Gly Asp Lys Leu Pro Ala Asp
545                 550                 555                 560

Asp Lys Thr Ala Ile Glu Ser Ala Leu Thr Ala Leu Glu Thr Ala Leu
                565                 570                 575

Lys Gly Glu Asp Lys Ala Ala Ile Glu Ala Lys Met Gln Glu Leu Ala
            580                 585                 590

Gln Val Ser Gln Lys Leu Met Glu Ile Ala Gln Gln Gln
            595                 600                 605

<210> SEQ ID NO 4
<211> LENGTH: 120
<212> TYPE: PRT
<213> ORGANISM: Caenorhabditis elegans

<400> SEQUENCE: 4

Met Gly Ser Ser His His His His Ser Ser Gly Leu Val Pro
1               5                   10                  15

Arg Gly Ser His Met Gly Leu Glu Ser Tyr Ala Phe Asn Leu Lys Gln
                20                  25                  30

Thr Ile Glu Asp Glu Lys Leu Lys Asp Lys Ile Ser Pro Glu Asp Lys
            35                  40                  45

Lys Lys Ile Glu Asp Lys Cys Asp Glu Ile Leu Lys Trp Leu Asp Ser
50                  55                  60

Asn Gln Thr Ala Glu Lys Glu Glu Phe Glu His Gln Gln Lys Asp Leu
65                  70                  75                  80

Glu Gly Leu Ala Asn Pro Ile Ile Ser Lys Leu Tyr Gln Ser Ala Gly
                85                  90                  95

Gly Ala Pro Pro Gly Ala Ala Pro Gly Gly Ala Ala Gly Gly Ala Gly
            100                 105                 110

Gly Pro Thr Ile Glu Glu Val Asp
            115                 120

<210> SEQ ID NO 5
<211> LENGTH: 16
<212> TYPE: PRT
<213> ORGANISM: Homo sapiens
```

```
<400> SEQUENCE: 5

Arg Phe His Asp Leu Leu Ser Gln Leu Asp Asp Gln Tyr Ser Arg Phe
1               5                   10                  15

<210> SEQ ID NO 6
<211> LENGTH: 19
<212> TYPE: PRT
<213> ORGANISM: Homo sapiens

<400> SEQUENCE: 6

Arg Phe Asn Gln Ala Gln Ser Gly Asn Ile Gln Ser Thr Val Met Leu
1               5                   10                  15

Asp Lys Gln

<210> SEQ ID NO 7
<211> LENGTH: 19
<212> TYPE: PRT
<213> ORGANISM: Homo sapiens

<400> SEQUENCE: 7

Arg Phe Asn Gln Ala Gln Ser Gly Asn Ile Gln Ser Thr Val Met Leu
1               5                   10                  15

Asp Lys Gln

<210> SEQ ID NO 8
<211> LENGTH: 15
<212> TYPE: PRT
<213> ORGANISM: Homo sapiens

<400> SEQUENCE: 8

Arg Gly Leu Asn Val Asp Gln Leu Asn Met Leu Gly Glu Lys Leu
1               5                   10                  15

<210> SEQ ID NO 9
<211> LENGTH: 18
<212> TYPE: PRT
<213> ORGANISM: Homo sapiens

<400> SEQUENCE: 9

Lys Leu Leu Gly Pro Asn Ala Ser Pro Asp Gly Leu Ile Pro Trp Thr
1               5                   10                  15

Arg Phe

<210> SEQ ID NO 10
<211> LENGTH: 14
<212> TYPE: PRT
<213> ORGANISM: Homo sapiens

<400> SEQUENCE: 10

Lys Ser Leu Glu Asp Leu Gln Asp Glu Tyr Asp Phe Lys Cys
1               5                   10

<210> SEQ ID NO 11
<211> LENGTH: 15
<212> TYPE: PRT
<213> ORGANISM: Homo sapiens

<400> SEQUENCE: 11

Lys Thr Glu Leu Ile Ser Val Ser Glu Val His Pro Ser Arg Leu
1               5                   10                  15
```

```
<210> SEQ ID NO 12
<211> LENGTH: 15
<212> TYPE: PRT
<213> ORGANISM: Homo sapiens

<400> SEQUENCE: 12

Lys Val Met Ala Ala Glu Asn Ile Pro Glu Asn Pro Leu Lys Tyr
1               5                   10                  15
```

HEAT SHOCK PROTEIN BINDING COMPOUNDS, COMPOSITIONS, AND METHODS FOR MAKING AND USING SAME

CROSS REFERENCE TO RELATED APPLICATIONS

This application is a continuation of U.S. application Ser. No. 15/230,700, filed Aug. 8, 2016, now U.S. Pat. No. 10,052,325, which is a divisional of U.S. application Ser. No. 13/391,148, filed Jun. 6, 2012, now U.S. Pat. No. 9,567,318, which is a U.S. National Phase Application under 35 U.S.C. § 371 of International Patent Application No. PCT/US2010/045817, filed Aug. 17, 2010, which claims priority to U.S. Provisional Application No. 61/272,101, filed Aug. 17, 2009, the entire contents of each of which are hereby incorporated by reference.

GOVERNMENT SUPPORT

This invention was made with government support under CA119001 awarded by the National Institutes of Health. The Government has certain rights in the invention.

FIELD

The present subject matter relates to a compound represented by the general formulae disclosed herein or a pharmacologically acceptable salt thereof; pharmaceutical compositions containing the compound; methods of making the compound; methods of using the compound for treating and/or preventing various malignancies or proliferation disorders; methods of using the compound to identify matter that treats and/or prevents various malignancies or proliferation disorders; methods of using the compound to identify biomarkers for the clinical development of matter to treat and/or prevent various malignancies or proliferation disorders; and methods of using the compound to identify its rational use in combination therapies. In particular, the present subject matter relates to a compound that is a small molecule modulator of heat shock protein 70 (Hsp70). In another embodiment, the subject matter relates to a small molecule that occupies an allosteric pocket of Hsp70 located outside the nucleotide binding site of Hsp70 and to methods for identifying, characterizing, and using such small molecule

BACKGROUND

Cancer cells often express high levels of several heat shock proteins (HSPs) which augment the aggressiveness of these tumors and also allow the cells to survive lethal conditions, including killing by therapies. In addition to conferring resistance to treatment, elevated HSP expression also facilitates cancer by inhibiting programmed cell death and by promoting autonomous growth.

Among the major HSPs are Hsp90 and Hsp70, proteins that act in an interconnected but also distinct fashion to regulate the malignant phenotype. Hsp90 maintains the transforming capacity of several onco-proteins, among which HER2, AKT, RAF1, IGF-IR, and HIF-1, function facilitated by Hsc70, the constitutive Hsp70, the inducible Hsp70 isoforms. Upon Hsp90 inhibition, the Hsp90-client onco-proteins become destabilized and are degraded by a proteasomal pathway (FIG. 1a). The transcription factor HSF-1, the master regulator of heat shock response, is another Hsp90 client, and unlike onco-proteins, it becomes activated when Hsp90 is inhibited. HSF-1 activation leads to an increase in Hsp70 levels, a feed-back response that limits the potency of Hsp90 inhibitors in certain tumors. Hsp70 in itself is a powerful anti-apoptotic molecule, suggesting that inhibition of both intrinsic and extrinsic apoptotic pathways by increased Hsp70 levels may be responsible for reducing the effect of Hsp90 inhibition. In addition to inhibiting apoptosis and assisting Hsp90, Hsp70 and its highly homologous cytosolic isoforms, serve many other overlapping chaperone functions and in some cases can substitute for each other.

The Hsp90 multi-chaperone complex, also called the Hsp90 super-chaperone machinery, has important roles in the development and progression of pathogenic cellular transformation through regulation of several malignancy driving and supporting client proteins. The activity of the Hsp90 multi-chaperone system is maintained and executed by a complex system of chaperones. The Hsp70s (constitutively expressed Hsc70 and the heat inducible Hsp70-1 and Hsp70-6) participate in the preliminary steps, whereas Hsp90 participates in the later stages (FIG. 1a). Their function requires a multitude of co-chaperones, such as the Hsp70-regulators, Hsp40, Hsp110, BAG and HIP; HSP-organizing protein (HOP), involved in the formation of the intermediate molecular chaperone complex where the client is passed from Hsp70 to Hsp90, and others such as p23, cdc37 and immunophilins, acting at the final or mature Hsp90 complex (FIG. 1a). Inhibition of the Hsp90 machinery through agents that act by direct binding to the regulatory ATPase pocket of Hsp90, such as geldanamycin (GM) and the PUderivatives PU24FC1 and PU-H71 (FIG. 1b), interferes with the formation of mature complexes, directing the client proteins towards proteasomal degradation (FIG. 1a). Interestingly, reduction in the activity of Hsp90, but not in the expression of Hsp70 or the co-chaperones HOP, HIP, p23, and Hsp40, was reported to dramatically activate HSF-1. An intriguing outcome of this observation is that HSF-1 activation does not require Hsp70, unlike the onco-protein clients of the Hsp90 machinery.

Whereas the significance of direct Hsp90 inhibition is now well understood, and has been harnessed in the development of small molecule inhibitors currently in clinical evaluation for multiple cancers, little is known about alternate ways to intervene in the activity of the Hsp90 machinery. Interfering with the chaperone machinery in ways other than direct Hsp90 inhibition may differentiate between several of its functions, and confer specific biological activities.

SUMMARY

All together, considering the complex interplay between HSPs in cancer and the intrinsic dependency of tumor cells on these proteins, it is not surprising that, upon inhibition of one HSP, cells develop mechanisms to balance this functional loss by the action of another HSP. Consequently, approaches such as those described in the subject matter herein that simultaneously target more than one HSP are more likely to succeed therapeutically.

Thus, the present subject matter provides compounds and methods to differentiate the two functions of the Hsp90 molecular machinery, namely regulation of onco-proteins and suppression of HSF-1, by specifically modulating the Hsp70 chaperones.

Described herein are novel compounds, and methods of making and using the same. In one embodiment of the present subject matter, the compounds described herein may be useful for modulating cell growth, such as, for example, inhibiting malignant cells and/or increasing cytotoxicity against cancer cells. In another embodiment, the compounds described herein may function as heat shock protein 70 (Hsp70) modulators. As such, it has been discovered that pharmacologic modulation of Hsp70 using these or other compounds has substantial and wide-ranging beneficial consequences in cancer cells. In yet other embodiments, the compounds described herein can disrupt the formation of Hsp90 machinery/onco-protein complexes, leading to proteasomal degradation of several onco-proteins, without disrupting or degrading non-oncogenic kinases. In further embodiments, the anti-cancer effects of the compounds described herein may comprise, for example, inhibition of proliferation, transformation-specific block of the cell cycle, induction of apoptosis, or reduction of invasiveness.

In another embodiment of this subject matter is described that important activity as described herein, may be achieved by compositions of matter that interact by either a irreversible or reversible binding mode. In a particular embodiment, these compounds interact with Hsp70. In a yet another embodiment, they interact with a herein described allosteric site on Hsp70.

In one embodiment, a homology model of human Hsp70 is presented. In another embodiment of the subject matter, the homology model is used to rationally design compounds that modulate the activity of mammalian Hsp70. This homology model will be useful for the discovery of compounds of the present subject matter by methods including but not limited to rational drug design and virtual screening.

In further embodiments, an allosteric pocket located outside the nucleotide binding site of Hsp70 and Hsc70 is presented. No natural or synthetic small molecule ligands are known for this pocket. In yet other embodiments, it is presented that occupying this pocket with a small molecule ligand will result in, for example, inhibition of proliferation, transformation-specific block of the cell cycle, induction of apoptosis, or reduction of invasiveness. This pocket will be useful for the discovery of compounds of the present subject matter. A candidate compound can be computationally provided by several methods. Examples of such methods include assembling molecular fragments into a candidate compounds, designing a candidate compound de novo, modifying a compound known to bind to the site, including the composition described herein, to form a candidate compound, and not lastly, by screening a database for a candidate compound.

In accordance with another embodiment, a cavity in the Hsp70 protein that has no known naturally occurring or synthetically created ligand, when occupied by a compound of the present subject matter as described herein, results in inhibition of malignant cell growth, inhibition of aberrant cell cycle progression, degradation and inhibition of several onco-proteins, induction of apoptosis and reduction in the invasive potential of cancer cells at doses that are not toxic to normal cells. In accordance with another embodiment, occupancy of this yet unexplored pocket by other small molecule ligands will lead to all or a subset of the following effects, but is not limited to: inhibition of malignant cell growth, inhibition of aberrant cell cycle progression, degradation and inhibition of several onco-proteins, induction of apoptosis and reduction in the invasive potential of cancer cells at doses that are not toxic to normal cells.

In further embodiments, methods of discovery of ligands that occupy this pocket are presented. In yet other embodiments, it is presented that occupying this pocket with a small molecule ligand will result in dual inhibition of the Hsp90 and Hsp70 oncogenic pathways. The novel binding cavity and interaction mode in Hsp70s described here also represent a valuable springboard for the design of inhibitors with a similar mechanism of action and therapeutic use. While targeting one HSP at a time has its clear therapeutic significance, embodiments presented here show that by simultaneously inhibiting Hsp70 and Hsc70, one could reap the beneficial effects of Hsp90 inhibition, namely depletion of tumors of onco-proteins driving malignant processes, such as proliferation, survival and metastasis, and the apoptotic effects of Hsp70 inhibition. In conclusion, one embodiment describes a novel cancer targeting strategy by inhibition of an allosteric pocket located outside the nucleotide binding site of Hsp70 and Hsc70.

In other embodiments of the present subject matter, a strategy comprising one or more of several methods to evaluate the ability of a candidate compound to act with the substantial and wide-ranging beneficial consequences in cancer cells of the herein described compounds of the present subject matter, is presented. The strategy includes testing for a herein described phenotypic outcome in select cancer cells, performing a competitive fluorescence polarization assay to test for Hsp90 and Hsp70 binding as described herein, and evaluating computationally the structural fit of the candidate compound into the herein mentioned pocket. The phenotypic test includes but is not limited to testing for growth inhibition in a large panel of cancer cells, HER2 and Raf-1 degradation in HER2+ SKBr3 breast cancer cells, FLT3 and p-STAT5 inactivation in MOLM-13 AML cells, p-STAT3 and p-PDK1 inactivation in MDA-MB-468 triple negative breast cancer cells, mutant AR degradation in LNCaP prostate cancer cells, PARP cleavage in a large panel of cancel cells, caspase 3,7 activation in MOLM-13 cells, augmenting the apoptotic effect of interferon and TNF in breast cancer cells, and lack of Hsp70 induction in a large panel of cancer cells. The Hsp70 and Hsp90 competitive assays test competitive binding of candidate compounds to HSP expressed in cancer cells.

In other embodiments it is shown that the compounds described herein isolate Hsp70 in complexes with its onco-client protein cargo. A solid-support immobilized version of a compound described herein therefore confers the unprecedented possibility to investigate the cancer Hsp70 interactome in an endogenous cellular environment.

In other embodiments, compounds of the herein described subject matter may also be derivatized to form biotin-containing compounds that can be attached onto streptavidin or avidin beads, or can be directly linked to a correspondingly functionalized resin, such as but not limited to agarose, sepharose and matrigel resin.

In yet another embodiment, the compounds described herein may be derivatized with a fluorescent dye, such as but not limited to Cy3B, FITC and BODiPY. When used in the context of the fluorescence polarization assay described herein, this compound may be used to screen for candidate compounds that interact with Hsp70 in a manner similar to compounds of the present subject matter described herein.

In further embodiment, the solid support immobilized compound described herein is used to identify that tumor-by-tumor components of oncogenically activated pathways are in complex with Hsp70. Addition of compositions described herein to specific cancer cells results in destabilization of these complexes, onco-protein degradation or inhibition, and cancer cell growth inhibition and death. These downstream events of tumor Hsp70 inhibition may be used to functionally monitor the effect of compounds of the present subject matter described herein. The method described herein thus provides effective analysis of functional molecular biomarkers associated with response to the described compounds of the present subject matter and to other therapy that acts by occupying the allosteric pocket described herein or that is identified through the assay described herein. It is proposed that these biomarkers are useful in the clinical development of compositions of matter described herein, of compositions of matter that occupy the pocket described herein or of compositions of matter that are identified by the assays described herein.

Interestingly, only reduction in the activity of Hsp90, but not of its Hsp90-machinery co-chaperones, such as Hsp70, or HOP, HIP, p23, or Hsp40, dramatically activates HSF-1, and using the compounds of the present subject matter it is possible to differentiate the two functions of the molecular machinery by specifically regulating its co-chaperones. Unlike a direct Hsp90 inhibitor, the compounds of the present subject matter might not, for example, activate HSF-1 nor induce a protective feed-back heat shock response. In one embodiment of the present subject matter, the compounds disrupt the formation of Hsp90 machinery/onco-protein complexes without activating HSF-1 and/or without inducing a protective feed-back heat shock response.

When compared to direct Hsp90 inhibition, pharmacologic administration of the compounds in some embodiments results in increased, but yet selective, cytotoxicity against cancer cells, due to apoptosis, for example. The biological consequence of pharmacologic inhibition of Hsp70 has been characterized in malignant cells by using the compounds of the present subject matter. It has been found that Hsp70 modulates dephosphorylation of the STAT1 tumor suppressor in breast cancer cells, a novel mechanism of inactivation of the STAT1 tumor suppressor. In another embodiment of the present subject matter, the compounds described herein inhibit or inactivate Hsp70 acceleration of STAT1 dephosphorylation in breast cancer cells, thereby promoting tumor suppression via continued activity of the tumor suppressor STAT1.

STAT1 is a major effector of interferon-(IFN)γ signaling. IFNγ is a cytokine produced by T-cells and natural killer cells with an essential immune-stimulating function that provides defense against the development of tumors. In a further embodiment it is found that compositions of matter presented herein augment the effect of IFNγ and of another cytokine, TNFα and could allow immune responses to much more potently wipe out tumors. This is an exciting finding for vaccine therapy trials, suggesting that co-administration of biologically active interferon with a compound of the present subject matter described herein, i.e., with a compound of the present subject matter that occupies the described pocket or with a compound of the present subject matter that is identified by the assay described herein, can improve the vaccine efficiency and allow the use of a smaller vaccination dose.

Figure 5:
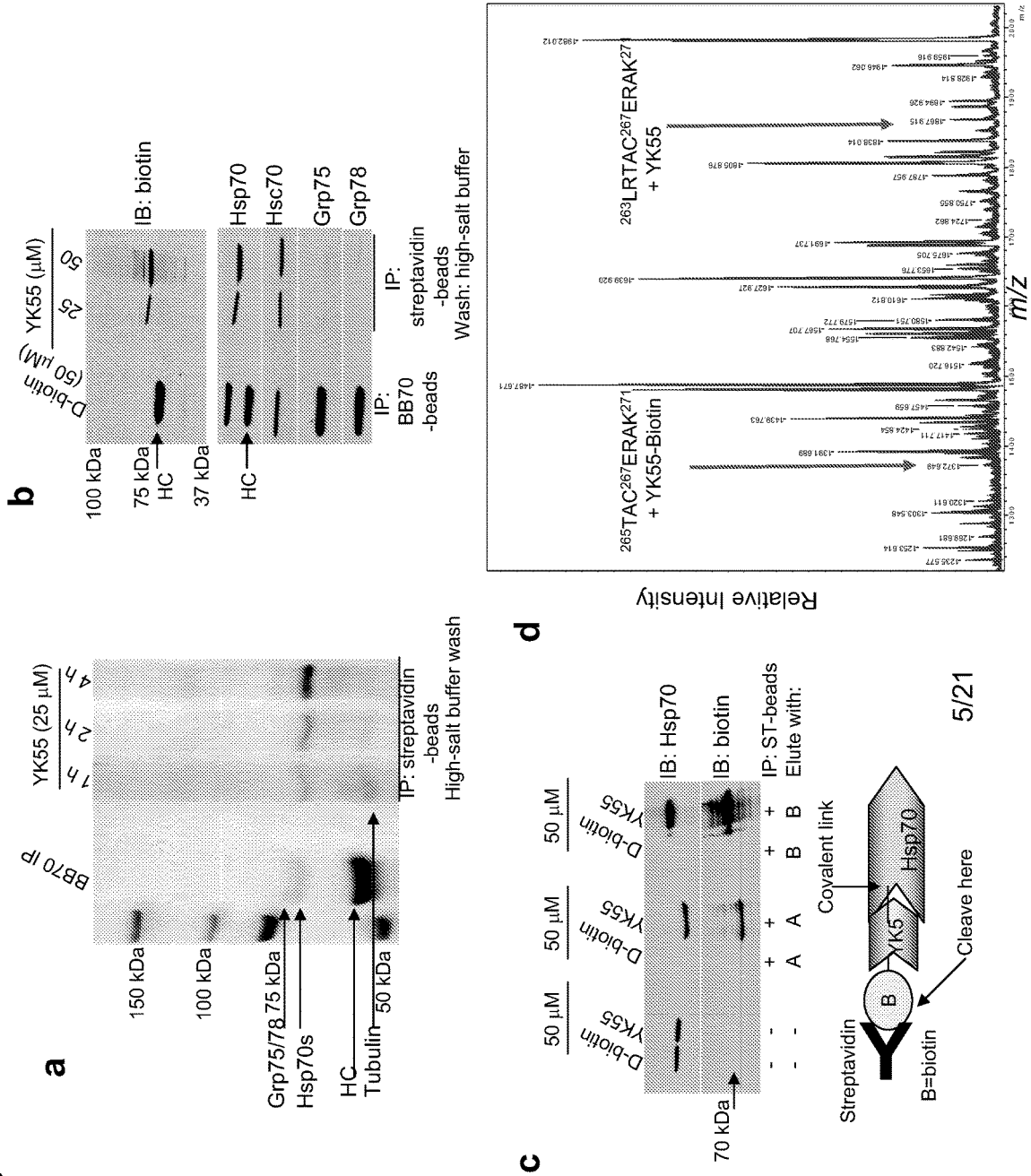

FIG. 5. YK5 forms a covalent link with Cys267 upon binding to Hsp70s. a) K562 cells were treated for the indicated times with YK55 (25 µM), prior to lysing and precipitation of protein complexes on streptavidin beads (50 µl) for 1 h at 4° C. Beads were washed with high-salt (1 M NaCl) buffer, proteins eluted by boiling in 2% SDS, separated on a denaturing gel and silver stained. BB70 Ab pull-downs were used to indicate the position of Hsp70s (BB70 IP; 2 µl). This antibody recognizes Hsp70, Hsc70, Grp75 and Grp78. HC=heavy chain. b) The experimental set-up was similar to panel a) but proteins were analyzed by WB. c) K562 cells were treated with YK55 or D-biotin (50 µM) for 6 h and lysed. Extracts (500 µg) were incubated for 1 h at 4° C. with streptavidin (ST)-beads and pull-downs washed with high-salt buffer (1M NaCl). Proteins were eluted by boiling in buffer A or B, as described in Methods. Following separation on a denaturing gel, proteins were visualized by WB. The data are consistent with those obtained from multiple repeat experiments (n≥2). d) MALDI-reTOF-MS/MS analysis of YK55 binding to Hsp70s in cancer cells. K562 cells were treated for 4 h with 100 µM YK55 and lysed. YK55 treated cell extract (500 µg) was incubated with streptavidin agarose beads for 1 h at 4° C. Beads were washed with high-salt buffer (1 M NaCl), proteins eluted by boiling in 2% SDS, separated on a denaturing gel and Coomassie stained. Gel-resolved proteins were digested with trypsin and peptides identified as indicated in Methods.

Figure 6:
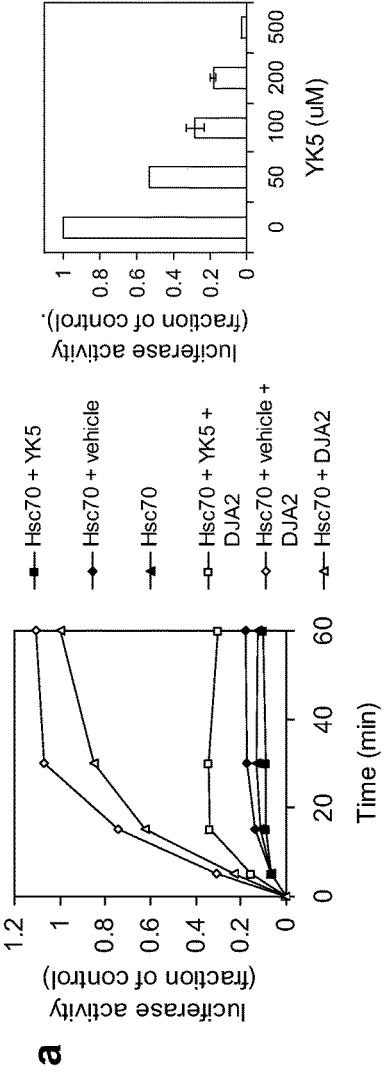
Figure 6:
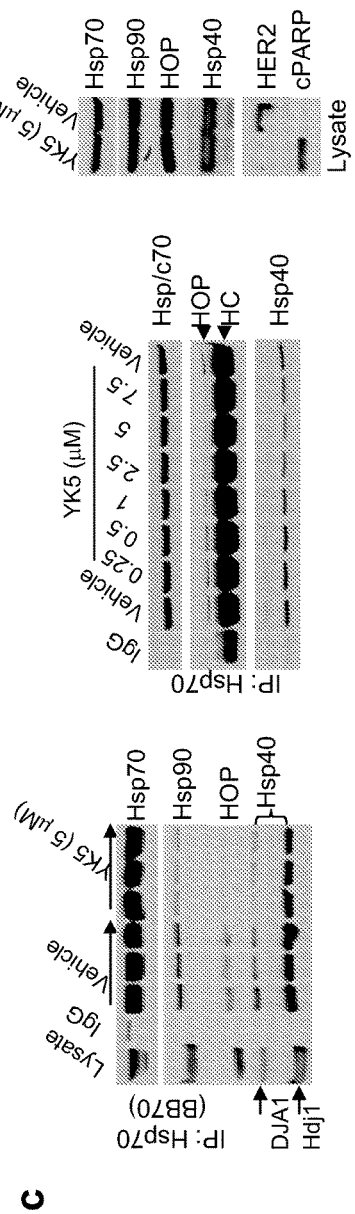
Figure 6:
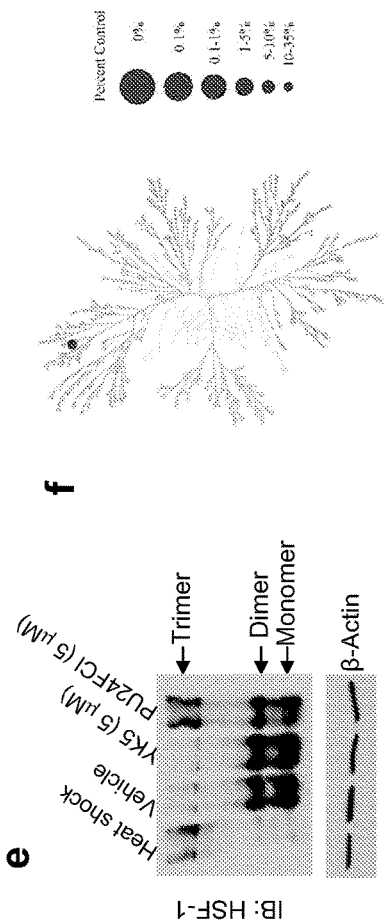

FIG. 6. YK5 inhibits core biochemical functions of Hsp70s and disrupts the Hsp90/Hsp70 interaction. a) Refolding of denatured luciferase by Hsc70 and DJA2 at 30° C. was measured for the indicated times in the presence of YK5 (100 µM) or vehicle (left), or at 60 min in the presence of indicated concentrations of YK5 (right). b) Hsc70 ATPase rates were measured for reactions at 30° C. with the indicated combinations of Hsc70 and co-chaperones in the presence of vehicle (DMSO) or YK5 (100 µM). ADP production was monitored by thin layer chromatography separation of radiolabeled ADP from ATP and phosphorimaging analysis (lower). The data are consistent with those obtained from multiple repeat experiments (n≥2). c,d) SKBr3 cells were treated for 24 h with vehicle or indicated concentrations of YK5 (c) or for the indicated times with YK5 (10 µM) (d). Proteins isolated with anti-Hsp90 and Hsp70s antibodies (IP: Hsp90 or Hsp70), or present in the cell extract (Lysate) were analyzed by WB. Specificity of binding was tested with a control IgG. HC=heavy chain; DJA1 and Hdj1=Hsp40 isoforms. e) Unlike Hsp90 inhibitors, YK5 fails to activate HSF-1. SKBr3 cells were heat shocked for 45 min at 42° C. or incubated with vehicle, YK5 or PU24FC1 (5 µM) for 3 h. Proteins were applied to a native gel and analyzed by immunoblotting. The data are consistent with those obtained from multiple repeat experiments (n≥3). f) YK5 was tested in the scanMAX screen (Ambit) against 359 kinases. The TREEspot™ Interaction Map for YK5 is presented. Only c-Met (red dot on the kinase tree) appears a potential low affinity kinase hit of YK5.

Figure 7:
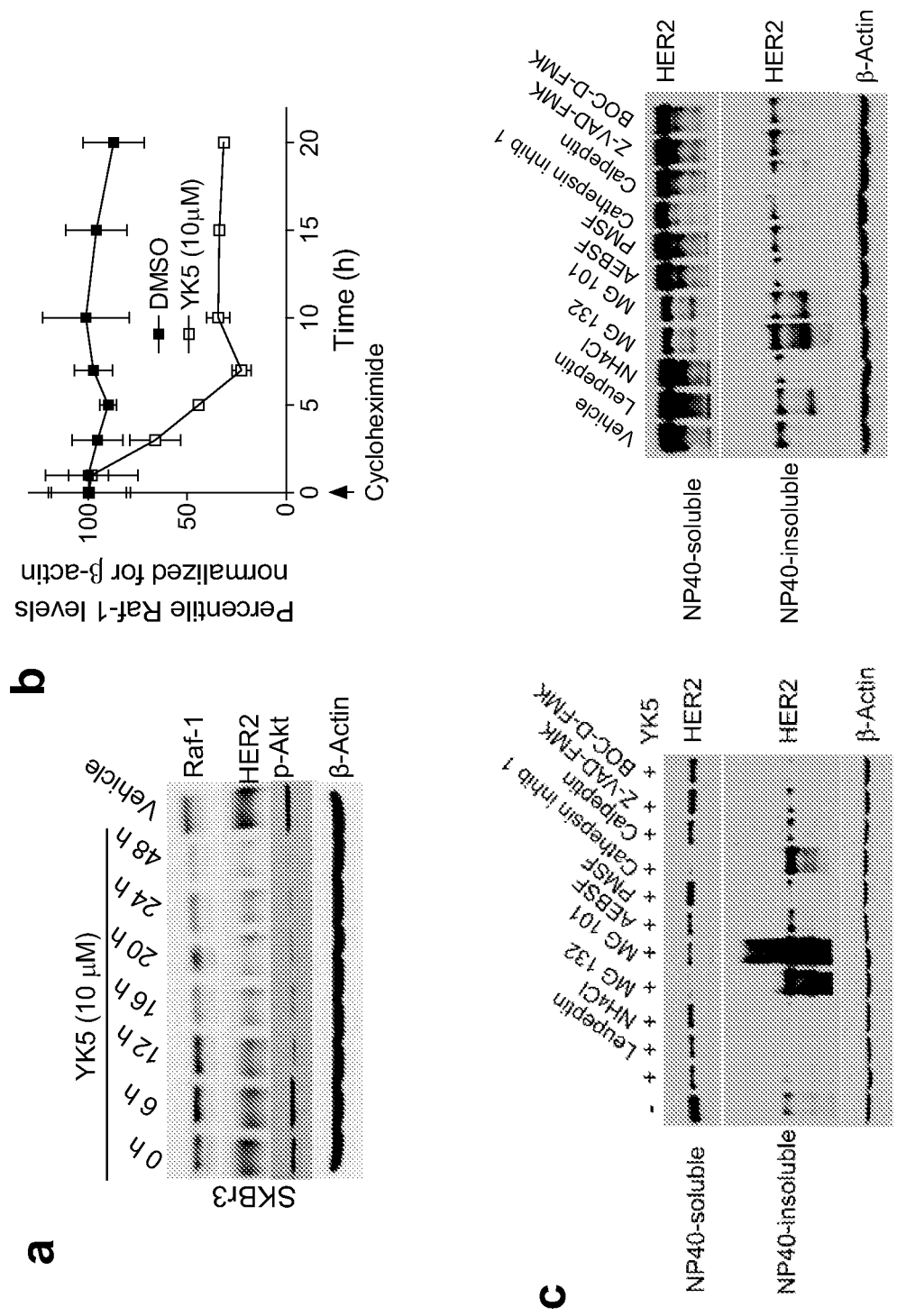

FIG. 7. YK5 disrupts the Hsp90/Hsp70/onco-client protein complexes resulting in oncoprotein destabilization and subsequent degradation by the proteasome. a) SKBr3 cells were treated for the indicated times with YK5 (10 µM). Proteins isolated with anti-Hsp90 antibody (IP: Hsp90), or present in the cell extract (Lysate) were analyzed by WB. Specificity of binding was tested with a control IgG. HC=heavy chain. b) SKBr3 cells were treated for the indicated times with the protein biosynthesis inhibitor cycloheximide (100 µg/ml) in the presence of vehicle (DMSO) or YK5 (10 µM). Following WB analysis, protein expression was quantified by densitometry and graphed against time of treatment. Points, mean; bars, s.d. c) SKBr3 cells were pre-treated with the indicated proteolysis machinery inhibitors prior to YK5 (10 µM) addition as described in Methods. After 24 h of treatment, protein expression in both detergent-soluble and insoluble fractions was determined by western blotting. The effects of inhibitors alone on protein processing are presented in the right side panel.

Figure 8:
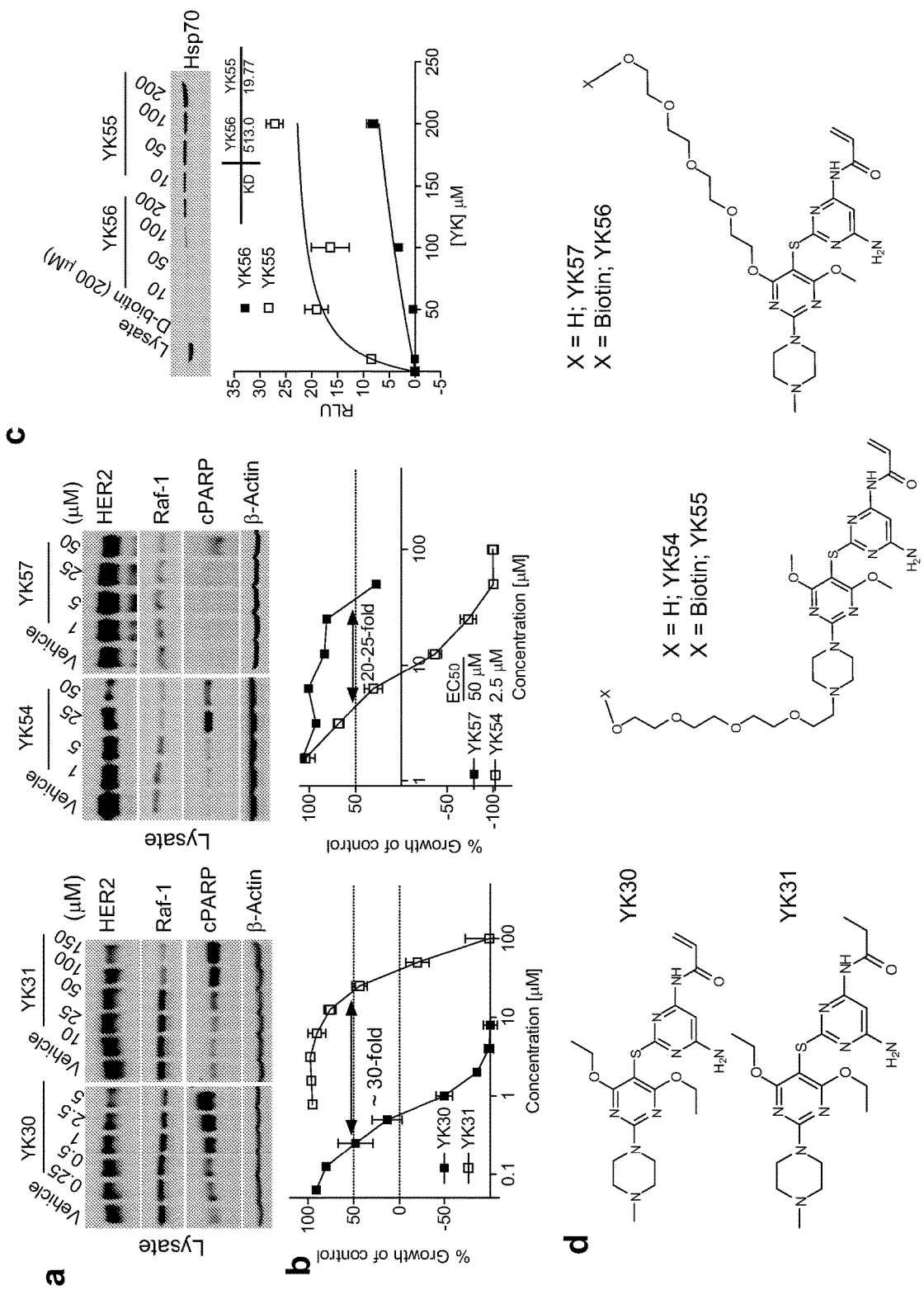

FIG. 8. Structure-activity relationship in the YK-series. a) SKBr3 breast cancer cells were treated for 24 h with indicated concentrations of YK-derivatives and proteins analyzed by Western blot. b) Kasumi-1 cells were incubated with increasing concentrations of YK-derivatives and inhibition of cell growth was analyzed with the Alamar blue assay as indicated in Methods. Points, mean; bars, s.d. Y axis values below 0% represent cell death of the starting population. c) Streptavidin beads (50 µl) were incubated with the indicated concentrations of YK55, YK56 or D-biotin to immobilize the corresponding compounds on beads. Beads (50 µl) were probed with SKBr3 cell extracts (500 µg), and the precipitated Hsp70 analyzed by western blot and quantified by dosimetry. Results from three independent experiments were graphed to determine the relative binding affinity of YKs. Points, mean; bars, s.d. d) Structure of representative YKs. YK55 and YK56 are the biotinylated derivatives of YK54 and YK57, respectively.

Figure 9:
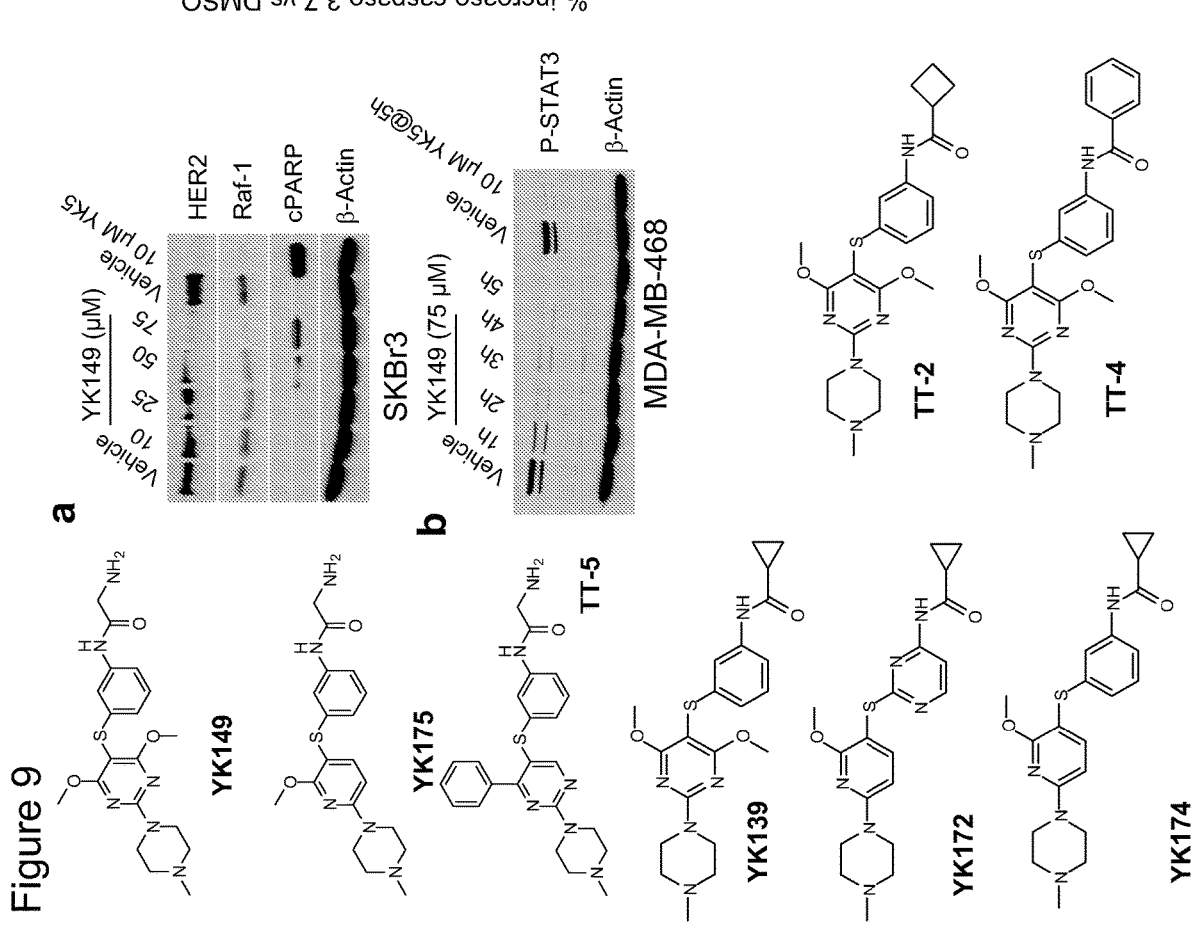

FIG. 9. (a) Examples of the compounds of the present subject matter dose-dependently reduce the steady-state levels of HER2 and Raf-1 onco-kinases in the SKBr3 HER2 overexpressing breast cancer cells, and induce apoptosis as indicated by PARP cleavage. Cells were treated for 24 h with the indicated concentrations of YK149 and YK5. Cells were lysed and proteins analyzed by western blotting. b) Examples of the compounds of the present subject matter inhibit the activity of the oncogenic STAT3 in the triple-negative breast cancer cells MDA-MB-468. Cells were treated for the indicated times with compounds or vehicle and proteins analyzed by western blot. (c) Examples of the compounds of the present subject matter dose-dependently induce apoptosis in the acute myeloid leukemia cells MOLM13. Cells were treated for 24 h with the indicated concentration of compounds and the increase in caspase3,7 activity was measured and compared to only vehicle (DMSO) treated cells. Caspase-3,7 activity was a measure of compound potency in cleaving the caspase substrate Z-DEVD-R110 and releasing rhodamine. The percentage increase in apoptotic cells was calculated by comparing the fluorescence readings obtained from compounds with those obtained from vehicle (DMSO)-treated cells.

Figure 10:
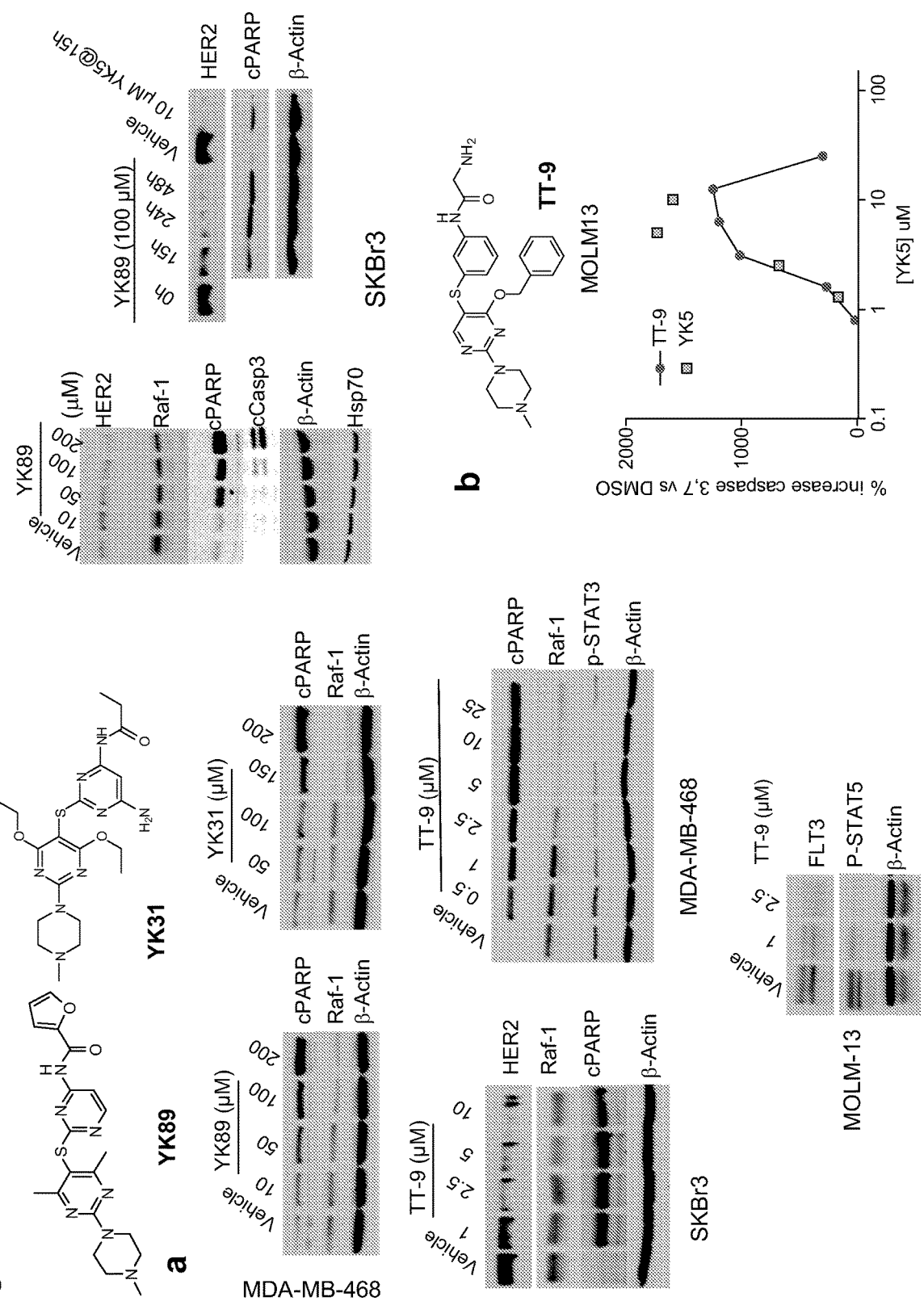

FIG. 10. (a) Examples of the compounds of the present subject matter dose-dependently reduce the steady-state levels of Raf-1 onco-kinase in the triple-negative breast cancer cells MDA-MB-468, and induce apoptosis as indicated by PARP cleavage. Examples of the compounds of the present subject matter dose-dependently reduce the steady-state levels of HER2 and Raf-1 onco-kinases in the SKBr3 HER2 overexpressing breast cancer cells, and induce apoptosis as indicated by PARP and caspase-3 cleavage. No associated induction of Hsp70 is observed. Example of the compounds of the present subject matter dose-dependently reduces the steady-state levels of FLT3 and p-STAT5 in the MOLM-13 mutant FLT3 expressing acute myeloid leukemia cells. Cells were treated for 24 h with the indicated concentrations of compounds or for the indicated times with the indicated concentration of compounds. Cells were lysed and proteins analyzed by western blotting. (b) Examples of the compounds of the present subject matter dose-dependently induce apoptosis in the acute myeloid leukemia cells MOLM13. Cells were treated for 24 h with the indicated concentration of compounds and the increase in caspase3,7 activity was measured and compared to only vehicle (DMSO) treated cells. Caspase-3,7 activity was a measure of compound potency in cleaving the caspase substrate Z-DEVD-R110 and releasing rhodamine. The percentage increase in apoptotic cells was calculated by comparing the fluorescence readings obtained from compounds with those obtained from vehicle (DMSO)-treated cells.

Figure 11:
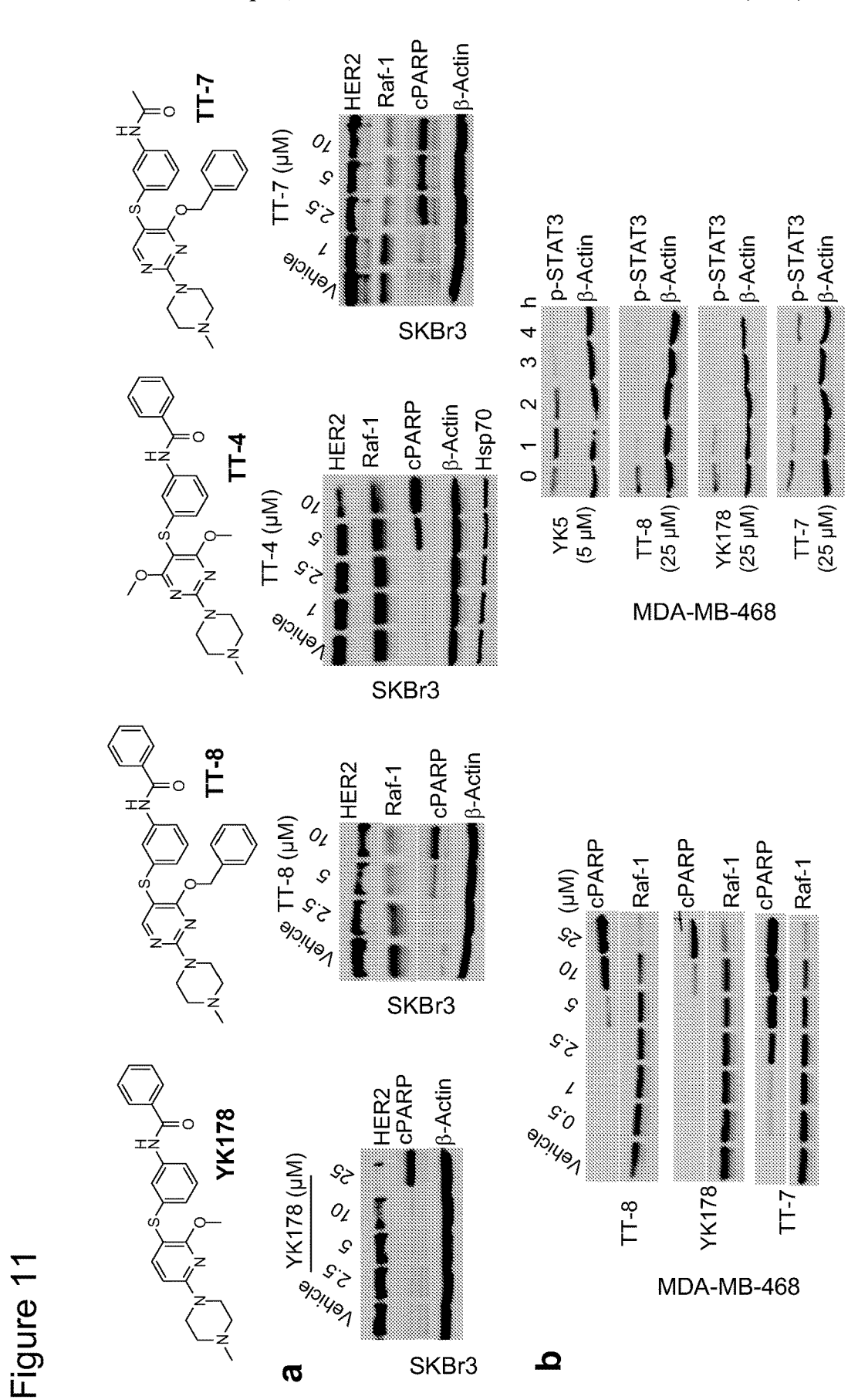

FIG. 11. (a) Examples of the compounds of the present subject matter reduce dose-dependently the steady-state levels of HER2 and Raf-1 oncokinases in the SKBr3 HER2 overexpressing breast cancer cells, and induce apoptosis as indicated by PARP cleavage. Cells were treated for 24 h with the indicated concentrations of agent. Cells were lysed and proteins analyzed by western blotting. (b) Examples of the compounds of the present subject matter inhibit the activity of the oncogenic STAT3, reduce the steady-state levels of Raf-1 and induce apoptosis in the triple-negative breast cancer cells MDA-MB-468. Cells were treated for 24 h with the indicated compounds or for the indicated times with the indicated concentrations of the compounds, and proteins analyzed by western blot.

Figure 12:
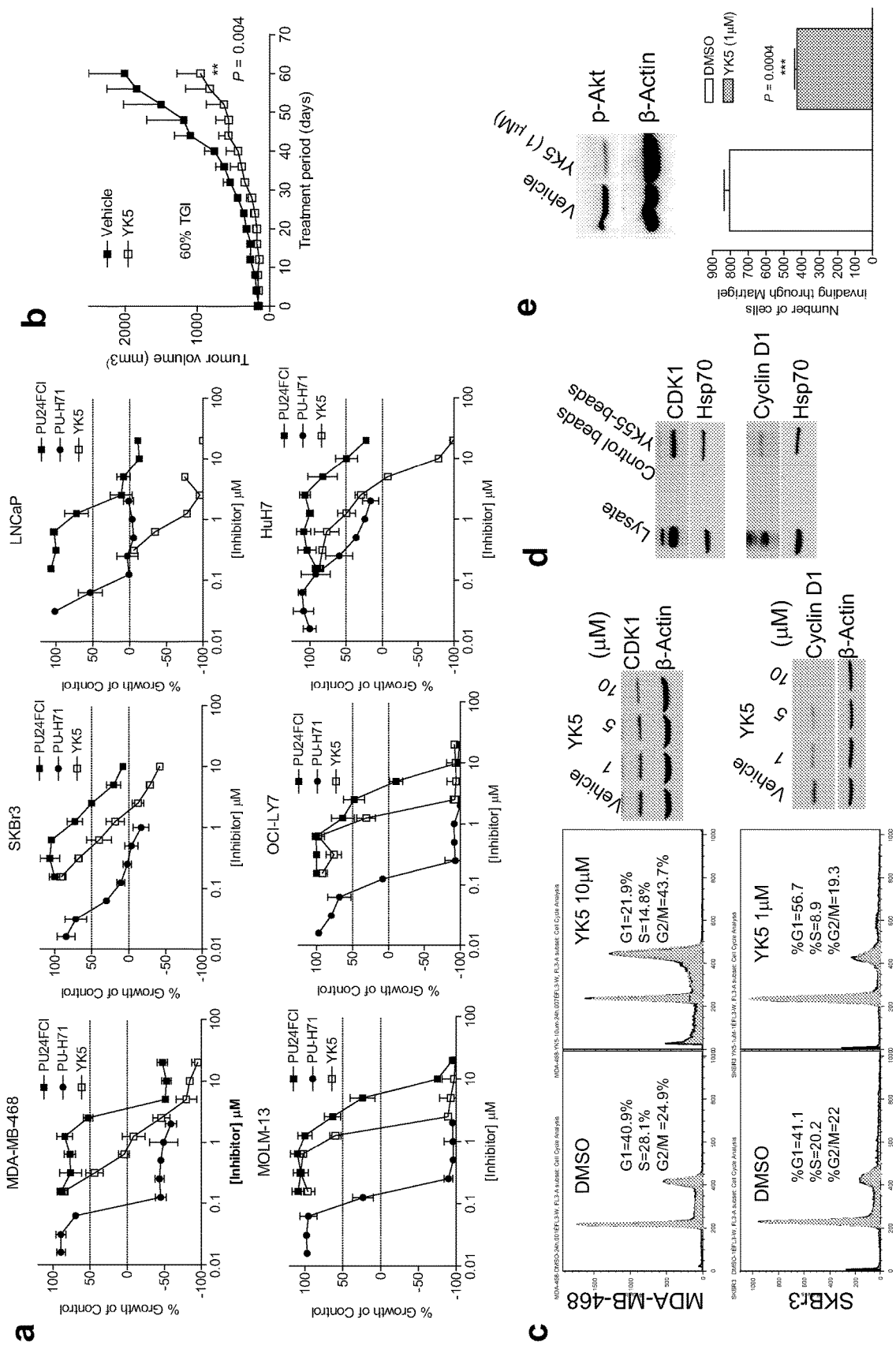

FIG. 12. YK5 affects the major hallmarks of cancer: inhibits proliferation and invasiveness and arrests cancer cells in the cell cycle. (a) The indicated cancer cells were incubated with increasing concentrations of inhibitors and growth over 72 h was assessed. Y-axis values below 0% represent cell death of the starting population. Drugs were assayed in triplicate. (b) Mice (n=5) bearing MDA-MB-468 subcutaneously (s.c.) xenografted tumors that reached a volume of approximately 100-200 mm$^3$, were administered i.t. YK5 or vehicle as described in Methods. Tumor volume (mm$^3$) was estimated from caliper measurements. (c) Cells were treated for 24 h with indicated concentrations of YK5. DNA content was analyzed by propidium iodide staining and flow cytometry (left), whereas proteins by western blotting (right). (d) Hsp70 client proteins isolated by YK55-beads from SKBr3 and MDA-MB-468 extracts (500 μg) were analyzed by western blotting. Control beads contain D-biotin (100 μM) attached. (e) MDA-MB-231 breast cancer cells were treated for 24 h with YK5 (1 μM) and protein extracts were subjected to immunoblotting (upper) or pretreated for 24 h with vehicle or YK5, and viable cells able to migrate through Matrigel over a 20 h period were quantified and data graphed (lower). Points, mean; bars, s.d. The data are consistent with those obtained from multiple repeat experiments (n≥3).

Figure 13:
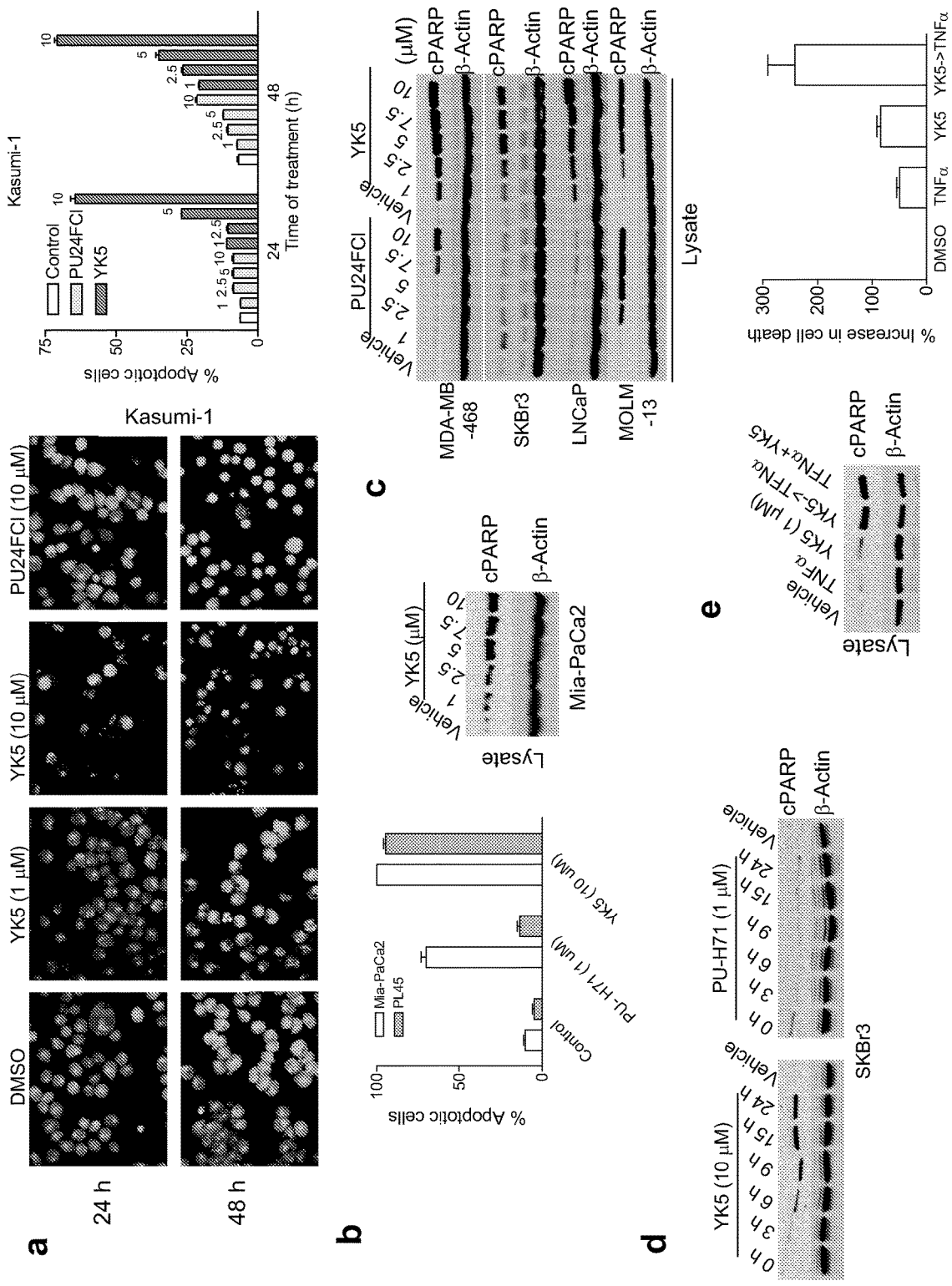

FIG. 13. YK5 has a higher apoptotic effect than Hsp90 inhibitors in select tumors. (a-d) Cells were treated with the indicated concentrations of inhibitors for the times presented. (a,b) Apoptotic cells were quantified by dual acridine orange/ethidium bromide staining as described in Methods. (c,d) Molecular markers of apoptosis (PARP cleavage) were analyzed in cells treated for 24 h with indicated concentrations of inhibitors (c) or for the indicated times with the indicated concentration of inhibitors (d) by western blotting. (e) MDAMB-468 cells were treated with vehicle, TNFα (20 ng/ml), YK5 (1 μM), pretreated with YK5 for 2 h before TNFα or co-treated, and cells were lysed for western blot analysis (left), or cell death was quantified by analyzing the hypodiploid population upon propidium iodine staining (right). The data are consistent with those obtained from multiple repeat experiments (n≥3). Points, mean; bars, s.d.

Figure 14:
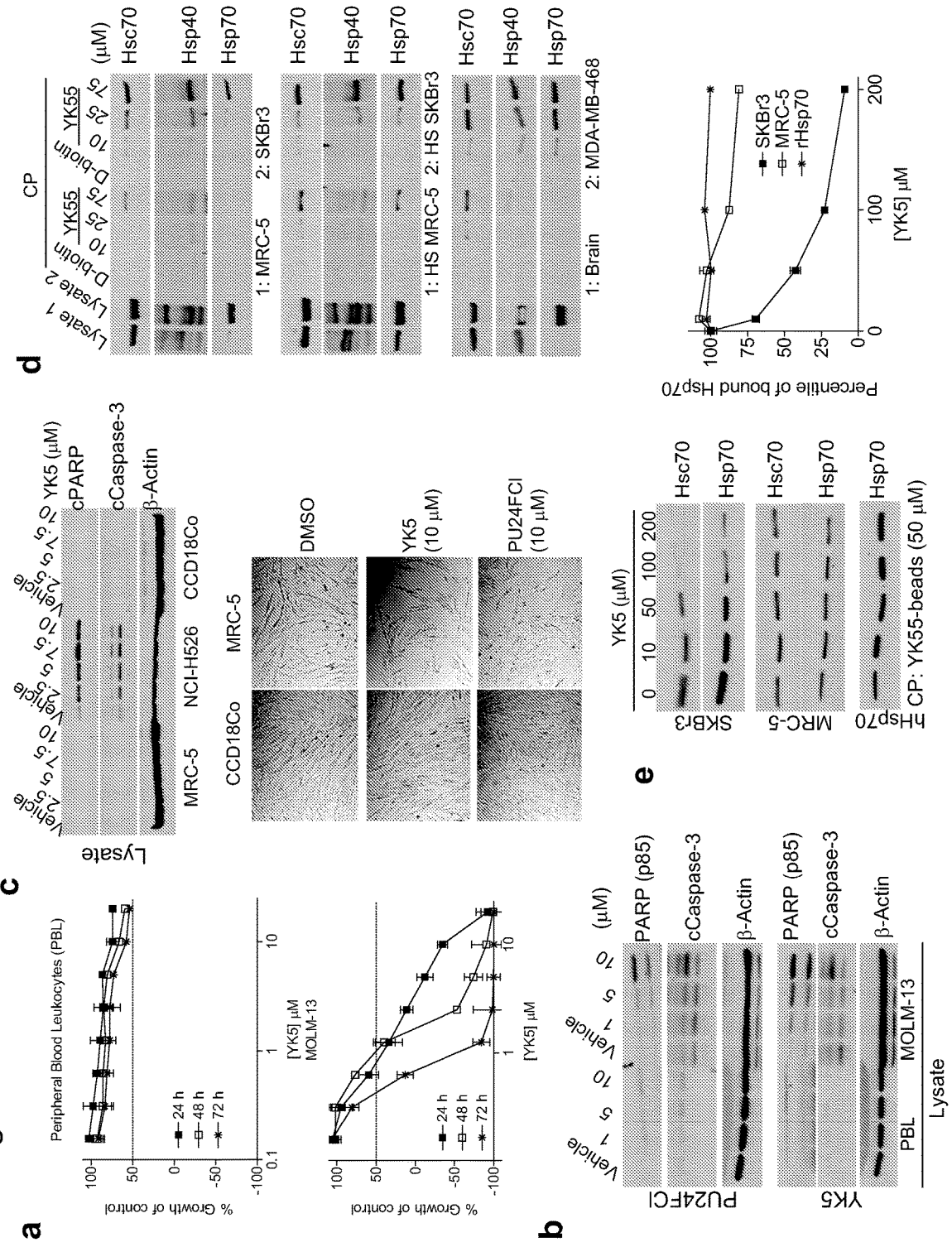

FIG. 14. YK5 has a higher affinity for tumor Hsp70s and selectively kills cancer cells. (a-c) Cells were treated with the indicated concentrations of inhibitors for the times presented, and metabolically viable cells by Alamar blue uptake as described in Methods (a). Molecular markers of apoptosis (PARP and caspase-3 cleavage) were analyzed in cells treated for 24 h with indicated concentrations of inhibitors, by western blotting (b, c). Morphology of cells treated for 24 h with vehicle or the indicated inhibitors was analyzed by light microscopy (c). (d) Extracts (500 μg) were incubated overnight with beads containing D-biotin (75 μM) or the indicated concentrations of YK55 added to 50 μl streptavidin beads. HS=heat shocked. (e) SKBr3 (200 μg) and MRC-5 (400 μg) extracts and recombinant human Hsp70 (2 μg) were incubated for 3 h with the indicated concentrations with YK5, followed by precipitation of Hsp70 complexes on YK55-beads (50 μM YK55 added to 50 μl streptavidin beads). Data obtained from three independent experiments were graphed (right). Points, mean; bars, s.d.

Figure 15:
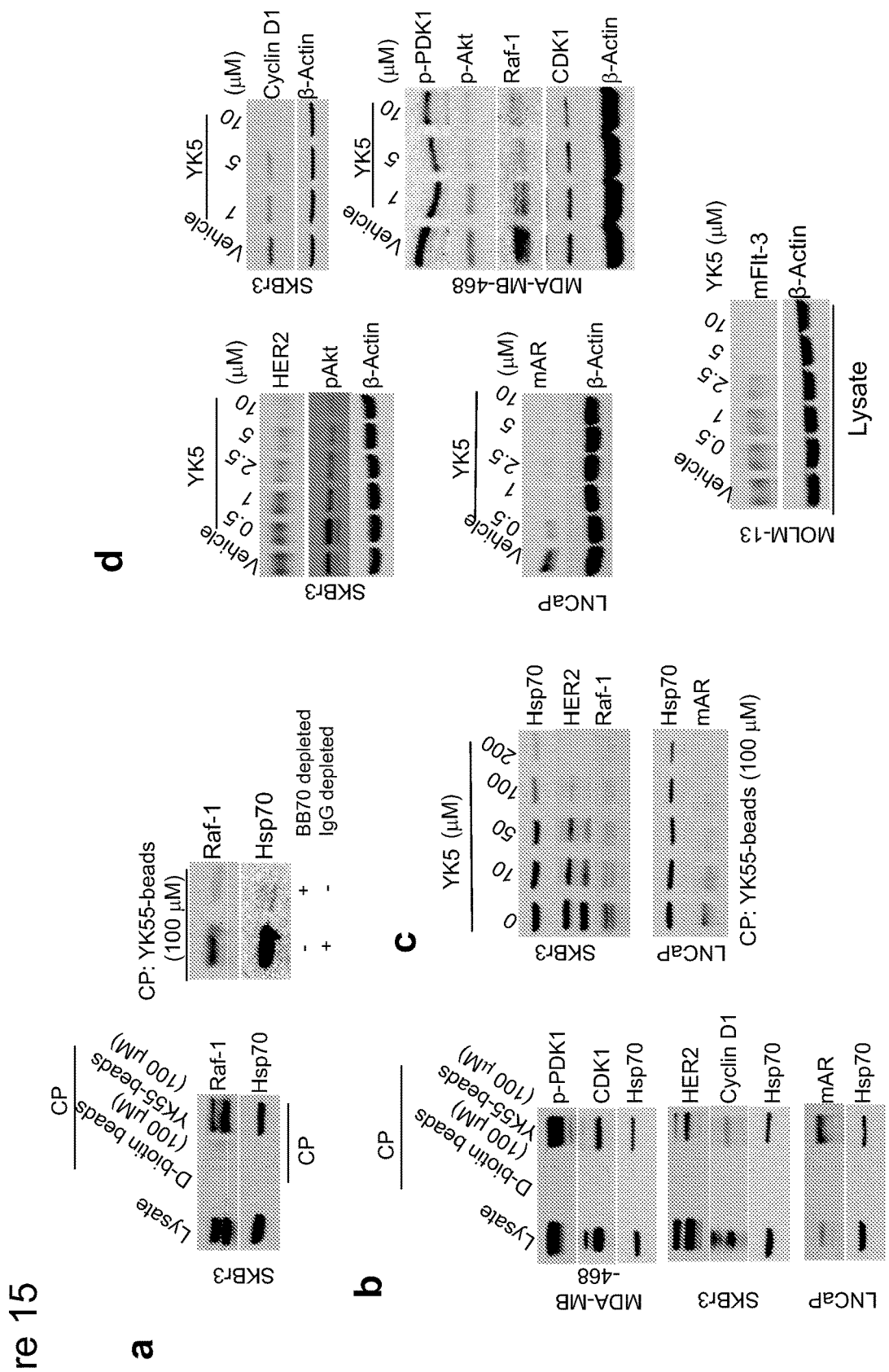

FIG. 15. A solid-support attached YK5, YK55-beads, isolates in a tumor-specific manner Hsp70 in complex with onco-proteins. (a, left and b) Hsp70 complexes precipitated from indicated cell extracts (500 μg) with YK55- or D-biotin-beads (100 μM YK55 or D-biotin added to 50 μl streptavidin beads, respectively) were analyzed by WB. (a, right) Binding of protein complexes to YK55 beads was probed in cell extracts in which Hsp/c70 levels were reduced by BB70 Ab or IgG immunoprecipitation, respectively. (c) Cell extracts were incubated for 3 h at 4° C. with the indicated concentrations of YK5, followed by precipitation of Hsp70s complexes on YK55-beads (100 μM YK55 added to 50 μl streptavidin beads). (d) YK5 reduces the steady-state levels of Hsp70-regulated oncoproteins. Cancer cells were treated for 24 h with the indicated concentrations of YK5 and cells were lysed for WB analysis. β-actin was used as loading control.

Figure 16:
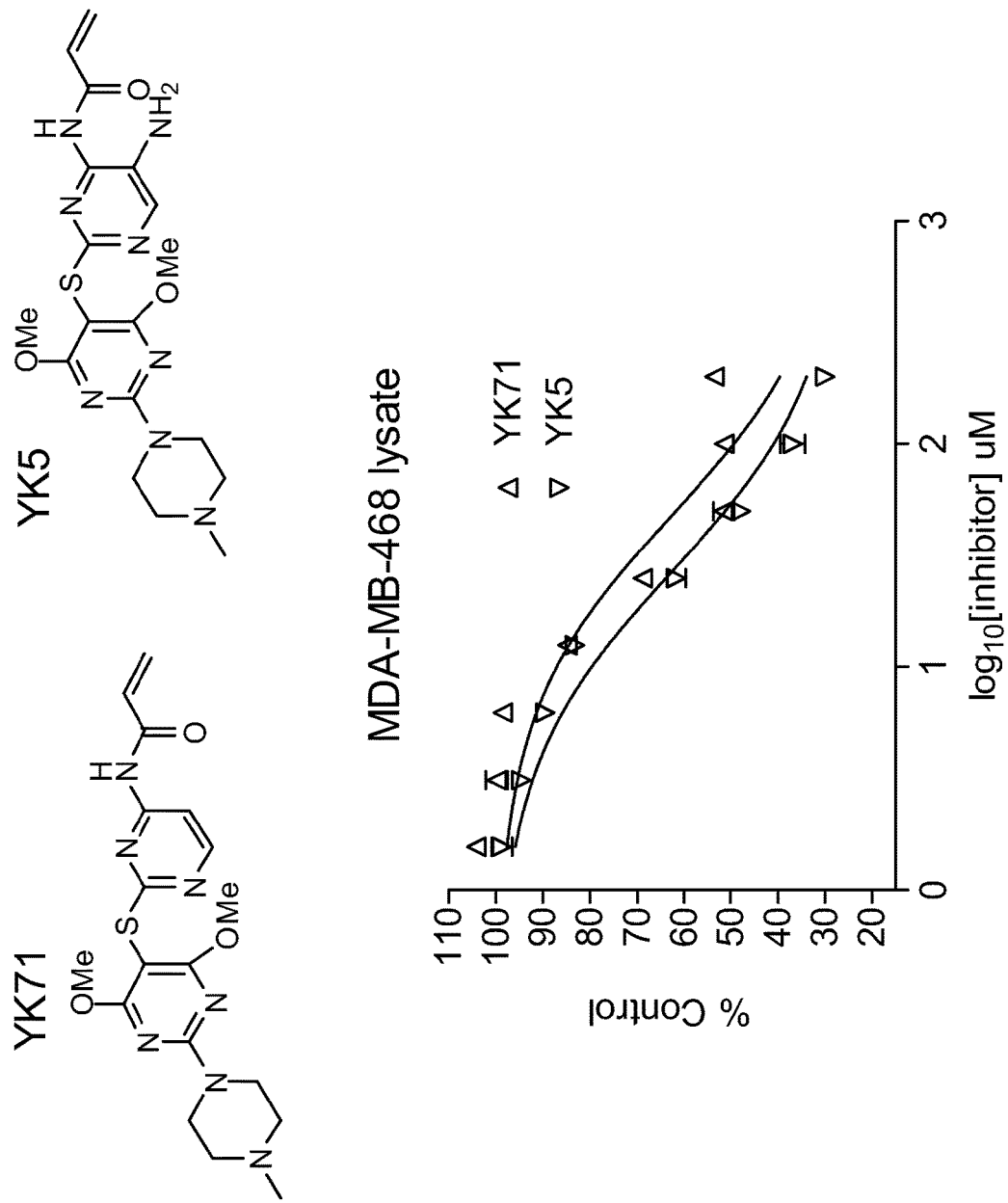

FIG. 16. Hsp70 competitive fluorescence polarization assay. Increasing concentrations of indicated inhibitors were added in triplicate to the assay plate and the Fluorescence Polarization (FP) assay was performed as indicated in Methods. The competitive effect was expressed as percentage of control and was calculated by dividing the millipolarization (mP; subtracting free cy3B-YK5) value from inhibitor wells by the average mP (subtracting free cy3B-YK5) from controls (cy3B-YK5 and cell lysate with vehicle DMSO) in each plate. Ligand binding was plotted against the $\log_{10}$ inhibitor concentration, and $EC_{50}$ values were calculated using a nonlinear least-square curve-fitting program in Prism 4.0. Points, mean; bars, s.d.

Figure 17:
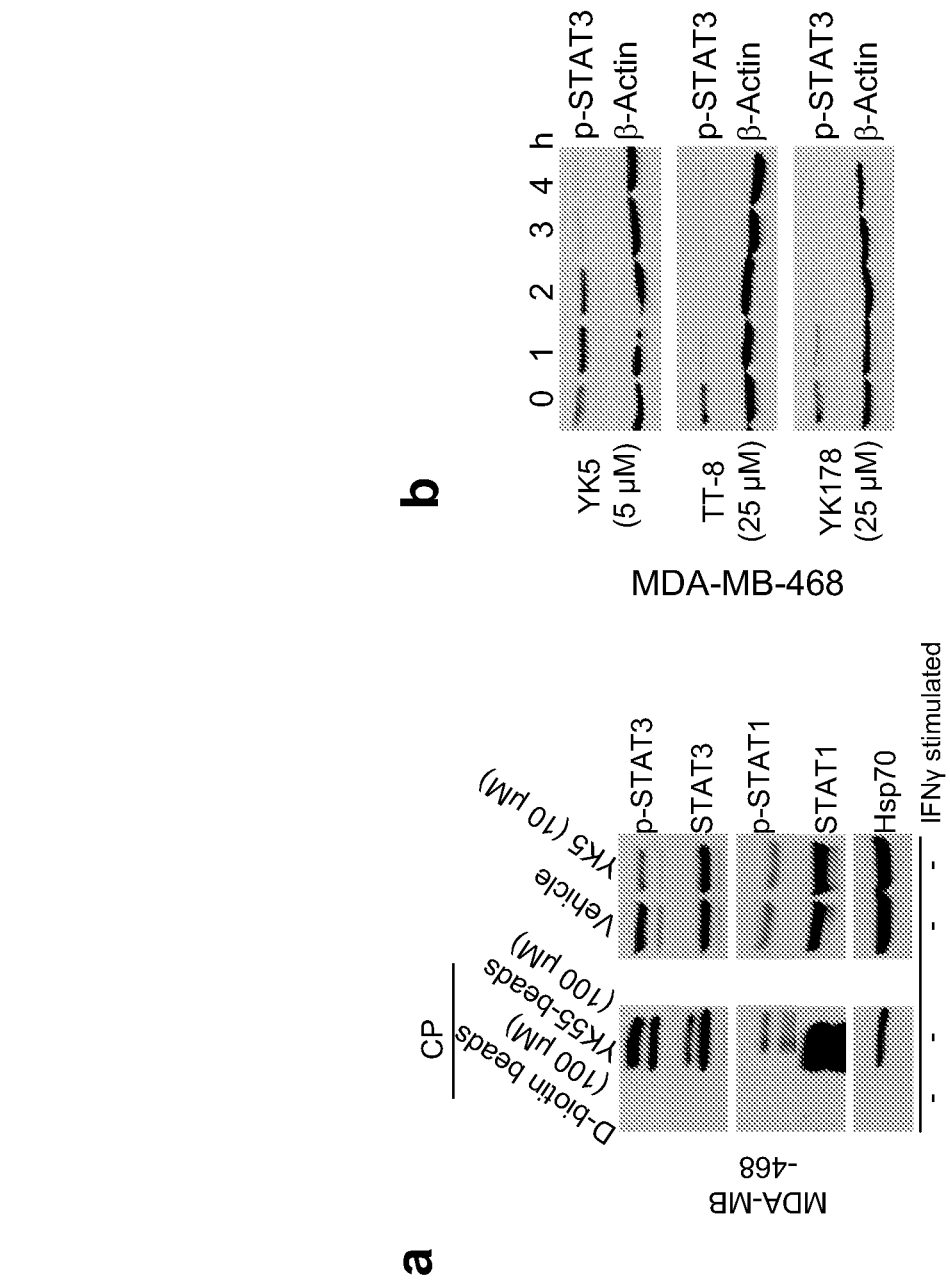

FIG. 17. YK5 identifies STAT1 and STAT3 as novel Hsp70s interacting oncogenic products in breast cancer cells. (a) YK55—but not biotin-beads recognize Hsp70 in complex with STAT1 and STAT3 in MDA-MB-468 extracts (left). To investigate the effect of YK5 on the steady-state levels and the activity of STATs, cells were treated for 24 h with vehicle (DMSO) or YK5 (10 µM) (right). (b) Example compositions of matter potently inhibit STAT3 in the triple-negative cells MDA-MB-468. Activated STAT3 is part of an important oncogenic pathway in triple-negative breast cancers.

Figure 18:
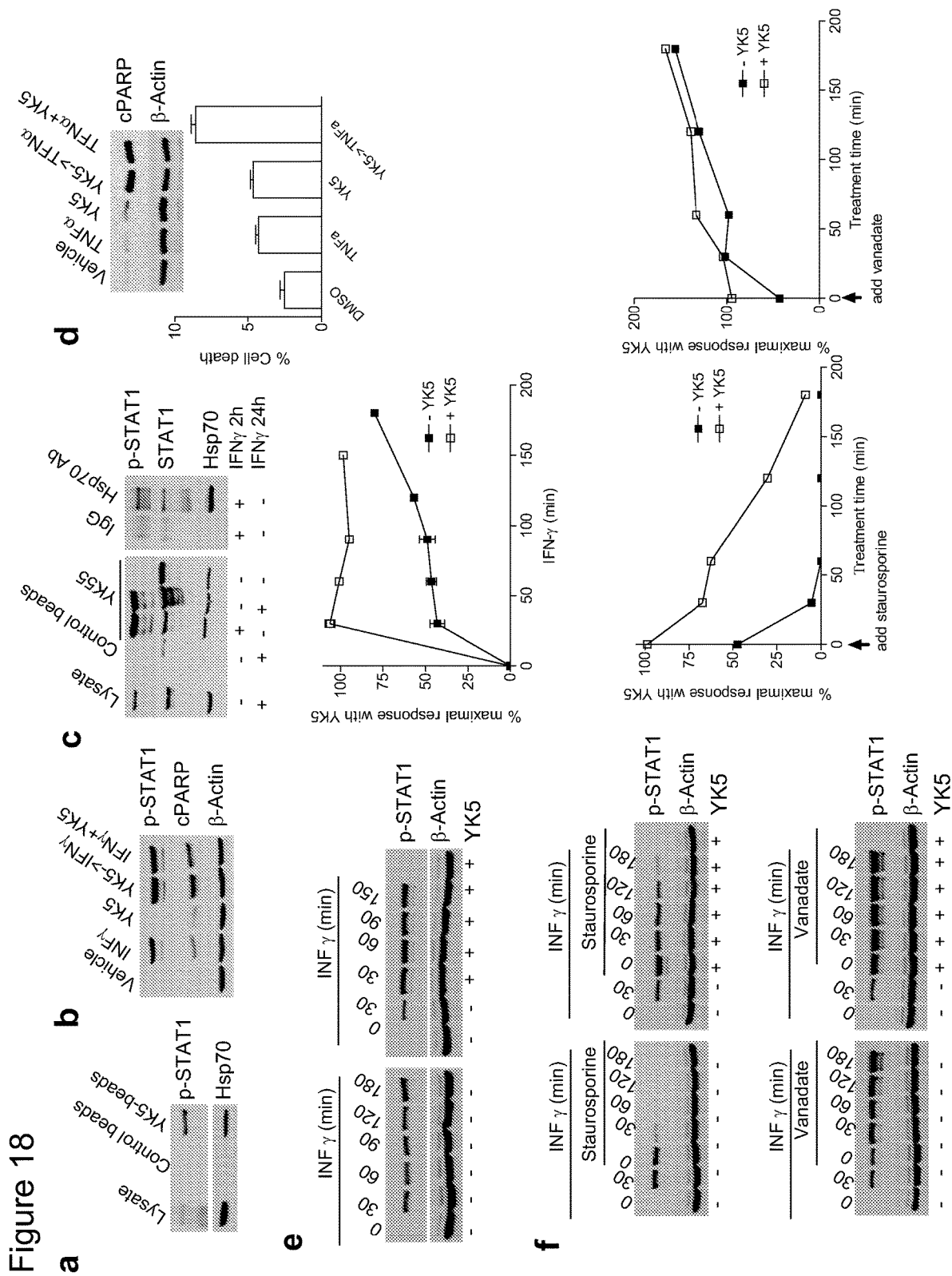

FIG. 18. YK5 uncovers a novel mechanism of inhibition of the pro-apoptotic effect of STAT1 tumor suppressor. (a) YK55 beads recognize Hsp70 in complex with p-STAT1 and STAT1 in MDA-MB-468 extracts (500 µg). (b) Binding of protein complexes to YK55 beads was probed in MDA-MB-468 cell extracts with Hsp/c70 levels reduced by BB70 Ab or IgG immunoprecipitation. (c) MDA-MB-468 cells were treated 7 h with vehicle, IFNγ100 ng/ml), YK5 (10 µM), pretreated with YK5 for 2 h before IFNγ stimulation or co-treated and cells were lysed for western blot analysis. (d) Cells were stimulated with IFNγ100 ng/ml), and Hsp70/STAT1 complexes in extracts (500 µg) analyzed by chemical and immuno-precipitation with D-biotin, YK55-beads and an Hsp70 Ab, respectively. (e,f) Cells were stimulated with IFNγ in the presence or absence of YK5 (10 µM) for the times shown, and with or without added staurosporine or orthovanadate as described in Methods. Levels of p-STAT1 were analyzed by western blotting and quantified by dosimetry. Data from two repeat experiments were graphed against the treatment time.

Figure 19:
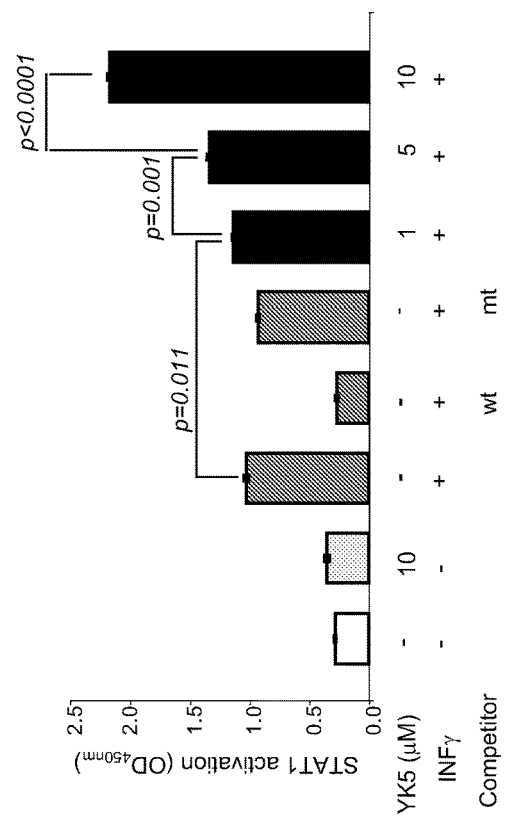
Figure 19:
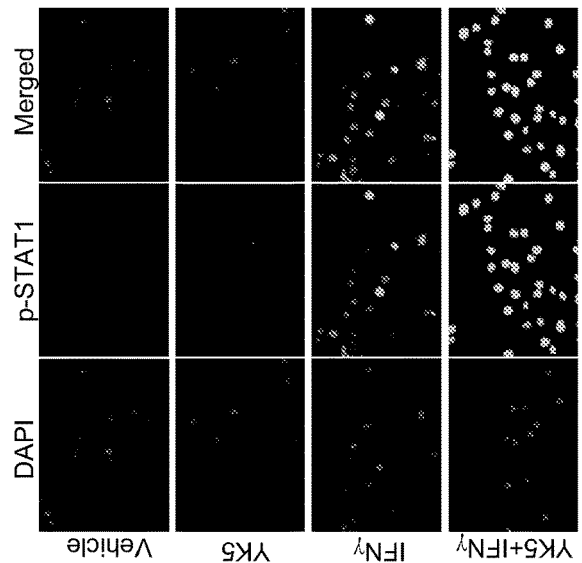

FIG. 19. YK5 enhances the nuclear content of IFNγ activated STAT1 and potentiates its binding to DNA. MDAMB-468 cells were treated with IFNγ (100 ng/ml) or co-treated with IFNγ (100 ng/ml) and YK5 (10 µM). (a) Activated STAT1 (pTyr701), was determined by immuno-fluorescent microscopy with a secondary antibody conjugated with FITC. Nuclear staining was performed with DAPI. (b) Activated STAT1 binding to STAT consensus binding site (5'-TTCCCGGAA-3') was determined by an ELISA-based assay. Activated STAT1, contained in lysates from untreated (white bar), treated with YK5 (light grey bar), IFNγ (dark grey bars) or the combination of IFNγ and YK5 (black bars) cells, and bound to the oligonucleotide, was detected through use of an anti-STAT1 antibody. Assays were performed in the absence or presence of 20 pmol of competitor oligonucleotide that contains either a wild-type or a mutated STAT consensus binding site using IFNγ-treated cells (dark grey bars). Experiments were carried out in four replicates. Results are expressed as mean absorbance values (OD450 nm) with SEM.

Figure 20:
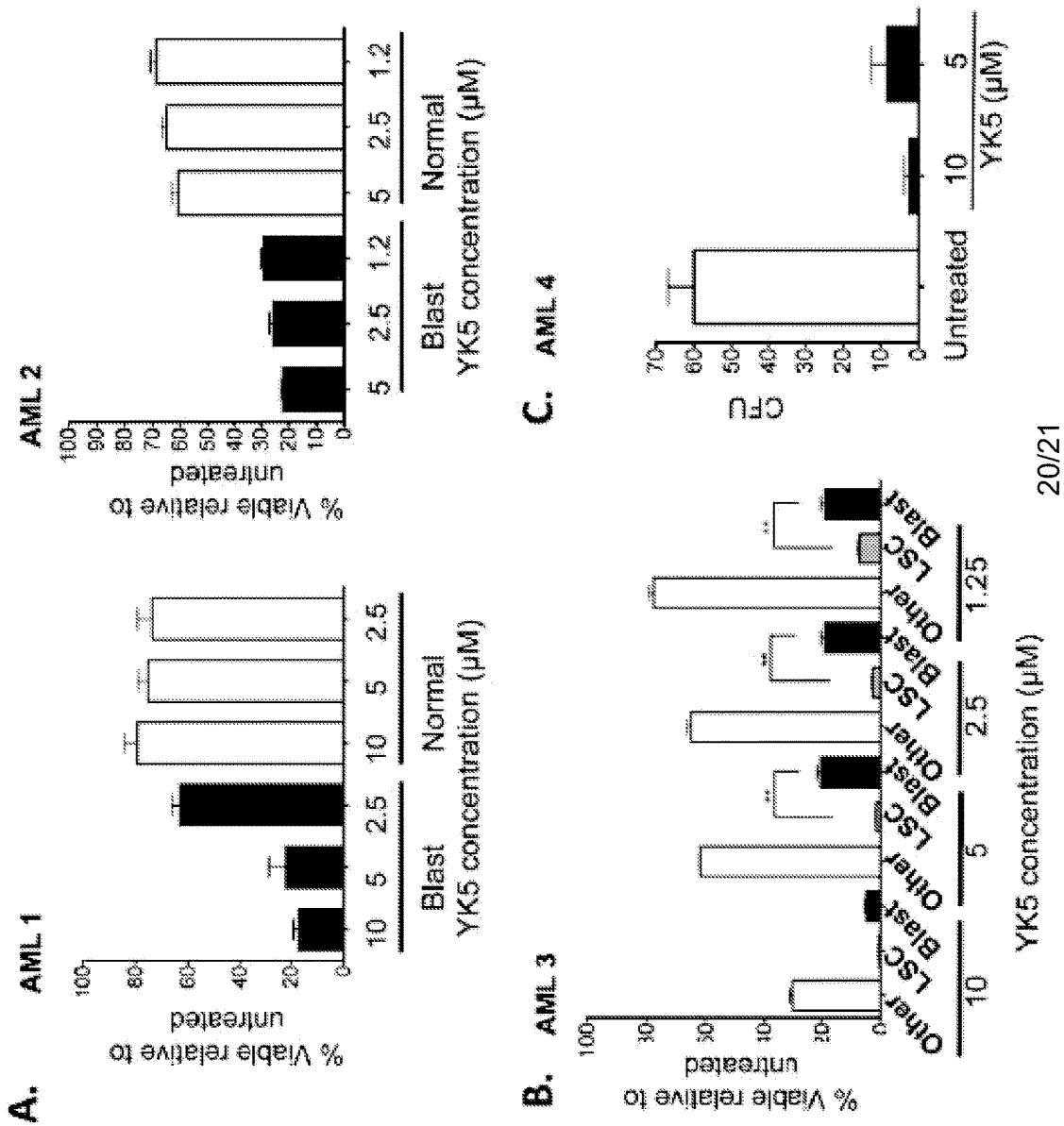

FIG. 20. Treatment of primary AML cells with YK5. YK5 kills both blast and cancer stem cells but not normal cells. Cells were treated with increasing concentrations of YK5 for 24 h. (a-b) % viability relative to untreated control is shown. Open bars: "Other" represent normal cells in the same patient (non-blast), Gray bars: Blasts (CD45 dim). red bars: leukemia stem cells (LSCs) (CD34+CD38-CD123+). (c) CFU (Colony forming units) decrease after treatment of primary AML cells with YK5. **p<0.001.

Figure 21:
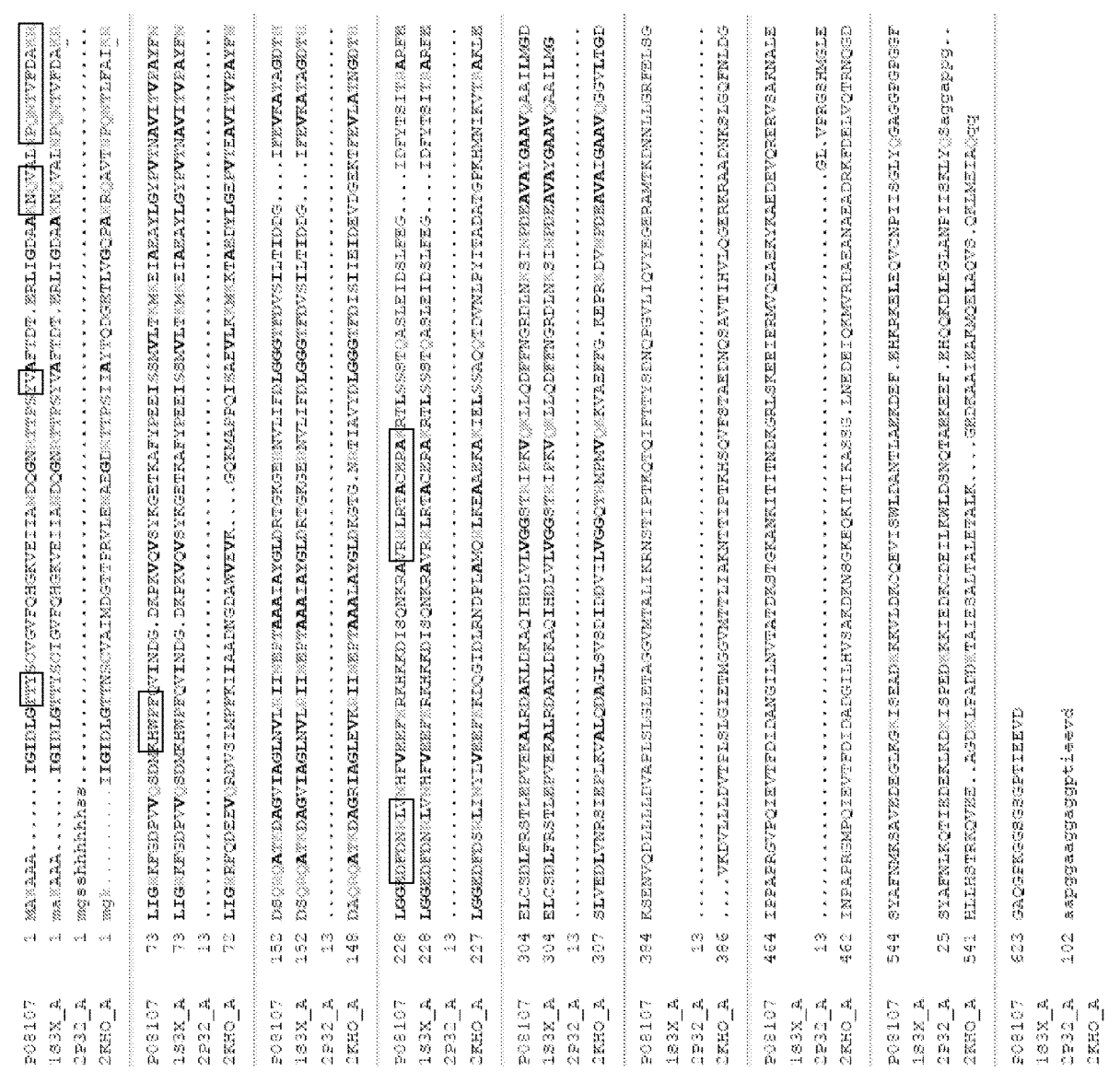

FIG. 21: Alignment of protein sequence of full length hHsp70 (SEQ ID NO:1) (Accession number: P08107), N-terminal hHsp70 protein (SEQ ID NO:2) (PDB ID: 1S3X), E. coli Hsp70 (DNAK) structure (SEQ ID NO:3) (PDB ID: 2KHO) and C. elegans (PDB ID: 2P32) (SEQ ID NO:4). Residue annotations are underlined and conserved residues are displayed in similar color. Sequences defining the allosteric pocket Site 1 are shown in boxes. Important amino acids in these sequences interact with the herein designed ligands.

DETAILED DESCRIPTION

Definitions

As used herein, the terms "administer," "administering," and "administration," refer to any method which, in sound medical practice, delivers the composition to a subject in such a manner as to provide a therapeutic effect.

The phrase "derivative" as used herein refers to any hydrate, solvate, salt, racemate, isomer, enantiomer, prodrug, metabolite, ester, or other analog or derivative of a particular chemical compound or molecule. The term "derivative" may also mean a modification to the disclosed compounds including, but not limited to, hydrolysis, reduction, or oxidation products of the disclosed compounds. Hydrolysis, reduction, and oxidation reactions are known in the art.

The term "modulating" refers to the process of producing an effect on biological activity, function, health, or condition of an organism in which such biological activity, function, health, or condition is maintained, enhanced, diminished, or treated in a manner which is consistent with the general health and well-being of the organism. The term "enhancing" the biological activity, function, health, or condition of an organism refers to the process of augmenting, fortifying, strengthening, or improving.

As used herein, the phrases an "effective amount" or a "therapeutically effective amount" of an active agent or ingredient, or pharmaceutically active agent or ingredient, which are synonymous herein, refer to an amount of the pharmaceutically active agent sufficient enough to have a therapeutic effect upon administration. A therapeutically effective amount of the pharmaceutically active agent may, will, or is expected to cause a relief of symptoms. Effective amounts of the pharmaceutically active agent will vary with the particular condition or conditions being treated, the severity of the condition, the duration of the treatment, the specific components of the composition being used, and like factors.

The phrase "any substituent," as used herein in defining formula (I) and (I'), means any substituent that may be replaced for hydrogen. In some embodiments, the term "any substituent," as used herein in defining formula (I) and (I'), is an optionally substituted straight or branched alkyl, alkenyl, or alkynyl group; an optionally substituted carbocyclic, heterocyclic, aryl, or heteroaryl group; halo; an optionally substituted $C_{2-22}$ acyl group; hydroxyl; nitro; cyano; aryloxy; alkoxy; halogenated alkoxy; alkenyloxy; hydroxyalkyl; amino; alkylamino; dialkylamino; cycloalkylamino; arylamino; diarylamino; acylamino; carbamyl; substituted or unsubstituted amido; alkylamido; alkylsulfonamido; sulfonamido; —$NHSO_2$alkenyl; —NHCOalkenyl; —NHCOalkynyl; —COalkenyl; —COalkynyl; trihalocarbon; thioalkyl; $SO_2$-alkyl; —COO-alkyl; —COalkyl; and alkyl-CN; or a pharmaceutically acceptable salt thereof or a hydrate thereof. In other embodiments, the phrase "any substituent" refers to a substituent that comprises a label or marker group useful for identifying, tracking, and or isolating the compound. Non-limiting examples of label groups and marker groups useful herein include, for example, fluorescent groups, biotin groups, avidin groups, and enzyme linker groups.

In naming substituent options, such as for Z and $W_1$-$W_4$ below, the name refers to the type of group that is directly attached to the central structure and does not preclude additional functionality attached to the base substituent.

Thus, the term "alkyl" refers to an optionally substituted linear, cyclic, or branched saturated hydrocarbon group, in which the atom attached to the remainder of the structure is a carbon atom. The alkyl group may have 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred "alkyl" groups herein contain 1 to 12 carbon atoms. "Lower alkyl" refers to an alkyl group of one to six, more preferably one to four, carbon atoms. The alkyl group may have substituents, for example halogen, hydroxy, alkoxy, amino, substituted and unsubstituted substituted and unsubstituted amido, sulfonamino, sulfonamido, sulphoxy, aryl, cyano, carboxy, carboxamide, acyl, nitro, thio.

The term "alkenyl" refers to an optionally substituted linear, cyclic, or branched unsaturated hydrocarbon group having a carbon-carbon double bond at one or more places, in which the atom attached to the remainder of the structure is a carbon atom. The alkenyl group may have 2-20 carbons, preferably 2-8 carbons. The linear alkenyl group includes, for example: a 1-alkenyl group such as an ethenyl group, 1-propenyl group, and 1-butenyl group; and a 2-alkenyl group such as a 2-butenyl group, and 2-pentenyl group. The alkenyl group may have substituents that are the same as for an alkyl group.

The term "alkynyl" refers to an optionally substituted branched or unbranched unsaturated hydrocarbon group having a carbon-carbon triple bond at one or more places, in which the atom attached to the remainder of the structure is a carbon atom. The alynyl group may have 2-20 carbons, preferably 2-8 carbons. Examples include: a 1-alkynyl group such as ethynyl group, 1-propynyl group, and 3,3-dimethyl-1-butynyl group; and a 2-alkynyl group such as a 2-propynyl group, 2-butynyl group, and 3-phenyl-2-propynyl group. The alkynyl group may have substituents that are the same as for an alkyl group.

The terms "halo" or "halogen" refer to fluoro, chloro, bromo or iodo, usually regarding halo substitution for a hydrogen atom in an organic compound. Of the halos, chloro and fluoro are generally preferred with chloro generally being the more preferred.

The term "amino" encompasses molecules in which an amine N is directly bonded to the central structure, including $NH_2$, alkylamino and alkenylamino groups.

The term "acyl" refers to hydrogen, alkyl, partially saturated or fully saturated cycloalkyl, partially saturated or fully saturated heterocycle, and aryl substituted carbonyl groups.

The term "aryl" refers to a substituted or unsubstituted aromatic hydrocarbon ring group having 5 to about 30 carbon atoms with from about 6 to about 14 carbon atoms being preferred. The "aryl" group can have a single ring or multiple condensed rings. When a substituent is identified as an aryl substituent, an atom of the aryl ring is bonded directly to an atom of the reminder of the structure. An aryloxy substituent is an aryl group connected to the remainder of the structure by an —O— bridge. The aryl group may have substituents that are the same as for an alkyl group, plus alkyl, alkenyl or alkynyl substituents. The term "aryl" includes, but is not limited to phenyl, α-naphthyl, β-naphthyl, biphenyl, anthryl, tetrahydronaphthyl, fluorenyl, indanyl, biphenylenyl, and acenaphthenyl. Specifically included within the definition of "aryl" are those aromatic groups that are optionally substituted. For example, in representative embodiments of the present subject matter, the, "aryl" groups are optionally substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, amino, amino substituted by one or two alkyl groups of from 1 to 6 carbon atoms, aminoacyl, acylamino, azido, cyano, halo, nitro, thioalkoxy, trihalomethyl, and aryl. The term "aralkyl" embraces aryl-substituted alkyl moieties. Preferable aralkyl groups are "lower aralkyl" groups having aryl groups attached to alkyl groups having one to six carbon atoms. Examples of such groups include benzyl, diphenylmethyl, triphenylmethyl, phenylethyl, and diphenylethyl.

The term "carbocyclic" refers to an optionally substituted group that contains one or more covalently closed ring structures, and that the atoms forming the backbone of the ring are all carbon atoms. The term thus distinguishes carbocyclic from heterocyclic rings in which the ring backbone contains at least one non-carbon atom. The terms "cycloalkane" or "cyclic alkane" or "cycloalkyl" refer to a carbocyclic group in which the ring is an optionally substituted cyclic aliphatic hydrocarbon, for example, a cyclic alkyl group preferably with 3 to 12 ring carbons. "Cycloalkyl" includes, by way of example, cyclopropyl, cyclobutyl, cyclopentyl, cyclohexyl, cycloheptyl, or cyclooctyl, and the like.

The term "heterocyclic or heterocycle" means an optionally substituted, saturated or unsaturated, aromatic or non-aromatic cyclic hydrocarbon group with 4 to about 20 carbon atoms, preferably about 5 to about 6, wherein 1 to about 4 carbon atoms are replaced by nitrogen, oxygen or sulfur. The preferred heterocycles are selected from the group consisting of benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperidine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine, and triazole. Structures of some heterocycles are as follows:

Heterocycles

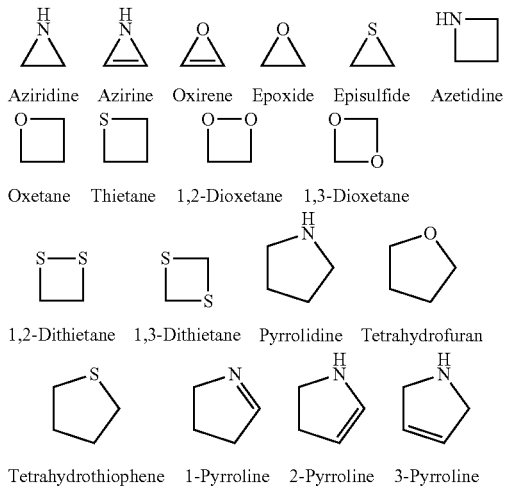

Aziridine   Azirine   Oxirene   Epoxide   Episulfide   Azetidine

Oxetane   Thietane   1,2-Dioxetane   1,3-Dioxetane 1,2-Dithietane   1,3-Dithietane   Pyrrolidine   Tetrahydrofuran Tetrahydrothiophene   1-Pyrroline   2-Pyrroline   3-Pyrroline

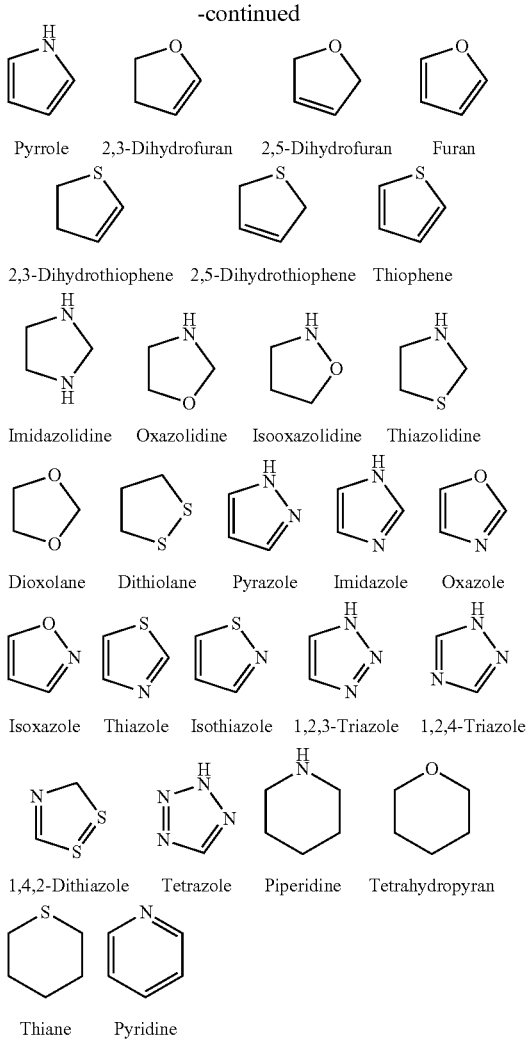

As used herein, the term "heteroaryl" is defined as a substituted or unsubstituted aromatic heterocyclic ring system (monocyclic or bicyclic). Heteroaryl groups can have, for example, from about 4 to about 20 carbon atoms (unless explicitly specified otherwise) with from about 4 to about 10 being preferred. In some embodiments, heteroaryl groups are aromatic heterocyclic rings systems having about 4 to about 14 ring atoms and containing carbon atoms and 1, 2, 3, or 4 heteroatoms selected from oxygen, nitrogen or sulfur. Representative heteroaryl groups are furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline.

The term "bridged ring" refers to group of 6 to 12 atoms that form an optionally substituted carbocycle, heterocycle, aryl, or heteroaryl comprising one or more rings wherein two or more non-adjacent ring atoms are connected. Non-limiting examples of a bridged ring structure may include a triccycloalkane, such as, for example, adamantanyl.

"Optional" or "optionally" means that the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution. "Optionally" is inclusive of embodiments in which the described conditions is present and embodiments in which the described condition is not present.

The compounds of the present subject matter can exist in tautomeric, geometric or stereoisomeric forms. The present subject matter contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the present subject matter.

The phrase "pharmaceutically acceptable carrier" as used in this regard refers to any inactive ingredient present in one of the herein described compositions in an amount effective to enhance the stability, effectiveness, or otherwise of said composition. Non-limiting examples of such pharmaceutically acceptable carriers include diluents, excipients, suspending agents, lubricating agents, adjuvants, vehicles, delivery systems, emulsifiers, disintegrants, absorbants, adsorbents, preservatives, surfactants, colorants, flavorants, emollients, buffers, pH modifiers, thickeners, water softening agents, humectants, fragrances, stabilizers, conditioning agents, chelating agents, sweeteners, propellants, anticaking agents, viscosity increasing agents, solubilizers, plasticizers, penetration enhancing agents, glidants, film forming agents, fillers, coating agents, binders, antioxidants, stiffening agents, wetting agents, or any mixture of these components.

As used herein, the phrase "pharmaceutically acceptable salts" refers to salts of certain ingredient(s) which possess the same activity as the unmodified compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, and naturally and synthetically derived amino acids.

As used herein, "subject" or "individual" or "animal" or "patient" or "mammal," refers to any subject, particularly a mammalian subject, for whom diagnosis, prognosis, or therapy is desired, for example, a human.

As used herein, a "treatment" or "treating" of a disease, disorder, or condition encompasses alleviation of at least one symptom thereof, a reduction in the severity thereof, or the delay, prevention, or inhibition of the progression thereof.

Treatment need not mean that the disease, disorder, or condition is totally cured. A useful composition herein needs only to reduce the severity of a disease, disorder, or condition, reduce the severity of symptoms associated therewith, provide improvement to a patient or subject's quality of life, or delay, prevent, or inhibit the onset of a disease, disorder, or condition.

As used herein, the term "modulating" means that a compound of the present subject matter may be an activator or inhibitor of Hsp70 or Hsc70. An activator would promote the HSP pathways. activators would be useful for diseases where increased proliferation may have a beneficial therapeutic effect. An inhibitor would inhibit Hsp70 or Hsc70 and thereby inhibit the HSP pathway and inhibit the growth of various cancers and proliferative disorders. Consequently, in conditions where increased activity of HSP pathways is required, then an activator is preferred. In conditions where inhibition of the HSP pathway is required, then an inhibitor is preferred.

In certain embodiments, the compounds of the present subject matter are useful in the treatment of proliferative disorders. The term "proliferative disorder" as used herein refers to cancer, including breast, prostate, lung, colon, stomach, pancreatic, ovarian, brain and hematopoietic cancers, esophageal carcinoma, renal cell carcinoma, bladder cancer, head and neck cancer, leukemias, and sarcomas such as cholangiosarcoma and esophageal sarcoma. In particular, this includes breast and ovarian cancers, prostate cancer, pancreatic cancer, hepatocellular carcinoma, non-small- and small-cell lung cancer (NSCLC and SCLC), colorectal cancer, leukemia, and lymphoma. Included are metastatic cancers, such as, for example, metastatic breast cancer.

As used herein, an "oncoprotein" means a protein that can potentially induce or facilitate neoplastic transformation of a cell. In one example, the protein can be encoded by an oncogene. An oncogene as used herein is a gene that produces a gene product that can potentially induce or facilitate neoplastic transformation of a cell. An oncogene can have a viral or cellular origin. Nonlimiting examples of oncoproteins include growth factor receptors, protein kinases, signal transducers, nuclear phosphoproteins, methyltransferases and transcription factors. When these proteins are aberrantly expressed, activated or translocated within the cell after structural and/or regulatory changes, uncontrolled cell proliferation and deficit in cell death can result. Nonlimiting examples of an oncoprotein of the present subject matter include ErbB2 (Her2/Neu), EGFR/ErbB1, ErbB3, ErbB4, ErbB5 and any other erbB family members, PDGFR, PML-RAR AKT, BCR-abl, src, Raf family members (e.g., C-Raf, B-Raf), dominant negative p53, HIF-1α, Telomerase, MTG8 (myeloid leukemia protein), Heat Shock factor, Hepatitis B virus reverse transcriptase, c-src, v-src, mutated or absent p53, estrogen receptor, mutant K-ras proteins, nitric oxide synthase and chimeric protein $p210_{BCR-ABL}$ individually and/or in any combination. The present invention further includes any other oncoprotein now known or later identified to be associated with Hsp70 or the Hsp70-Hsp90 complex. In some embodiments, the oncoproteins present in a patient are measured before, during, and after therapy. In other embodiments, administering compounds of the present subject matter to a patient in need thereof results in the destabilization and degradation of one or more oncoproteins in the patient.

Any concentration ranges, percentage range, or ratio range recited herein are to be understood to include concentrations, percentages or ratios of any integer within that range and fractions thereof, such as one tenth and one hundredth of an integer, unless otherwise indicated.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application. For example, "a" polymer refers to both one polymer or a mixture comprising two or more polymers.

Throughout the application, descriptions of various embodiments use "comprising" language; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Other terms as used herein are meant to be defined by their well-known meanings in the art.

Compounds of the Present Subject Matter

In accordance with a first general embodiment, the present subject matter relates to compounds having the formulas:

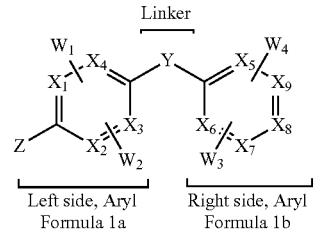

Formula I

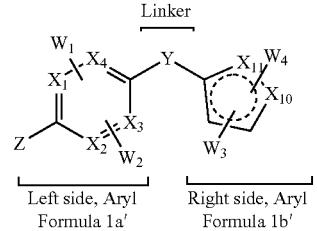

Formula I' their stereoisomers, tautomers, and pharmaceutically acceptable salts thereof, wherein, $X_1$, $X_2$, $X_3$, $X_4$, $X_5$, $X_6$, $X_7$, $X_8$, and $X_9$ are independently selected from CH, substituted C, and substituted N;

$X_{10}$ and $X_{11}$ are independently selected from CH, $CH_2$, NH, NR, O, and S such that aromaticity is maintained; R is an alkyl or substituted alkyl chain;

Y is S, SO, $SO_2$, $CH_2$, CHR, CRR, CO, O, NH, or NR, wherein R is a lower alkyl or alkoxyl chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, $_{and}$ alkyl-CN;

$W_1$ and $W_2$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_1$ and $W_2$ may be joined together via a linker, so as to form a fused 5- or 6-membered ring; and $W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_3$ and $W_4$ may be joined together via a linker, so as to form a fused 5- or 6-membered ring.

Furthermore, $W_2$ may be joined to the right side aryl ring directly to form a 5-membered ring or via a linker to form a 6 or 7-membered ring.

In preferred embodiments of formula (1a) and formula (1b), $X_1$-$X_4$ are independently selected from but not limited to:

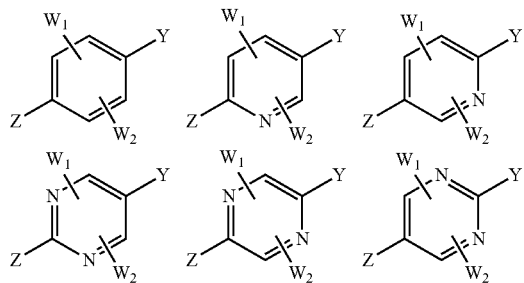

In preferred embodiments of formula (1a), $X_5$-$X_9$ are independently selected from but not limited to:

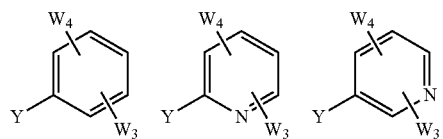

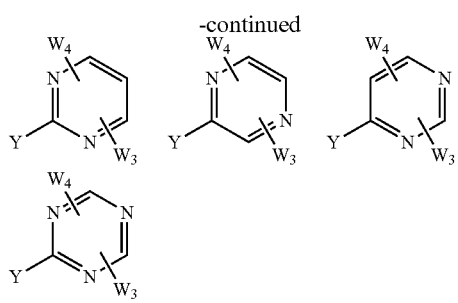

In preferred embodiments of formula (1b'), $X_{10}$ is $CH_2$, NH, NR', O, and S; wherein R' is a lower alkyl chain;

In preferred embodiments of formula (I) and formula (I') Y is S, SO, $SO_2$, O or CH2.

In preferred embodiments of formula (1a) and formula (1a') Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted substituted and unsubstituted amido, alkylamido, and dialkylamido.

In preferred embodiments of formula (1a) and formula (1a') $W_1$ and $W_2$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted substituted and unsubstituted amido, alkylamido, and dialkylamido; $W_1$ and $W_2$ may be joined together via a linker, so as to form a fused 5- or 6-membered ring.

In preferred embodiments of formula (1b) and formula (1b') $W_3$ and $W_4$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido; $W_3$ and $W_4$ may be joined together via a linker, so as to form a fused 5- or 6-membered ring.

In one embodiment, the compound of formula (I) or (I') is as defined above, provided that: (1) Y is selected from the group consisting of S, SO, and SO2; (2) Z is selected from the group consisting of hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, and diarylamino; (3) the left-side aryl of formula 1a or 1a' contains at least one ring nitrogen; (4) at least one of W1 and W2 is selected from the group consisting of alkyl, alkenyl, alkynyl, aryl, alkoxy, amino, alkylamino, dialkylamino, cycloalkylamino, arylamino, and diarylamino; and (5) at least one of W3 and W4 is selected from the group consisting of amino, alkylamino, dialkylamino, cycloalkylamino, arylamino, diarylamino, acylamino, carbamyl, substituted or unsubstituted amido, —NHSO2alkenyl, —NHCOalkenyl, —NHCOalkynyl, —COalkenyl, —COalkynyl, alkylamido, alkylsulfonamido, and sulfonamido.

In another embodiment, the compound of formula (I) or (I') is as defined above, provided that: (1) Z is selected from the group consisting of aryl, saturated or unsaturated cycloalkyl, saturated or unsaturated heterocycle, halogen, alkylamino, dialkyl amino, cycloalkylamino, arylamino, and diarylamino; (2) at least one of W1 and W2 is selected from the group consisting of alkyl, alkenyl, alkynyl, aryl, alkoxy, amino, alkylamino, dialkylamino, cycloalkylamino, arylamino, and diarylamino; and (3) at least one of W3 and (4) W4 is selected from the group consisting of amino, alkylamino, dialkylamino, cycloalkylamino, arylamino, diarylamino, acylamino, carbamyl, substituted or unsubstituted amido, —NHSO$_2$alkenyl, —NHCOalkenyl, —NHCOalkynyl, —COalkenyl, —COalkynyl, alkylamido, alkylsulfonamido, and sulfonamido.

In a further embodiment, the compound of formula (I) or (I') is as defined above, provided that: (1) Y is selected from the group consisting of S, SO, and SO2; (2) Z is selected from the group consisting of hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, and diarylamino; (3) at least one of W1 and W2 is selected from the group consisting of alkyl, alkenyl, alkynyl, aryl, alkoxy, amino, alkylamino, dialkylamino, cycloalkylamino, arylamino, and diarylamino; and (4) at least one of W3 and W4 is selected from the group consisting of amino, alkylamino, dialkylamino, cycloalkylamino, arylamino, diarylamino, acylamino, carbamyl, substituted or unsubstituted amido, —NHSO$_2$alkenyl, —NHCOalkenyl, —NHCOalkynyl, —COalkenyl, —COalkynyl, alkylamido, alkylsulfonamido, and sulfonamido.

In a further embodiment, the compound of formula (I) or (I') is as defined above, provided that: (1) Z is selected from the group consisting of aryl, saturated or unsaturated cycloalkyl, saturated or unsaturated heterocycle, halogen, hydroxyl, alkoxy, alkylamino, dialkyl amino, cycloalkylamino, arylamino, and diarylamino; (2) both W1 and W2 are selected from the group consisting of alkyl, alkenyl, alkynyl, aryl, alkoxy, amino, alkylamino, dialkylamino, cycloalkylamino, arylamino, and diarylamino; and (3) at least one of W3 and W4 is selected from the group consisting of amino, alkylamino, dialkylamino, cycloalkylamino, arylamino, diarylamino, acylamino, carbamyl, substituted or unsubstituted amido, —NHSO$_2$alkenyl, —NHCOalkenyl, —NHCOalkynyl, —COalkenyl, —COalkynyl, alkylamido, alkylsulfonamido, and sulfonamido.

In a further embodiment, the compound of formula (I) or (I') is as defined above, provided that: (1) both W1 and W2 are selected from the group consisting of aryl, heterocycle, alkoxy, amino, alkylamino, dialkylamino, cycloalkylamino, arylamino, and diarylamino; and (4) at least one of W3 and W4 is selected from the group consisting of amino, alkylamino, dialkylamino, cycloalkylamino, arylamino, diarylamino, acylamino, carbamyl, substituted or unsubstituted amido, —NHSO$_2$alkenyl, —NHCOalkenyl, —NHCOalkynyl, —COalkenyl, —COalkynyl, alkylamido, alkylsulfonamido, and sulfonamido.

In one embodiment, the compound of formula (I) or (I') is as defined above, provided that: (1) Y is selected from the group consisting of S, SO, and S02; (2) Z is selected from the group consisting of hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, and diarylamino; (3) either the left-side aryl or the right-side aryl of formula 1a or 1a' contains at least two ring nitrogens; (4) at least one of W1 and W2 is selected from the group consisting of alkyl, alkenyl, alkynyl, aryl, alkoxy, amino, alkylamino, dialkylamino, cycloalkylamino, arylamino, and diarylamino; and (5) at least one of W3 and W4 is selected from the group consisting of amino, alkylamino, dialkylamino, cycloalkylamino, arylamino, diarylamino, acylamino, carbamyl, substituted or unsubstituted amido, —NHSO$_2$alkenyl, —NHCOalkenyl, —NHCOalkynyl, —COalkenyl, —COalkynyl, alkylamido, alkylsulfonamido, and sulfonamido.

In one embodiment, the compound of formula (I) or (I') is as defined above, provided that: (1) Y is selected from the group consisting of S, SO, and SO2; (2) Z is selected from the group consisting of aryl, saturated or unsaturated cycloalkyl, saturated or unsaturated heterocycle, halogen, alkoxy, alkylamino, dialkyl amino, cycloalkylamino, arylamino, and diarylamino; (3) either the left-side aryl or the right-side aryl or both aryls of formula 1a or 1a' contain at least two ring nitrogens; (4) at least one of W1 and W2 is selected from the group consisting of alkoxy, alkylamino, dialkylamino, cycloalkylamino, arylamino, and diarylamino; and (5) at least one of W3 and W4 is selected from the group consisting of alkylamino, dialkylamino, cycloalkylamino, arylamino, diarylamino, acylamino, carbamyl, substituted or unsubstituted amido, —NHSO$_2$alkenyl, —NHCOalkenyl, —NHCOalkynyl, —COalkenyl, —COalkynyl, alkylamido, alkylsulfonamido, and sulfonamido.

Another embodiment of the present subject matter relates to compounds having the formula:

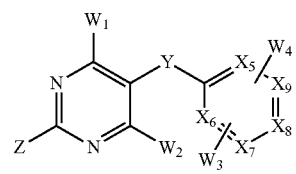

Formula 2a their stereoisomers, tautomers, and pharmaceutically acceptable salts thereof, wherein, $X_5$-$X_9$ are independently selected from CH, substituted C, and substituted N;

Y is S, SO, SO$_2$, CH$_2$, CHR, CRR, CO, O, NH, or NR, wherein R is a lower alkyl or alkoxyl chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, SO$_2$-alkyl, —COO-alkyl, —COalkyl, and alkyl-CN;

$W_1$ and $W_2$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; and;

$W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_3$ and $W_4$ may be joined together via a linker, so as to form a fused 5- or 6-membered ring.

Furthermore, $W_2$ may be joined to the right side aryl ring directly to form a 5-membered ring or via a linker to form a 6 or 7-membered ring.

In preferred embodiments of formula (2a), $X_5$-$X_9$ are independently selected from but not limited to:

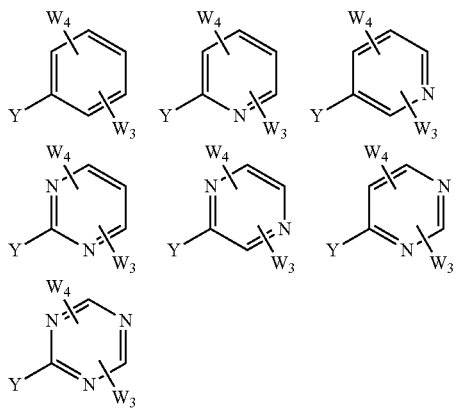

In preferred embodiments of formula (2a), Y is S, SO, $SO_2$, O or $CH_2$.

In preferred embodiments of formula (2a), Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (2a), $W_1$ and $W_2$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (2a), $W_3$ and $W_4$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In particular preferred embodiments of formula (2a), $X_5$-$X_9$ are

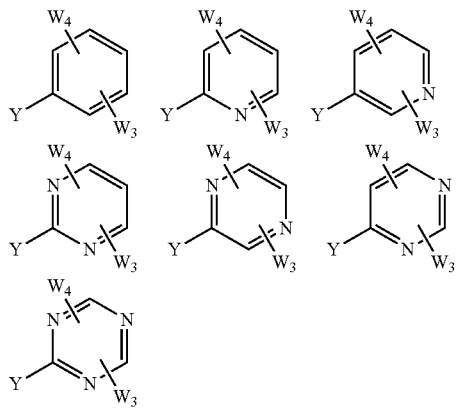

In particular preferred embodiments of formula (2a), Y is S, SO, or $SO_2$.

In particular preferred embodiments of formula (2a), Z is hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, or diarylamino.

In particular preferred embodiments of formula (2a), $W_1$ and $W_2$ are independently hydrogen, alkyl, alkenyl, alkynyl, aryl, alkoxy, amino, alkylamino, dialkylamino, cycloalkylamino, arylamino, or diarylamino.

In particular preferred embodiments of formula (2a), $W_3$ and $W_4$ are independently hydrogen, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN.

Table 1 shows examples of specific compounds exemplifying this embodiment. The IC50 values listed for some of these compounds illustrate the antiproliferative effects of the subject compounds and were obtained using the Growth Inhibition assays described herein.

TABLE 1

| ID # | Compound Name | $IC_{50}$ (μM) Kasumi | $IC_{50}$ (μM) SKBr3 |
|---|---|---|---|
| YK1 | N,N'-(2-(4,6-dimethoxy-2-(4-methylpiperazin-1-yl)pyrimidin-5-ylthio)pyrimidine-4,6-diyl)diacetamide | 15 | |
| YK2 | 2-(4,6-dimethoxy-2-(4-methylpiperazin-1-yl)pyrimidin-5-ylthio)pyrimidine-4,6-diamine | 57.2 | |

TABLE 1-continued

| ID # | Compound Name | IC$_{50}$ (μM) Kasumi | IC$_{50}$ (μM) SKBr3 |
|---|---|---|---|
| YK3 | N,N'-(2-(4,6-dimethoxy-2-(4-methylpiperazin-1-yl)pyrimidin-5-ylsulfinyl)pyrimidine-4,6-diyl)diacetamide | | |
| YK4 | N-(6-amino-2-(2-amino-4,6-dimethoxypyrimidin-5-ylthio)pyrimidin-4-yl)-3-(diethylamino)propanamide | | |
| YK5 | N-(6-amino-2-(4,6-dimethoxy-2-(4-methylpiperazin-1-yl)pyrimidin-5-ylthio)pyrimidin-4-yl)acrylamide | 0.4-0.6 | 0.455 |
| YK6 | N-(6-amino-2-(2-amino-4,6-dimethoxypyrimidin-5-ylthio)pyrimidin-4-yl)-3-(4-methylpiperazin-1-yl)propanamide | 23 | |
| YK7 | N,N'-(2-(2-(4-(2-hydroxyethyl)piperazin-1-yl)-4,6-dimethoxypyrimidin-5-ylthio)pyrimidine-4,6-diyl)diacetamide | | |
| YK8 | N,N'-(2-(4,6-dimethoxy-2-morpholinopyrimidin-5-ylthio)pyrimidine-4,6-diyl)diacetamide | >100 | |
| YK9 | N,N'-(2-(4,6-dimethoxy-2-(piperidin-1-yl)pyrimidin-5-ylthio)pyrimidine-4,6-diyl)diacetamide | >100 | |
| YK10 | 2-(4-(5-(4,6-diaminopyrimidin-2-ylthio)-4,6-dimethoxypyrimidin-2-yl)piperazin-1-yl)ethanol | | |
| YK11 | 2-(4,6-dimethoxy-2-morpholinopyrimidin-5-ylthio)pyrimidine-4,6-diamine | >100 | |
| YK12 | 2-(4,6-dimethoxy-2-(piperidin-1-yl)pyrimidin-5-ylthio)pyrimidine-4,6-diamine | >100 | |
| YK13 | N-(6-amino-2-(4,6-dimethoxy-2-(4-methylpiperazin-1-yl)pyrimidin-5-ylthio)pyrimidin-4-yl)propionamide | >100 (>100) | |
| YK14 | N-(6-amino-2-(2-(4-(2-hydroxyethyl)piperazin-1-yl)-4,6-dimethoxypyrimidin-5-ylthio)pyrimidin-4-yl)propionamide | >100 | |
| YK15 | N-(6-amino-2-(4,6-dimethoxy-2-morpholinopyrimidin-5-ylthio)pyrimidin-4-yl)propionamide | >100 | |
| YK16 | N-(6-amino-2-(4,6-dimethoxy-2-(piperidin-1-yl)pyrimidin-5-ylthio)pyrimidin-4-yl)propionamide | >100 | |
| YK17 | N-(6-amino-2-(2-(4-(2-hydroxyethyl)piperazin-1-yl)-4,6-dimethoxypyrimidin-5-ylthio)pyrimidin-4-yl)acrylamide | | |
| YK18 | N-(6-amino-2-(4,6-dimethoxy-2-morpholinopyrimidin-5-ylthio)pyrimidin-4-yl)acrylamide | 3 | |
| YK19 | N-(6-amino-2-(4,6-dimethoxy-2-(piperidin-1-yl)pyrimidin-5-ylthio)pyrimidin-4-yl)acrylamide | 2.5 | |
| YK20 | N-(6-amino-2-(4,6-dimethoxy-2-(4-methylpiperazin-1-yl)pyrimidin-5-ylthio)pyrimidin-4-yl)octanamide | 6.3 | |
| YK21 | N-(6-amino-2-(2-(4-(2-hydroxyethyl)piperazin-1-yl)-4,6-dimethoxypyrimidin-5-ylthio)pyrimidin-4-yl)octanamide | 7.2 | |
| YK22 | N-(6-amino-2-(4,6-dimethoxy-2-morpholinopyrimidin-5-ylthio)pyrimidin-4-yl)octanamide | 12.3 | |
| YK23 | N-(6-amino-2-(4,6-dimethoxy-2-(piperidin-1-yl)pyrimidin-5-ylthio)pyrimidin-4-yl)octanamide | 13.2 | |
| YK24 | N,N'-(2-(2-(4-butylpiperazin-1-yl)-4,6-dimethoxypyrimidin-5-ylthio)pyrimidine-4,6-diyl)diacetamide | 16.8 | |
| YK25 | 2-(2-(4-butylpiperazin-1-yl)-4,6-dimethoxypyrimidin-5-ylthio)pyrimidine-4,6-diamine | >100 | |
| YK26 | N-(6-amino-2-(2-(4-butylpiperazin-1-yl)-4,6-dimethoxypyrimidin-5-ylthio)pyrimidin-4-yl)acrylamide | | |
| YK27 | N-(6-amino-2-(2-(4-butylpiperazin-1-yl)-4,6-dimethoxypyrimidin-5-ylthio)pyrimidin-4-yl)octanamide | | |
| YK28 | 2-(4,6-diethoxy-2-(4-methylpiperazin-1-yl)pyrimidin-5-ylthio)pyrimidine-4,6-diamine | | |
| YK29 | N,N'-(2-(4,6-diethoxy-2-(4-methylpiperazin-1-yl)pyrimidin-5-ylthio)pyrimidine-4,6-diyl)diacetamide | 76.7 | |

TABLE 1-continued

| ID # | Compound Name | IC$_{50}$ (μM) Kasumi | IC$_{50}$ (μM) SKBr3 |
|---|---|---|---|
| YK30 | N-(6-amino-2-(4,6-diethoxy-2-(4-methylpiperazin-1-yl)pyrimidin-5-ylthio)pyrimidin-4-yl)acrylamide | 0.48 | |
| YK31 | N-(6-amino-2-(4,6-diethoxy-2-(4-methylpiperazin-1-yl)pyrimidin-5-ylthio)pyrimidin-4-yl)propionamide | 34.1 | |
| YK32 | N-(6-amino-2-(4,6-diethoxy-2-(4-methylpiperazin-1-yl)pyrimidin-5-ylthio)pyrimidin-4-yl)-3-chloropropanamide | | |
| YK33 | N-(6-amino-2-(4,6-diethoxy-2-(4-methylpiperazin-1-yl)pyrimidin-5-ylthio)pyrimidin-4-yl)cyclopropanecarboxamide | 88.7 (14.2) | |
| YK34 | (E)-N-(6-amino-2-(4,6-diethoxy-2-(4-methylpiperazin-1-yl)pyrimidin-5-ylthio)pyrimidin-4-yl)but-2-enamide | 55 | |
| YK35 | 2-(4,6-diethoxy-2-(piperidin-1-yl)pyrimidin-5-ylthio)pyrimidine-4,6-diamine | | |
| YK36 | N,N'-(2-(4,6-diethoxy-2-(piperidin-1-yl)pyrimidin-5-ylthio)pyrimidine-4,6-diyl)diacetamide | | |
| YK37 | N-(6-amino-2-(4,6-diethoxy-2-(piperidin-1-yl)pyrimidin-5-ylthio)pyrimidin-4-yl)acrylamide | 2.5 | |
| YK38 | N-(6-amino-2-(4,6-diethoxy-2-(piperidin-1-yl)pyrimidin-5-ylthio)pyrimidin-4-yl)propionamide | 50 | |
| YK39 | N-(6-amino-2-(4,6-diethoxy-2-(piperidin-1-yl)pyrimidin-5-ylthio)pyrimidin-4-yl)-2-bromoacetamide | | |
| YK40 | N-(6-amino-2-(4,6-diethoxy-2-(piperidin-1-yl)pyrimidin-5-ylthio)pyrimidin-4-yl)cyclopropanecarboxamide | 38.3 | |
| YK41 | N,N'-(2-(4,6-diethoxy-2-(piperidin-1-yl)pyrimidin-5-ylthio)pyrimidine-4,6-diyl)dicyclopropanecarboxamide | >100 | |
| YK42 | (E)-N-(6-amino-2-(4,6-diethoxy-2-(piperidin-1-yl)pyrimidin-5-ylthio)pyrimidin-4-yl)but-2-enamide | | |
| YK43 | N,N'-(2-(4,6-diethoxy-2-morpholinopyrimidin-5-ylthio)pyrimidine-4,6-diyl)diacetamide | | |
| YK44 | N-(6-amino-2-(4,6-diethoxy-2-morpholinopyrimidin-5-ylthio)pyrimidin-4-yl)acrylamide | 1.2 | |
| YK45 | N-(6-amino-2-(4,6-diethoxy-2-morpholinopyrimidin-5-ylthio)pyrimidin-4-yl)propionamide | | |
| YK46 | N-(6-amino-2-(4,6-diethoxy-2-morpholinopyrimidin-5-ylthio)pyrimidin-4-yl)-2-bromoacetamide | | |
| YK47 | N-(6-amino-2-(4,6-diethoxy-2-morpholinopyrimidin-5-ylthio)pyrimidin-4-yl)cyclopropanecarboxamide | | |
| YK48 | (E)-N-(6-amino-2-(4,6-diethoxy-2-morpholinopyrimidin-5-ylthio)pyrimidin-4-yl)but-2-enamide | | |
| YK49 | N-(6-amino-2-(4,6-diethoxy-2-morpholinopyrimidin-5-ylthio)pyrimidin-4-yl)furan-2-carboxamide | >100 | |
| YK50 | N-(6-amino-2-(2-amino-4,6-dimethoxypyrimidin-5-ylthio)pyrimidin-4-yl)acrylamide | 1.5 | |
| YK51 | N-(6-amino-2-(4,6-dimethoxy-2-(4-methylpiperazin-1-yl)pyrimidin-5-ylthio)pyrimidin-4-yl)-3-(dimethylamino)propanamide | 8 | |
| YK52 | 6-(5-(4,6-diaminopyrimidin-2-ylthio)-4,6-dimethoxypyrimidin-2-ylamino)hexan-1-ol | 779 | |
| YK53 | N-(6-amino-2-(4,6-dimethoxy-2-(4-methylpiperazin-1-yl)pyrimidin-5-ylthio)pyrimidin-4-yl)acetamide | 16 | |
| YK54 | N-(6-amino-2-(2-(4-(2-(2-(2-hydroxyethoxy)ethoxy)ethyl)piperazin-1-yl)-4,6-dimethoxypyrimidin-5-ylthio)pyrimidin-4-yl)acrylamide | 4.8 | |
| YK55 | 2-(2-(2-(2-(4-(5-(4-acrylamido-6-aminopyrimidin-2-ylthio)-4,6-dimethoxypyrimidin-2-yl)piperazin-1-yl)ethoxy)ethoxy)ethoxy)ethyl 5-(2-oxohexahydro-1H-thieno[3,4-d]imidazol-4-yl)pentanoate | 13.1 | |

TABLE 1-continued

| ID # | Compound Name | IC$_{50}$ (μM) Kasumi | IC$_{50}$ (μM) SKBr3 |
|---|---|---|---|
| YK56 | 2-(2-(2-(2-(5-(4-acrylamido-6-aminopyrimidin-2-ylthio)-6-methoxy-2-(4-methylpiperazin-1-yl)pyrimidin-4-yloxy)ethoxy)ethoxy)ethoxy)ethyl 5-((3aR,4R,6aS)-2-oxohexahydro-1H-thieno[3,4-d]imidazol-4-yl)pentanoate | | |
| YK57 | N-(6-amino-2-(4-(2-(2-(2-hydroxyethoxy)ethoxy)ethoxy)-6-methoxy-2-(4-methylpiperazin-1-yl)pyrimidin-5-ylthio)pyrimidin-4-yl)acrylamide | | |
| YK58 | N-(6-amino-2-(2-amino-4-methoxy-6-(4-methylpiperazin-1-yl)pyrimidin-5-ylthio)pyrimidin-4-yl)acrylamide | | |
| YK59 | 2-(2-(2-(2-(4-(5-(4-amino-6-propionamidopyrimidin-2-ylthio)-4,6-diethoxypyrimidin-2-yl)piperazin-1-yl)ethoxy)ethoxy)ethoxy)ethyl 5-((3aS,4S,6aR)-2-oxohexahydro-1H-thieno[3,4-d]imidazol-4-yl)pentanoate | | |
| YK60 | 2-(2-(2-(2-(4-(5-(4-amino-6-(3-(dimethylamino)propanamido)pyrimidin-2-ylthio)-4,6-dimethoxypyrimidin-2-yl)piperazin-1-yl)ethoxy)ethoxy)ethoxy)ethyl 5-((3aS,4S,6aR)-2-oxohexahydro-1H-thieno[3,4-d]imidazol-4-yl)pentanoate | | |
| YK61 | N-(2-(2-amino-4,6-dimethoxypyrimidin-5-ylthio)pyrimidin-4-yl)acetamide | 94.4 | |
| YK62 | N-(2-(2-fluoro-4,6-dimethoxypyrimidin-5-ylthio)pyrimidin-4-yl)acetamide | >100 | |
| YK63 | N-(2-(4,6-dimethoxy-2-(4-methylpiperazin-1-yl)pyrimidin-5-ylthio)pyrimidin-4-yl)acetamide | 11.2 | |
| YK64 | N-(2-(4,6-dimethoxy-2-(piperidin-1-yl)pyrimidin-5-ylthio)pyrimidin-4-yl)acetamide | 4 | |
| YK65 | N-(2-(4,6-dimethoxy-2-morpholinopyrimidin-5-ylthio)pyrimidin-4-yl)acetamide | 15.7 | |
| YK66 | N-(2-(4,6-dimethoxy-2-(pyrrolidin-1-yl)pyrimidin-5-ylthio)pyrimidin-4-yl)acetamide | 48.3 | |
| YK67 | 2-(4,6-dimethoxy-2-(4-methylpiperazin-1-yl)pyrimidin-5-ylthio)pyrimidin-4-amine | 93.5 | |
| YK68 | 2-(4,6-dimethoxy-2-(piperidin-1-yl)pyrimidin-5-ylthio)pyrimidin-4-amine | 14.7 | |
| YK69 | 2-(4,6-dimethoxy-2-morpholinopyrimidin-5-ylthio)pyrimidin-4-amine | 54.2 | |
| YK70 | 2-(4,6-dimethoxy-2-(pyrrolidin-1-yl)pyrimidin-5-ylthio)pyrimidin-4-amine | 25.2 | |
| YK71 | N-(2-(4,6-dimethoxy-2-(4-methylpiperazin-1-yl)pyrimidin-5-ylthio)pyrimidin-4-yl)acrylamide | 0.8 | 1.2 |
| YK72 | N-(2-(4,6-dimethoxy-2-(piperidin-1-yl)pyrimidin-5-ylthio)pyrimidin-4-yl)acrylamide | 2 | |
| YK73 | N-(2-(4,6-dimethoxy-2-morpholinopyrimidin-5-ylthio)pyrimidin-4-yl)acrylamide | 1.9 | 11.6 |
| YK74 | N-(2-(4,6-dimethoxy-2-(pyrrolidin-1-yl)pyrimidin-5-ylthio)pyrimidin-4-yl)acrylamide | 42.2 | 4.3 |
| YK75 | 4-(5-(4-acetamidopyrimidin-2-ylthio)-4,6-dimethoxypyrimidin-2-yl)-1-methylpiperazine 1-oxide | | >100 |
| YK76 | N-(2-(2,4,6-trimethoxypyrimidin-5-ylthio)pyrimidin-4-yl)acrylamide | 22.5 | 2.4 |
| YK77 | N-(2-(2,4,6-trimethoxypyrimidin-5-ylthio)pyrimidin-4-yl)propionamide | 62.3 | 79.2 |
| YK78 | N-(2-(2,4,6-trimethoxypyrimidin-5-ylthio)pyrimidin-4-yl)cyclopropanecarboxamide | | |
| YK79 | 4-(5-(4-aminopyrimidin-2-ylthio)-4,6-dimethoxypyrimidin-2-yl)-1-methylpiperazine 1-oxide | | |
| YK80 | 4-(5-(4-acrylamidopyrimidin-2-ylthio)-4,6-dimethoxypyrimidin-2-yl)-1-methylpiperazine 1-oxide | >100 | 31.1 |
| YK81 | N-(2-(4,6-dimethoxy-2-(4-methylpiperazin-1-yl)pyrimidin-5-ylthio)pyrimidin-4-yl)propionamide | | |
| YK82 | 4-(4,6-dimethoxy-5-(4-propionamidopyrimidin-2-ylsulfonyl)pyrimidin-2-yl)-1-methylpiperazine 1-oxide | | |
| YK83 | 4-(5-(4-aminopyrimidin-2-ylsulfinyl)-4,6-dimethoxypyrimidin-2-yl)-1-methylpiperazine 1-oxide | | |

TABLE 1-continued

| ID # | Compound Name | IC$_{50}$ (μM) Kasumi | IC$_{50}$ (μM) SKBr3 |
|---|---|---|---|
| YK84 | 2-(4,6-dimethyl-2-(4-methylpiperazin-1-yl)pyrimidin-5-ylthio)pyrimidin-4-amine | | |
| YK85 | N-(2-(4,6-dimethyl-2-(4-methylpiperazin-1-yl)pyrimidin-5-ylthio)pyrimidin-4-yl)acrylamide | 4.8 | 1.8 |
| YK86 | N-(2-(4,6-dimethyl-2-(4-methylpiperazin-1-yl)pyrimidin-5-ylthio)pyrimidin-4-yl)propionamide | 26.2 | 44.4 |
| YK87 | (E)-N-(2-(4,6-dimethyl-2-(4-methylpiperazin-1-yl)pyrimidin-5-ylthio)pyrimidin-4-yl)but-2-enamide | 16.0 | |
| YK88 | N-(2-(4,6-dimethyl-2-(4-methylpiperazin-1-yl)pyrimidin-5-ylthio)pyrimidin-4-yl)methacrylamide | 13.1 | 16.7 |
| YK89 | N-(2-(4,6-dimethyl-2-(4-methylpiperazin-1-yl)pyrimidin-5-ylthio)pyrimidin-4-yl)furan-2-carboxamide | 12.0, 7.5 | 6.8 |
| YK90 | N-(2-(4,6-dimethyl-2-(4-methylpiperazin-1-yl)pyrimidin-5-ylthio)pyrimidin-4-yl)cyclopropanecarboxamide | 20.1, 27.1 | 25.8 |
| YK91 | 2-(2-(4-(4-aminobutyl)piperazin-1-yl)-4,6-dimethoxypyrimidin-5-ylthio)pyrimidine-4,6-diamine | | |
| YK92 | N-(6-amino-2-(2-(4-(4-aminobutyl)piperazin-1-yl)-4,6-dimethoxypyrimidin-5-ylthio)pyrimidin-4-yl)acrylamide | | |
| YK93 | 2-(2-(4-(4-aminobutyl)piperazin-1-yl)-4,6-dimethoxypyrimidin-5-ylthio)pyrimidin-4-amine | | |
| YK94 | N-(2-(2-(4-(4-aminobutyl)piperazin-1-yl)-4,6-dimethoxypyrimidin-5-ylthio)pyrimidin-4-yl)acrylamide | | |
| YK95 | N-(2-(2-(4-(4-aminobutyl)piperazin-1-yl)-4,6-dimethoxypyrimidin-5-ylthio)pyrimidin-4-yl)furan-2-carboxamide | | |
| YK96 | N-(2-(4,6-dimethoxy-2-(4-methylpiperazin-1-yl)pyrimidin-5-ylthio)pyrimidin-4-yl)propionamide | | |
| YK97 | (E)-N-(2-(4,6-dimethoxy-2-(4-methylpiperazin-1-yl)pyrimidin-5-ylthio)pyrimidin-4-yl)but-2-enamide | | |
| YK98 | N-(2-(4,6-dimethoxy-2-(4-methylpiperazin-1-yl)pyrimidin-5-ylthio)pyrimidin-4-yl)methacrylamide | | |
| YK99 | N-(2-(4,6-dimethoxy-2-(4-methylpiperazin-1-yl)pyrimidin-5-ylthio)pyrimidin-4-yl)furan-2-carboxamide | | |
| YK100 | N-(2-(4,6-dimethoxy-2-(4-methylpiperazin-1-yl)pyrimidin-5-ylthio)pyrimidin-4-yl)furan-2-carboxamide | | |
| YK101 | N-(2-(4,6-dimethoxy-2-(piperidin-1-yl)pyrimidin-5-ylthio)pyrimidin-4-yl)propionamide | | |
| YK102 | (E)-N-(2-(4,6-dimethoxy-2-(piperidin-1-yl)pyrimidin-5-ylthio)pyrimidin-4-yl)but-2-enamide | | |
| YK103 | N-(2-(4,6-dimethoxy-2-(piperidin-1-yl)pyrimidin-5-ylthio)pyrimidin-4-yl)methacrylamide | | |
| YK104 | N-(2-(4,6-dimethoxy-2-(piperidin-1-yl)pyrimidin-5-ylthio)pyrimidin-4-yl)furan-2-carboxamide | | |
| YK105 | N-(2-(4,6-dimethoxy-2-(piperidin-1-yl)pyrimidin-5-ylthio)pyrimidin-4-yl)cyclopropanecarboxamide | | |
| YK106 | N-(2-(4,6-dimethoxy-2-(pyrrolidin-1-yl)pyrimidin-5-ylthio)pyrimidin-4-yl)propionamide | >100 | 99.5 |
| YK107 | (E)-N-(2-(4,6-dimethoxy-2-(pyrrolidin-1-yl)pyrimidin-5-ylthio)pyrimidin-4-yl)but-2-enamide | | |
| YK108 | N-(2-(4,6-dimethoxy-2-(pyrrolidin-1-yl)pyrimidin-5-ylthio)pyrimidin-4-yl)methacrylamide | 9.5 | |
| YK109 | N-(2-(4,6-dimethoxy-2-(pyrrolidin-1-yl)pyrimidin-5-ylthio)pyrimidin-4-yl)furan-2-carboxamide | | |
| YK110 | N-(2-(4,6-dimethoxy-2-(pyrrolidin-1-yl)pyrimidin-5-ylthio)pyrimidin-4-yl)cyclopropanecarboxamide | >100, >100 | >100 |
| YK111 | N-(2-(4,6-dimethoxy-2-morpholinopyrimidin-5-ylthio)pyrimidin-4-yl)propionamide | | |
| YK112 | (E)-N-(2-(4,6-dimethoxy-2-morpholinopyrimidin-5-ylthio)pyrimidin-4-yl)but-2-enamide | | |
| YK113 | N-(2-(4,6-dimethoxy-2-morpholinopyrimidin-5-ylthio)pyrimidin-4-yl)methacrylamide | | |
| YK114 | N-(2-(4,6-dimethoxy-2-morpholinopyrimidin-5-ylthio)pyrimidin-4-yl)furan-2-carboxamide | | |

TABLE 1-continued

| ID # | Compound Name | IC$_{50}$ (µM) Kasumi | IC$_{50}$ (µM) SKBr3 |
|---|---|---|---|
| YK115 | N-(2-(4,6-dimethoxy-2-morpholinopyrimidin-5-ylthio)pyrimidin-4-yl)cyclopropanecarboxamide | | |
| PDP2 | 3-(4,6-dimethoxy-2-morpholinopyrimidin-5-ylthio)aniline | 79.7 | >100 |
| PDP3 | N-(3-(4,6-dimethoxy-2-morpholinopyrimidin-5-ylthio)phenyl)acrylamide | 11.4 | 16.5 |
| PDP4 | N-(3-(4,6-dimethoxy-2-morpholinopyrimidin-5-ylthio)phenyl)propionamide | >100 | >100 |
| PDP5 | N-(3-(4,6-dimethoxy-2-morpholinopyrimidin-5-ylthio)phenyl)methacrylamide | | 18.1 |
| PDP6 | N-(3-(4,6-dimethoxy-2-morpholinopyrimidin-5-ylthio)phenyl)cyclopropanecarboxamide | ? | 9.9(?) |
| PDP7 | 2-(4,6-dimethoxy-2-morpholinopyrimidin-5-ylthio)-6-(trifluoromethyl)pyrimidin-4-ol | | |
| PDP8 | 2-(4,6-dimethoxy-2-morpholinopyrimidin-5-ylthio)-6-(trifluoromethyl)pyrimidin-4-yl acrylate | | |
| PDP9 | 2-(4,6-dimethoxy-2-morpholinopyrimidin-5-ylthio)-6-(trifluoromethyl)pyrimidin-4-yl cyclopropanecarboxylate | | |
| PDP10 | 2-(4,6-dimethoxy-2-morpholinopyrimidin-5-ylthio)-6-(trifluoromethyl)pyrimidin-4-yl methacrylate | | |
| YK116 | 2-(4,6-dimethyl-2-morpholinopyrimidin-5-ylthio)pyrimidin-4-amine | | |
| YK117 | N-(2-(4,6-dimethyl-2-morpholinopyrimidin-5-ylthio)pyrimidin-4-yl)acrylamide | 6.2 | 14.4 |
| YK118 | N-(2-(4,6-dimethyl-2-morpholinopyrimidin-5-ylthio)pyrimidin-4-yl)propionamide | >100 | >100 |
| YK119 | (E)-N-(2-(4,6-dimethyl-2-morpholinopyrimidin-5-ylthio)pyrimidin-4-yl)but-2-enamide | | |
| YK120 | N-(2-(4,6-dimethyl-2-morpholinopyrimidin-5-ylthio)pyrimidin-4-yl)methacrylamide | | |
| YK121 | N-(2-(4,6-dimethyl-2-morpholinopyrimidin-5-ylthio)pyrimidin-4-yl)furan-2-carboxamide | | |
| YK122 | N-(2-(4,6-dimethyl-2-morpholinopyrimidin-5-ylthio)pyrimidin-4-yl)cyclopropanecarboxamide | | |
| YK123 | N-(2-(4,6-dimethyl-2-morpholinopyrimidin-5-ylthio)pyrimidin-4-yl)-2-methoxyacetamide | 58.1 | >100 |
| YK124 | 2-(4,6-dimethyl-2-(piperazin-1-yl)pyrimidin-5-ylthio)pyrimidin-4-amine | | |
| YK125 | N-(2-(4,6-dimethyl-2-(piperazin-1-yl)pyrimidin-5-ylthio)pyrimidin-4-yl)acrylamide | | |
| YK126 | N-(2-(4,6-dimethyl-2-(piperazin-1-yl)pyrimidin-5-ylthio)pyrimidin-4-yl)propionamide | | |
| YK127 | (E)-N-(2-(4,6-dimethyl-2-(piperazin-1-yl)pyrimidin-5-ylthio)pyrimidin-4-yl)but-2-enamide | | |
| YK128 | N-(2-(4,6-dimethyl-2-(piperazin-1-yl)pyrimidin-5-ylthio)pyrimidin-4-yl)methacrylamide | | |
| YK129 | N-(3-(4,6-dimethoxy-2-(4-methylpiperazin-1-yl)pyrimidin-5-ylthio)phenyl)acrylamide | 7.7, 9.9 | 6.8 |
| YK130 | N-(3-(4,6-dimethoxy-2-(4-methylpiperazin-1-yl)pyrimidin-5-ylthio)phenyl)propionamide | 10.4, 21.2 | 18.3 |
| YK131 | (E)-N-(3-(4,6-dimethoxy-2-(4-methylpiperazin-1-yl)pyrimidin-5-ylthio)phenyl)but-2-enamide | 15.0 | 20.7 |
| YK132 | N-(3-(4,6-dimethoxy-2-(4-methyipiperazin-1-yl)pyrimidin-5-ylthio)phenyl)methacrylamideN-(3-(4,6-dimethoxy-2-(4-methylpiperazin-1-yl)pyrimidin-5-ylthio)phenyl)methacrylamide | 7.7 | 17.8 |
| YK133 | 3-(4,6-dimethoxy-2-(4-methylpiperazin-1-yl)pyrimidin-5-ylthio)aniline | 30.5, 25.4 | 37.3 |
| YK134 | N-(3-(4,6-dimethyl-2-(4-methylpiperazin-1-yl)pyrimidin-5-ylthio)phenyl)propionamide | | |
| YK135 | N-(3-(4,6-dimethyl-2-(4-methylpiperazin-1-yl)pyrimidin-5-ylthio)phenyl)propionamide | | |
| YK136 | (E)-N-(3-(4,6-dimethyl-2-(4-methylpiperazin-1-yl)pyrimidin-5-ylthio)phenyl)but-2-enamide | | |
| YK137 | N-(3-(4,6-dimethyl-2-(4-methylpiperazin-1-yl)pyrimidin-5-ylthio)phenyl)methacrylamide | | |
| YK138 | 3-(4,6-dimethyl-2-(4-methylpiperazin-1-yl)pyrimidin-5-ylthio)aniline | | |
| YK139 | N-(3-(4,6-dimethoxy-2-(4-methylpiperazin-1-yl)pyrimidin-5-ylthio)phenyl)cyclopropanecarboxamide | 8.9, 7.9 | 7.7 |
| YK140 | N-(3-(2-amino-4,6-dimethoxypyrimidin-5-ylthio)phenyl)propionamide | 35.2 | 99.5 |

TABLE 1-continued

| ID # | Compound Name | IC$_{50}$ (μM) Kasumi | IC$_{50}$ (μM) SKBr3 |
|---|---|---|---|
| YK141 | N-(3-(2-(4-(2-(2-(2-(2-hydroxyethoxy)ethoxy)ethoxy)ethyl)piperazin-1-yl)-4,6-dimethoxypyrimidin-5-ylthio)phenyl)propionamide | | 38.9 |
| YK142 | 2-(2-(2-(2-(4-(4,6-dimethoxy-5-(3-propionamidophenylthio)pyrimidin-2-yl)piperazin-1-yl)ethoxy)ethoxy)ethoxy)ethyl 5-(2-oxohexahydro-1H-thieno[3,4-d]imidazol-4-yl)pentanoate | | 47.9 |
| YK144 | N-(2-(2-(4-(2-(2-(2-(2-hydroxyethoxy)ethoxy)ethoxy)ethyl)piperazin-1-yl)-4,6-dimethylpyrimidin-5-ylthio)pyrimidin-4-yl)furan-2-carboxamide | | |
| YK145 | 2-(2-(2-(2-(4-(5-(4-(furan-2-carboxamido)pyrimidin-2-ylthio)-4,6-dimethylpyrimidin-2-yl)piperazin-1-yl)ethoxy)ethoxy)ethoxy)ethyl 5-(2-oxohexahydro-1H-thieno[3,4-d]imidazol-4-yl)pentanoate | | |
| YK146 | N-(3-(4,6-dimethyl-2-(piperazin-1-yl)pyrimidin-5-ylthio)phenyl)propionamide | 8.8, 9.0 | |
| YK147 | N-(3-(4,6-dimethyl-2-(piperazin-1-yl)pyrimidin-5-ylthio)phenyl)but-3-enamide | | |
| YK148 | N-(3-(4,6-dimethyl-2-(piperazin-1-yl)pyrimidin-5-ylthio)phenyl)methacrylamide | | |
| YK149 | 2-amino-N-(3-(4,6-dimethoxy-2-(4-methylpiperazin-1-yl)pyrimidin-5-ylthio)phenyl)acetamide | 13.9, 21.0 | |
| YK177 | methyl 2-(5-(3-acetamidophenylthio)-2-amino-6-methylpyrimidin-4-yloxy)propanoate | | |
| TT-2 | N-(3-(4,6-dimethoxy-2-(4-methylpiperazin-1-yl)pyrimidin-5-ylthio)phenyl)cyclobutanecarboxamide | | |
| TT-3 | N-(3-(4,6-dimethoxy-2-(4-methylpiperazin-1-yl)pyrimidin-5-ylthio)phenyl)cyclohexanecarboxamide | | |
| TT-4 | N-(3-(4,6-dimethoxy-2-(4-methylpiperazin-1-yl)pyrimidin-5-ylthio)phenyl)benzamide | | |
| TT-5 | 2-amino-N-(3-(2-(4-methylpiperazin-1-yl)-4-phenylpyrimidin-5-ylthio)phenyl)acetamide | | |
| TT-6 | N-(2-(2-(2-(2-(4-(5-(4-acrylamido-6-aminopyrimidin-2-ylthio)-4,6-dimethoxypyrimidin-2-yl)piperazin-1-yl)ethoxy)ethoxy)ethoxy)ethyl)-5-(2-oxohexahydro-1H-thieno[3,4-d]imidazol-4-yl)pentanamide | | |
| TT-7 | N-(3-(4-(benzyloxy)-2-(4-methylpiperazin-1-yl)pyrimidin-5-ylthio)phenyl)acetamide | | |
| TT-8 | N-(3-(4-(benzyloxy)-2-(4-methylpiperazin-1-yl)pyrimidin-5-ylthio)phenyl)benzamide | | |
| TT-9 | 2-amino-N-(3-(4-(benzyloxy)-2-(4-methylpiperazin-1-yl)pyrimidin-5-ylthio)phenyl)acetamide | | |
| TT-10 | 2-amino-N-(3-(4-(4-methoxybenzyloxy)-2-(4-methylpiperazin-1-yl)pyrimidin-5-ylthio)phenyl)acetamide | | |
| TT-11 | N-(3-(4-(4-methoxybenzyloxy)-2-(4-methylpiperazin-1-yl)pyrimidin-5-ylthio)phenyl)acetamide | | |
| TT-12 | 2-amino-N-(3-(4-(cyclopentylmethoxy)-2-(4-methylpiperazin-1-yl)pyrimidin-5-ylthio)phenyl)acetamide | | |
| TT-13 | 2-amino-N-(3-(2-(4-methylpiperazin-1-yl)-4-phenoxypyrimidin-5-ylthio)phenyl)acetamide | | |
| TT-14 | 2-amino-N-(3-(4-(cyclopentyloxy)-2-(4-methylpiperazin-1-yl)pyrimidin-5-ylthio)phenyl)acetamide | | |
| TT-15 | 2-amino-N-(3-(4-(cyclohexyloxy)-2-(4-methylpiperazin-1-yl)pyrimidin-5-ylthio)phenyl)acetamide | | |
| TT-16 | 2-amino-N-(3-(2-(4-methylpiperazin-1-yl)-4-(pyridin-3-ylmethoxy)pyrimidin-5-ylthio)phenyl)acetamide | | |
| TT-17 | 2-amino-N-(3-(2-(4-methylpiperazin-1-yl)-4-(pyridin-4-ylmethoxy)pyrimidin-5-ylthio)phenyl)acetamide | | |

TABLE 1-continued

| ID # | Compound Name | IC$_{50}$ (μM) Kasumi | IC$_{50}$ (μM) SKBr3 |
|---|---|---|---|
| TT-18 | 2-amino-N-(3-(4-(benzyloxy)-2-(4-methylpiperazin-1-yl)pyrimidin-5-ylthio)phenyl)propanamide | | |
| TT-19 | 2-amino-N-(3-(4-(benzyloxy)-2-(4-methylpiperazin-1-yl)pyrimidin-5-ylthio)phenyl)-3-methylbutanamide | | |
| TT-20 | N-(3-(4-(benzyloxy)-2-(4-methylpiperazin-1-yl)pyrimidin-5-ylthio)phenyl)pyrrolidine-2-carboxamide | | |
| TT-21 | 2-amino-N-(3-(4-benzyl-2-(4-methylpiperazin-1-yl)pyrimidin-5-ylthio)phenyl)acetamide | | |
| TT-22 | 2-amino-N-(3-(4-(4-chlorobenzyloxy)-2-(4-methylpiperazin-1-yl)pyrimidin-5-ylthio) phenyl)acetamide | | |
| TT-23 | 2-amino-N-(3-(4-methoxy-2-(4-methylpiperazin-1-yl)pyrimidin-5-ylthio)phenyl)acetamide | | |
| TT-24 | 2-amino-N-(3-(4-(3-aminobenzyloxy)-2-(4-methylpiperazin-1-yl)pyrimidin-5-ylthio)phenyl)acetamide | | |
| TT-25 | 2-amino-N-(3-(4-(2-aminobenzyloxy)-2-(4-methylpiperazin-1-yl)pyrimidin-5-ylthio)phenyl) acetamide | | |
| TT-26 | 2-amino-N-(3-(4-(difluoro(phenyl)methoxy)-2-(4-methylpiperazin-1-yl)pyrimidin-5-ylthio)phenyl)acetamide | | |
| TT-27 | 2-amino-N-(3-(4-(3,5-difluorobenzyloxy)-2-(4-methylpiperazin-1-yl)pyrimidin-5-ylthio)phenyl) acetamide | | |
| TT-28 | N-(3-(4-(benzyloxy)-2-(4-methylpiperazin-1-yl)pyrimidin-5-ylthio)phenyl)acrylamide | | |
| TT-29 | N-(2-(4-(benzyloxy)-2-(4-methylpiperazin-1-yl)pyrimidin-5-ylthio)pyrimidin-4-yl)acrylamide | | |
| TT-30 | N-(6-amino-2-(4-(benzyloxy)-2-(4-ethylpiperazin-1-yl)pyrimidin-5-ylthio)pyrimidin-4-yl)acrylamide | | |
| 1-01 | 2-amino-N-(3-(4-(3-(dimethylamino)phenyl)-2-(4-methylpiperazin-1-yl)pyrimidin-5-ylthio)phenyl)acetamide | | |
| 1-02 | 2-amino-N-(3-(4-(4-(dimethylamino)phenyl)-2-(4-methylpiperazin-1-yl)pyrimidin-5-ylthio)phenyl)acetamide | | |
| 1-03 | 2-amino-N-(3-(4-(3-cyanophenyl)-2-(4-methylpiperazin-1-yl)pyrimidin-5-ylthio)phenyl)acetamide | | |
| 1-04 | 2-amino-N-(3-(2-(4-methylpiperazin-1-yl)-4-(3-nitrophenyl)pyrimidin-5-ylthio)phenyl)acetamide | | |
| 1-05 | 2-amino-N-(3-(2-(4-methylpiperazin-1-yl)-4-(3-sulfamoylphenyl)pyrimidin-5-ylthio)phenyl)acetamide | | |
| 1-06 | 2-amino-N-(3-(4-(furan-2-yl)-2-(4-methylpiperazin-1-yl)pyrimidin-5-ylthio)phenyl)acetamide | | |
| 1-07 | N-(3-(4-(furan-3-yl)-2-(4-methylpiperazin-1-yl)pyrimidin-5-ylthio)phenyl)benzamide | | |
| 1-08 | 3-(4-(benzyloxy)-2-(4-methylpiperazin-1-yl)pyrimidin-5-ylthio)-N-cyclopropylbenzamide | | |
| 1-09 | 3-(3-(4-(benzyloxy)-2-(4-methylpiperazin-1-yl)pyrimidin-5-ylthio)phenoxy)-2-methylpropanamide | | |
| 1-10 | 2-amino-N-(3-amino-5-(2-(4-methylpiperazin-1-yl)-4-(1H-pyrrol-2-yl)pyrimidin-5-ylthio)phenyl)acetamide | | |
| 1-11 | 2-amino-N-(3-(2-(4-methylpiperazin-1-yl)-4-(1H-pyrrol-3-yl)pyrimidin-5-ylthio)phenyl)propanamide | | |
| 1-12 | 2-amino-N-(3-chloro-5-(2-(4-methylpiperazin-1-yl)-4-(1H-pyrazol-3-yl)pyrimidin-5-ylthio)phenyl)acetamide | | |
| 1-13 | N-(3-(4-(cyclohexyloxy)-2-(4-methylpiperazin-1-yl)pyrimidin-5-ylthio)phenyl)benzamide | | |
| 1-14 | 2-amino-N-(3-amino-5-(4-(2-(dimethylamino)ethoxy)-2-(4-methylpiperazin-1-yl)pyrimidin-5-ylthio)phenyl)acetamide | | |
| 1-15 | 2-amino-N-(3-(4-(2-methoxyethyl)-2-(4-methylpiperazin-1-yl)pyrimidin-5-ylthio)phenyl)propanamide | | |

TABLE 1-continued

| ID # | Compound Name | IC$_{50}$ (μM) Kasumi | IC$_{50}$ (μM) SKBr3 |
|---|---|---|---|
| 1-16 | N-(3-(4-acetyl-2-(4-methylpiperazin-1-yl)pyrimidin-5-ylthio)-5-chlorophenyl)-2-aminoacetamide | | |
| 1-17 | N-(4-methyl-2-(4-methylpiperazin-1-yl)-10H-thiochromeno[3,2-d]pyrimidin-7-yl)propionamide | | |
| 1-18 | 2-amino-N-(3-(2-(4-methylpiperazin-1-yl)-4-(pyrrolidin-2-ylmethoxy)pyrimidin-5-ylthio)phenyl)acetamide | | |
| 1-19 | 2-amino-N-(3-(2-(4-methylpiperazin-1-yl)-4-(piperidin-4-yloxy)pyrimidin-5-ylthio)phenyl)acetamide | | |
| 1-20 | 2-amino-N-(3-(4-(benzyloxy)-2-(4-methylpiperazin-1-yl)-6-(trifluoromethyl)pyrimidin-5-ylthio)-5-methoxyphenyl)acetamide | | |
| 1-21 | 2-amino-N-(3-(4-(benzyloxy)-2-(4-methylpiperazin-1-yl)pyrimidin-5-ylthio)phenyl)-3-(1H-imidazol-4-yl)propanamide | | |
| 1-22 | 5-(4-(benzyloxy)-2-(4-methylpiperazin-1-yl)pyrimidin-5-ylthio)quinolin-2(1H)-one | | |
| 1-23 | 2-amino-N-(3-(4-(benzyloxy)-2-(4-methylpiperazin-1-yl)pyrimidin-5-ylthio)phenyl)-3-methylbutanamide | | |
| 1-24 | N-(4-(4-(3-(dimethylamino)phenoxy)-2-(4-methylpiperazin-1-yl)pyrimidin-5-ylthio)pyridin-2-yl)propionamide | | |
| 1-25 | N-(3-(2-(4-methylpiperazin-1-yl)-4-(piperidin-3-yloxy)pyrimidin-5-ylthio)phenyl)methanesulfonamide | | |
| 1-26 | 4-(benzyloxy)-6-(2-methoxyethoxy)-2-(4-methylpiperazin-1-yl)-5-(3-(1-phenylethyl)phenylthio)pyrimidine | | |
| 1-27 | 7-(2-(4-methylpiperazin-1-yl)-4-(quinolin-8-ylmethoxy)pyrimidin-5-ylthio)quinolin-2(1H)-one | | |
| 1-28 | N-(3-(4-(benzyloxy)-2-(4-methylpiperazin-1-yl)pyrimidin-5-ylthio)phenyl)pyrrolidine-2-carboxamide | | |
| 1-29 | 2-amino-N-(3-(4-(benzyloxy)-2-(4-methylpiperazin-1-yl)pyrimidin-5-ylthio)phenyl)propanamide compound with N-(3-(4-(benzyloxy)-2-(4-methylpiperazin-1-yl)pyrimidin-5-ylthio)phenyl)pyrrolidine-2-carboxamide (1:1) | | |
| 1-30 | 2-amino-N-(5-(4-(3-aminophenoxy)-2-(4-methylpiperazin-1-yl)pyrimidin-5-ylthio)pyridin-3-yl)acetamide | | |
| 1-31 | 2-amino-N-(4-(4-(4-aminocyclohexyloxy)-2-(4-methylpiperazin-1-yl)pyrimidin-5-ylthio)-6-methylpyrimidin-2-yl)acetamide | | |
| 1-32 | 2-amino-3-methyl-N-(3-(2-(4-methylpiperazin-1-yl)-4-(pyridin-3-ylmethoxy)pyrimidin-5-ylsulfonyl)phenyl)pentanamide | | |
| 1-33 | 2-amino-N-(6-(4-(benzyloxy)-2-(4-methylpiperazin-1-yl)pyrimidin-5-ylthio)benzo[d][1,3]dioxol-4-yl)acetamide | | |
| 1-34 | (3-(4-(3-aminocyclohexyloxy)-2-(4-methylpiperazin-1-yl)pyrimidin-5-ylthio)phenyl)methanol | | |
| 1-35 | 2-amino-N-(4-(4-(benzyloxy)-6-(2-methoxyethoxy)-2-(4-methylpiperazin-1-yl)pyrimidin-5-ylthio)phenyl)acetamide | | |
| 1-36 | 2-amino-N-(3-(furan-3-ylamino)-5-(2-(4-methylpiperazin-1-yl)-4-(pyrimidin-2-ylmethoxy)pyrimidin-5-ylsulfinyl)phenyl)-4-methylpentanamide | | |
| 1-37 | 2-amino-N-(3-(4-(3-bromo-2-methoxybenzyloxy)-2-(4-methylpiperazin-1-yl)pyrimidin-5-ylthio)-5-methoxyphenyl)acetamide | | |
| 1-38 | 2-amino-N-(6-(4-(3-aminocyclopentyloxy)-2-(4-methylpiperazin-1-yl)pyrimidin-5-ylthio)pyrazin-2-yl)acetamide | | |
| 1-39 | 2-amino-N-(4-(4-(benzyloxy)-6-methoxy-2-(4-methylpiperazin-1-yl)pyrimidin-5-ylthio)-1,3,5-triazin-2-yl)propanamide | | |

TABLE 1-continued

| ID # | Compound Name | IC$_{50}$ (μM) Kasumi | IC$_{50}$ (μM) SKBr3 |
|---|---|---|---|
| 1-40 | 2-amino-N-(6-(2-(4-methylpiperazin-1-yl)-4-(pyridin-3-yloxy)pyrimidin-5-ylthio)pyridin-2-yl)propanamide | | |
| 1-41 | 2-amino-N-(3-(4-(benzyloxy)-2-(4-methylpiperazin-1-yl)pyrimidin-5-ylthio)-5-(dimethylamino)phenyl)acetamide | | |
| 1-42 | 5-(4-(benzyloxy)-2-(4-methylpiperazin-1-yl)pyrimidin-5-ylthio)-3,4-dihydroquinolin-2(1H)-one | | |
| 1-43 | 2-amino-N-(2-(4-(3-carbamimidoylphenoxy)-2-(4-methylpiperazin-1-yl)pyrimidin-5-ylthio)pyrimidin-4-yl)acetamide | | |
| 1-44 | N-(3-(4-(2-(dimethylamino)ethoxy)-2-(4-methylpiperazin-1-yl)pyrimidin-5-ylthio)phenyl)acrylamide | | |
| 1-45 | 2-amino-N-(2-(2-(4-methylpiperazin-1-yl)-4-(pyridin-2-yloxy)pyrimidin-5-ylsulfonyl)pyridin-4-yl)propanamide | | |
| 1-46 | 2-amino-N-(3-amino-5-(4-(benzyloxy)-2-(4-methylpiperazin-1-yl)pyrimidin-5-ylthio)phenyl)acetamide | | |
| 1-47 | 7-(4-(benzyloxy)-2-(4-methylpiperazin-1-yl)pyrimidin-5-ylthio)-3,4-dihydroquinolin-2(1H)-one | | |
| 1-48 | N-(3-(2-(4-methylpiperazin-1-yl)-4-(pyridin-4-yloxy)pyrimidin-5-ylsulfinyl)phenyl)benzamide | | |
| 1-49 | N-(2-amino-6-(4,6-dimethoxy-2-(4-methylpiperazin-1-yl)pyrimidin-5-ylthio)pyridin-4-yl)acrylamide | | |
| 1-50 | N-(2-(4,6-dimethoxy-2-(4-methylpiperazin-1-yl)pyrimidin-5-ylthio)pyridin-4-yl)acrylamide | | |
| 1-51 | N-(3-amino-5-(4,6-dimethoxy-2-(4-methylpiperazin-1-yl)pyrimidin-5-ylthio)phenyl)acrylamide | | |
| 1-52 | N-(3-(4,6-dimethoxy-2-(4-methylpiperazin-1-yl)pyrimidin-5-ylthio)phenyl)acrylamide | | |
| 1-53 | N-(6-amino-2-(4,6-dimethoxy-2-(4-methylpiperazin-1-yl)pyrimidin-5-ylthio)pyrimidin-4-yl)methacrylamide | | |
| 1-54 | N-(2-(4,6-dimethoxy-2-(4-methylpiperazin-1-yl)pyrimidin-5-ylthio)pyrimidin-4-yl)methacrylamide | | |
| 1-55 | (Z)-N-(6-amino-2-(4,6-dimethoxy-2-(4-methylpiperazin-1-yl)pyrimidin-5-ylthio)pyrimidin-4-yl)but-2-enamide | | |
| 1-56 | (Z)-N-(2-(4,6-dimethoxy-2-(4-methylpiperazin-1-yl)pyrimidin-5-ylthio)pyrimidin-4-yl)but-2-enamide | | |
| 1-57 | (E)-N-(6-amino-2-(4,6-dimethoxy-2-(4-methylpiperazin-1-yl)pyrimidin-5-ylthio)pyrimidin-4-yl)but-2-enamide | | |
| 1-58 | (E)-N-(2-(4,6-dimethoxy-2-(4-methylpiperazin-1-yl)pyrimidin-5-ylthio)pyrimidin-4-yl)but-2-enamide | | |
| 1-59 | N-(6-amino-2-(4,6-dimethoxy-2-(4-methylpiperazin-1-yl)pyrimidin-5-ylthio)pyrimidin-4-yl)-N-methylacrylamide | | |
| 1-60 | N-(2-(4,6-dimethoxy-2-(4-methylpiperazin-1-yl)pyrimidin-5-ylthio)pyrimidin-4-yl)-N-methylacrylamide | | |
| 1-61 | N-(6-amino-2-(4,6-dimethoxy-2-(4-methylpiperazin-1-yl)pyrimidin-5-ylthio)pyrimidin-4-yl)propiolamide | | |
| 1-62 | N-(2-(4,6-dimethoxy-2-(4-methylpiperazin-1-yl)pyrimidin-5-ylthio)pyrimidin-4-yl)propiolamide | | |
| 1-63 | N-(2-(4,6-dimethoxy-2-(4-methylpiperazin-1-yl)pyrimidin-5-ylthio)-6-methoxypyrimidin-4-yl)acrylamide | | |
| 1-64 | N4-allyl-2-(4,6-dimethoxy-2-(4-methylpiperazin-1-yl)pyrimidin-5-ylthio)pyrimidine-4,6-diamine | | |
| 1-65 | N-allyl-2-(4,6-dimethoxy-2-(4-methylpiperazin-1-yl)pyrimidin-5-ylthio)pyrimidin-4-amine | | |
| 1-66 | 2-(4,6-dimethoxy-2-(4-methylpiperazin-1-yl)pyrimidin-5-ylthio)-N4-(prop-2-ynyl)pyrimidine-4,6-diamine | | |

TABLE 1-continued

| ID # | Compound Name | IC$_{50}$ (μM) Kasumi | IC$_{50}$ (μM) SKBr3 |
|---|---|---|---|
| 1-67 | 2-(4,6-dimethoxy-2-(4-methylpiperazin-1-yl)pyrimidin-5-ylthio)-N-(prop-2-ynyl)pyrimidin-4-amine | | |
| 1-68 | N-(6-amino-2-(4,6-dimethoxy-2-(4-(2-(2-methoxyethoxy)ethyl)piperazin-1-yl)pyrimidin-5-ylthio)pyrimidin-4-yl)acrylamide | | |
| 1-69 | N-(2-(4,6-dimethoxy-2-(4-(2-(2-methoxyethoxy)ethyl)piperazin-1-yl)pyrimidin-5-ylthio)pyrimidin-4-yl)acrylamide | | |
| 1-70 | N-(6-amino-2-(4,6-dimethoxy-2-(4-(2-(2-morpholinoethoxy)ethyl)piperazin-1-yl)pyrimidin-5-ylthio)pyrimidin-4-yl)acrylamide | | |
| 1-71 | N-(2-(4,6-dimethoxy-2-(4-(2-(2-morpholinoethoxy)ethyl)piperazin-1-yl)pyrimidin-5-ylthio)pyrimidin-4-yl)acrylamide | | |
| 1-72 | N-(6-amino-2-(2-(4-(2-(2-(dimethylamino)ethoxy)ethyl)piperazin-1-yl)-4,6-dimethoxypyrimidin-5-ylthio)pyrimidin-4-yl)acrylamide | | |
| 1-73 | N-(2-(2-(4-(2-(2-(dimethylamino)ethoxy)ethyl)piperazin-1-yl)-4,6-dimethoxypyrimidin-5-ylthio)pyrimidin-4-yl)acrylamide | | |
| 1-74 | N-(2-(4,6-dimethoxy-2-(4-methylpiperazin-1-yl)pyrimidin-5-ylthio)-6-(3-morpholinopropylamino)pyrimidin-4-yl)acrylamide | | |
| 1-75 | N-(2-(4,6-dimethoxy-2-(4-methylpiperazin-1-yl)pyrimidin-5-ylthio)-6-(3-(dimethylamino)propylamino)pyrimidin-4-yl)acrylamide | | |
| 1-76 | (E)-N-(6-amino-2-(4,6-dimethoxy-2-(4-methylpiperazin-1-yl)pyrimidin-5-ylthio)pyrimidin-4-yl)-4-(dimethylamino)but-2-enamide | | |
| 1-77 | (E)-N-(2-(4,6-dimethoxy-2-(4-methylpiperazin-1-yl)pyrimidin-5-ylthio)pyrimidin-4-yl)-4-(dimethylamino)but-2-enamide | | |
| 1-78 | (E)-N-(6-amino-2-(4,6-dimethoxy-2-(4-methylpiperazin-1-yl)pyrimidin-5-ylthio)pyrimidin-4-yl)-3-(furan-2-yl)acrylamide | | |
| 1-79 | (E)-N-(6-amino-2-(4,6-dimethoxy-2-(4-methylpiperazin-1-yl)pyrimidin-5-ylthio)pyrimidin-4-yl)-3-(furan-2-yl)acrylamide | | |
| 1-80 | (E)-N-(6-amino-2-(4,6-dimethoxy-2-(4-methylpiperazin-1-yl)pyrimidin-5-ylthio)pyrimidin-4-yl)-3-(thiophen-2-yl)acrylamide | | |
| 1-81 | (E)-N-(2-(4,6-dimethoxy-2-(4-methylpiperazin-1-yl)pyrimidin-5-ylthio)pyrimidin-4-yl)-3-(thiophen-2-yl)acrylamide | | |
| 1-82 | (E)-N-(6-amino-2-(4,6-dimethoxy-2-(4-methylpiperazin-1-yl)pyrimidin-5-ylthio)pyrimidin-4-yl)-3-(pyridin-3-yl)acrylamide | | |
| 1-83 | (E)-N-(2-(4,6-dimethoxy-2-(4-methylpiperazin-1-yl)pyrimidin-5-ylthio)pyrimidin-4-yl)-3-(pyridin-3-yl)acrylamide | | |
| 1-84 | 5-(3-(4,6-dimethoxy-2-(4-methylpiperazin-1-yl)pyrimidin-5-ylthio)phenyl)-1H-pyrrol-2(5H)-one | | |
| 1-85 | N-(1-(4-methoxy-2-(4-methylpiperazin-1-yl)pyrimidin-5-ylthio)isoquinolin-3-yl)acrylamide | | |
| 1-86 | N-(4-(4,6-dimethoxy-2-(4-methylpiperazin-1-yl)pyrimidin-5-ylthio)phenyl)acrylamide | | |
| 1-87 | 5-(4-(4,6-dimethoxy-2-(4-methylpiperazin-1-yl)pyrimidin-5-ylthio)phenyl)pent-1-en-3-one | | |
| 1-88 | N-(6-amino-2-(4,6-dimethoxy-2-(4-methylpiperazin-1-yl)pyrimidin-5-ylthio)pyrimidin-4-yl)ethenesulfonamide | | |
| 1-89 | N-(6-amino-2-(4,6-dimethoxy-2-(4-methylpiperazin-1-yl)pyrimidin-5-ylthio)pyrimidin-4-yl)propiolamide | | |
| 1-90 | 1-(2-(4,6-dimethoxy-2-(4-methylpiperazin-1-yl)pyrimidin-5-ylthio)pyrimidin-4-yl)but-3-en-2-one | | |

TABLE 1-continued

| ID # | Compound Name | IC$_{50}$ (µM) Kasumi | IC$_{50}$ (µM) SKBr3 |
|---|---|---|---|
| 1-91 | 2-amino-N-(3-(4-(4-chlorobenzyloxy)-2-(4-methylpiperazin-1-yl)pyrimidin-5-ylthio)phenyl)acetamide | | |
| 1-92 | 2-amino-N-(3-(4-(furan-2-ylmethoxy)-2-(4-methylpiperazin-1-yl)pyrimidin-5-ylthio)phenyl)acetamide | | |
| 1-93 | 2-amino-N-(3-(4-(furan-3-ylmethoxy)-2-(4-methylpiperazin-1-yl)pyrimidin-5-ylthio)phenyl)acetamide | | |
| 1-94 | 2-amino-N-(3-(2-(4-methylpiperazin-1-yl)-4-phenethoxypyrimidin-5-ylthio)phenyl)acetamide | | |
| 1-95 | 2-amino-N-(3-(4-(2-cyclopentylethoxy)-2-(4-methylpiperazin-1-yl)pyrimidin-5-ylthio)phenyl)acetamide | | |
| 1-96 | 2-amino-N-(3-(4-methoxy-2-(4-methylpiperazin-1-yl)pyrimidin-5-ylthio)phenyl)acetamide | | |

One embodiment of the compound of formula 2a is a compound of formula 2a'

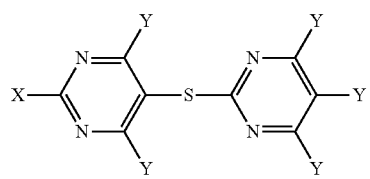

2a' or a stereoisomer, tautomer, or pharmaceutically acceptable salt thereof, wherein: each X and Y is independently selected from the group consisting of optionally substituted straight or branched alkyl, alkenyl, or alkynyl; an optionally substituted carbocyclic, heterocyclic, aryl, or heteroaryl group; halo; an optionally substituted $C_{2-22}$ acyl group; a —NR$_4$R$_5$ group; a —C(O)R$_6$ group; an -(ethoxy)$_n$-R$_6$ group, wherein n is 1-12; an optionally substituted alkoxycarbonyl group; an optionally substituted alkyloxy group; an optionally substituted amino group; a nitro group; and a carboxyl group; R$_4$ and R$_5$ are each independently selected from the group consisting of H; optionally substituted straight or branched alkyl, alkenyl, or alkynyl; and —C(O) R$_6$; and each R$_6$ is independently selected from the group consisting of an optionally substituted straight or branched alkyl, alkenyl, or alkynyl; an optionally substituted carbocyclic, heterocyclic, aryl, or heteroaryl group; an optionally substituted alkyloxy group; and an alkylacrylate group (such as ethyl acrylate).

In another embodiment, the compound of formula 2a' is as described above, provided that X does not comprise a bridged ring structure.

In another embodiment, the compound of formula 2a' is as described above, provided that at least one of the X or Y substituents comprises at least one label or marker group useful for identifying, tracking, and or isolating the compound. Non-limiting examples of label groups and marker groups useful herein include, for example, fluorescent groups, biotin groups, avidin groups, and enzyme linker groups.

Another embodiment of the present subject matter is a compound of formula 2a″

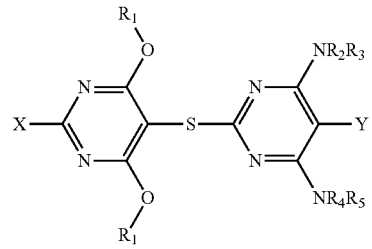

2a″ or a stereoisomer, tautomer, or pharmaceutically acceptable salt thereof, wherein: each R$_1$ is independently selected from the group consisting of H; optionally substituted straight or branched alkyl, alkenyl, or alkynyl; an optionally substituted carbocyclic, heterocyclic, aryl, or heteroaryl group; halo; an optionally substituted $C_{2-22}$ acyl group; a —C(O)R$_6$ group; and an -(ethoxy)$_n$-R$_6$ group, wherein n is 1-12; R$_2$, R$_3$, R$_4$, and R$_5$ are each independently selected from the group consisting of H; optionally substituted straight or branched alkyl, alkenyl, or alkynyl; an optionally substituted carbocyclic, heterocyclic, aryl, or heteroaryl group; an optionally substituted $C_{2-22}$ acyl group; a —C(O)R$_6$ group; and an optionally substituted alkoxycarbonyl group; and X is selected from the group consisting of optionally substituted straight or branched alkyl, alkenyl, or alkynyl; an optionally substituted carbocyclic, heterocyclic (e.g. 4-alkylpiperazine), aryl, or heteroaryl group; halo; an optionally substituted $C_{2-22}$ acyl group; a —NR$_4$R$_5$ group; a —C(O)R$_6$ group; an -(ethoxy)$_n$-R$_6$ group, wherein n is 1-12; an optionally substituted alkoxycarbonyl group; an optionally substituted alkyloxy group; an optionally substituted amino group; a nitro group; and a carboxyl group; and each R$_6$ is independently selected from the group consisting of an optionally substituted straight or branched alkyl, alkenyl, or alkynyl; an optionally substituted carbocyclic, heterocyclic, aryl, or heteroaryl group; an optionally substituted alkyloxy group; and an alkylacrylate group (such as ethyl acrylate); provided that X does not comprise a bridged ring structure.

In another embodiment, the compound of formula 2a' is as described above, provided that the compound is not N-(6-amino-2-(4,6-dimethoxy-2-(4-methylpiperazin-1-yl)pyrimidin-5-ylthio) pyrimidin-4-yl)octanamide (YK20).

In still another embodiment, the compound of formula 2a″ is as described above, and wherein: each R$_1$ is independently selected from the group consisting of H; and optionally substituted straight or branched alkyl, alkenyl, or alkynyl; $R_2$, $R_3$, $R_4$, and $R_5$ are each independently selected from the group consisting of H; optionally substituted straight or branched C1-C6 alkyl; and —C(O) $R_6$ wherein $R_6$ is an optionally substituted straight or branched C1-C6 alkyl, alkenyl, or alkynyl; and X is selected from the group consisting of an optionally substituted straight or branched alkyl, alkenyl, or alkynyl group; an optionally substituted carbocyclic, heterocyclic, aryl, or heteroaryl group; and halo. In a further embodiment, X is piperazine ring linked at a nitrogen atom, wherein the piperazine is optionally substituted with at least one group selected from the group consisting of halo, haloalkyl, straight or branched alkyl, substituted straight or branched alkyl, and HO-(ethoxy)$_n$-C1-C6 alkyl- where n=1-8 (such as, for example, HO-(ethoxy)$_3$-C$_2$H$_4$—).

In another embodiment, the compound of formula 2a' is as described above, wherein: each $R_1$ is independently selected from the group consisting of straight or branched C1-C6 alkyl and substituted straight or branched C1-C6 alkyl. For example, $R_1$ may be selected from the group consisting of methyl, ethyl, ethenyl, propyl, and butyl.

In another embodiment, the compound of formula 2a' is as described above, wherein: each $R_1$ is independently selected from methyl and ethyl; $NR_2R_3$ is $NH_2$; $NR_4R_5$ is NHC(O)—C1-C6 alkyl or NHC(O)—C2-C6 alkenyl; and X is piperazine ring linked at a nitrogen atom, and the piperazine ring is optionally substituted with halo, haloalkyl, or straight or branched C1-C6 alkyl.

In another embodiment, the compound of formula 2a' is as described above, wherein: each $R_1$ is the same or different and is methyl or ethyl; $R_2$, $R_3$, and $R_4$ are each H; $R_5$ is —C(O)-methyl, —C(O)-ethyl, or —C(O)-ethenyl; X is piperazine, 4-methylpiperazin-1-yl or 4-(2-(2-(2-(2-hydroxyethoxy)ethoxy)ethoxy)ethyl)piperazin-1-yl.

Another embodiment of the present subject matter relates to compounds having the formula:

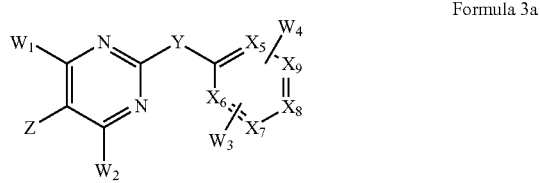

Formula 3a their stereoisomers, tautomers, and pharmaceutically acceptable salts thereof, wherein, $X_5$-$X_9$ are independently selected from CH, substituted C, and substituted N;

Y is S, SO, SO$_2$, CH$_2$, CHR, CRR, CO, O, NH, or NR, wherein R is a lower alkyl or alkoxyl chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, SO$_2$-alkyl, —COO-alkyl, —COalkyl, and alkyl-CN;

$W_1$ and $W_2$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, SO$_2$-alkyl, —COO-alkyl, —COalkyl, and alkyl-CN; and $W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, SO$_2$-alkyl, —COO-alkyl, —COalkyl, and alkyl-CN; or $W_3$ and $W_4$ may be joined together via a linker, so as to form a fused 5- or 6-membered ring. Furthermore, $W_2$ may be joined to the right side aryl ring directly to form a 5-membered ring or via a linker to form a 6 or 7-membered ring.

In preferred embodiments of formula (3a), $X_5$-$X_9$ are independently selected from but not limited to:

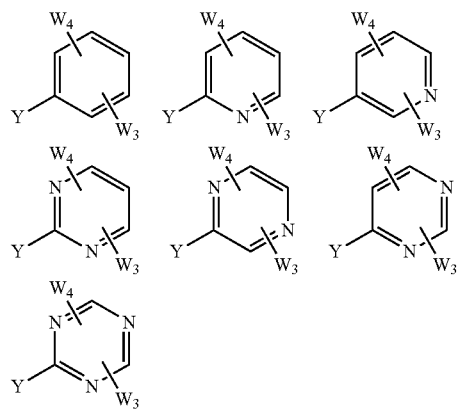

In preferred embodiments of formula (3a) Y is is S, SO, SO$_2$, O or CH$_2$.

In preferred embodiments of formula (3a) Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (3a) $W_1$ and $W_2$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (3a) $W_3$ and $W_4$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In particular preferred embodiments of formula (3a), $X_5$-$X_9$ are

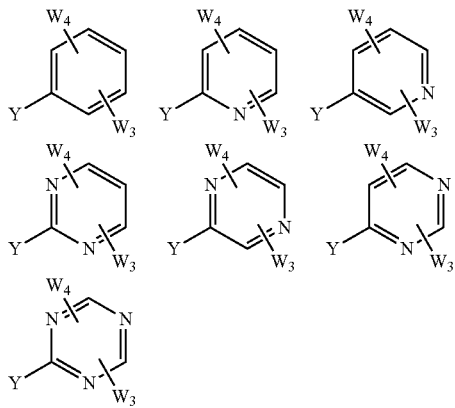

In particular preferred embodiments of formula (3a), Y is S, SO, or $SO_2$.

In particular preferred embodiments of formula (3a), Z is hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, or diarylamino.

In particular preferred embodiments of formula (3a), $W_1$ and $W_2$ are independently hydrogen, alkyl, alkenyl, alkynyl, aryl, alkoxy, amino, alkylamino, dialkylamino, cycloalkylamino, arylamino, or diarylamino.

In particular preferred embodiments of formula (3a), $W_3$ and $W_4$ are independently hydrogen, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COOalkyl, —COalkyl, and alkyl-CN.

Table 2 show examples of specific compounds exemplifying this embodiment.

TABLE 2

| ID # | Compound Name |
|---|---|
| 2-01 | N-(3-(4,6-dimethoxy-5-(4-methylpiperazin-1-yl)pyrimidin-2-ylthio)phenyl)acrylamide |
| 2-02 | 4,6-dimethoxy-2-(3-phenoxyphenylthio)pyrimidine |
| 2-03 | N-(3-(4-(cyclopropylamino)-5-(5,6-dihydropyridin-1(2H)-yl)-6-methoxypyrimidin-2-ylthio)phenyl)acrylamide |
| 2-04 | 3-(5-hydroxy-4,6-dimethoxypyrimidin-2-ylthio)benzenesulfinamide |
| 2-05 | 7-(4-methoxy-5-(4-methylpiperazin-1-yl)pyrimidin-2-ylthio)-3,4-dihydroquinolin-2(1H)-one |
| 2-06 | 7-(4-methoxy-5-(4-methylpiperazin-1-yl)pyrimidin-2-ylthio)quinolin-2(1H)-one |
| 2-07 | 2-(4,6-dichloropyridin-2-ylthio)-4-methoxy-5-(4-methylpiperazin-1-yl)pyrimidine |
| 2-08 | N-(2-(4-amino-5-ethyl-6-methoxypyrimidin-2-ylsulfinyl)-6-methoxypyridin-4-yl)acetamide |
| 2-09 | 2-(6-chloro-4-(cyclopentylamino)pyridin-2-ylthio)-N5,N5-diethyl-N4-phenylpyrimidine-4,5-diamine |
| 2-10 | (2-chloro-6-(5-ethoxy-4-methoxypyrimidin-2-ylthio)pyridin-4-yl)methanesulfinamide |
| 2-11 | 2-(2-(4-methoxy-5-(4-methylpiperazin-1-yl)pyrimidin-2-ylthio)pyridin-4-yl)acetonitrile |
| 2-12 | 2-amino-N-(2-(4-(furan-2-yl)-5-(4-methylpiperazin-1-yl)pyrimidin-2-ylthio)pyridin-4-yl)acetamide |
| 2-13 | N-(5-(4,6-dimethyl-5-(4-methylpiperazin-1-yl)pyrimidin-2-ylthio)pyridin-3-yl)cyclopropanecarboxamide |
| 2-14 | N-methyl-2-(5-(trifluoromethoxy)pyridin-3-ylsulfonyl)-5-vinylpyrimidin-4-amine |
| 2-15 | ethyl 5-(4-(diphenylamino)-5-(pyrrolidin-1-yl)pyrimidin-2-ylthio)pyridin-3-ylcarbamate |
| 2-16 | N-isopropyl-4,6-dimethyl-2-(5-(trifluoromethyl)pyridin-3-ylthio)pyrimidin-5-amine |
| 2-17 | N-(5-(4,6-dimethyl-5-(4-methylpiperazin-1-yl)pyrimidin-2-ylthio)pyridin-3-yl)picolinamide |
| 2-18 | N-(5-(4-methyl-6-(5-methylfuran-2-yl)-5-(piperazin-1-yl)pyrimidin-2-ylthio)pyridin-3-yl)cyclopropanecarboxamide |
| 2-19 | N-(6-hydroxy-2-(4-methoxy-5-(4-methylpiperazin-1-yl)-6-vinylpyrimidin-2-ylthio)pyrimidin-4-yl)acetamide |
| 2-20 | N-(2-(4-(dimethylamino)-5-(prop-1-ynyl)pyrimidin-2-ylthio)-6-(vinyloxy)pyrimidin-4-yl)acetamide |
| 2-21 | 1-(6-hydroxy-2-(4-methoxy-5-(1H-pyrrol-1-yl)-6-vinylpyrimidin-2-ylthio)pyrimidin-4-yl)ethanone |
| 2-22 | 2-(5-(diethylamino)-4-methoxy-6-vinylpyrimidin-2-ylthio)-6-(methylthio)pyrimidin-4-ol |
| 2-23 | N-(6-hydroxy-2-(4-methoxy-5-(4-methylpiperazin-1-yl)-6-vinylpyrimidin-2-ylthio)pyrimidin-4-yl)nicotinamide |
| 2-24 | N-(6-hydroxy-2-(4-methoxy-5-(4-methylpiperazin-1-yl)-6-(1H-pyrrol-2-yl)pyrimidin-2-ylthio)pyrimidin-4-yl)acetamide |
| 2-25 | 4-(4-methoxy-2-(6-nitropyrazin-2-ylthio)-6-phenylpyrimidin-5-yl)morpholine |
| 2-26 | 2-(6-(4-(cyclopentylamino)-6-methoxy-5-(pyridin-4-yl)pyrimidin-2-ylsulfinyl)pyrazin-2-yl)ethanol |
| 2-27 | 2-(5-(4-methoxy-6-phenyl-5-(piperidin-1-yl)pyrimidin-2-ylthio)pyrazin-2-yl)acetamide |
| 2-28 | N-cyclopentyl-4-methoxy-2-(6-(methylsulfonyl)pyrazin-2-ylthio)-6-phenylpyrimidin-5-amine |
| 2-29 | 4-(6-methoxy-5-morpholino-2-(6-nitropyrazin-2-ylthio)pyrimidin-4-yl)-N,N-dimethylaniline |
| 2-30 | 4-methoxy-5-(4-methylpiperazin-1-yl)-2-(6-nitropyrazin-2-ylthio)-6-(1H-pyrazol-3-yl)pyrimidine |
| 2-31 | 6-(4-ethynyl-6-methoxy-5-(piperidin-1-yl)pyrimidin-2-ylthio)pyrimidine-4-carbonitrile |
| 2-32 | 2-(6-aminopyrimidin-4-ylsulfonyl)-5-cyclohexyl-N-phenylpyrimidin-4-amine |
| 2-33 | N-(6-(4-ethynyl-5-fluoro-6-methoxypyrimidin-2-ylthio)pyrimidin-4-yl)acetamide |
| 2-34 | isopropyl 6-(4-ethynyl-6-methoxy-5-(phenylamino)pyrimidin-2-ylthio)pyrimidine-4-carboxylate |
| 2-35 | 6-(4-(3-(dimethylamino)phenyl)-5-(piperidin-1-yl)pyrimidin-2-ylthio)pyrimidine-4-carbonitrile |
| 2-36 | 6-(4-methoxy-5-(piperidin-1-yl)-6-(thiophen-2-yl)pyrimidin-2-ylthio)pyrimidine-4-carbonitrile |
| 2-37 | N-(4-amino-6-(5-(4-hydroxypiperidin-1-yl)-4-phenoxypyrimidin-2-ylthio)-1,3,5-triazin-2-yl)benzamide |
| 2-38 | 6-(5-cyclohexenylpyrimidin-2-ylthio)-N2-ethyl-N4,N4-dimethyl-1,3,5-triazine-2,4-diamine |
| 2-39 | N-acetyl-N-(4-amino-6-(5-bromo-4-phenoxypyrimidin-2-ylthio)-1,3,5-triazin-2-yl)acetamide |
| 2-40 | (4-amino-6-(4-phenoxy-5-(pyrimidin-5-ylamino)pyrimidin-2-ylthio)-1,3,5-triazin-2-yl)(cyclopentyl)methanone |
| 2-41 | N-(4-amino-6-(4-(3-(dimethylamino)phenoxy)-5-(4-hydroxypiperidin-1-yl)pyrimidin-2-ylthio)-1,3,5-triazin-2-yl)benzamide |
| 2-42 | N-(4-(4-allyl-5-(4-hydroxypiperidin-1-yl)pyrimidin-2-ylthio)-6-amino-1,3,5-triazin-2-yl)-2-aminopropanamide |
| 2-43 | 6-(5-(4-hydroxycyclohexylamino)-4-methoxy-6-(thiophen-2-yl)pyrimidin-2-ylthio)pyrimidine-4-carbonitrile |
| 2-44 | N-(4-amino-6-(5-(4-hydroxycyclohexylamino)-4-phenoxypyrimidin-2-ylthio)-1,3,5-triazin-2-yl)benzamide |
| 2-45 | 2-amino-N-(3-(5-(4-methylpiperazin-1-yl)-4-(pyrrolidin-2-ylmethoxy)pyrimidin-2-ylthio)phenyl)acetamide |

TABLE 2-continued

| ID # | Compound Name |
|---|---|
| 2-46 | 2-amino-N-(3-(5-(4-methylpiperazin-1-yl)-4-(piperidin-4-yloxy)pyrimidin-2-ylthio)phenyl)acetamide |
| 2-47 | 2-amino-N-(3-(4-(benzyloxy)-5-(4-methylpiperazin-1-yl)-6-(trifluoromethyl)pyrimidin-2-ylthio)-5-methoxyphenyl)acetamide |
| 2-48 | 2-amino-N-(3-(4-(benzyloxy)-5-(4-methylpiperazin-1-yl)pyrimidin-2-ylthio)phenyl)-3-(1H-imidazol-4-yl)propanamide |
| 2-49 | 5-(4-(benzyloxy)-5-(4-methylpiperazin-1-yl)pyrimidin-2-ylthio)quinolin-2(1H)-one |
| 2-50 | 2-amino-N-(3-(4-(benzyloxy)-5-(4-methylpiperazin-1-yl)pyrimidin-2-ylthio)phenyl)-3-methylbutanamide |
| 2-51 | N-(4-(4-(3-(dimethylamino)phenoxy)-5-(4-methylpiperazin-1-yl)pyrimidin-2-ylthio)pyridin-2-yl)propionamide |
| 2-52 | N-(3-(5-(4-methylpiperazin-1-yl)-4-(piperidin-3-yloxy)pyrimidin-2-ylthio)phenyl)methanesulfonamide |
| 2-53 | 4-(2-methoxyethoxy)-5-(4-methylpiperazin-1-yl)-6-phenoxy-2-(3-(1-phenylethyl)phenylthio)pyrimidine |
| 2-54 | 7-(5-(4-methylpiperazin-1-yl)-4-(quinolin-8-yloxy)pyrimidin-2-ylthio)quinolin-2(1H)-one |
| 2-55 | N-(3-(4-(benzyloxy)-5-(4-methylpiperazin-1-yl)pyrimidin-2-ylthio)phenyl)pyrrolidine-2-carboxamide |
| 2-56 | 2-amino-N-(3-(4-(benzyloxy)-5-(4-methylpiperazin-1-yl)pyrimidin-2-ylthio)phenyl)propanamide |
| 2-57 | 2-amino-N-(5-(4-(3-aminophenoxy)-5-(4-methylpiperazin-1-yl)pyrimidin-2-ylthio)pyridin-3-yl)acetamide |
| 2-58 | 2-amino-N-(4-(4-(4-aminocyclohexyloxy)-5-(4-methylpiperazin-1-yl)pyrimidin-2-ylthio)-6-methylpyrimidin-2-yl)acetamide |
| 2-59 | 2-amino-3-methyl-N-(3-(5-(4-methylpiperazin-1-yl)-4-(pyridin-3-ylmethoxy)pyrimidin-2-ylsulfonyl)phenyl)pentanamide |
| 2-60 | 2-amino-N-(6-(4-(benzyloxy)-5-(4-methylpiperazin-1-yl)pyrimidin-2-ylthio)benzo[d][1,3]dioxol-4-yl)acetamide |
| 2-61 | (3-(4-(3-(dimethylamino)cyclohexyloxy)-5-(4-methylpiperazin-1-yl)pyrimidin-2-ylthio)phenyl)methanol |
| 2-62 | 2-amino-N-(4-(4-(benzyloxy)-6-(2-methoxyethoxy)-5-(4-methylpiperazin-1-yl)pyrimidin-2-ylthio)phenyl)acetamide |
| 2-63 | 2-amino-N-(3-(furan-3-ylamino)-5-(5-(4-methylpiperazin-1-yl)-4-(pyrimidin-2-ylmethoxy)pyrimidin-2-ylsulfinyl)phenyl)-4-methylpentanamide |
| 2-64 | 2-amino-N-(6-(4-(3-aminocyclopentyloxy)-5-(4-methylpiperazin-1-yl)pyrimidin-2-ylthio)pyrazin-2-yl)acetamide |
| 2-65 | 2-amino-N-(4-(4-methoxy-5-(4-methylpiperazin-1-yl)-6-phenethylpyrimidin-2-ylthio)-1,3,5-triazin-2-yl)propanamide |
| 2-66 | 2-amino-N-(6-(5-(4-methylpiperazin-1-yl)-4-(pyridin-3-yloxy)pyrimidin-2-ylthio)pyridin-2-yl)propanamide |
| 2-67 | 2-amino-N-(2-(4-(3-carbamimidoylphenoxy)-5-(4-methylpiperazin-1-yl)pyrimidin-2-ylthio)pyrimidin-4-yl)acetamide |
| 2-68 | N-(3-(4-(2-(dimethylamino)ethoxy)-5-(4-methylpiperazin-1-yl)pyrimidin-2-ylthio)phenyl)acrylamide |
| 2-69 | 2-amino-N-(2-(5-(4-methylpiperazin-1-yl)-4-(pyridin-2-yloxy)pyrimidin-2-ylsulfonyl)pyridin-4-yl)propanamide |
| 2-70 | N-(3-(5-(4-methylpiperazin-1-yl)-4-(pyridin-4-yloxy)pyrimidin-2-ylsulfinyl)phenyl)benzamide |
| 2-71 | 2-amino-N-(3-(dimethylamino)-5-(5-(4-methylpiperazin-1-yl)-4-phenoxypyrimidin-2-ylthio)phenyl)acetamide |
| 2-72 | 5-(4-(benzyloxy)-5-(4-methylpiperazin-1-yl)pyrimidin-2-ylthio)-3,4-dihydroquinolin-2(1H)-one |
| 2-73 | 2-amino-N-(3-amino-5-(4-(cyclopentyloxy)-5-(4-methylpiperazin-1-yl)pyrimidin-2-ylthio)phenyl)acetamide |
| 2-74 | 7-(4-(cyclopropylmethoxy)-6-methoxy-5-(4-methylpiperazin-1-yl)pyrimidin-2-ylthio)-3,4-dihydroquinolin-2(1H)-one |

Another embodiment of the present subject matter relates to compounds having the formula:

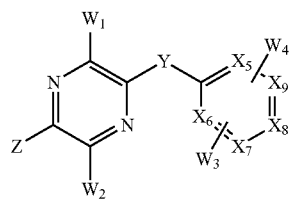

Formula 4a their stereoisomers, tautomers, and pharmaceutically acceptable salts thereof, wherein, $X_5$-$X_9$ are independently selected from CH, substituted C, and substituted N;

Y is S, SO, $SO_2$, $CH_2$, CHR, CRR, CO, O, NH, or NR, wherein R is a lower alkyl or alkoxyl chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN;

$W_1$ and $W_2$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; and $W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_3$ and $W_4$ may be joined together via a linker, so as to form a fused 5- or 6-membered ring. Furthermore, $W_2$ may be joined to the right side aryl ring directly to form a 5-membered ring or via a linker to form a 6 or 7-membered ring.

In preferred embodiments of formula (4a), $X_5$-$X_9$ are independently selected from but not limited to:

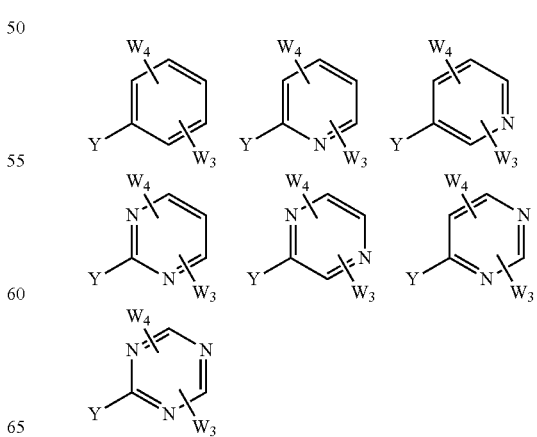

In preferred embodiments of formula (4a) Y is is S, SO, SO$_2$, O or CH$_2$.

In preferred embodiments of formula (4a) Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (4a) W$_1$ and W$_2$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (4a) W$_3$ and W$_4$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In particular preferred embodiments of formula (4a), X$_5$—X$_9$ are

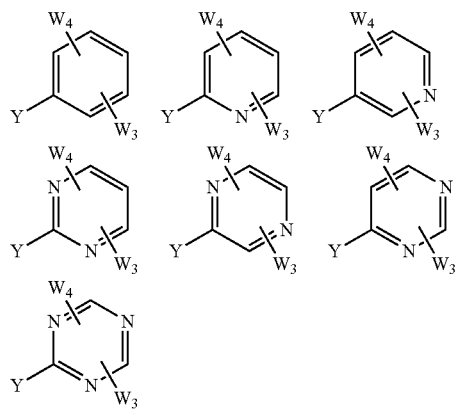

In particular preferred embodiments of formula (4a), Y is S, SO, or SO$_2$.

In particular preferred embodiments of formula (4a), Z is hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, or diarylamino.

In particular preferred embodiments of formula (4a), W$_1$ and W$_2$ are independently hydrogen, alkyl, alkenyl, alkynyl, aryl, alkoxy, amino, alkylamino, dialkylamino, cycloalkylamino, arylamino, or diarylamino.

In particular preferred embodiments of formula (4a), W$_3$ and W$_4$ are independently hydrogen, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, SO$_2$-alkyl, —COO-alkyl, —COalkyl, and alkyl-CN.

Table 3 show examples of specific compounds exemplifying this embodiment.

TABLE 3

| ID # | Compound Name |
|---|---|
| 3-01 | N-(3-(3,6-dimethoxy-5-(4-methylpiperazin-1-yl)pyrazin-2-ylthio)phenyl)acrylamide |
| 3-02 | 2,5-dimethoxy-3-(3-phenoxyphenylthio)pyrazine |
| 3-03 | N-(3-(6-(cyclopropylamino)-5-(5,6-dihydropyridin-1(2H)-yl)-3-methoxypyrazin-2-ylthio)phenyl)acrylamide |
| 3-04 | 3-(5-hydroxy-3,6-dimethoxypyrazin-2-ylthio)benzenesulfinamide |
| 3-05 | 7-(6-methoxy-5-(4-methylpiperazin-1-yl)pyrazin-2-ylthio)-3,4-dihydroquinolin-2(1H)-one |
| 3-06 | 7-(6-methoxy-5-(4-methylpiperazin-1-yl)pyrazin-2-ylthio)quinolin-2(1H)-one |
| 3-07 | 5-(4,6-dichloropyridin-2-ylthio)-3-methoxy-2-(4-methylpiperazin-1-yl)pyrazine |
| 3-08 | N-(2-(3-amino-5-ethyl-6-methoxypyrazin-2-ylsulfinyl)-6-methoxypyridin-4-yl)acetamide |
| 3-09 | 5-(6-chloro-4-(cyclopentylamino)pyridin-2-ylthio)-N2,N2-diethyl-N3-phenylpyrazine-2,3-diamine |
| 3-10 | (2-chloro-6-(5-ethoxy-6-methoxypyrazin-2-ylthio)pyridin-4-yl)methanesulfinamide |
| 3-11 | 2-(2-(6-methoxy-5-(4-methylpiperazin-1-yl)pyrazin-2-ylthio)pyridin-4-yl)acetonitrile |
| 3-12 | 2-amino-N-(2-(6-(furan-2-yl)-5-(4-methylpiperazin-1-yl)pyrazin-2-ylthio)pyridin-4-yl)acetamide |
| 3-13 | N-(5-(6-methyl-5-(4-methylpiperazin-1-yl)pyrazin-2-ylthio)pyridin-3-yl)cyclopropanecarboxamide |
| 3-14 | N-methyl-3-(5-(trifluoromethoxy)pyridin-3-ylsulfonyl)-6-vinylpyrazin-2-amine |
| 3-15 | ethyl 5-(6-(diphenylamino)-5-(pyrrolidin-1-yl)pyrazin-2-ylthio)pyridin-3-ylcarbamate |
| 3-16 | N-isopropyl-3,6-dimethyl-5-(5-(trifluoromethyl)pyridin-3-ylthio)pyrazin-2-amine |
| 3-17 | N-(5-(3,6-dimethyl-5-(4-methylpiperazin-1-yl)pyrazin-2-ylthio)pyridin-3-yl)picolinamide |
| 3-18 | N-(5-(3-methyl-6-(5-methylfuran-2-yl)-5-(piperazin-1-yl)pyrazin-2-ylthio)pyridin-3-yl)cyclopropanecarboxamide |
| 3-19 | N-(6-hydroxy-2-(3-methoxy-5-(4-methylpiperazin-1-yl)-6-vinylpyrazin-2-ylthio)pyrimidin-4-yl)acetamide |
| 3-20 | N-(2-(3-(dimethylamino)-5-(prop-1-ynyl)pyrazin-2-ylthio)-6-(vinyloxy)pyrimidin-4-yl)acetamide |
| 3-21 | 1-(6-hydroxy-2-(3-methoxy-5-(1H-pyrrol-1-yl)-6-vinylpyrazin-2-ylthio)pyrimidin-4-yl)ethanone |
| 3-22 | 2-(5-(diethylamino)-3-methoxy-6-vinylpyrazin-2-ylthio)-6-(methylthio)pyrimidin-4-ol |
| 3-23 | N-(6-hydroxy-2-(3-methoxy-5-(4-methylpiperazin-1-yl)-6-vinylpyrazin-2-ylthio)pyrimidin-4-yl)nicotinamide |
| 3-24 | N-(6-hydroxy-2-(3-methoxy-5-(4-methylpiperazin-1-yl)-6-(1H-pyrrol-2-yl)pyrazin-2-ylthio)pyrimidin-4-yl)acetamide |
| 3-25 | 4-(3-methoxy-5-(6-nitropyrazin-2-ylthio)pyrazin-2-yl)morpholine |
| 3-26 | 2-(6-(3-(cyclopentylamino)-6-methoxy-5-(pyridin-4-yl)pyrazin-2-ylsulfinyl)pyrazin-2-yl)ethanol |
| 3-27 | 2-(5-(6-methoxy-3-phenyl-5-(piperidin-1-yl)pyrazin-2-ylthio)pyrazin-2-yl)acetamide |
| 3-28 | N-cyclopentyl-3-methoxy-5-(6-(methylsulfonyl)pyrazin-2-ylthio)-6-phenylpyrazin-2-amine |
| 3-29 | 4-(5-methoxy-6-morpholino-3-(6-nitropyrazin-2-ylthio)pyrazin-2-yl)-N,N-dimethylaniline |
| 3-30 | 2-methoxy-3-(4-methylpiperazin-1-yl)-6-(6-nitropyrazin-2-ylthio)-5-(1H-pyrazol-3-yl)pyrazine |
| 3-31 | 6-(3-ethynyl-6-methoxy-5-(piperidin-1-yl)pyrazin-2-ylthio)pyrimidine-4-carbonitrile |
| 3-32 | 6-(5-cyclohexyl-3-(phenylamino)pyrazin-2-ylsulfonyl)pyrimidin-4-amine |
| 3-33 | N-(6-(3-ethynyl-5-fluoro-6-methoxypyrazin-2-ylthio)pyrimidin-4-yl)acetamide |
| 3-34 | isopropyl 6-(3-ethynyl-6-methoxy-5-(phenylamino)pyrazin-2-ylthio)pyrimidine-4-carboxylate |
| 3-35 | 6-(3-(3-(dimethylamino)phenyl)-5-(piperidin-1-yl)pyrazin-2-ylthio)pyrimidine-4-carbonitrile |
| 3-36 | 6-(6-methoxy-5-(piperidin-1-yl)-3-(thiophen-2-yl)pyrazin-2-ylthio)pyrimidine-4-carbonitrile |
| 3-37 | N-(4-amino-6-(5-(4-hydroxypiperidin-1-yl)-3-phenoxypyrazin-2-ylthio)-1,3,5-triazin-2-yl)benzamide |
| 3-38 | 6-(5-cyclohexenylpyrazin-2-ylthio)-N2-ethyl-N4,N4-dimethyl-1,3,5-triazine-2,4-diamine |

TABLE 3-continued

| ID # | Compound Name |
|---|---|
| 3-39 | N-acetyl-N-(4-amino-6-(5-bromo-3-phenoxypyrazin-2-ylthio)-1,3,5-triazin-2-yl)acetamide |
| 3-40 | (4-amino-6-(3-phenoxy-5-(pyrimidin-5-ylamino)pyrazin-2-ylthio)-1,3,5-triazin-2-yl)(cyclopentyl)methanone |
| 3-41 | N-(4-amino-6-(3-(3-(dimethylamino)phenoxy)-5-(4-hydroxypiperidin-1-yl)pyrazin-2-ylthio)-1,3,5-triazin-2-yl)benzamide |
| 3-42 | N-(4-(3-allyl-5-(4-hydroxypiperidin-1-yl)pyrazin-2-ylthio)-6-amino-1,3,5-triazin-2-yl)-2-aminopropanamide |
| 3-43 | N-(3-(5-(4-hydroxycyclohexylamino)-3,6-dimethoxypyrazin-2-ylthio)phenyl)acrylamide |
| 3-44 | 2-amino-N-(3-(5-(4-methylpiperazin-1-yl)-6-(pyrrolidin-2-ylmethoxy)pyrazin-2-ylthio)phenyl)acetamide |
| 3-45 | 2-amino-N-(3-(5-(4-methylpiperazin-1-yl)-6-(piperidin-4-yloxy)pyrazin-2-ylthio)phenyl)acetamide |
| 3-46 | 2-amino-N-(3-(6-(benzyloxy)-3-methoxy-5-(4-methylpiperazin-1-yl)pyrazin-2-ylthio)-5-methoxyphenyl)acetamide |
| 3-47 | 2-amino-N-(3-(6-(benzyloxy)-5-(4-methylpiperazin-1-yl)pyrazin-2-ylthio)phenyl)-3-(1H-imidazol-4-yl)propanamide |
| 3-48 | 5-(6-(benzyloxy)-5-(4-methylpiperazin-1-yl)pyrazin-2-ylthio)quinolin-2(1H)-one |
| 3-49 | 2-amino-N-(3-(6-(benzyloxy)-5-(4-methylpiperazin-1-yl)pyrazin-2-ylthio)phenyl)-3-methylbutanamide |
| 3-50 | N-(4-(6-(3-(dimethylamino)phenoxy)-5-(4-methylpiperazin-1-yl)pyrazin-2-ylthio)pyridin-2-yl)propionamide |
| 3-51 | N-(3-(5-(4-methylpiperazin-1-yl)-6-(piperidin-3-yloxy)pyrazin-2-ylthio)phenyl)methanesulfonamide |
| 3-52 | N,N-dimethyl-2-(6-(4-methylpiperazin-1-yl)-5-phenoxy-3-(3-(1-phenylethyl)phenylthio)pyrazin-2-yloxy)ethanamine |
| 3-53 | 7-(5-(4-methylpiperazin-1-yl)-6-(quinolin-8-yloxy)pyrazin-2-ylthio)quinolin-2(1H)-one |
| 3-54 | N-(3-(6-(benzyloxy)-5-(4-methylpiperazin-1-yl)pyrazin-2-ylthio)phenyl)pyrrolidine-2-carboxamide |
| 3-55 | 2-amino-N-(3-(6-(benzyloxy)-5-(4-methylpiperazin-1-yl)pyrazin-2-ylthio)phenyl)propanamide |
| 3-56 | 2-amino-N-(5-(6-(3-aminophenoxy)-5-(4-methylpiperazin-1-yl)pyrazin-2-ylthio)pyridin-3-yl)acetamide |
| 3-57 | 2-amino-N-(4-(6-(4-aminocyclohexyloxy)-5-(4-methylpiperazin-1-yl)pyrazin-2-ylthio)-6-methylpyrimidin-2-yl)acetamide |
| 3-58 | 2-amino-3-methyl-N-(3-(5-(4-methylpiperazin-1-yl)-6-(pyridin-3-ylmethoxy)pyrazin-2-ylsulfonyl)phenyl)pentanamide |
| 3-59 | 2-amino-N-(6-(6-(benzyloxy)-5-(4-methylpiperazin-1-yl)pyrazin-2-ylthio)benzo[d][1,3]dioxol-4-yl)acetamide |
| 3-60 | (3-(6-(3-(dimethylamino)cyclohexyloxy)-5-(4-methylpiperazin-1-yl)pyrazin-2-ylthio)phenyl)methanol |
| 3-61 | 2-amino-N-(4-(6-(benzyloxy)-3-(2-methoxyethoxy)-5-(4-methylpiperazin-1-yl)pyrazin-2-ylthio)phenyl)acetamide |
| 3-62 | 2-amino-N-(3-(furan-3-ylamino)-5-(5-(4-methylpiperazin-1-yl)-6-(pyrimidin-2-ylmethoxy)pyrazin-2-ylsulfinyl)phenyl)-4-methylpentanamide |
| 3-63 | 2-amino-N-(3-(6-(2,3-dimethoxybenzyloxy)-5-(4-methylpiperazin-1-yl)pyrazin-2-ylthio)-5-methoxyphenyl)acetamide |
| 3-64 | 2-amino-N-(6-(6-(3-aminocyclopentyloxy)-5-(4-methylpiperazin-1-yl)pyrazin-2-ylthio)pyrazin-2-yl)acetamide |
| 3-65 | 2-amino-N-(4-(3-methoxy-5-(4-methylpiperazin-1-yl)-6-phenethylpyrazin-2-ylthio)-1,3,5-triazin-2-yl)propanamide |
| 3-66 | 2-amino-N-(6-(5-(4-methylpiperazin-1-yl)-6-(pyridin-3-yloxy)pyrazin-2-ylthio)pyridin-2-yl)propanamide |
| 3-67 | 2-amino-N-(3-(3-amino-5-(4-methylpiperazin-1-yl)-6-phenoxypyrazin-2-ylthio)phenyl)acetamide |
| 3-68 | 5-(6-(benzyloxy)-5-(4-methylpiperazin-1-yl)pyrazin-2-ylthio)-3,4-dihydroquinolin-2(1H)-one |
| 3-69 | 2-amino-N-(2-(6-(3-carbamimidoylphenoxy)-5-(4-methylpiperazin-1-yl)pyrazin-2-ylthio)pyrimidin-4-yl)acetamide |
| 3-70 | N-(3-(6-(2-(dimethylamino)ethoxy)-5-(4-methylpiperazin-1-yl)pyrazin-2-ylthio)phenyl)acrylamide |
| 3-71 | 2-amino-N-(2-(5-(4-methylpiperazin-1-yl)-6-(pyridin-2-yloxy)pyrazin-2-ylsulfonyl)pyridin-4-yl)propanamide |
| 3-72 | 2-amino-N-(3-amino-5-(6-(cyclopentyloxy)-5-(4-methylpiperazin-1-yl)pyrazin-2-ylthio)phenyl)acetamide |
| 3-73 | 7-(6-(cyclopropylmethoxy)-3-methoxy-5-(4-methylpiperazin-1-yl)pyrazin-2-ylthio)-3,4-dihydroquinolin-2(1H)-one |
| 3-74 | N-(3-(5-(4-methylpiperazin-1-yl)-6-(pyridin-4-yloxy)pyrazin-2-ylsulfinyl)phenyl)benzamide |

Another embodiment of the present subject matter relates to compounds having the formula:

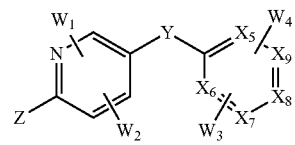

Formula 5a their stereoisomers, tautomers, and pharmaceutically acceptable salts thereof, wherein, $X_5$-$X_9$ are independently selected from CH, substituted C, and substituted N;

Y is S, SO, $SO_2$, $CH_2$, CHR, CRR, CO, O, NH, or NR, wherein R is a lower alkyl or alkoxyl chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN;

$W_1$ and $W_2$ independently at each occurrence are independently selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_1$ and $W_2$ may be joined together via a linker, so as to form a fused 5- or 6-membered ring; and $W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_3$ and $W_4$ may be joined together via a linker, so as to form a fused 5- or 6-membered ring.

Furthermore, $W_2$ may be joined to the right side aryl ring directly to form a 5-membered ring or via a linker to form a 6 or 7-membered ring.

In preferred embodiments of formula (5a), $X_5$-$X_9$ are independently selected from but not limited to:

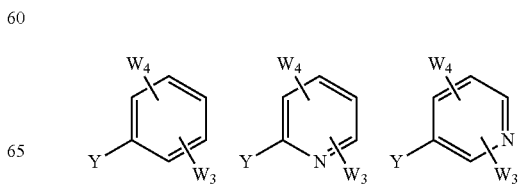

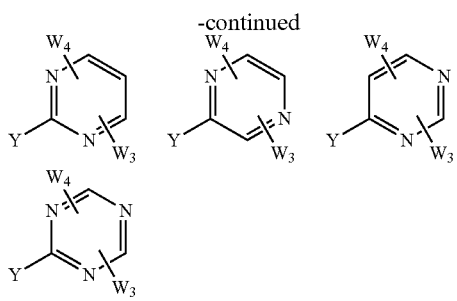

In preferred embodiments of formula (5a) Y is is S, SO, SO₂, O or CH2.

In preferred embodiments of formula (5a) Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (5a) W₁ and W₂ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (5a) W₃ and W₄ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In particular preferred embodiments of formula (5a), X₅-X₉ are

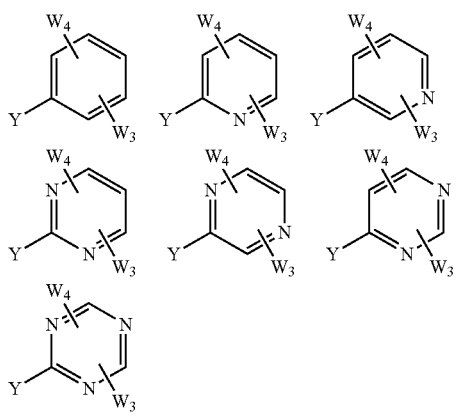

In particular preferred embodiments of formula (5a), Y is S, SO, or SO₂.

In particular preferred embodiments of formula (5a), Z is hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, or diarylamino.

In particular preferred embodiments of formula (5a), W₁ and W₂ are independently hydrogen, alkyl, alkenyl, alkynyl, aryl, alkoxy, amino, alkylamino, dialkylamino, cycloalkylamino, arylamino, or diarylamino.

In particular preferred embodiments of formula (5a), W₃ and W₄ are independently hydrogen, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, SO₂-alkyl, —COOalkyl, —COalkyl, and alkyl-CN.

Table 4 show examples of specific compounds exemplifying this embodiment.

TABLE 4

| ID # | Compound Name |
| --- | --- |
| YK171 | N-(2-(2-methoxy-6-(4-methylpiperazin-1-yl)pyridin-3-ylthio)pyrimidin-4-yl)propionamide |
| YK172 | N-(2-(2-methoxy-6-(4-methylpiperazin-1-yl)pyridin-3-ylthio)pyrimidin-4-yl)cyclopropanecarboxamide |
| YK173 | N-(3-(2-methoxy-6-(4-methylpiperazin-1-yl)pyridin-3-ylthio)phenyl)propionamide |
| YK174 | N-(3-(2-methoxy-6-(4-methylpiperazin-1-yl)pyridin-3-ylthio)phenyl)cyclopropanecarboxamide |
| YK175 | 2-amino-N-(3-(2-methoxy-6-(4-methylpiperazin-1-yl)pyridin-3-ylthio)phenyl)acetamide |
| YK176 | 1-(5-(3,5-dichlorophenylthio)-6-methoxypyridin-2-yl)-4-methylpiperazine |
| YK178 | N-(3-(2-methoxy-6-(4-methylpiperazin-1-yl)pyridin-3-ylthio)phenyl)benzamide |
| YK179 | 2-amino-N-(3-(2-hydroxy-6-(4-methylpiperazin-1-yl)pyridin-3-ylthio)phenyl)acetamide |
| YK180 | 2-amino-N-(3-(2-(benzyloxy)-6-(4-methylpiperazin-1-yl)pyridin-3-ylthio)phenyl)acetamide |
| YK181 | 2-amino-N-(3-(2-(4-methoxybenzyloxy)-6-(4-methylpiperazin-1-yl)pyridin-3-ylthio)phenyl)acetamide |
| 4-01 | 2-(2-(5-methoxy-6-(4-methylpiperazin-1-yl)pyridin-3-ylthio)pyridin-4-yl)acetonitrile |
| 4-02 | 2-amino-N-(2-(5-(furan-2-yl)-6-(4-methylpiperazin-1-yl)pyridin-3-ylthio)pyridin-4-yl)acetamide |
| 4-03 | N-(5-(5-methyl-6-(4-methylpiperazin-1-yl)pyridin-3-ylthio)pyridin-3-yl)cyclopropanecarboxamide |
| 4-04 | N-methyl-3-(5-(trifluoromethoxy)pyridin-3-ylsulfonyl)-6-vinylpyridin-2-amine |
| 4-05 | ethyl 5-(5-(diphenylamino)-6-(pyrrolidin-1-yl)pyridin-3-ylthio)pyridin-3-ylcarbamate |
| 4-06 | N-isopropyl-3,6-dimethyl-5-(5-(trifluoromethyl)pyridin-3-ylthio)pyridin-2-amine |
| 4-07 | N-(5-(2,5-dimethyl-6-(4-methylpiperazin-1-yl)pyridin-3-ylthio)pyridin-3-yl)picolinamide |
| 4-08 | N-(5-(2-methyl-5-(5-methylfuran-2-yl)-6-(piperazin-1-yl)pyridin-3-ylthio)pyridin-3-yl)cyclopropanecarboxamide |
| 4-09 | N-(6-hydroxy-2-(2-methoxy-6-(4-methylpiperazin-1-yl)-5-vinylpyridin-3-ylthio)pyrimidin-4-yl)acetamide |
| 4-10 | N-(2-(2-(dimethylamino)-6-(prop-1-ynyl)pyridin-3-ylthio)-6-(vinyloxy)pyrimidin-4-yl)acetamide |
| 4-11 | 1-(6-hydroxy-2-(2-methoxy-6-(1H-pyrrol-1-yl)-5-vinylpyridin-3-ylthio)pyrimidin-4-yl)ethanone |
| 4-12 | 2-(6-(diethylamino)-2-methoxy-5-vinylpyridin-3-ylthio)-6-(methylthio)pyrimidin-4-ol |
| 4-13 | N-(6-hydroxy-2-(2-methoxy-6-(4-methylpiperazin-1-yl)-5-vinylpyridin-3-ylthio)pyrimidin-4-yl)nicotinamide |
| 4-14 | N-(6-hydroxy-2-(2-methoxy-6-(4-methylpiperazin-1-yl)-5-(1H-pyrrol-2-yl)pyridin-3-ylthio)pyrimidin-4-yl)acetamide |
| 4-15 | 4-(3-methoxy-5-(6-nitropyrazin-2-ylthio)pyridin-2-yl)morpholine |
| 4-16 | 2-(6-(6-(cyclopentylamino)-3-methoxy-2,4'-bipyridin-5-ylsulfinyl)pyrazin-2-yl)ethanol |
| 4-17 | 2-(5-(5-methoxy-2-phenyl-6-(piperidin-1-yl)pyridin-3-ylthio)pyrazin-2-yl)acetamide |
| 4-18 | N-cyclopentyl-3-methoxy-5-(6-(methylsulfonyl)pyrazin-2-ylthio)-6-phenylpyridin-2-amine |

TABLE 4-continued

| ID # | Compound Name |
|---|---|
| 4-19 | 4-(5-methoxy-6-morpholino-3-(6-nitropyrazin-2-ylthio)pyridin-2-yl)-N,N-dimethylaniline |
| 4-20 | 2-(5-methoxy-6-(4-methylpiperazin-1-yl)-2-(1H-pyrazol-3-yl)pyridin-3-ylthio)-6-nitropyrazine |
| 4-21 | 6-(2-ethynyl-5-methoxy-6-(piperidin-1-yl)pyridin-3-ylthio)pyrimidine-4-carbonitrile |
| 4-22 | 6-(6-cyclohexyl-2-(phenylamino)pyridin-3-ylsulfonyl)pyrimidin-4-amine |
| 4-23 | N-(6-(2-ethynyl-6-fluoro-5-methoxypyridin-3-ylthio)pyrimidin-4-yl)acetamide |
| 4-24 | isopropyl 6-(2-ethynyl-5-methoxy-6-(phenylamino)pyridin-3-ylthio)pyrimidine-4-carboxylate |
| 4-25 | 6-(2-(3-(dimethylamino)phenyl)-6-(piperidin-1-yl)pyridin-3-ylthio)pyrimidine-4-carbonitrile |
| 4-26 | 6-(5-methoxy-6-(piperidin-1-yl)-2-(thiophen-2-yl)pyridin-3-ylthio)pyrimidine-4-carbonitrile |
| 4-27 | N-(4-amino-6-(6-(4-hydroxypiperidin-1-yl)-2-phenoxypyridin-3-ylthio)-1,3,5-triazin-2-yl)benzamide |
| 4-28 | 6-(6-cyclohexenylpyridin-3-ylthio)-N2-ethyl-N4,N4-dimethyl-1,3,5-triazine-2,4-diamine |
| 4-29 | N-acetyl-N-(4-amino-6-(6-bromo-2-phenoxypyridin-3-ylthio)-1,3,5-triazin-2-yl)acetamide |
| 4-30 | (4-amino-6-(2-phenoxy-6-(pyridin-3-ylamino)pyridin-3-ylthio)-1,3,5-triazin-2-yl)(cyclopentyl)methanone |
| 4-31 | N-(4-amino-6-(2-(3-(dimethylamino)phenoxy)-6-(4-hydroxypiperidin-1-yl)pyridin-3-ylthio)-1,3,5-triazin-2-yl)benzamide |
| 4-32 | N-(4-(2-allyl-6-(4-hydroxypiperidin-1-yl)pyridin-3-ylthio)-6-amino-1,3,5-triazin-2-yl)-2-aminopropanamide |
| 4-33 | N-(3-(6-(4-hydroxycyclohexylamino)-2,5-dimethoxypyridin-3-ylthio)phenyl)acrylamide |
| 4-34 | N-(3-(2-methoxy-6-(4-methylpiperazin-1-yl)pyridin-3-ylthio)phenyl)acetamide |
| 4-35 | 2-amino-N-(2-(2-(furan-2-yl)-6-(4-methylpiperazin-1-yl)pyridin-3-ylthio)pyridin-4-yl)acetamide |
| 4-36 | N-(5-(4-methoxy-6-(piperazin-1-yl)pyridin-3-ylthio)pyridin-3-yl)cyclopropanecarboxamide |
| 4-37 | 2-amino-N-(3-(6-(4-methylpiperazin-1-yl)-5-(pyrrolidin-2-ylmethoxy)pyridin-3-ylthio)phenyl)acetamide |
| 4-38 | 2-amino-N-(3-(6-(4-methylpiperazin-1-yl)-5-(piperidin-4-yloxy)pyridin-3-ylthio)phenyl)acetamide |
| 4-39 | 2-amino-N-(3-methoxy-5-(2-methoxy-6-(4-methylpiperazin-1-yl)pyridin-3-ylthio)phenyl)acetamide |
| 4-40 | 2-amino-N-(3-(2-(benzyloxy)-6-(4-methylpiperazin-1-yl)pyridin-3-ylthio)phenyl)-3-(1H-imidazol-4-yl)propanamide |
| 4-41 | 5-(5-(benzyloxy)-6-(4-methylpiperazin-1-yl)pyridin-3-ylthio)quinolin-2(1H)-one |
| 4-42 | 2-amino-N-(3-(2-(benzyloxy)-6-(4-methylpiperazin-1-yl)pyridin-3-ylthio)phenyl)-3-methylbutanamide |
| 4-43 | N-(4-(2-(3-(dimethylamino)phenoxy)-6-(4-methylpiperazin-1-yl)pyridin-3-ylthio)pyridin-2-yl)propionamide |
| 4-44 | N-(3-(6-(4-methylpiperazin-1-yl)-5-(piperidin-3-yloxy)pyridin-3-ylthio)phenyl)methanesulfonamide |
| 4-45 | N,N-dimethyl-2-(6-(4-methylpiperazin-1-yl)-5-phenoxy-3-(3-(1-phenylethyl)phenylthio)pyridin-2-yloxy)ethanamine |
| 4-46 | 7-(6-(4-methylpiperazin-1-yl)-5-(quinolin-8-yloxy)pyridin-3-ylthio)quinolin-2(1H)-one |
| 4-47 | N-(3-(2-(benzyloxy)-6-(4-methylpiperazin-1-yl)pyridin-3-ylthio)phenyl)pyrrolidine-2-carboxamide |
| 4-48 | 2-amino-N-(3-(5-(benzyloxy)-6-(4-methylpiperazin-1-yl)pyridin-3-ylthio)phenyl)propanamide |
| 4-49 | 2-amino-N-(5-(5-(3-aminophenoxy)-6-(4-methylpiperazin-1-yl)pyridin-3-ylthio)pyridin-3-yl)acetamide |
| 4-50 | 2-amino-N-(4-(5-(4-aminocyclohexyloxy)-6-(4-methylpiperazin-1-yl)pyridin-3-ylthio)-6-methylpyrimidin-2-yl)acetamide |
| 4-51 | 2-amino-3-methyl-N-(3-(6-(4-methylpiperazin-1-yl)-5-(pyridin-3-ylmethoxy)pyridin-3-ylsulfonyl)phenyl)pentanamide |
| 4-52 | 2-amino-N-(6-(6-(4-methylpiperazin-1-yl)-2-phenoxypyridin-3-ylthio)benzo[d][1,3]dioxol-4-yl)acetamide |
| 4-53 | (3-(5-(3-(dimethylamino)cyclohexyloxy)-6-(4-methylpiperazin-1-yl)pyridin-3-ylthio)phenyl)methanol |
| 4-54 | 2-amino-N-(4-(2-(2-methoxyethoxy)-6-(4-methylpiperazin-1-yl)pyridin-3-ylthio)phenyl)acetamide |
| 4-55 | 2-amino-N-(3-(furan-3-ylamino)-5-(6-(4-methylpiperazin-1-yl)-5-(pyrimidin-2-ylmethoxy)pyridin-3-ylsulfinyl)phenyl)-4-methylpentanamide |
| 4-56 | 2-amino-N-(3-(5-(2,3-dimethoxybenzyloxy)-6-(4-methylpiperazin-1-yl)pyridin-3-ylthio)-5-methoxyphenyl)acetamide |
| 4-57 | 2-amino-N-(6-(5-(3-aminocyclopentyloxy)-6-(4-methylpiperazin-1-yl)pyridin-3-ylthio)pyrazin-2-yl)acetamide |
| 4-58 | 2-amino-N-(4-(2-(furan-2-yloxy)-6-(4-methylpiperazin-1-yl)pyridin-3-ylthio)-1,3,5-triazin-2-yl)propanamide |
| 4-59 | 2-amino-N-(6-(6-(4-methylpiperazin-1-yl)-5-(pyridin-3-yloxy)pyridin-3-ylthio)pyridin-2-yl)propanamide |
| 4-60 | 2-amino-N-(3-(2-amino-6-(4-methylpiperazin-1-yl)-5-phenoxypyridin-3-ylthio)phenyl)acetamide |
| 4-61 | 5-(5-(benzyloxy)-6-(4-methylpiperazin-1-yl)pyridin-3-ylthio)-3,4-dihydroquinolin-2(1H)-one |
| 4-62 | 2-amino-N-(2-(5-(3-carbamimidoylphenoxy)-6-(4-methylpiperazin-1-yl)pyridin-3-ylthio)pyrimidin-4-yl)acetamide |
| 4-63 | N-(3-(2-(furan-3-ylmethyl)-6-(4-methylpiperazin-1-yl)pyridin-3-ylthio)phenyl)acrylamide |
| 4-64 | 2-amino-N-(2-(6-(4-methylpiperazin-1-yl)-5-(pyridin-2-yloxy)pyridin-3-ylsulfonyl)pyridin-4-yl)propanamide |
| 4-65 | 2-amino-N-(3-amino-5-(5-(cyclopentyloxy)-6-(4-methylpiperazin-1-yl)pyridin-3-ylthio)phenyl)acetamide |
| 4-66 | 7-(5-(cyclopropylmethoxy)-2-methoxy-6-(4-methylpiperazin-1-yl)pyridin-3-ylthio)-3,4-dihydroquinolin-2(1H)-one |
| 4-67 | N-(3-(6-(4-methylpiperazin-1-yl)-5-(pyridin-4-yloxy)pyridin-3-ylsulfinyl)phenyl)benzamide |
| 4-68 | N-(6-amino-2-(7-amino-3-methoxy-1-(4-methylpiperazin-1-yl)isoquinolin-4-ylthio)pyrimidin-4-yl)acrylamide |

Another embodiment of the present subject matter relates to compounds having the formula:

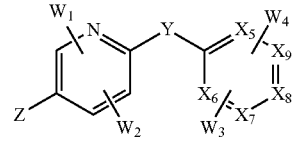

Formula 6a their stereoisomers, tautomers, and pharmaceutically acceptable salts thereof, wherein, $X_5$-$X_9$ are independently selected from CH, substituted C, and substituted N;

Y is S, SO, $SO_2$, $CH_2$, CHR, CRR, CO, O, NH, or NR, wherein R is a lower alkyl or alkoxyl chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, SO2-alkyl, —COO-alkyl, —COalkyl, and alkyl-CN;

$W_1$ and $W_2$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COOalkyl, —COalkyl, and alkyl-CN; or $W_1$ and $W_2$ may be joined together via a linker, so as to form a fused 5- or 6-membered ring; and $W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_3$ and $W_4$ may be joined together via a linker, so as to form a fused 5- or 6-membered ring.

Furthermore, $W_2$ may be joined to the right side aryl ring directly to form a 5-membered ring or via a linker to form a 6 or 7-membered ring.

In preferred embodiments of formula (6a), $X_5$-$X_9$ are independently selected from but not limited to:

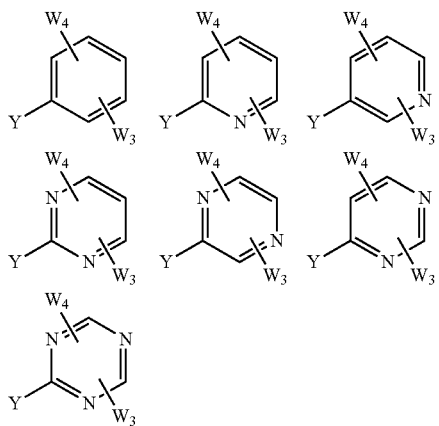

In preferred embodiments of formula (6a) Y is is S, SO, $SO_2$, O or CH2.

In preferred embodiments of formula (6a) Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (6a) $W_1$ and $W_2$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (6a) $W_3$ and $W_4$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In particular preferred embodiments of formula (6a), $X_5$-$X_9$ are

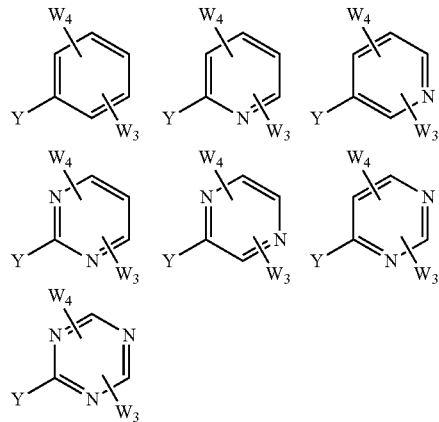

In particular preferred embodiments of formula (6a), Y is S, SO, or $SO_2$.

In particular preferred embodiments of formula (6a), Z is hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, or diarylamino.

In particular preferred embodiments of formula (6a), W and $W_2$ are independently hydrogen, alkyl, alkenyl, alkynyl, aryl, alkoxy, amino, alkylamino, dialkylamino, cycloalkylamino, arylamino, or diarylamino.

In particular preferred embodiments of formula (6a), $W_3$ and $W_4$ are independently hydrogen, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN.

Table 5 show examples of specific compounds exemplifying this embodiment.

TABLE 5

| ID # | Compound Name |
|---|---|
| 5-01 | N-(3-(4,6-dimethoxy-5-(4-methylpiperazin-1-yl)pyridin-2-ylthio)phenyl)acrylamide |
| 5-02 | 2,4-dimethoxy-6-(3-phenoxyphenylthio)pyridine |
| 5-03 | N-(3-(4-(cyclopropylamino)-5-(5,6-dihydropyridin-1(2H)-yl)-6-methoxypyridin-2-ylthio)phenyl)acrylamide |
| 5-04 | 3-(5-hydroxy-4,6-dimethoxypyridin-2-ylthio)benzenesulfinamide |
| 5-05 | 7-(4-methoxy-5-(4-methylpiperazin-1-yl)pyridin-2-ylthio)-3,4-dihydroquinolin-2(1H)-one |
| 5-06 | 7-(4-methoxy-5-(4-methylpiperazin-1-yl)pyridin-2-ylthio)quinolin-2(1H)-one |
| 5-07 | 1-(6-(4,6-dichloropyridin-2-ylthio)-4-methoxypyridin-3-yl)-4-methylpiperazine |
| 5-08 | N-(2-(6-amino-5-ethyl-4-methoxypyridin-2-ylsulfinyl)-6-methoxypyridin-4-yl)acetamide |
| 5-09 | 6-(6-chloro-4-(cyclopentylamino)pyridin-2-ylthio)-N3,N3-diethyl-N4-phenylpyridine-3,4-diamine |
| 5-10 | (2-chloro-6-(5-ethoxy-4-methoxypyridin-2-ylthio)pyridin-4-yl)methanesulfinamide |
| 5-11 | 2-(2-(4-methoxy-5-(4-methylpiperazin-1-yl)pyridin-2-ylthio)pyridin-4-yl)acetonitrile |

TABLE 5-continued

| ID # | Compound Name |
|---|---|
| 5-12 | 2-amino-N-(2-(4-(furan-2-yl)-5-(4-methylpiperazin-1-yl)pyridin-2-ylthio)pyridin-4-yl)acetamide |
| 5-13 | N-(5-(4,6-dimethyl-5-(4-methylpiperazin-1-yl)pyridin-2-ylthio)pyridin-3-yl)cyclopropanecarboxamide |
| 5-14 | N-methyl-6-(5-(trifluoromethoxy)pyridin-3-ylsulfonyl)-3-vinylpyridin-2-amine |
| 5-15 | ethyl 5-(4-(diphenylamino)-5-(pyrrolidin-1-yl)pyridin-2-ylthio)pyridin-3-ylcarbamate |
| 5-16 | N-isopropyl-2,4-dimethyl-6-(5-(trifluoromethyl)pyridin-3-ylthio)pyridin-3-amine |
| 5-17 | N-(5-(4,6-dimethyl-5-(4-methylpiperazin-1-yl)pyridin-2-ylthio)pyridin-3-yl)picolinamide |
| 5-18 | N-(5-(6-methyl-4-(5-methylfuran-2-yl)-5-(piperazin-1-yl)pyridin-2-ylthio)pyridin-3-yl)cyclopropanecarboxamide |
| 5-19 | N-(6-hydroxy-2-(6-methoxy-5-(4-methylpiperazin-1-yl)-4-vinylpyridin-2-ylthio)pyrimidin-4-yl)acetamide |
| 5-20 | N-(2-(6-(dimethylamino)-5-(prop-1-ynyl)pyridin-2-ylthio)-6-(vinyloxy)pyrimidin-4-yl)acetamide |
| 5-21 | 1-(6-hydroxy-2-(6-methoxy-5-(1H-pyrrol-1-yl)-4-vinylpyridin-2-ylthio)pyrimidin-4-yl)ethanone |
| 5-22 | 2-(5-(diethylamino)-6-methoxy-4-vinylpyridin-2-ylthio)-6-(methylthio)pyrimidin-4-ol |
| 5-23 | N-(5-(6-hydroxy-6-methoxy-5-(4-methylpiperazin-1-yl)-4-vinylpyridin-2-ylthio)pyrimidin-4-yl)nicotinamide |
| 5-24 | N-(6-hydroxy-2-(6-methoxy-5-(4-methylpiperazin-1-yl)-4-(1H-pyrrol-2-yl)pyridin-2-ylthio)pyrimidin-4-yl)acetamide |
| 5-25 | 4-(4-methoxy-6-(6-nitropyrazin-2-ylthio)-2-phenylpyridin-3-yl)morpholine |
| 5-26 | 2-(6-(2-(cyclopentylamino)-4-methoxy-3,4'-bipyridin-6-ylsulfinyl)pyrazin-2-yl)ethanol |
| 5-27 | 2-(5-(4-methoxy-6-phenyl-5-(piperidin-1-yl)pyridin-2-ylthio)pyrazin-2-yl)acetamide |
| 5-28 | N-cyclopentyl-4-methoxy-6-(6-(methylsulfonyl)pyrazin-2-ylthio)-2-phenylpyridin-3-amine |
| 5-29 | 4-(4-methoxy-3-morpholino-6-(6-nitropyrazin-2-ylthio)pyridin-2-yl)-N,N-dimethylaniline |
| 5-30 | 2-methoxy-5-(4-methylpiperazin-1-yl)-6-(1H-pyrazol-3-yl)pyridin-2-ylthio)-6-nitropyrazine |
| 5-31 | 6-(6-ethynyl-4-methoxy-5-(piperidin-1-yl)pyridin-2-ylthio)pyrimidine-4-carbonitrile |
| 5-32 | 6-(5-cyclohexyl-6-(phenylamino)pyridin-2-ylsulfonyl)pyrimidin-4-amine |
| 5-33 | N-(6-(6-ethynyl-5-fluoro-4-methoxypyridin-2-ylthio)pyrimidin-4-yl)acetamide |
| 5-34 | isopropyl 6-(6-ethynyl-4-methoxy-5-(phenylamino)pyridin-2-ylthio)pyrimidine-4-carboxylate |
| 5-35 | 6-(6-(3-(dimethylamino)phenyl)-5-(piperidin-1-yl)pyridin-2-ylthio)pyrimidine-4-carbonitrile |
| 5-36 | 6-(4-methoxy-5-(piperidin-1-yl)-6-(thiophen-2-yl)pyridin-2-ylthio)pyrimidine-4-carbonitrile |
| 5-37 | N-(4-amino-6-(5-(4-hydroxypiperidin-1-yl)-6-phenoxypyridin-2-ylthio)-1,3,5-triazin-2-yl)benzamide |
| 5-38 | 6-(5-cyclohexenylpyridin-2-ylthio)-N2-ethyl-N4,N4-dimethyl-1,3,5-triazine-2,4-diamine |
| 5-39 | N-acetyl-N-(4-amino-6-(5-bromo-6-phenoxypyridin-2-ylthio)-1,3,5-triazin-2-yl)acetamide |
| 5-40 | (4-amino-6-(6-phenoxy-5-(pyrimidin-5-ylamino)pyridin-2-ylthio)-1,3,5-triazin-2-yl)(cyclopentyl)methanone |
| 5-41 | N-(4-amino-6-(6-(3-(dimethylamino)phenoxy)-5-(4-hydroxypiperidin-1-yl)pyridin-2-ylthio)-1,3,5-triazin-2-yl)benzamide |
| 5-42 | N-(4-(6-allyl-5-(4-hydroxypiperidin-1-yl)pyridin-2-ylthio)-6-amino-1,3,5-triazin-2-yl)-2-aminopropanamide |
| 5-43 | N-(3-(5-(4-hydroxycyclohexylamino)-4,6-dimethoxypyridin-2-ylthio)phenyl)acrylamide |
| 5-44 | N-(2-methoxy-5-(6-methoxy-5-(4-methylpiperazin-1-yl)pyridin-2-ylthio)phenyl)acrylamide |
| 5-45 | 1-(6-(4,6-dichloropyridin-2-ylthio)-5-methoxypyridin-3-yl)-4-methylpiperazine |
| 5-46 | N-(5-(3,6-dimethyl-5-(4-methylpiperazin-1-yl)pyridin-2-ylthio)pyridin-3-yl)cyclopropanecarboxamide |
| 5-47 | N-(2-(3-cyclopropoxy-5-(4-methylpiperazin-1-yl)pyridin-2-ylthio)-6-hydroxypyrimidin-4-yl)acetamide |
| 5-48 | 4-(5-methoxy-6-(6-nitropyrazin-2-ylthio)-2-phenylpyridin-3-yl)morpholine |
| 5-49 | 2-amino-N-(3-(5-(4-methylpiperazin-1-yl)-4-(pyrrolidin-2-ylmethoxy)pyridin-2-ylthio)phenyl)acetamide |
| 5-50 | 2-amino-N-(3-(5-(4-methylpiperazin-1-yl)-3-(piperidin-4-yloxy)pyridin-2-ylthio)phenyl)acetamide |
| 5-51 | 2-amino-N-(3-(4-(benzyloxy)-5-(4-methylpiperazin-1-yl)pyridin-2-ylthio)-5-methoxyphenyl)acetamide |
| 5-52 | 2-amino-N-(3-(4-(benzyloxy)-5-(4-methylpiperazin-1-yl)pyridin-2-ylthio)phenyl)-3-(1H-imidazol-4-yl)propanamide |
| 5-53 | 5-(4-(benzyloxy)-5-(4-methylpiperazin-1-yl)pyridin-2-ylthio)quinolin-2(1H)-one |
| 5-54 | 2-amino-N-(3-(4-(benzyloxy)-5-(4-methylpiperazin-1-yl)pyridin-2-ylthio)phenyl)-3-methylbutanamide |
| 5-55 | N-(4-(3-(3-(dimethylamino)phenoxy)-5-(4-methylpiperazin-1-yl)pyridin-2-ylthio)pyridin-2-yl)propionamide |
| 5-56 | N-(3-(5-(4-methylpiperazin-1-yl)-4-(piperidin-3-yloxy)pyridin-2-ylthio)phenyl)methanesulfonamide |
| 5-57 | 1-(2-(2-methoxyethoxy)-4-phenoxy-6-(3-(1-phenylethyl)phenylthio)pyridin-3-yl)-4-methylpiperazine |
| 5-58 | 7-(5-(4-methylpiperazin-1-yl)-4-(quinolin-8-yloxy)pyridin-2-ylthio)quinolin-2(1H)-one |
| 5-59 | N-(3-(4-(benzyloxy)-5-(4-methylpiperazin-1-yl)pyridin-2-ylthio)phenyl)pyrrolidine-2-carboxamide |
| 5-60 | 2-amino-N-(3-(4-(benzyloxy)-5-(4-methylpiperazin-1-yl)pyridin-2-ylthio)phenyl)propanamide |
| 5-61 | 2-amino-N-(5-(4-(3-aminophenoxy)-5-(4-methylpiperazin-1-yl)pyridin-2-ylthio)pyridin-3-yl)acetamide |
| 5-62 | 2-amino-N-(4-(4-(4-aminocyclohexyloxy)-5-(4-methylpiperazin-1-yl)pyridin-2-ylthio)-6-methylpyrimidin-2-yl)acetamide |
| 5-63 | 2-amino-3-methyl-N-(3-(5-(4-methylpiperazin-1-yl)-4-(pyridin-3-ylmethoxy)pyridin-2-ylsulfonyl)phenyl)pentanamide |
| 5-64 | 2-amino-N-(6-(3-(benzyloxy)-5-(4-methylpiperazin-1-yl)pyridin-2-ylthio)benzo[d][1,3]dioxol-4-yl)acetamide |
| 5-65 | (3-(4-(3-(dimethylamino)cyclohexyloxy)-5-(4-methylpiperazin-1-yl)pyridin-2-ylthio)phenyl)methanol |
| 5-66 | 2-amino-N-(4-(4-(benzyloxy)-6-(2-methoxyethoxy)-5-(4-methylpiperazin-1-yl)pyridin-2-ylthio)phenyl)acetamide |
| 5-67 | 2-amino-N-(3-(furan-3-ylamino)-5-(5-(4-methylpiperazin-1-yl)-3-(pyrimidin-2-ylmethoxy)pyridin-2-ylsulfinyl)phenyl)-4-methylpentanamide |
| 5-68 | 2-amino-N-(3-(4-(2,3-dimethoxybenzyloxy)-5-(4-methylpiperazin-1-yl)pyridin-2-ylthio)-5-methoxyphenyl)acetamide |
| 5-69 | 2-amino-N-(6-(4-(3-aminocyclopentyloxy)-5-(4-methylpiperazin-1-yl)pyridin-2-ylthio)pyrazin-2-yl)acetamide |
| 5-70 | (E)-2-amino-N-(4-(6-methoxy-5-(4-methylpiperazin-1-yl)-4-styrylpyridin-2-ylthio)-1,3,5-triazin-2-yl)propanamide |
| 5-71 | 2-amino-N-(6-(5-(4-methylpiperazin-1-yl)-4-(pyridin-3-yloxy)pyridin-2-ylthio)pyridin-2-yl)propanamide |
| 5-72 | 2-amino-N-(3-(dimethylamino)-5-(5-(4-methylpiperazin-1-yl)-4-phenoxypyridin-2-ylthio)phenyl)acetamide |
| 5-73 | 5-(5-(4-methylpiperazin-1-yl)-3-(pyridin-3-ylmethoxy)pyridin-2-ylthio)-3,4-dihydroquinolin-2(1H)-one |
| 5-74 | 2-amino-N-(2-(4-(3-carbamimidoylphenoxy)-5-(4-methylpiperazin-1-yl)pyridin-2-ylthio)pyrimidin-4-yl)acetamide |
| 5-75 | 2-amino-N-(4-(2-(dimethylamino)ethoxy)-5-(4-methylpiperazin-1-yl)pyridin-2-ylthio)phenyl)acrylamide |
| 5-76 | 2-amino-N-(2-(5-(4-methylpiperazin-1-yl)-3-(pyridin-2-yloxy)pyridin-2-ylsulfonyl)pyridin-4-yl)propanamide |
| 5-77 | 2-amino-N-(3-amino-5-(4-(cyclopentyloxy)-5-(4-methylpiperazin-1-yl)pyridin-2-ylthio)phenyl)acetamide |
| 5-78 | 7-(4-(cyclopropylmethoxy)-6-methoxy-5-(4-methylpiperazin-1-yl)pyridin-2-ylthio)-3,4-dihydroquinolin-2(1H)-one |
| 5-79 | N-(3-(5-(4-methylpiperazin-1-yl)-4-(pyridin-4-yloxy)pyridin-2-ylsulfinyl)phenyl)benzamide |
| 5-80 | N-(6-amino-2-(6-amino-4-(4-methylpiperazin-1-yl)isoquinolin-1-ylthio)pyrimidin-4-yl)acrylamide |

Another embodiment of the present subject matter relates to compounds having the formula:

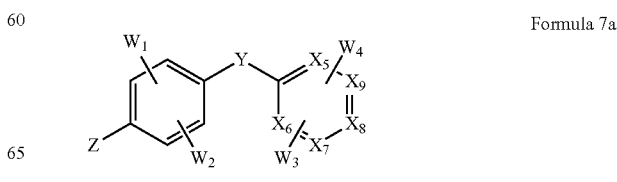

Formula 7a their stereoisomers, tautomers, and pharmaceutically acceptable salts thereof, wherein, $X_5$-$X_9$ are independently selected from CH, substituted C, and substituted N;

Y is S, SO, $SO_2$, $CH_2$, CHR, CRR, CO, O, NH, or NR, wherein R is a lower alkyl or alkoxyl chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN;

$W_1$ and $W_2$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_1$ and $W_2$ may be joined together via a linker, so as to form a fused 5- or 6-membered ring; and $W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_3$ and $W_4$ may be joined together via a linker, so as to form a fused 5- or 6-membered ring.

Furthermore, $W_2$ may be joined to the right side aryl ring directly to form a 5-membered ring or via a linker to form a 6 or 7-membered ring.

In preferred embodiments of formula (7a), $X_5$-$X_9$ are independently selected from but not limited to:

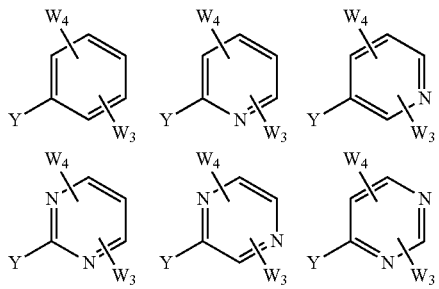

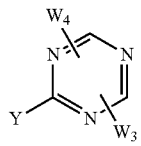

In preferred embodiments of formula (7a) Y is is S, SO, $SO_2$, O or CH2.

In preferred embodiments of formula (7a) Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (7a) $W_1$ and $W_2$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (7a) $W_3$ and $W_4$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In particular preferred embodiments of formula (7a), $X_5$-$X_9$ are

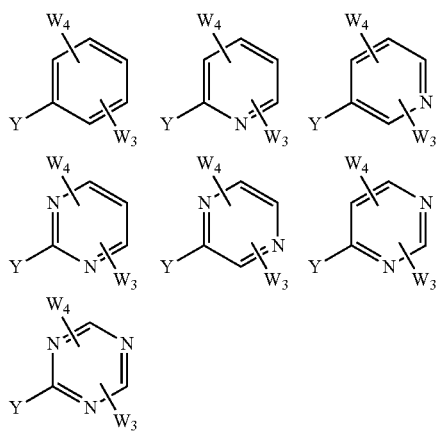

In particular preferred embodiments of formula (7a), Y is S, SO, or $SO_2$.

In particular preferred embodiments of formula (7a), Z is hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, or diarylamino.

In particular preferred embodiments of formula (7a), $W_1$ and $W_2$ are independently hydrogen, alkyl, alkenyl, alkynyl, aryl, alkoxy, amino, alkylamino, dialkylamino, cycloalkylamino, arylamino, or diarylamino.

In particular preferred embodiments of formula (7a), $W_3$ and $W_4$ are independently hydrogen, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COOalkyl, —COalkyl, and alkyl-CN.

Table 6 show examples of specific compounds exemplifying this embodiment.

TABLE 6

| ID # | Compound Name |
|---|---|
| 6-01 | N-(3-(2,6-dimethoxy-4-(4-methylpiperazin-1-yl)phenylthio)phenyl)acrylamide |
| 6-02 | (2,5-dimethoxyphenyl)(3-phenoxyphenyl)sulfane |
| 6-03 | N-(3-(3-(cyclopropylamino)-4-(5,6-dihydropyridin-1(2H)-yl)-5-methoxyphenylthio)phenyl)acrylamide |
| 6-04 | 3-(4-hydroxy-2,6-dimethoxyphenylthio)benzenesulfinamide |
| 6-05 | 7-(3-methoxy-4-(4-methylpiperazin-1-yl)phenylthio)-3,4-dihydroquinolin-2(1H)-one |
| 6-06 | 7-(3-methoxy-4-(4-methylpiperazin-1-yl)phenylthio)quinolin-2(1H)-one |
| 6-07 | 1-(4-(4,6-dichloropyridin-2-ylthio)-2-methoxyphenyl)-4-methylpiperazine |
| 6-08 | N-(2-(5-amino-2-ethoxy-4-ethylphenylsulfinyl)-6-methoxypyridin-4-yl)acetamide |
| 6-09 | 4-(6-chloro-4-(cyclopentylamino)pyridin-2-ylthio)-N1,N1-diethyl-N2-phenylbenzene-1,2-diamine |
| 6-10 | (2-chloro-6-(2-(cyclopentyloxy)-4-ethoxyphenylthio)pyridin-4-yl)methanesulfinamide |
| 6-11 | 2-(2-(3-methoxy-4-(4-methylpiperazin-1-yl)phenylthio)pyridin-4-yl)acetonitrile |
| 6-12 | 2-amino-N-(2-(3-(furan-2-yl)-4-(4-methylpiperazin-1-yl)phenylthio)pyridin-4-yl)acetamide |
| 6-13 | N-(5-(2,6-diethyl-4-(4-methylpiperazin-1-yl)phenylthio)pyridin-3-yl)cyclopropanecarboxamide |
| 6-14 | N-methyl-5-(5-(trifluoromethoxy)pyridin-3-ylsulfonyl)-2-vinylaniline |
| 6-15 | ethyl 5-(3-(diphenylamino)-4-(pyrrolidin-1-yl)phenylthio)pyridin-3-ylcarbamate |
| 6-16 | N-isopropyl-2,6-dimethyl-4-(5-(trifluoromethyl)pyridin-3-ylthio)aniline |
| 6-17 | N-(5-(2-(cyclopentylamino)-6-methoxy-4-(4-methylpiperazin-1-yl)phenylthio)pyridin-3-yl)picolinamide |
| 6-18 | N-(5-(3-methyl-5-(5-methylfuran-2-yl)-4-(piperazin-1-yl)phenylthio)pyridin-3-yl)cyclopropanecarboxamide |
| 6-19 | N-(6-hydroxy-2-(3-methoxy-4-(4-methylpiperazin-1-yl)-5-vinylphenylthio)pyrimidin-4-yl)acetamide |
| 6-20 | N-(2-(2-(dimethylamino)-4-(prop-1-ynyl)phenylthio)-6-(vinyloxy)pyrimidin-4-yl)acetamide |
| 6-21 | 1-(6-hydroxy-2-(5-methoxy-4-(1H-pyrrol-1-yl)-2-vinylphenylthio)pyrimidin-4-yl)ethanone |
| 6-22 | 2-(4-(diethylamino)-3-methoxy-5-vinylphenylthio)-6-(methylthio)pyrimidin-4-ol |
| 6-23 | N-(2-(2,5-dimethoxy-4-(4-methylpiperazin-1-yl)phenylthio)-6-hydroxypyrimidin-4-yl)nicotinamide |
| 6-24 | N-(2-(2-(furan-2-yl)-4-(4-methylpiperazin-1-yl)-5-(1H-pyrrol-2-yl)phenylthio)-6-hydroxypyrimidin-4-yl)acetamide |
| 6-25 | 4-(3-methoxy-5-(6-nitropyrazin-2-ylthio)biphenyl-2-yl)morpholine |
| 6-26 | 2-(6-(3-(cyclopentylamino)-5-methoxy-4-(pyridin-4-yl)phenylsulfinyl)pyrazin-2-yl)ethanol |
| 6-27 | 2-(5-(5-methoxy-6-(piperidin-1-yl)biphenyl-3-ylthio)pyrazin-2-yl)acetamide |
| 6-28 | N-cyclopentyl-3-methoxy-5-(6-(methylsulfonyl)pyrazin-2-ylthio)biphenyl-2-amine |
| 6-29 | 3'-methoxy-N,N-dimethyl-2'-morpholino-5'-(6-nitropyrazin-2-ylthio)biphenyl-4-amine |
| 6-30 | 2-(3-methoxy-4-(4-methylpiperazin-1-yl)-5-(1H-pyrazol-3-yl)phenylthio)-6-nitropyrazine |
| 6-31 | 6-(3-ethynyl-5-methoxy-4-(piperidin-1-yl)phenylthio)pyrimidine-4-carbonitrile |
| 6-32 | 6-(4-cyclohexyl-3-(phenylamino)phenylsulfonyl)pyrimidin-4-amine |
| 6-33 | N-(6-(6-ethynyl-5-fluoro-4-methoxypyridin-2-ylthio)pyrimidin-4-yl)acetamide |
| 6-34 | isopropyl 6-(3-ethynyl-5-methoxy-4-(phenylamino)phenylthio)pyrimidine-4-carboxylate |
| 6-35 | 6-(3'-(dimethylamino)-6-(piperidin-1-yl)biphenyl-3-ylthio)pyrimidine-4-carbonitrile |
| 6-36 | 6-(3-methoxy-4-(piperidin-1-yl)-5-(thiophen-2-yl)phenylthio)pyrimidine-4-carbonitrile |
| 6-37 | N-(4-amino-6-(4-(4-hydroxypiperidin-1-yl)-3-phenoxyphenylthio)-1,3,5-triazin-2-yl)benzamide |

TABLE 6-continued

| ID # | Compound Name |
|---|---|
| 6-38 | 6-(4-cyclohexenylphenylthio)-N2-ethyl-N4,N4-dimethyl-1,3,5-triazine-2,4-diamine |
| 6-39 | N-acetyl-N-(4-amino-6-(4-bromo-3-phenoxyphenylthio)-1,3,5-triazin-2-yl)acetamide |
| 6-40 | (4-amino-6-(3-phenoxy-4-(pyrimidin-5-ylamino)phenylthio)-1,3,5-triazin-2-yl)(cyclopentyl)methanone |
| 6-41 | N-(4-amino-6-(3-(3-(dimethylamino)phenoxy)-4-(4-hydroxypiperidin-1-yl)phenylthio)-1,3,5-triazin-2-yl)benzamide |
| 6-42 | N-(4-(3-allyl-4-(4-hydroxypiperidin-1-yl)phenylthio)-6-amino-1,3,5-triazin-2-yl)-2-aminopropanamide |
| 6-43 | N-(3-(4-(4-hydroxycyclohexylamino)-2,6-dimethoxyphenylthio)phenyl)acrylamide |
| 6-44 | 2-amino-N-(3-(4-(4-methylpiperazin-1-yl)-3-(pyrrolidin-2-ylmethoxy)phenylthio)phenyl)acetamide |
| 6-45 | 2-amino-N-(3-(4-(4-methylpiperazin-1-yl)-2-(piperidin-4-yloxy)phenylthio)phenyl)acetamide |
| 6-46 | 2-amino-N-(3-(2-(benzyloxy)-4-(4-methylpiperazin-1-yl)phenylthio)-5-methoxyphenyl)acetamide |
| 6-47 | 2-amino-N-(3-(3-(benzyloxy)-4-(4-methylpiperazin-1-yl)phenylthio)phenyl)-3-(1H-imidazol-4-yl)propanamide |
| 6-48 | 5-(3-(benzyloxy)-4-(4-methylpiperazin-1-yl)phenylthio)quinolin-2(1H)-one |
| 6-49 | 2-amino-N-(3-(3-(benzyloxy)-4-(4-methylpiperazin-1-yl)phenylthio)phenyl)-3-methylbutanamide |
| 6-50 | N-(4-(2-(3-(dimethylamino)phenoxy)-4-(4-methylpiperazin-1-yl)phenylthio)pyridin-2-yl)propionamide |
| 6-51 | N-(3-(4-(4-methylpiperazin-1-yl)-3-(piperidin-3-yloxy)phenylthio)phenyl)methanesulfonamide |
| 6-52 | 1-(2-(2-methoxyethoxy)-6-phenoxy-4-(3-(1-phenylethyl)phenylthio)phenyl)-4-methylpiperazine |
| 6-53 | 7-(4-(4-methylpiperazin-1-yl)-3-(quinolin-8-yloxy)phenylthio)quinolin-2(1H)-one |
| 6-54 | N-(3-(3-(benzyloxy)-4-(4-methylpiperazin-1-yl)phenylthio)phenyl)pyrrolidine-2-carboxamide |
| 6-55 | 2-amino-N-(3-(3-(benzyloxy)-4-(4-methylpiperazin-1-yl)phenylthio)phenyl)propanamide |
| 6-56 | 2-amino-N-(5-(3-(3-aminophenoxy)-4-(4-methylpiperazin-1-yl)phenylthio)pyridin-3-yl)acetamide |
| 6-57 | 2-amino-N-(4-(3-(4-aminocyclohexyloxy)-4-(4-methylpiperazin-1-yl)phenylthio)-6-methylpyrimidin-2-yl)acetamide |
| 6-58 | 2-amino-3-methyl-N-(3-(4-(4-methylpiperazin-1-yl)-3-(pyridin-3-ylmethoxy)phenylsulfonyl)phenyl)pentanamide |
| 6-59 | 2-amino-N-(6-(2-(benzyloxy)-4-(4-methylpiperazin-1-yl)phenylthio)benzo[d][1,3]dioxol-4-yl)acetamide |
| 6-60 | (3-(3-(dimethylamino)cyclohexyloxy)-4-(4-methylpiperazin-1-yl)phenylthio)phenyl)methanol |
| 6-61 | 2-amino-N-(4-(3-(benzyloxy)-5-(2-methoxyethoxy)-4-(4-methylpiperazin-1-yl)phenylthio)phenyl)acetamide |
| 6-62 | 2-amino-N-(3-(furan-3-ylamino)-5-(4-(4-methylpiperazin-1-yl)-2-(pyrimidin-2-ylmethoxy)phenylsulfinyl)phenyl)-4-methylpentanamide |
| 6-63 | 2-amino-N-(3-(3-(2,3-dimethoxybenzyloxy)-4-(4-methylpiperazin-1-yl)phenylthio)-5-methoxyphenyl)acetamide |
| 6-64 | 2-amino-N-(9-methoxy-8-(4-methylpiperazin-1-yl)dibenzo[b,d]thiophen-3-yl)acetamide |
| 6-65 | 2-amino-N-(6-(3-(3-aminocyclopentyloxy)-4-(4-methylpiperazin-1-yl)phenylthio)pyrazin-2-yl)acetamide |
| 6-66 | (E)-2-amino-N-(4-(3-methoxy-4-(4-methylpiperazin-1-yl)-5-styrylphenylthio)-1,3,5-triazin-2-yl)propanamide |
| 6-67 | 2-amino-N-(6-(4-(4-methylpiperazin-1-yl)-3-(pyridin-3-yloxy)phenylthio)pyridin-2-yl)propanamide |
| 6-68 | 2-amino-N-(3-(dimethylamino)-5-(4-(4-methylpiperazin-1-yl)-3-phenoxyphenylthio)phenyl)acetamide |
| 6-69 | 5-(4-(4-methylpiperazin-1-yl)-2-(pyridin-3-ylmethoxy)phenylthio)-3,4-dihydroquinolin-2(1H)-one |
| 6-70 | 2-amino-N-(2-(3-(3-carbamimidoylphenoxy)-4-(4-methylpiperazin-1-yl)phenylthio)pyrimidin-4-yl)acetamide |
| 6-71 | N-(3-(3-(2-(dimethylamino)ethoxy)-4-(4-methylpiperazin-1-yl)phenylthio)phenyl)acrylamide |
| 6-72 | 2-amino-N-(2-(4-(4-methylpiperazin-1-yl)-2-(pyridin-2-yloxy)phenylsulfonyl)pyridin-4-yl)propanamide |
| 6-73 | 2-amino-N-(3-amino-5-(3-(cyclopentyloxy)-4-(4-methylpiperazin-1-yl)phenylthio)phenyl)acetamide |
| 6-74 | 7-(3-(cyclopropylmethoxy)-5-methoxy-4-(4-methylpiperazin-1-yl)phenylthio)-3,4-dihydroquinolin-2(1H)-one |
| 6-75 | N-(3-(4-(4-methylpiperazin-1-yl)-3-(pyridin-4-yloxy)phenylsulfinyl)phenyl)benzamide |

TABLE 6-continued

| ID # | Compound Name |
|---|---|
| 6-76 | 2-amino-N-(2-(6-amino-4-(4-methylpiperazin-1-yl)naphthalen-1-ylthio)pyrimidin-4-yl)acetamide |

Another embodiment of the present subject matter relates to compounds having the formula:

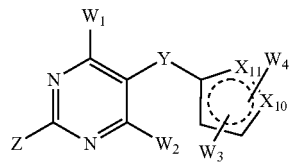

Formula 2b their stereoisomers, tautomers, and pharmaceutically acceptable salts thereof, wherein, $X_{10}$ and $X_{11}$ are independently selected from CH, $CH_2$, NH, NR', O, and S such that aromaticity is maintained, wherein R' is an alkyl or substituted alkyl chain;

Y is S, SO, $SO_2$, $CH_2$, CHR, CRR, CO, O, NH, or NR, wherein R is a lower alkyl or alkoxyl chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN;

$W_1$ and $W_2$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; and $W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_3$ and $W_4$ may be joined together via a linker, so as to form a fused 5- or 6-membered ring.

Furthermore, $W_2$ may be joined to the right side aryl ring directly to form a 5-membered ring or via a linker to form a 6 or 7-membered ring.

In preferred embodiments of formula (2b), $X_{10}$ and $X_{11}$ are independently selected from but not limited to:

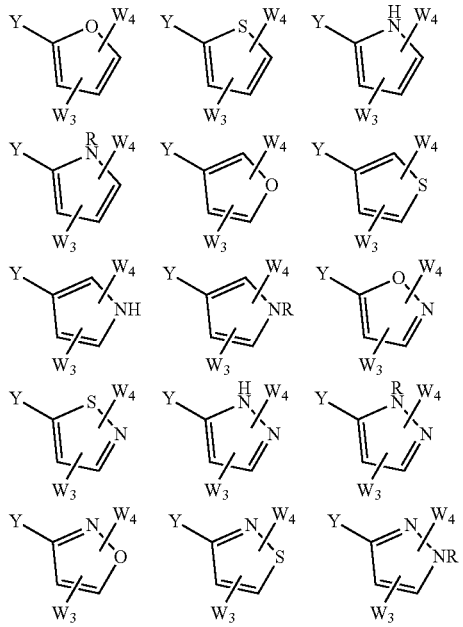

wherein R is an alkyl or substituted alkyl chain.

In preferred embodiments of formula (2b) Y is is S, SO, $SO_2$, O or CH2.

In preferred embodiments of formula (2b) Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (2b) $W_1$ and $W_2$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (2b) $W_3$ and $W_4$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In particular preferred embodiments of formula (2b), $X_{10}$ and $X_{11}$ are independently selected from;

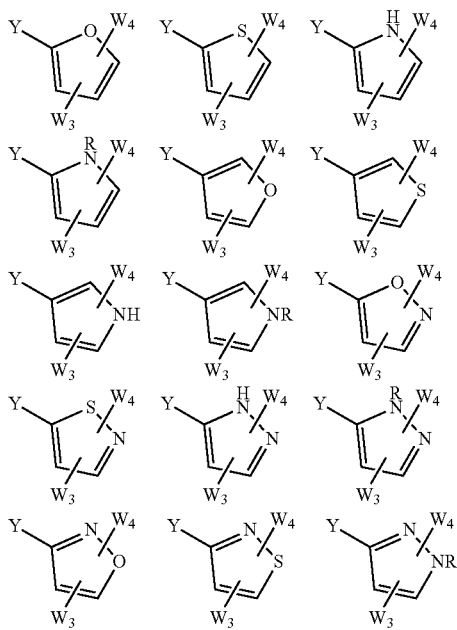

wherein R is an alkyl or substituted alkyl chain.

In particular preferred embodiments of formula (2b), Y is S, SO, or $SO_2$.

In particular preferred embodiments of formula (2b), Z is hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, or diarylamino.

In particular preferred embodiments of formula (2b), $W_1$ and $W_2$ are independently hydrogen, alkyl, alkenyl, alkynyl, aryl, alkoxy, amino, alkylamino, dialkylamino, cycloalkylamino, arylamino, or diarylamino.

In particular preferred embodiments of formula (2b), $W_3$ and $W_4$ are independently hydrogen, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN.

Table 7 show examples of specific compounds exemplifying this embodiment.

TABLE 7

| ID # | Compound Name |
|---|---|
| 7-01 | 4-(4-(3-(dimethylamino)phenyl)-2-(4-methylpiperazin-1-yl)pyrimidin-5-ylthio)-1H-pyrrol-3-ol |
| 7-02 | 4-(4-(3-(dimethylamino)phenyl)-5-(2-phenyl-1H-pyrrol-3-ylsulfonyl)pyrimidin-2-ylamino)cyclohexanol |
| 7-03 | (E)-4-(2-(ethylamino)-4-(prop-1-enyl)pyrimidin-5-ylthio)-1H-pyrrol-3-ol |
| 7-04 | 4-(2-methoxypyrimidin-5-ylthio)-1H-pyrrol-3-ol |
| 7-05 | 2-methoxy-5-(5-methoxy-4-methyl-1H-pyrrol-3-ylthio)-6-methylpyrimidin-4-amine |
| 7-06 | 4-(4-methoxy-5-(2-(methylthio)-1H-pyrrol-3-ylsulfonyl)pyrimidin-2-ylamino)cyclohexanol |
| 7-07 | 5-(1-methyl-1H-pyrrol-3-ylthio)-4-phenyl-2-(piperidin-1-yl)pyrimidine |
| 7-08 | 1-methyl-4-(4-phenyl-2-(pyridin-4-yl)pyrimidin-5-ylthio)-1H-pyrrol-3-amine |
| 7-09 | 4-(4-ethynyl-2-vinylpyrimidin-5-ylthio)-N,N,1-trimethyl-1H-pyrrol-3-amine |
| 7-10 | 5-(1-methyl-4-nitro-1H-pyrrol-3-ylthio)-2-phenoxy-4-phenylpyrimidine |
| 7-11 | N-(4-(2-ethoxy-4-(3-sulfamoylphenyl)pyrimidin-5-ylthio)-1-ethyl-1H-pyrrol-3-yl)acetamide |
| 7-12 | 4-(3,5-bis(trifluoromethyl)phenyl)-5-(1-methyl-4-(methylsulfonyl)-1H-pyrrol-3-ylthio)-2-(pyridin-4-yl)pyrimidine |
| 7-13 | 1-(2-(diethylamino)-5-(5-methylfuran-3-ylthio)pyrimidin-4-yl)ethanone |
| 7-14 | 1-(5-(4-(ethylamino)furan-3-ylthio)-2-(pyridin-3-yl)pyrimidin-4-yl)ethanone |
| 7-15 | 2-ethynyl-5-(5-(pyrrolidin-1-yl)furan-3-ylthio)pyrimidin-4-amine |
| 7-16 | 1-(5-(5-methylfuran-3-ylthio)-2-(phenylamino)pyrimidin-4-yl)ethanone |
| 7-17 | isopropyl 4-(4-acetyl-2-(1H-pyrrol-1-yl)pyrimidin-5-ylthio)furan-2-ylcarbamate |
| 7-18 | methyl 4-(4-(1H-pyrazol-3-yl)-2-(pyridin-3-yl)pyrimidin-5-ylthio)furan-2-carboxylate |
| 7-19 | 1-(3-(5-(5-chlorothiophen-3-ylthio)-2-(5,6-dihydropyridin-1(2H)-yl)pyrimidin-4-yl)phenyl)ethanone |
| 7-20 | N-(4-(4-(3-acetylphenyl)-2-(4-methylpiperazin-1-yl)pyrimidin-5-ylsulfinyl)thiophen-3-yl)acetamide |
| 7-21 | 1-(3-(5-(5-bromothiophen-3-ylthio)-2-(5,6-dihydropyridin-1(2H)-yl)pyrimidin-4-yl)phenyl)ethanone |
| 7-22 | 1-(3-(2-(5,6-dihydropyridin-1(2H)-yl)-5-(5-ethoxythiophen-3-ylthio)pyrimidin-4-yl)phenyl)ethanone |
| 7-23 | 4-(4-(3-acetylphenyl)-2-(4-methylpiperazin-1-yl)pyrimidin-5-ylthio)thiophene-3-sulfonamide |
| 7-24 | N-(4-(4-(cyclopentylamino)-6-methyl-2-(4-methylpiperazin-1-yl)pyrimidin-5-ylsulfinyl)thiophen-3-yl)acetamide |
| 7-25 | 5-(4-methoxy-2-(4-methylpiperazin-1-yl)pyrimidin-5-ylthio)-N-methyl-1H-pyrrole-3-carboxamide |

TABLE 7-continued

| ID # | Compound Name |
|---|---|
| 7-26 | 4-(benzyloxy)-5-(3-methoxy-1H-pyrrol-2-ylthio)-2-(4-methylpiperazin-1-yl)pyrimidine |
| 7-27 | 1-ethyl-5-(4-methoxy-2-(4-methylpiperazin-1-yl)pyrimidin-5-ylthio)-N-methyl-1H-pyrrole-3-carboxamide |
| 7-28 | 1-(5-(5-(hydroxymethyl)-1H-pyrrol-2-ylthio)-2-(4-methylpiperazin-1-yl)pyrimidin-4-yl)urea |
| 7-29 | 5-(4-methoxy-2-(4-methylpiperazin-1-yl)pyrimidin-5-ylthio)-N-methylfuran-3-carboxamide |
| 7-30 | 2-amino-N-(2-(4-methoxy-2-(4-methylpiperazin-1-yl)pyrimidin-5-ylthio)furan-3-yl)acetamide |
| 7-31 | 1-(5-(4-(cyclopropylamino)-2-(4-methylpiperazin-1-yl)pyrimidin-5-ylthio)furan-2-yl)ethanone |
| 7-32 | 2-amino-N-(2-(4-methoxy-6-methyl-2-(4-methylpiperazin-1-yl)pyrimidin-5-ylthio)thiophen-3-yl)propanamide |
| 7-33 | 5-(4-methoxy-2-(4-methylpiperazin-1-yl)pyrimidin-5-ylthio)-N-methyl-4-(trifluoromethoxy)thiophene-3-carboxamide |
| 7-34 | 5-methyl-3-(2-(pyridin-3-yl)pyrimidin-5-ylsulfinyl)isoxazole |
| 7-35 | 1-(3-(4-amino-2-(4-methylpiperazin-1-yl)pyrimidin-5-ylthio)isoxazol-4-yl)ethanone |
| 7-36 | 3-(4,6-dimethyl-2-(piperidin-1-yl)pyrimidin-5-ylthio)isothiazole |
| 7-37 | 4-(4-(benzyloxy)-5-(5-(furan-2-yl)isothiazol-3-ylthio)pyrimidin-2-yl)morpholine |
| 7-38 | 5-(4-methoxy-2-(4-methylpiperazin-1-yl)pyrimidin-5-ylthio)-N-methyl-1H-pyrazole-3-carboxamide |
| 7-39 | 4-(benzyloxy)-5-(4-methoxy-1H-pyrazol-5-ylthio)-2-(4-methylpiperazin-1-yl)pyrimidine |
| 7-40 | 1-ethyl-5-(4-methoxy-2-(4-methylpiperazin-1-yl)pyrimidin-5-ylthio)-N-methyl-1H-pyrazole-3-carboxamide |
| 7-41 | 2-(3-(4-ethyl-2-(4-methylpiperazin-1-yl)pyrimidin-5-ylthio)-1-methyl-1H-pyrazol-4-yloxy)ethanamine |
| 7-42 | 5-(4-methoxy-2-(4-methylpiperazin-1-yl)pyrimidin-5-ylthio)-N-methylisoxazole-3-carboxamide |
| 7-43 | 2-amino-N-(5-(4-methoxy-2-(4-methylpiperazin-1-yl)pyrimidin-5-ylthio)isoxazol-4-yl)acetamide |
| 7-44 | N-cyclopropyl-5-(isoxazol-5-ylthio)-2-(4-methylpiperazin-1-yl)pyrimidin-4-amine |
| 7-45 | 2-amino-N-(5-(4-methoxy-6-methyl-2-(4-methylpiperazin-1-yl)pyrimidin-5-ylthio)isothiazol-4-yl)propanamide |
| 7-46 | 5-(4-methoxy-2-(4-methylpiperazin-1-yl)pyrimidin-5-ylthio)-N-methyl-4-(trifluoromethoxy)isothiazole-3-carboxamide |

Another embodiment of the present subject matter relates to compounds having the formula:

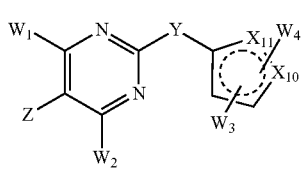

Formula 3b their stereoisomers, tautomers, and pharmaceutically acceptable salts thereof, wherein, $X_{10}$ and $X_{11}$ are independently selected from CH, $CH_2$, NH, NR', O, and S such that aromaticity is maintained, wherein R' is an alkyl or substituted alkyl chain;

Y is S, SO, $SO_2$, $CH_2$, CHR, CRR, CO, O, NH, or NR, wherein R is a lower alkyl or alkoxyl chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN;

$W_1$ and $W_2$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; and $W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_3$ and $W_4$ may be joined together via a linker, so as to form a fused 5- or 6-membered ring.

Furthermore, $W_2$ may be joined to the right side aryl ring directly to form a 5-membered ring or via a linker to form a 6 or 7-membered ring.

In preferred embodiments of formula (3b), $X_{10}$ and $X_{11}$ are independently selected from but not limited to:

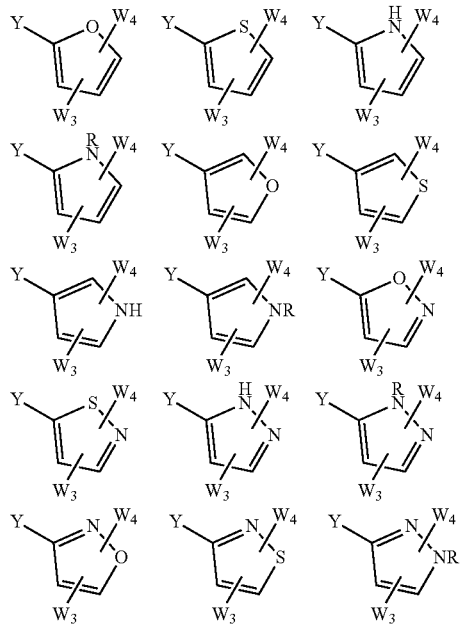

In particular preferred embodiments of formula (3b), $X_{10}$ and $X_{11}$ are independently selected from;

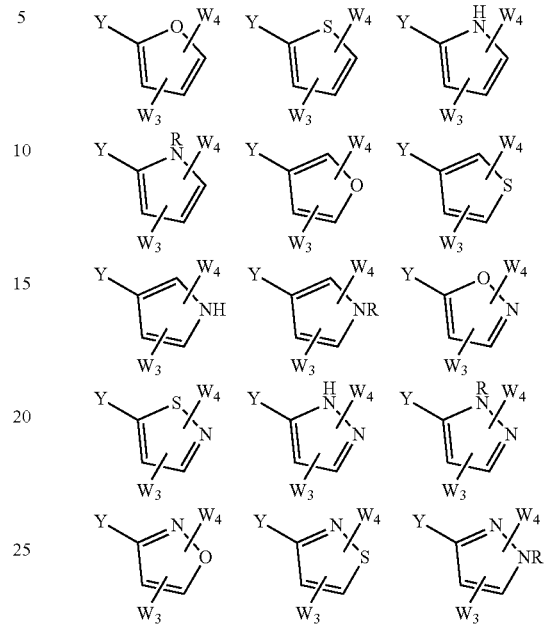

wherein R is an alkyl or substituted alkyl chain.

In preferred embodiments of formula (3b) Y is is S, SO, $SO_2$, O or CH2.

In preferred embodiments of formula (3b) Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (3b) $W_1$ and $W_2$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (3b) $W_3$ and $W_4$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

wherein R is an alkyl or substituted alkyl chain.

In particular preferred embodiments of formula (3b), Y is S, SO, or $SO_2$.

In particular preferred embodiments of formula (3b), Z is hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, or diarylamino.

In particular preferred embodiments of formula (3b), $W_1$ and $W_2$ are independently hydrogen, alkyl, alkenyl, alkynyl, aryl, alkoxy, amino, alkylamino, dialkylamino, cycloalkylamino, arylamino, or diarylamino.

In particular preferred embodiments of formula (3b), $W_3$ and $W_4$ are independently hydrogen, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN.

Table 8 show examples of specific compounds exemplifying this embodiment.

TABLE 8

| ID # | Compound Name |
|---|---|
| 8-01 | 4-(4-(4-(dimethylamino)phenyl)-5-(4-methylpiperazin-1-yl)pyrimidin-2-ylthio)-1H-pyrrol-3-ol |
| 8-02 | 3-(5-(4-hydroxycyclohexylamino)-2-(2-phenyl-1H-pyrrol-3-ylsulfonyl)pyrimidin-4-yl)benzimidamide |
| 8-03 | (E)-4-(5-(ethylamino)-4-(prop-1-enyl)pyrimidin-2-ylthio)-1H-pyrrol-3-ol |
| 8-04 | 4-(5-methoxypyrimidin-2-ylthio)-1H-pyrrol-3-ol |
| 8-05 | 5-methoxy-2-(5-methoxy-4-methyl-1H-pyrrol-3-ylthio)-6-methylpyrimidin-4-amine |

TABLE 8-continued

| ID # | Compound Name |
|---|---|
| 8-06 | 4-(4-methoxy-2-(2-(methylthio)-1H-pyrrol-3-ylsulfonyl)pyrimidin-5-ylamino)cyclohexanol |
| 8-07 | 2-(1-methyl-1H-pyrrol-3-ylthio)-4-phenyl-5-(piperidin-1-yl)pyrimidine |
| 8-08 | 1-methyl-4-(4-phenyl-5-(pyridin-4-yl)pyrimidin-2-ylthio)-1H-pyrrol-3-amine |
| 8-09 | 4-(4-ethynyl-5-vinylpyrimidin-2-ylthio)-N,N,1-trimethyl-1H-pyrrol-3-amine |
| 8-10 | 2-(1-methyl-4-nitro-1H-pyrrol-3-ylthio)-5-phenoxy-4-phenylpyrimidine |
| 8-11 | N-(4-(5-ethoxy-4-(3-sulfamoylphenyl)pyrimidin-2-ylthio)-1-ethyl-1H-pyrrol-3-yl)acetamide |
| 8-12 | 4-(3,5-bis(trifluoromethyl)phenyl)-2-(1-methyl-4-(methylsulfonyl)-1H-pyrrol-3-ylthio)-5-(pyridin-4-yl)pyrimidine |
| 8-13 | 1-(5-(diethylamino)-2-(5-methylfuran-3-ylthio)pyrimidin-4-yl)ethanone |
| 8-14 | 4-(4,5-di(pyridin-3-yl)-6-(pyrrolidin-1-yl)pyrimidin-2-ylthio)-N-ethylfuran-3-amine |
| 8-15 | 5-ethynyl-2-(5-(pyrrolidin-1-yl)furan-3-ylthio)pyrimidin-4-amine |
| 8-16 | 2-(5-methylfuran-3-ylthio)-N-phenyl-4-(thiophen-3-yl)pyrimidin-5-amine |
| 8-17 | isopropyl 4-(4-acetyl-5-(1H-pyrrol-1-yl)pyrimidin-2-ylthio)furan-2-ylcarbamate |
| 8-18 | methyl 4-(4-(1H-pyrazol-3-yl)-5-(pyridin-3-yl)pyrimidin-2-ylthio)furan-2-carboxylate |
| 8-19 | 1-(3-(2-(5-chlorothiophen-3-ylthio)-5-(5,6-dihydropyridin-1(2H)-yl)pyrimidin-4-yl)phenyl)ethanone |
| 8-20 | N-(4-(4-(2-(dimethylamino)ethoxy)-5-(4-methylpiperazin-1-yl)pyrimidin-2-ylsulfinyl)thiophen-3-yl)acetamide |
| 8-21 | 1-(3-(2-(5-bromothiophen-3-ylthio)-5-(5,6-dihydropyridin-1(2H)-yl)pyrimidin-4-yl)phenyl)ethanone |
| 8-22 | 5-(5,6-dihydropyridin-1(2H)-yl)-2-(5-ethoxythiophen-3-ylthio)-4-(furan-2-yl)pyrimidine |
| 8-23 | 4-(4-(cyclopentyloxy)-5-(4-methylpiperazin-1-yl)pyrimidin-2-ylthio)thiophene-3-sulfonamide |
| 8-24 | N-(4-(4-(cyclopentylamino)-6-methyl-5-(4-methylpiperazin-1-yl)pyrimidin-2-ylsulfinyl)thiophen-3-yl)acetamide |
| 8-25 | 5-(6-methoxy-5-(4-methylpiperazin-1-yl)pyrazin-2-ylthio)-N-methyl-1H-pyrrole-3-carboxamide |
| 8-26 | 3-(benzyloxy)-5-(3-methoxy-1H-pyrrol-2-ylthio)-2-(4-methylpiperazin-1-yl)pyrazine |
| 8-27 | 1-ethyl-5-(6-methoxy-5-(4-methylpiperazin-1-yl)pyrazin-2-ylthio)-N-methyl-1H-pyrrole-3-carboxamide |
| 8-28 | 1-(6-(5-(hydroxymethyl)-1H-pyrrol-2-ylthio)-3-(4-methylpiperazin-1-yl)pyrazin-2-yl)urea |
| 8-29 | 5-(6-methoxy-3-methyl-5-(4-methylpiperazin-1-yl)pyrazin-2-ylthio)-N-methylfuran-3-carboxamide |
| 8-30 | 2-amino-N-(2-(6-methoxy-5-(4-methylpiperazin-1-yl)pyrazin-2-ylthio)furan-3-yl)acetamide |
| 8-31 | 1-(5-(6-(cyclopropylamino)-5-(4-methylpiperazin-1-yl)pyrazin-2-ylthio)furan-2-yl)ethanone |
| 8-32 | 2-amino-N-(2-(6-methoxy-5-(4-methylpiperazin-1-yl)pyrazin-2-ylthio)thiophen-3-yl)propanamide |
| 8-33 | 5-(6-methoxy-5-(4-methylpiperazin-1-yl)pyrazin-2-ylthio)-N-methyl-4-(trifluoromethoxy)thiophene-3-carboxamide |
| 8-34 | 3-(6-methoxy-5-(pyridin-3-yl)pyrazin-2-ylsulfinyl)-5-methylisoxazole |
| 8-35 | 1-(3-(6-amino-5-(4-methylpiperazin-1-yl)pyrazin-2-ylthio)isoxazol-4-yl)ethanone |
| 8-36 | 3-(6-methyl-5-(piperidin-1-yl)pyrazin-2-ylthio)isothiazole |
| 8-37 | 4-(3-(benzyloxy)-5-(5-(furan-2-yl)isothiazol-3-ylthio)pyrazin-2-yl)morpholine |
| 8-38 | 5-(6-methoxy-5-(4-methylpiperazin-1-yl)pyrazin-2-ylthio)-N-methyl-1H-pyrazole-3-carboxamide |
| 8-39 | 3-(benzyloxy)-5-(4-methoxy-1H-pyrazol-5-ylthio)-2-(4-methylpiperazin-1-yl)pyrazine |
| 8-40 | 1-ethyl-5-(6-methoxy-5-(4-methylpiperazin-1-yl)pyrazin-2-ylthio)-N-methyl-1H-pyrazole-3-carboxamide |
| 8-41 | 2-(3-(6-ethyl-3-methyl-5-(4-methylpiperazin-1-yl)pyrazin-2-ylthio)-1-methyl-1H-pyrazol-4-yloxy)ethanamine |
| 8-42 | 5-(6-methoxy-5-(4-methylpiperazin-1-yl)pyrazin-2-ylthio)-N-methylisoxazole-3-carboxamide |
| 8-43 | 2-amino-N-(5-(6-methoxy-5-(4-methylpiperazin-1-yl)pyrazin-2-ylthio)isoxazol-4-yl)acetamide |
| 8-44 | N-cyclopropyl-6-(isoxazol-5-ylthio)-3-(4-methylpiperazin-1-yl)pyrazin-2-amine |
| 8-45 | 2-amino-N-(5-(6-methoxy-5-(4-methylpiperazin-1-yl)pyrazin-2-ylthio)isothiazol-4-yl)propanamide |
| 8-46 | 5-(6-methoxy-5-(4-methylpiperazin-1-yl)pyrazin-2-ylthio)-N-methyl-4-(trifluoromethoxy)isothiazole-3-carboxamide |

Another embodiment of the present subject matter relates to compounds having the formula:

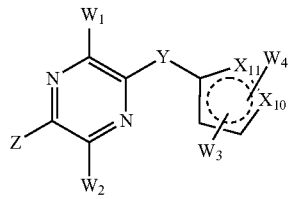

Formula 4b their stereoisomers, tautomers, and pharmaceutically acceptable salts thereof, wherein, $X_{10}$ and $X_{11}$ are independently selected from CH, $CH_2$, NH, NR', O, and S such that aromaticity is maintained, wherein R' is an alkyl or substituted alkyl chain;

Y is S, SO, $SO_2$, $CH_2$, CHR, CRR, CO, O, NH, or NR, wherein R is a lower alkyl or alkoxyl chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN;

$W_1$ and $W_2$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, SO2-alkyl, —COO-alkyl, —COalkyl, and alkyl-CN; and $W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_3$ and $W_4$ may be joined together via a linker, so as to form a fused 5- or 6-membered ring.

Furthermore, $W_2$ may be joined to the right side aryl ring directly to form a 5-membered ring or via a linker to form a 6 or 7-membered ring.

In preferred embodiments of formula (4b), $X_{10}$ and $X_{11}$ are independently selected from but not limited to:

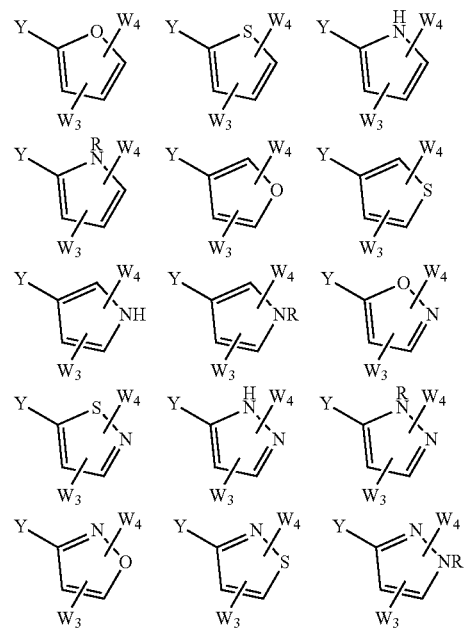

wherein R is an alkyl or substituted alkyl chain.

In preferred embodiments of formula (4b) Y is is S, SO, $SO_2$, O or CH2.

In preferred embodiments of formula (4b) Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (4b) $W_1$ and $W_2$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (4b) $W_3$ and $W_4$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In particular preferred embodiments of formula (4b), $X_{10}$ and $X_{11}$ are independently selected from;

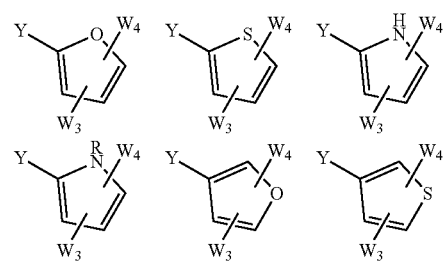

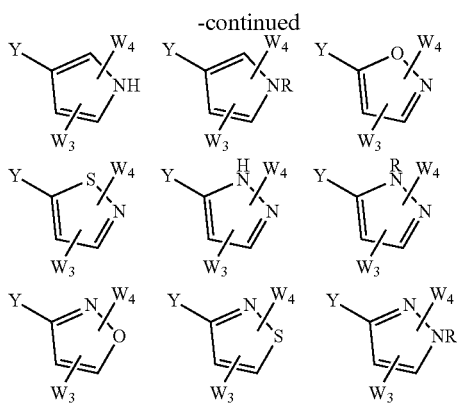

wherein R is an alkyl or substituted alkyl chain.

In particular preferred embodiments of formula (4b), Y is S, SO, or $SO_2$.

In particular preferred embodiments of formula (4b), Z is hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, or diarylamino.

In particular preferred embodiments of formula (4b), $W_1$ and $W_2$ are independently hydrogen, alkyl, alkenyl, alkynyl, aryl, alkoxy, amino, alkylamino, dialkylamino, cycloalkylamino, arylamino, or diarylamino.

In particular preferred embodiments of formula (4b), $W_3$ and $W_4$ are independently hydrogen, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN.

Table 9 show examples of specific compounds exemplifying this embodiment.

TABLE 9

| ID # | Compound Name |
|---|---|
| 9-01 | 4-(6-(4-(dimethylamino)phenyl)-5-(4-methylpiperazin-1-yl)pyrazin-2-ylthio)-1H-pyrrol-3-ol |
| 9-02 | 3-(3-(4-hydroxycyclohexylamino)-6-(2-phenyl-1H-pyrrol-3-ylsulfonyl)pyrazin-2-yl)benzimidamide |
| 9-03 | (E)-4-(5-(ethylamino)-6-(prop-1-enyl)pyrazin-2-ylthio)-1H-pyrrol-3-ol |
| 9-04 | 4-(5-methoxypyrazin-2-ylthio)-1H-pyrrol-3-ol |
| 9-05 | 3-methoxy-6-(5-methoxy-4-methyl-1H-pyrrol-3-ylthio)-5-methylpyrazin-2-amine |
| 9-06 | 4-(3-methoxy-5-(2-(methylthio)-1H-pyrrol-3-ylsulfonyl)pyrazin-2-ylamino)cyclohexanol |
| 9-07 | 4-(3-methoxy-5-(2-(methylthio)-1H-pyrrol-3-ylsulfonyl)pyrazin-2-ylamino)cyclohexanol |
| 9-08 | 1-methyl-4-(6-phenyl-5-(pyridin-4-yl)pyrazin-2-ylthio)-1H-pyrrol-3-amine |
| 9-09 | 4-(6-ethynyl-5-vinylpyrazin-2-ylthio)-N,N,1-trimethyl-1H-pyrrol-3-amine |
| 9-10 | 3-methyl-2-(1-methyl-4-nitro-1H-pyrrol-3-ylthio)-5-phenoxypyrazine |
| 9-11 | N-(4-(5-ethoxy-6-(3-sulfamoylphenyl)pyrazin-2-ylthio)-1-ethyl-1H-pyrrol-3-yl)acetamide |
| 9-12 | 3-(3,5-bis(trifluoromethyl)phenyl)-5-(1-methyl-4-(methylsulfonyl)-1H-pyrrol-3-ylthio)-2-(pyridin-4-yl)pyrazine |
| 9-13 | 1-(3-(diethylamino)-6-(5-methylfuran-3-ylthio)pyrazin-2-yl)ethanone |
| 9-14 | 3-(4-(ethylamino)furan-3-ylthio)-5,6-di(pyridin-3-yl)pyrazin-2-amine |
| 9-15 | 3-ethynyl-6-(5-(pyrrolidin-1-yl)furan-3-ylthio)pyrazin-2-amine |
| 9-16 | 5-(5-methylfuran-3-ylthio)-N-phenyl-3-(thiophen-3-yl)pyrazin-2-amine |
| 9-17 | isopropyl 4-(6-acetyl-5-(1H-pyrrol-1-yl)pyrazin-2-ylthio)furan-2-ylcarbamate |
| 9-18 | methyl 4-(6-(1H-pyrazol-3-yl)-5-(pyridin-3-yl)pyrazin-2-ylthio)furan-2-carboxylate |
| 9-19 | 1-(3-(6-(5-chlorothiophen-3-ylthio)-3-(5,6-dihydropyridin-1(2H)-yl)pyrazin-2-yl)phenyl)ethanone |
| 9-20 | N-(4-(6-(2-(dimethylamino)ethoxy)-5-(4-methylpiperazin-1-yl)pyrazin-2-ylsulfinyl)thiophen-3-yl)acetamide |
| 9-21 | 1-(3-(6-(5-bromothiophen-3-ylthio)-3-(5,6-dihydropyridin-1(2H)-yl)pyrazin-2-yl)phenyl)ethanone |
| 9-22 | 2-(5,6-dihydropyridin-1(2H)-yl)-5-(5-ethoxythiophen-3-ylthio)-3-(furan-2-yl)pyrazine |
| 9-23 | 4-(6-(cyclopentyloxy)-5-(4-methylpiperazin-1-yl)pyrazin-2-ylthio)thiophene-3-sulfonamide |
| 9-24 | N-(4-(6-(cyclopentylamino)-3-methyl-5-(4-methylpiperazin-1-yl)pyrazin-2-ylsulfinyl)thiophen-3-yl)acetamide |
| 9-25 | 5-(6-methoxy-5-(4-methylpiperazin-1-yl)pyrazin-2-ylthio)-N-methyl-1H-pyrrole-3-carboxamide |
| 9-26 | 3-(benzyloxy)-5-(3-methoxy-1H-pyrrol-2-ylthio)-2-(4-methylpiperazin-1-yl)pyrazine |
| 9-27 | 1-ethyl-5-(6-methoxy-5-(4-methylpiperazin-1-yl)pyrazin-2-ylthio)-N-methyl-1H-pyrrole-3-carboxamide |
| 9-28 | 1-(6-(5-(hydroxymethyl)-1H-pyrrol-2-ylthio)-3-(4-methylpiperazin-1-yl)pyrazin-2-yl)urea |
| 9-29 | 5-(6-methoxy-3-methyl-5-(4-methylpiperazin-1-yl)pyrazin-2-ylthio)-N-methylfuran-3-carboxainide |

TABLE 9-continued

| ID # | Compound Name |
| --- | --- |
| 9-30 | 2-amino-N-(2-(6-methoxy-5-(4-methylpiperazin-1-yl)pyrazin-2-ylthio)furan-3-yl)acetamide |
| 9-31 | 1-(5-(6-(cyclopropylamino)-5-(4-methylpiperazin-1-yl)pyrazin-2-ylthio)furan-2-yl)ethanone |
| 9-32 | 2-amino-N-(2-(6-methoxy-5-(4-methylpiperazin-1-yl)pyrazin-2-ylthio)thiophen-3-yl)propanamide |
| 9-33 | 5-(6-methoxy-5-(4-methylpiperazin-1-yl)pyrazin-2-ylthio)-N-methyl-4-(trifluoromethoxy)thiophene-3-carboxamide |
| 9-34 | 3-(6-methoxy-5-(pyridin-3-yl)pyrazin-2-ylsulfinyl)-5-methylisoxazole |
| 9-35 | 1-(3-(6-amino-5-(4-methylpiperazin-1-yl)pyrazin-2-ylthio)isoxazol-4-yl)ethanone |
| 9-36 | 3-(6-methyl-5-(piperidin-1-yl)pyrazin-2-ylthio)isothiazole |
| 9-37 | 4-(3-(benzyloxy)-5-(5-(furan-2-yl)isothiazol-3-ylthio)pyrazin-2-yl)morpholine |
| 9-38 | 5-(6-methoxy-5-(4-methylpiperazin-1-yl)pyrazin-2-ylthio)-N-methyl-1H-pyrazole-3-carboxamide |
| 9-39 | 3-(benzyloxy)-5-(4-methoxy-1H-pyrazol-5-ylthio)-2-(4-methylpiperazin-1-yl)pyrazine |
| 9-40 | 1-ethyl-5-(6-methoxy-5-(4-methylpiperazin-1-yl)pyrazin-2-ylthio)-N-methyl-1H-pyrazole-3-carboxamide |
| 9-41 | 2-(3-(6-ethyl-3-methyl-5-(4-methylpiperazin-1-yl)pyrazin-2-ylthio)-1-methyl-1H-pyrazol-4-yloxy)ethanamine |
| 9-42 | 5-(6-methoxy-5-(4-methylpiperazin-1-yl)pyrazin-2-ylthio)-N-methylisoxazole-3-carboxamide |
| 9-43 | 2-amino-N-(5-(6-methoxy-5-(4-methylpiperazin-1-yl)pyrazin-2-ylthio)isoxazol-4-yl)acetamide |
| 9-44 | N-cyclopropyl-6-(isoxazol-5-ylthio)-3-(4-methylpiperazin-1-yl)pyrazin-2-amine |
| 9-45 | 2-amino-N-(5-(6-methoxy-5-(4-methylpiperazin-1-yl)pyrazin-2-ylthio)isothiazol-4-yl)propanamide |
| 9-46 | 5-(6-methoxy-5-(4-methylpiperazin-1-yl)pyrazin-2-ylthio)-N-methyl-4-(trifluoromethoxy)isothiazole-3-carboxamide |

Another embodiment of the present subject matter relates to compounds having the formula:

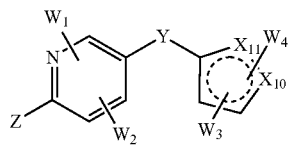

Formula 5b their stereoisomers, tautomers, and pharmaceutically acceptable salts thereof, wherein, $X_{10}$ and $X_{11}$ are independently selected from CH, $CH_2$, NH, NR', O, and S such that aromaticity is maintained, wherein R' is an alkyl or substituted alkyl chain;

Y is S, SO, $SO_2$, $CH_2$, CHR, CRR, CO, O, NH, or NR, wherein R is a lower alkyl or alkoxyl chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN;

$W_1$ and $W_2$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_1$ and $W_2$ may be joined together via a linker, so as to form a fused 5- or 6-membered ring; and $W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_3$ and $W_4$ may be joined together via a linker, so as to form a fused 5- or 6-membered ring.

Furthermore, $W_2$ may be joined to the right side aryl ring directly to form a 5-membered ring or via a linker to form a 6 or 7-membered ring.

In preferred embodiments of formula (5b), $X_{10}$ and $X_{11}$ are independently selected from but not limited to:

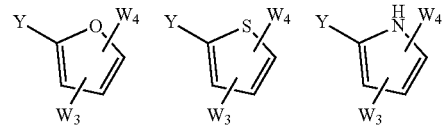

-continued

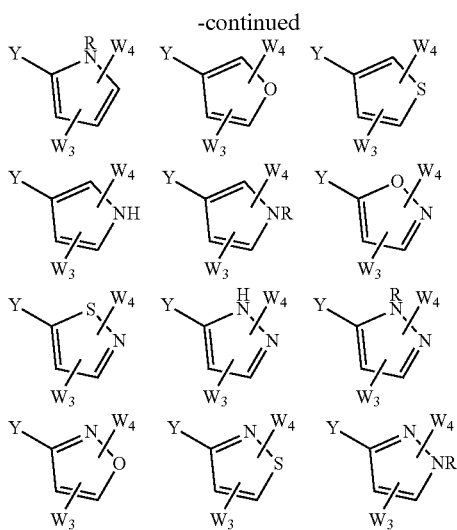

wherein R is an alkyl or substituted alkyl chain.

In preferred embodiments of formula (5b) Y is is S, SO, $SO_2$, O or CH2.

In preferred embodiments of formula (5b) Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (5b) $W_1$ and $W_2$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (5b) $W_3$ and $W_4$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In particular preferred embodiments of formula (5b), $X_{10}$ and $X_{11}$ are independently selected from;

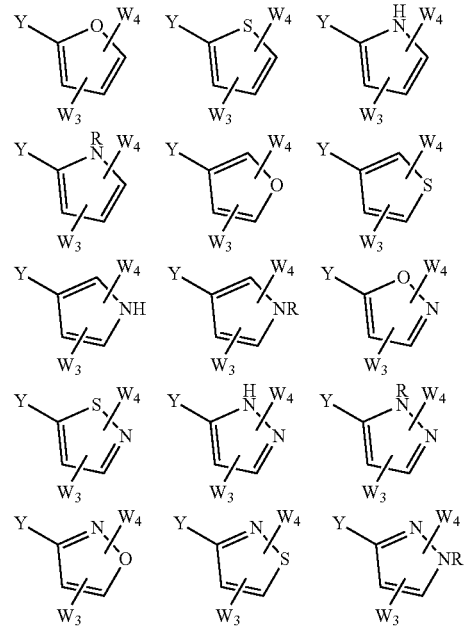

wherein R is an alkyl or substituted alkyl chain.

In particular preferred embodiments of formula (5b), Y is S, SO, or $SO_2$.

In particular preferred embodiments of formula (5b), Z is hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, or diarylamino.

In particular preferred embodiments of formula (5b), $W_1$ and $W_2$ are independently hydrogen, alkyl, alkenyl, alkynyl, aryl, alkoxy, amino, alkylamino, dialkylamino, cycloalkylamino, arylamino, or diarylamino.

In particular preferred embodiments of formula (5b), $W_3$ and $W_4$ are independently hydrogen, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COOalkyl, —COalkyl, and alkyl-CN.

Table 10 show examples of specific compounds exemplifying this embodiment.

TABLE 10

| ID # | Compound Name |
|---|---|
| 10-01 | 4-(5-(4-(dimethylamino)phenyl)-6-(4-methylpiperazin-1-yl)pyridin-3-ylthio)-1H-pyrrol-3-ol |
| 10-02 | 3-(2-(4-hydroxycyclohexylamino)-5-(2-phenyl-1H-pyrrol-3-ylsulfonyl)pyridin-3-yl)benzimidamide |
| 10-03 | (E)-4-(6-(ethylamino)-5-(prop-1-enyl)pyridin-3-ylthio)-1H-pyrrol-3-ol |
| 10-04 | 4-(6-methoxypyridin-3-ylthio)-1H-pyrrol-3-ol |
| 10-05 | 2-methoxy-5-(5-methoxy-4-methyl-1H-pyrrol-3-ylthio)-6-methylpyridin-3-amine |
| 10-06 | 4-(3-methoxy-5-(2-(methylthio)-1H-pyrrol-3-ylsulfonyl)pyridin-2-ylamino)cyclohexanol |
| 10-07 | 5-(1-methyl-1H-pyrrol-3-ylthio)-3-phenyl-2-(piperidin-1-yl)pyridine |
| 10-08 | 1-methyl-4-(3-phenyl-2,4'-bipyridin-5-ylthio)-1H-pyrrol-3-amine |
| 10-09 | 4-(5-ethynyl-6-vinylpyridin-3-ylthio)-N,N,1-trimethyl-1H-pyrrol-3-amine |
| 10-10 | 2-methyl-3-(1-methyl-4-nitro-1H-pyrrol-3-ylthio)-6-phenoxypyridine |

TABLE 10-continued

| ID # | Compound Name |
|---|---|
| 10-11 | N-(4-(6-ethoxy-5-(3-sulfamoylphenyl)pyridin-3-ylthio)-1-ethyl-1H-pyrrol-3-yl)acetamide |
| 10-12 | 3-(3,5-bis(trifluoromethyl)phenyl)-5-(1-methyl-4-(methylsulfonyl)-1H-pyrrol-3-ylthio)-2,4'-bipyridine |
| 10-13 | 1-(2-(diethylamino)-5-(5-methylfuran-3-ylthio)pyridin-3-yl)ethanone |
| 10-14 | A name could not be generated for this structure. |
| 10-15 | 2-ethynyl-5-(5-(pyrrolidin-1-yl)furan-3-ylthio)pyridin-3-amine |
| 10-16 | 5-(5-methylfuran-3-ylthio)-N-phenyl-3-(thiophen-3-yl)pyridin-2-amine |
| 10-17 | isopropyl 4-(5-acetyl-6-(1H-pyrrol-1-yl)pyridin-3-ylthio)furan-2-ylcarbamate |
| 10-18 | methyl 4-(3-(1H-pyrazol-3-yl)-2,3'-bipyridin-5-ylthio)furan-2-carboxylate |
| 10-19 | 1-(3-(5-(5-chlorothiophen-3-ylthio)-2-(5,6-dihydropyridin-1(2H)-yl)pyridin-3-yl)phenyl)ethanone |
| 10-20 | N-(4-(5-(2-(dimethylamino)ethoxy)-6-(4-methylpiperazin-1-yl)pyridin-3-ylsulfinyl)thiophen-3-yl)acetamide |
| 10-21 | 1-(3-(5-(5-bromothiophen-3-ylthio)-2-(5,6-dihydropyridin-1(2H)-yl)pyridin-3-yl)phenyl)ethanone |
| 10-22 | 2-(5,6-dihydropyridin-1(2H)-yl)-5-(5-ethoxythiophen-3-ylthio)-3-(furan-2-yl)pyridine |
| 10-23 | 4-(5-(cyclopentyloxy)-6-(4-methylpiperazin-1-yl)pyridin-3-ylthio)thiophene-3-sulfonamide |
| 10-24 | N-(4-(5-(cyclopentylamino)-2-methyl-6-(4-methylpiperazin-1-yl)pyridin-3-ylsulfinyl)thiophen-3-yl)acetamide |
| 10-25 | 5-(5-methoxy-6-(4-methylpiperazin-1-yl)pyridin-3-ylthio)-N-methyl-1H-pyrrole-3-carboxamide |
| 10-26 | 1-(3-(benzyloxy)-5-(3-methoxy-1H-pyrrol-2-ylthio)pyridin-2-yl)-4-methylpiperazine |
| 10-27 | 1-ethyl-5-(5-methoxy-6-(4-methylpiperazin-1-yl)pyridin-3-ylthio)-N-methyl-1H-pyrrole-3-carboxamide |
| 10-28 | 1-(5-(5-(hydroxymethyl)-1H-pyrrol-2-ylthio)-2-(4-methylpiperazin-1-yl)pyridin-3-yl)urea |
| 10-29 | 5-(5-methoxy-2-methyl-6-(4-methylpiperazin-1-yl)pyridin-3-ylthio)-N-methylfuran-3-carboxamide |
| 10-30 | 2-amino-N-(2-(5-methoxy-6-(4-methylpiperazin-1-yl)pyridin-3-ylthio)furan-3-yl)acetamide |
| 10-31 | 1-(5-(5-(cyclopropylamino)-6-(4-methylpiperazin-1-yl)pyridin-3-ylthio)furan-2-yl)ethanone |
| 10-32 | 2-amino-N-(2-(5-methoxy-6-(4-methylpiperazin-1-yl)pyridin-3-ylthio)thiophen-3-yl)propanamide |
| 10-33 | 5-(5-methoxy-6-(4-methylpiperazin-1-yl)pyridin-3-ylthio)-N-methyl-4-(trifluoromethoxy)thiophene-3-carboxamide |
| 10-34 | 4-(3-(benzyloxy)-5-(5-(furan-2-yl)isothiazol-3-ylthio)pyridin-2-yl)morpholine |
| 10-35 | 5-(5-methoxy-6-(4-methylpiperazin-1-yl)pyridin-3-ylthio)-N-methyl-1H-pyrazole-3-carboxamide |
| 10-36 | 1-(3-(benzyloxy)-5-(4-methoxy-1H-pyrazol-5-ylthio)pyridin-2-yl)-4-methylpiperazine |
| 10-37 | 1-ethyl-5-(5-methoxy-6-(4-methylpiperazin-1-yl)pyridin-3-ylthio)-N-methyl-1H-pyrazole-3-carboxamide |
| 10-38 | 2-(3-(5-ethyl-2-methyl-6-(4-methylpiperazin-1-yl)pyridin-3-ylthio)-1-methyl-1H-pyrazol-4-yloxy)ethanamine |
| 10-39 | 5-(5-methoxy-6-(4-methylpiperazin-1-yl)pyridin-3-ylthio)-N-methylisoxazole-3-carboxamide |
| 10-40 | 2-amino-N-(5-(5-methoxy-6-(4-methylpiperazin-1-yl)pyridin-3-ylthio)isoxazol-4-yl)acetamide |
| 10-41 | N-cyclopropyl-5-(isoxazol-5-ylthio)-2-(4-methylpiperazin-1-yl)pyridin-3-amine |
| 10-42 | 2-amino-N-(5-(5-methoxy-6-(4-methylpiperazin-1-yl)pyridin-3-ylthio)isothiazol-4-yl)propanamide |
| 10-43 | 2-amino-N-(5-(5-methoxy-6-(4-methylpiperazin-1-yl)pyridin-3-ylthio)isoxazol-4-yl)acetamide |
| 10-44 | N-cyclopropyl-5-(isoxazol-5-ylthio)-2-(4-methylpiperazin-1-yl)pyridin-3-amine |
| 10-45 | 2-amino-N-(5-(5-methoxy-6-(4-methylpiperazin-1-yl)pyridin-3-ylthio)isothiazol-4-yl)propanamide |
| 10-46 | 5-(5-methoxy-6-(4-methylpiperazin-1-yl)pyridin-3-ylthio)-N-methyl-4-(trifluoromethoxy)isothiazole-3-carboxamide |

Another embodiment of the present subject matter relates to compounds having the formula:

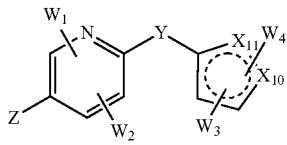

Formula 6b their stereoisomers, tautomers, and pharmaceutically acceptable salts thereof, wherein, $X_{10}$ and $X_{11}$ are independently selected from CH, $CH_2$, NH, NR', O, and S such that aromaticity is maintained, wherein R' is an alkyl or substituted alkyl chain;

Y is S, SO, $SO_2$, $CH_2$, CHR, CRR, CO, O, NH, or NR, wherein R is a lower alkyl or alkoxy chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN;

$W_1$ and $W_2$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_1$ and $W_2$ may be joined together via a linker, so as to form a fused 5- or 6-membered ring; and $W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_3$ and $W_4$ may be joined together via a linker, so as to form a fused 5- or 6-membered ring.

Furthermore, $W_2$ may be joined to the right side aryl ring directly to form a 5-membered ring or via a linker to form a 6 or 7-membered ring.

In preferred embodiments of formula (6b), $X_{10}$ and $X_{11}$ are independently selected from but not limited to:

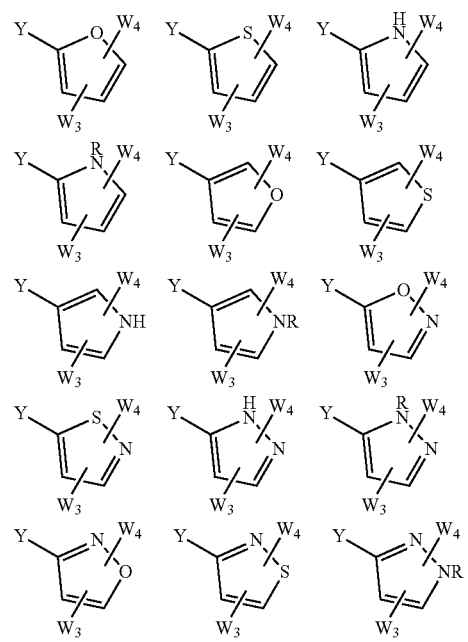

wherein R is an alkyl or substituted alkyl chain.

In preferred embodiments of formula (6b) Y is is S, SO, $SO_2$, O or CH2.

In preferred embodiments of formula (6b) Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamino.

In preferred embodiments of formula (6b) $W_1$ and $W_2$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (6b) $W_3$ and $W_4$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In particular preferred embodiments of formula (6b), $X_{10}$ and $X_{11}$ are independently selected from;

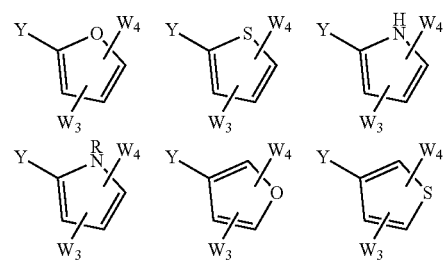

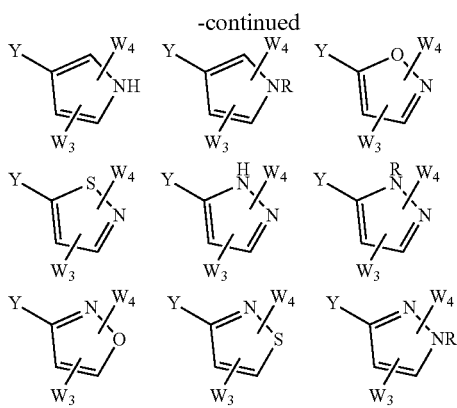

wherein R is an alkyl or substituted alkyl chain.

In particular preferred embodiments of formula (6b), Y is S, SO, or SO$_2$.

In particular preferred embodiments of formula (6b), Z is hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, or diarylamino.

In particular preferred embodiments of formula (6b), W$_1$ and W$_2$ are independently hydrogen, alkyl, alkenyl, alkynyl, aryl, alkoxy, amino, alkylamino, dialkylamino, cycloalkylamino, arylamino, or diarylamino.

In particular preferred embodiments of formula (6b), W$_3$ and W$_4$ are independently hydrogen, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, SO$_2$-alkyl, —COO-alkyl, —COalkyl, and alkyl-CN.

Table 11 show examples of specific compounds exemplifying this embodiment.

TABLE 11

| ID # | Compound Name |
|---|---|
| 11-01 | 4-(4-(4-(dimethylamino)phenyl)-5-(4-methylpiperazin-1-yl)pyridin-2-ylthio)-1H-pyrrol-3-ol |
| 11-02 | 3-(5-(4-hydroxycyclohexylamino)-2-(2-phenyl-1H-pyrrol-3-ylsulfonyl)pyridin-4-yl)benzimidamide |
| 11-03 | (E)-4-(5-(ethylamino)-4-(prop-1-enyl)pyridin-2-ylthio)-1H-pyrrol-3-ol |
| 11-04 | 4-(5-methoxypyridin-2-ylthio)-1H-pyrrol-3-ol |
| 11-05 | 3-methoxy-6-(5-methoxy-4-methyl-1H-pyrrol-3-ylthio)-2-methylpyridin-4-amine |
| 11-06 | 4-(4-methoxy-6-(2-(methylthio)-1H-pyrrol-3-ylsulfonyl)pyridin-3-ylamino)cyclohexanol |
| 11-07 | 2-(1-methyl-1H-pyrrol-3-ylthio)-4-phenyl-5-(piperidin-1-yl)pyridine |
| 11-08 | 1-methyl-4-(4-phenyl-3,4'-bipyridin-6-ylthio)-1H-pyrrol-3-amine |
| 11-09 | 4-(4-ethynyl-5-vinylpyridin-2-ylthio)-N,N,1-trimethyl-1H-pyrrol-3-amine |
| 11-10 | 6-(1-methyl-4-nitro-1H-pyrrol-3-ylthio)-3-phenoxy-2-phenylpyridine |
| 11-11 | N-(4-(5-ethoxy-6-(3-sulfamoylphenyl)pyridin-2-ylthio)-1-ethyl-1H-pyrrol-3-yl)acetamide |
| 11-12 | 4-(3,5-bis(trifluoromethyl)phenyl)-6-(1-methyl-4-(methylsulfonyl)-1H-pyrrol-3-ylthio)-3,4'-bipyridine |
| 11-13 | 1-(5-(diethylamino)-2-(5-methylfuran-3-ylthio)pyridin-4-yl)ethanone |
| 11-14 | 4-(3,3'-bipyridin-6-ylthio)-N-ethylfuran-3-amine |
| 11-15 | 5-ethynyl-2-(5-(pyrrolidin-1-yl)furan-3-ylthio)pyridin-4-amine |
| 11-16 | 6-(5-methylfuran-3-ylthio)-N-phenyl-4-(thiophen-3-yl)pyridin-3-amine |
| 11-17 | isopropyl 4-(4-acetyl-5-(1H-pyrrol-1-yl)pyridin-2-ylthio)furan-2-ylcarbamate |
| 11-18 | methyl 4-(4-(1H-pyrazol-3-yl)-3,3'-bipyridin-6-ylthio)furan-2-carboxylate |
| 11-19 | 1-(3-(2-(5-chlorothiophen-3-ylthio)-5-(5,6-dihydropyridin-1(2H)-yl)pyridin-4-yl)phenyl)ethanone |
| 11-20 | N-(4-(4-(2-(dimethylamino)ethoxy)-5-(4-methylpiperazin-1-yl)pyridin-2-ylsulfinyl)thiophen-3-yl)acetamide |
| 11-21 | 1-(3-(2-(5-bromothiophen-3-ylthio)-5-(5,6-dihydropyridin-1(2H)-yl)pyridin-4-yl)phenyl)ethanone |
| 11-22 | 5-(5,6-dihydropyridin-1(2H)-yl)-2-(5-ethoxythiophen-3-ylthio)-4-(furan-2-yl)pyridine |
| 11-23 | 4-(4-(cyclopentyloxy)-5-(4-methylpiperazin-1-yl)pyridin-2-ylthio)thiophene-3-sulfonamide |
| 11-24 | N-(4-(4-(cyclopentylamino)-6-methyl-5-(4-methylpiperazin-1-yl)pyridin-2-ylsulfinyl)thiophen-3-yl)acetamide |
| 11-25 | 5-(4-methoxy-5-(4-methylpiperazin-1-yl)pyridin-2-ylthio)-N-methyl-1H-pyrrole-3-carboxamide |
| 11-26 | 1-(4-(benzyloxy)-6-(3-methoxy-1H-pyrrol-2-ylthio)pyridin-3-yl)-4-methylpiperazine |
| 11-27 | 1-ethyl-5-(4-methoxy-5-(4-methylpiperazin-1-yl)pyridin-2-ylthio)-N-methyl-1H-pyrrole-3-carboxamide |
| 11-28 | 1-(2-(5-(hydroxymethyl)-1H-pyrrol-2-ylthio)-5-(4-methylpiperazin-1-yl)pyridin-4-yl)urea |
| 11-29 | 5-(4-methoxy-5-(4-methylpiperazin-1-yl)pyridin-2-ylthio)-N-methylfuran-3-carboxamide |
| 11-30 | 2-amino-N-(2-(4-methoxy-5-(4-methylpiperazin-1-yl)pyridin-2-ylthio)furan-3-yl)acetamide |
| 11-31 | 1-(5-(4-(cyclopropylamino)-5-(4-methylpiperazin-1-yl)pyridin-2-ylthio)furan-2-yl)ethanone |

TABLE 11-continued

| ID # | Compound Name |
|---|---|
| 11-32 | 2-amino-N-(2-(4-methoxy-6-methyl-5-(4-methylpiperazin-1-yl)pyridin-2-ylthio)thiophen-3-yl)propanamide |
| 11-33 | 5-(4-methoxy-5-(4-methylpiperazin-1-yl)pyridin-2-ylthio)-N-methyl-4-(trifluoromethoxy)thiophene-3-carboxamide |
| 11-34 | 3-(4-methoxy-3,3'-bipyridin-6-ylsulfinyl)-5-methylisoxazole |
| 11-35 | 1-(3-(4-amino-5-(4-methylpiperazin-1-yl)pyridin-2-ylthio)isoxazol-4-yl)ethanone |
| 11-36 | 3-(4,6-dimethyl-5-(piperidin-1-yl)pyridin-2-ylthio)isothiazole |
| 11-37 | 4-(4-(benzyloxy)-6-(5-(furan-2-yl)isothiazol-3-ylthio)pyridin-3-yl)morpholine |
| 11-38 | 5-(4-methoxy-5-(4-methylpiperazin-1-yl)pyridin-2-ylthio)-N-methyl-1H-pyrazole-3-carboxamide |
| 11-39 | 1-(4-(benzyloxy)-6-(4-methoxy-1H-pyrazol-5-ylthio)pyridin-3-yl)-4-methylpiperazine |
| 11-40 | 1-ethyl-5-(4-methoxy-5-(4-methylpiperazin-1-yl)pyridin-2-ylthio)-N-methyl-1H-pyrazole-3-carboxamide |
| 11-41 | 2-(3-(4-ethyl-5-(4-methylpiperazin-1-yl)pyridin-2-ylthio)-1-methyl-1H-pyrazol-4-yloxy)ethanamine |
| 11-42 | 5-(4-methoxy-5-(4-methylpiperazin-1-yl)pyridin-2-ylthio)-N-methylisoxazole-3-carboxamide |
| 11-43 | 2-amino-N-(5-(4-methoxy-5-(4-methylpiperazin-1-yl)pyridin-2-ylthio)isoxazol-4-yl)acetamide |
| 11-44 | N-cyclopropyl-2-(isoxazol-5-ylthio)-5-(4-methylpiperazin-1-yl)pyridin-4-amine |
| 11-45 | 2-amino-N-(5-(4-methoxy-6-methyl-5-(4-methylpiperazin-1-yl)pyridin-2-ylthio)isothiazol-4-yl)propanamide |
| 11-46 | 5-(4-methoxy-5-(4-methylpiperazin-1-yl)pyridin-2-ylthio)-N-methyl-4-(trifluoromethoxy)isothiazole-3-carboxamide |

Another embodiment of the present subject matter relates to compounds having the formula:

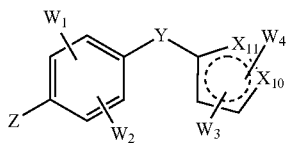

Formula 7b their stereoisomers, tautomers, and pharmaceutically acceptable salts thereof, wherein, $X_{10}$ and $X_{11}$ are independently selected from CH, $CH_2$, NH, NR', O, and S such that aromaticity is maintained, wherein R' is an alkyl or substituted alkyl chain;

Y is S, SO, $SO_2$, $CH_2$, CHR, CRR, CO, O, NH, or NR, wherein R is a lower alkyl or alkoxyl chain;

Z is selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN;

$W_1$ and $W_2$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_1$ and $W_2$ may be joined together via a linker, so as to form a fused 5- or 6-membered ring; and $W_3$ and $W_4$ independently at each occurrence can be selected from the group consisting of hydrogen, alkyl, alkenyl, alkynyl, aryl, saturated or unsaturated cycloalkyl, saturated or unsaturated heterocycle, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN; or $W_3$ and $W_4$ may be joined together via a linker, so as to form a fused 5- or 6-membered ring.

Furthermore, $W_2$ may be joined to the right side aryl ring directly to form a 5-membered ring or via a linker to form a 6 or 7-membered ring.

In preferred embodiments of formula (7b), $X_{10}$ and $X_{11}$ are independently selected from but not limited to:

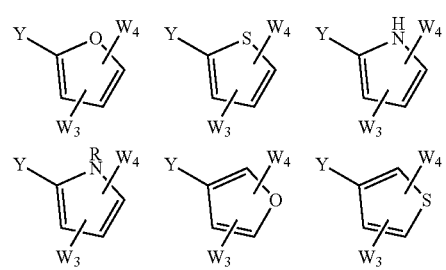

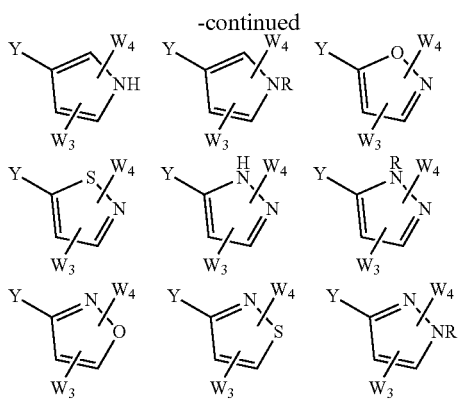

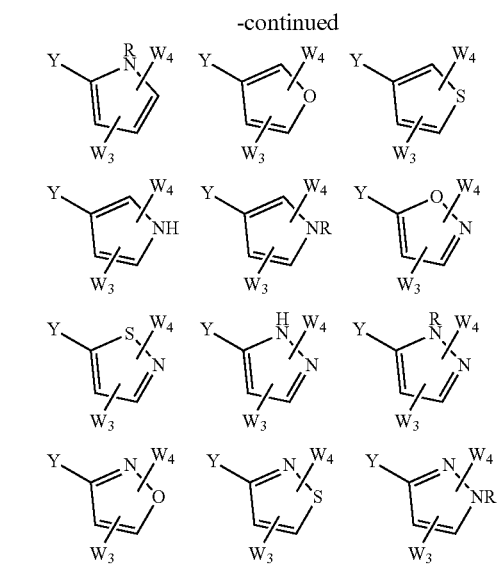

wherein R is an alkyl or substituted alkyl chain.

In preferred embodiments of formula (7b) Y is is S, SO, $SO_2$, O or CH2.

In preferred embodiments of formula (7b) Z is alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (7b) $W_1$ and $W_2$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In preferred embodiments of formula (7b) $W_3$ and $W_4$ at each occurrence are independently selected from the group consisting of hydrogen, alkyl, aryl, saturated or unsaturated cycloalkyl, saturated or unsaturated heterocycle, halogen, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, and dialkylamido.

In particular preferred embodiments of formula (7b), $X_{10}$ and $X_{11}$ are independently selected from;

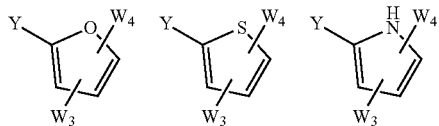

wherein R is an alkyl or substituted alkyl chain.

In particular preferred embodiments of formula (7b), Y is S, SO, or $SO_2$.

In particular preferred embodiments of formula (7b), Z is hydrogen, alkyl, alkenyl, alkynyl, aryl, saturated or unsaturated cycloalkyl, saturated or unsaturated heterocycle, halogen, hydroxyl, alkoxy, alkylamino, dialkyl amino, cycloalkylamino, arylamino, or diarylamino.

In particular preferred embodiments of formula (7b), $W_1$ and $W_2$ are independently hydrogen, alkyl, alkenyl, alkynyl, aryl, alkoxy, amino, alkylamino, dialkylamino, cycloalkylamino, arylamino, or diarylamino.

In particular preferred embodiments of formula (7b), $W_3$ and $W_4$ are independently hydrogen, halogen, hydroxyl, nitro, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, substituted and unsubstituted amido, alkylamido, alkylsulfonamido, sufonamido, —NHSO2alkenyl, —NHCOalkenyl, —NHCOalkynyl, —COalkenyl, —COalkynyl, trihalocarbon, thioalkyl, $SO_2$-alkyl, —COO-alkyl, —COalkyl, and alkyl-CN.

Table 12 show examples of specific compounds exemplifying this embodiment.

TABLE 12

| ID # | Compound Name |
|---|---|
| 12-01 | 4-(4'-(dimethylamino)-6-(4-methylpiperazin-1-yl)biphenyl-3-ylthio)-1H-pyrrol-3-ol |
| 12-02 | 2'-(4-hydroxycyclohexylamino)-5'-(2-phenyl-1H-pyrrol-3-ylsulfonyl)biphenyl-3-carboximidamide |
| 12-03 | (E)-4-(4-(ethylamino)-3-(prop-1-enyl)phenylthio)-1H-pyrrol-3-ol |
| 12-04 | 4-(4-methoxyphenylthio)-1H-pyrrol-3-ol |
| 12-05 | 2-methoxy-5-(5-methoxy-4-methyl-1H-pyrrol-3-ylthio)-3-methylaniline |
| 12-06 | 4-(2-methoxy-4-(2-(methylthio)-1H-pyrrol-3-ylsulfonyl)phenylamino)cyclohexanol |
| 12-07 | 1-(5-(1-methyl-1H-pyrrol-3-ylthio)biphenyl-2-yl)piperidine |
| 12-08 | 1-methyl-4-(6-(pyridin-4-yl)biphenyl-3-ylthio)-1H-pyrrol-3-amine |
| 12-09 | 4-(3-ethynyl-4-vinylphenylthio)-N,N,1-trimethyl-1H-pyrrol-3-amine |
| 12-10 | 1-methyl-3-nitro-4-(6-phenoxybiphenyl-3-ylthio)-1H-pyrrole |

TABLE 12-continued

| ID # | Compound Name |
|---|---|
| 12-11 | N-(4-(6-ethoxy-3'-sulfamoylbiphenyl-3-ylthio)-1-ethyl-1H-pyrrol-3-yl)acetamide |
| 12-12 | 4-(5-(1-methyl-4-(methylsulfonyl)-1H-pyrrol-3-ylthio)-3',5'-bis(trifluoromethyl)biphenyl-2-yl)pyridine |
| 12-13 | 1-(2-(diethylamino)-5-(5-methylfuran-3-ylthio)phenyl)ethanone |
| 12-14 | 4-(3,4-di(pyridin-3-yl)-5-(pyrrolidin-1-yl)phenylthio)-N-ethylfuran-3-amine |
| 12-15 | 2-ethynyl-5-(5-(pyrrolidin-1-yl)furan-3-ylthio)aniline |
| 12-16 | 4-(5-methylfuran-3-ylthio)-N-phenyl-2-(thiophen-3-yl)aniline |
| 12-17 | isopropyl 4-(3-acetyl-4-(1H-pyrrol-1-yl)phenylthio)furan-2-ylcarbamate |
| 12-18 | methyl 4-(3-(1H-pyrazol-3-yl)-4-(pyridin-3-yl)phenylthio)furan-2-carboxylate |
| 12-19 | 1-(5'-(5-chlorothiophen-3-ylthio)-2'-(5,6-dihydropyridin-1(2H)-yl)biphenyl-3-yl)ethanone |
| 12-20 | N-(4-(3-(2-(dimethylamino)ethoxy)-4-(4-methylpiperazin-1-yl)phenylsulfinyl)thiophen-3-yl)acetamide |
| 12-21 | 1-(5'-(5-bromothiophen-3-ylthio)-2'-(5,6-dihydropyridin-1(2H)-yl)biphenyl-3-yl)ethanone |
| 12-22 | 1-(4-(5-ethoxythiophen-3-ylthio)-2-(furan-2-yl)phenyl)-1,2,3,6-tetrahydropyridine |
| 12-23 | 4-(3-(cyclopentyloxy)-4-(4-methylpiperazin-1-yl)phenylthio)thiophene-3-sulfonamide |
| 12-24 | N-(4-(3-(cyclopentylamino)-5-methyl-4-(4-methylpiperazin-1-yl)phenylsulfinyl)thiophen-3-yl)acetamide |
| 12-25 | 5-(3-methoxy-4-(4-methylpiperazin-1-yl)phenylthio)-N-methyl-1H-pyrrole-3-carboxamide |
| 12-26 | 1-(2-(benzyloxy)-4-(3-methoxy-1H-pyrrol-2-ylthio)phenyl)-4-methylpiperazine |
| 12-27 | 1-ethyl-5-(3-methoxy-4-(4-methylpiperazin-1-yl)phenylthio)-N-methyl-1H-pyrrole-3-carboxamide |
| 12-28 | 1-(5-(5-(hydroxymethyl)-1H-pyrrol-2-ylthio)-2-(4-methylpiperazin-1-yl)phenyl)urea |
| 12-29 | 5-(5-methoxy-2-methyl-4-(4-methylpiperazin-1-yl)phenylthio)-N-methylfuran-3-carboxamide |
| 12-30 | 2-amino-N-(2-(3-methoxy-4-(4-methylpiperazin-1-yl)phenylthio)furan-3-yl)acetamide |
| 12-31 | 1-(5-(3-(cyclopropylamino)-4-(4-methylpiperazin-1-yl)phenylthio)furan-2-yl)ethanone |
| 12-32 | 2-amino-N-(2-(3-methoxy-4-(4-methylpiperazin-1-yl)phenylthio)thiophen-3-yl)propanamide |
| 12-33 | 5-(3-methoxy-4-(4-methylpiperazin-1-yl)phenylthio)-N-methyl-4-(trifluoromethoxy)thiophene-3-carboxamide |
| 12-34 | 3-(3-methoxy-4-(pyridin-3-yl)phenylsulfinyl)-5-methylisoxazole |
| 12-35 | 1-(3-(3-amino-4-(4-methylpiperazin-1-yl)phenylthio)isoxazol-4-yl)ethanone |
| 12-36 | 3-(3-methyl-4-(piperidin-1-yl)phenylthio)isothiazole |
| 12-37 | 4-(2-(benzyloxy)-4-(5-(furan-2-yl)isothiazol-3-ylthio)phenyl)morpholine |
| 12-38 | 5-(3-methoxy-4-(4-methylpiperazin-1-yl)phenylthio)-N-methyl-1H-pyrazole-3-carboxamide |
| 12-39 | 1-(2-(benzyloxy)-4-(4-methoxy-1H-pyrazol-5-ylthio)phenyl)-4-methylpiperazine |
| 12-40 | 1-ethyl-5-(3-methoxy-4-(4-methylpiperazin-1-yl)phenylthio)-N-methyl-1H-pyrazole-3-carboxamide |
| 12-41 | 2-(3-(5-ethyl-2-methyl-4-(4-methylpiperazin-1-yl)phenylthio)-1-methyl-1H-pyrazol-4-yloxy)ethanamine |
| 12-42 | 5-(3-methoxy-4-(4-methylpiperazin-1-yl)phenylthio)-N-methylisoxazole-3-carboxamide |
| 12-43 | 2-amino-N-(5-(3-methoxy-4-(4-methylpiperazin-1-yl)phenylthio)isoxazol-4-yl)acetamide |
| 12-44 | N-cyclopropyl-5-(isoxazol-5-ylthio)-2-(4-methylpiperazin-1-yl)aniline |
| 12-45 | 2-amino-N-(5-(3-methoxy-4-(4-methylpiperazin-1-yl)phenylthio)isothiazol-4-yl)propanamide |
| 12-46 | 5-(3-methoxy-4-(4-methylpiperazin-1-yl)phenylthio)-N-methyl-4-(trifluoromethoxy)isothiazole-3-carboxamide |

In one embodiment of the present subject matter, the compound of the present subject matter is a compound selected from the group consisting of compounds of Table 1, compounds of Table 2, compounds of Table 3, compounds of Table 4, compounds of Table 5, compounds of Table 6, compounds of Table 7, compounds of Table 8, compounds of Table 9, compounds of Table 10, compounds of Table 11, and compounds of Table 12.

In another embodiment, the present subject matter relates to a method of making a compound, or an intermediate thereof, comprising performing at least one of the synthetic steps described in the examples herein.

Description of an Unexplored Allosteric Site (Site 1) on hHsp70 of Whose Occupancy Confers Anticancer Activity In accordance with another embodiment, a cavity in the Hsp70 protein that has no known naturally occurring or synthetically created ligand, when occupied by compounds of the present subject matter as described herein, results in inhibition of malignant cell growth, inhibition of aberrant cell cycle progression, degradation and inhibition of one or more onco-proteins, induction of apoptosis, reduction in the invasive potential of cancer cells at doses that are not toxic to normal cells, or combinations thereof. In accordance with another embodiment, occupancy of this previously unexplored pocket by other small molecule ligands will lead to all or a subset of the following effects, but is not limited to: inhibition of malignant cell growth, inhibition of aberrant cell cycle progression, degradation and inhibition of several onco-proteins, induction of apoptosis, reduction in the invasive potential of cancer cells at doses that are not toxic to normal cells, or combinations thereof.

The pocket, referred to herein as an allosteric Site 1, is next to the ATP/ADP binding pocket, and is comprised of a hydrophilic sub-pocket lined by but not limited to Thr13, Thr14, Tyr15, Lys56, Lys271, Arg269, Glu268, Arg264 and Thr265 polar amino acids. There is a Cysteine residue (Cys267) embedded in this sub-pocket that could covalently link to a ligand containing the appropriate Cys-reactive functionality, such as but not limited to acrylamide, vinyl sulfonamide, propiolamide or α-halocarbonyl. Adjacent to the hydrophilic sub-pocket there is a large sub-pocket comprised of both non-polar and polar amino acid residues, such as but not limited to Leu237, Val238, Val260, Arg261, Val59, Pro63, Thr66, Asn235, Asp234, Glu231, Asp69, Phe68 Arg 72 and Tyr41, which provide hydrophobic and electrostatic (x-x) interactions with the ligand. Providing interactions with the ligand are amino acids such as but not limited to Lys88, His89, Trp90, Pro91 and Phe92.

Because no full-length crystal structure of human Hsp70 was available, a homology model of full-length human Hsp70 was created. Whereas in the available crystal structures Cys267 is unexposed, in the homology model of the full length Hsp70 the pocket containing Cys267 becomes exposed. The identified interaction of YK5 is with full length homology model of human Hsp70.

In one embodiment, a method of treating or preventing a tumor or proliferative disorder in an animal is provided, comprising administering a therapeutically effective amount of an Hsp70 inhibitor to an animal in need thereof; contacting the Hsp70 inhibitor with an allosteric binding domain located outside the nucleotide binding site of Hsp70 and Hsc70; simultaneously inhibiting both Hsp70 and Hsc70; inducing apoptosis in tumor cells or cells with a proliferative disorder, and not inducing increased apoptosis in normal cells, stroma, or blood vessels. In a further embodiment, the Hsp70 inhibitor used in the above method is a compound selected from formula (I) or (I').

In a yet further embodiment, the allosteric binding domain is located on SEQ ID NO:1 and said domain is defined by one or more amino acid residues selected from the group consisting of Thr13, Thr14, Tyr15, Lys56, Lys271, Arg269, Glu268, Arg264, Thr265, Cys267, Leu237, Val238, Val260, Arg261, Val59, Pro63, Thr66, Asn235, Asp234, Glu231, Asp69, Phe68, Tyr41, Lys88, His89, Trp90, Pro91, Phe92, and combinations thereof. In another embodiment, the allosteric binding domain is 1 defined by three or more amino acid residues recited above. In another embodiment, the allosteric binding domain is 1 defined by four or more amino acid residues recited above. In another embodiment, the allosteric binding domain is 1 defined by five or more amino acid residues recited above. In another embodiment, the allosteric binding domain is 1 defined by 3, 4, 5, 6, 7, 8, 9, 10, 11, 12, 13, 14, 15 or more amino acid residues recited above. In some embodiments, a compound of the present subject matter binds to this allosteric binding domain and causes the inhibition of Hsp70, Hsc70, or both simultaneously.

In a another embodiment, the allosteric binding domain is located on SEQ ID NO:1 and said domain is defined by one or more amino acid residues selected from the group consisting of Cys267, Leu237, Arg264, Asp234, Arg261, Tyr41, Phe68, Trp90, His89, and combinations thereof. In yet another embodiment, the allosteric binding domain is located on SEQ ID NO:1 and said domain is defined by one or more amino acid residues selected from the group consisting of Cys267, Arg264, Arg261, Phe68, His89, and combinations thereof.

Another embodiment relates to a method of activating Hsp70, wherein the Hsp70 comprises a binding pocket on SEQ ID NO:1 having a Site 1 located in a cleft region outside the ATP/ADP binding domain, and flanked by sub-regions Ib and IIb, and which comprises contacting Site 1 of the binding pocket with a ligand which binds to the binding pocket so as to activate the activity of Hsp70. A further embodiments involves a method of activating Hsp70 according to claim 27, wherein Site 1 has a first large hydrophilic pocket comprising Tyr15, Lys56, Lys271, Arg269, Glu268, Arg264 and Thr265 polar amino acids; a Cysteine residue (Cys267) embedded in this pocket; and adjacent to this pocket there is a second larger pocket on Hsp70 comprising both non-polar and polar amino acid residues, such as Leu237, Val238, Val260, Arg261, Val59, Pro63, Thr66, Asn235, Asp234, Glu231, Asp69, Phe68 and Tyr41, which may form hydrophobic and electrostatic (π-π) interactions.

In a further embodiment, a three-dimensional structure is provided of binding site 1 of Hsp70 or a variant thereof for screening a modulator that modulates the activity of Hsp-70 or Hsc-70, wherein said binding site comprises a ligand binding domain on SEQ ID NO:1 defined by amino acid residue selected from a group consisting of Thr13, Thr14, Tyr15, Lys56, Lys271, Arg269, Glu268, Arg264, Thr265, Cys267, Leu237, Val238, Val260, Arg261, Val59, Pro63, Thr66, Asn235, Asp234, Glu231, Asp69, Phe68, Tyr41, Lys88, His89, Trp90, Pro91, Phe92, and combinations thereof.

One embodiment relates to computer assisted system for producing a three-dimensional structure of binding site 1 of Hsp70 or a variant thereof of claim 1, wherein the system comprises: (a) a computer readable data storage medium comprising a data storage material encoded with computer readable data, wherein said data comprises at least a portion of peptide sequence SEQ ID NO: 1 and the sequences shown in boxes in FIG. 21 (b) a working memory having stored instructions for processing said computer readable data; (c) a central processing unit coupled to said computer readable data storage medium and said working memory for processing said computer readable data into said three-dimensional structure; and (d) a display coupled to said central processing unit for displaying said three-dimensional structure. In a further embodiment, the binding site 1 of Hsp70 or a variant thereof on SEQ ID NO:1 is defined by amino acid residue selected from a group consisting of Thr13, Thr14, Tyr15, Lys56, Lys271, Arg269, Glu268, Arg264, Thr265, Cys267, Leu237, Val238, Val260, Arg261, Val59, Pro63, Thr66, Asn235, Asp234, Glu231, Asp69, Phe68, Tyr41, Lys88, His89, Trp90, Pro91, Phe92, and combinations thereof.

Pharmaceutical Composition Containing a Compound of the Present Subject Matter

In one embodiment, the present subject matter relates to compositions comprising a compound as described herein. In another embodiment, the present subject matter relates to pharmaceutical compositions comprising a compound as described herein, and a pharmaceutically acceptable carrier. The carriers useful herein may further include one or more compatible solid or liquid filler, diluents, or encapsulating materials which are suitable for human or animal administration.

Biocompatible carriers, as used herein, are components that do not cause any interactions which substantially reduce the efficacy of the pharmaceutical composition in an ordinary user environment. Possible pharmaceutical carriers must be of sufficiently low toxicity to make them suitable for administration to the subject being treated.

Any non-toxic, inert, and effective carrier may be used to formulate the compositions contemplated herein. Suitable pharmaceutically acceptable carriers, excipients, and diluents in this regard are well known to those of skill in the art, such as those described in *The Merck Index*, Thirteenth Edition, Budavari et al., Eds., Merck & Co., Inc., Rahway, N.J. (2001); and the "Inactive Ingredient Guide", U.S. Food and Drug Administration (FDA) Center for Drug Evaluation and Research (CDER) Office of Management, the contents of all of which are hereby incorporated by reference in their entirety. Examples of preferred pharmaceutically acceptable excipients, carriers and diluents useful in the present compositions include distilled water, physiological saline, Ringer's solution, dextrose solution, Hank's solution, and DMSO.

These additional inactive components, as well as effective formulations and administration procedures, are well known in the art and are described in standard textbooks, such as *Goodman and Gillman's: The Pharmacological Bases of Therapeutics,* 8th Ed., Gilman et al. Eds. Pergamon Press (1990) and *Remington's Pharmaceutical Sciences,* 18th Ed., Mack Publishing Co., Easton, Pa. (1990), both of which are incorporated by reference herein in their entirety. The carrier may comprise, in total, from about 0.1% to about 99.99999% by weight of the compositions presented herein.

Therapeutic Applications

In some embodiments, the compounds of formula (I) and formula (I') have been found to possess anti-proliferative activity and are therefore believed to be of use in the treatment of proliferative disorders such as cancers and other disorders associated with uncontrolled cellular proliferation. As defined herein, an anti-proliferative effect within the scope of the present subject matter may be demonstrated, for example, by the ability to inhibit cell proliferation specific kinases in vitro or in vivo, or inhibit cell proliferation in an in vitro whole cell assay, in an in vivo animal model, or in human clinical administration.

Administration

The pharmaceutical compositions of the present subject matter may be adapted for oral, rectal, vaginal, parenteral, intramuscular, intraperitoneal, intraarterial, intrathecal, intrabronchial, subcutaneous, intradermal, intravenous, nasal, buccal, or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present subject matter may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

Appropriate dosage levels on the order of about 0.001 mg to about 5,000 mg per kilogram body weight of the compound active agent may be useful in the treatment of the diseases, disorders, and conditions contemplated herein. Typically, this effective amount of the active agent will generally comprise from about 0.001 mg to about 100 mg per kilogram of patient body weight per day. Moreover, it will be understood that this dosage of active agent can be administered in a single or multiple dosage units to provide the desired therapeutic effect.

In one embodiment, the preferred therapeutically effective dosage will be the amount of a compound of the present subject matter required to obtain a serum, but more preferably tumor, concentration equivalent to the concentration to achieve phenotypic effects in any of the many assays described herein, such as but not limited to growth inhibition of AML Kasumi-1 cells, induction of apoptosis as indicated by caspase 3,7 activation in MOLM-13 AML cells, degradation of HER-2 and Raf-1 kinases in SKBr3 breast cancer cells, inactivation of p-STAT3 in MDA-MB-468 breast cancer cells selected from the group consisting of 1 nM to 200 uM; 1 nM to 100 uM; 1 nM to 50 uM; 100 nM to 100 uM; 100 nM to 50 uM; 100 nM to 20 uM; 1 nM to 1 uM; and 1 nM to 100 nM. In one embodiment, the phenotypic effect is the IC50 value for the assay. In a further embodiment, the preferred therapeutically effective dosage will be the amount required to obtain a serum, but more preferably tumor, concentration equivalent to the concentration equivalent to the concentration to achieve phenotypic effects in any of the many assays described herein, such as but not limited to growth inhibition of AML Kasumi-1 cells, induction of apoptosis as indicated by caspase 3,7 activation in MOLM-13 AML cells, degradation of HER-2 and Raf-1 kinases in SKBr3 breast cancer cells, inactivation of p-STAT3 in MDA-MB-468 breast cancer cells selected from the group consisting of less than 200 uM; less than 100 uM; less than 50 uM; less than 25 uM; less than 15 uM; less than 10 uM; less than 5 uM; less than 2 uM; less than 1 uM; less than 500 nM; less than 200 nM; or less than 100 nM. In a further embodiment, the phenotypic effect is the IC50 value for the assay.

If desired, other therapeutic agents can be employed in conjunction with those provided in the above-described compositions. The amount of pharmaceutically active ingredients that may be combined with the carrier materials to produce a single dosage form will vary depending upon the host treated, the nature of the disease, disorder, or condition, and the nature of the active ingredients.

The preferred pharmaceutical compositions may be given in a single or multiple doses daily. In an embodiment, the pharmaceutical compositions are given from one to three times daily. Starting with a low dose twice daily and slowly working up to higher doses if needed is a strategy. The amount of pharmaceutically active ingredients that may be combined with the carrier materials to produce a single dosage form will vary depending upon the host treated, the nature of the disease, disorder, or condition, and the nature of the active ingredients. It is understood, however, that a specific dose level for any particular patient will vary depending upon a variety of factors, including the activity of the specific pharmaceutically active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time are well known in the art.

The optimal pharmaceutical formulations will be determined by one skilled in the art depending upon considerations such as the particular pharmaceutically active agent combination and the desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the essential lipids.

In an embodiment, the present pharmaceutical composition in accordance with the subject matter described herein may be an intravenous form or an oral dosage form, for example, a capsule, a tablet, liquid, and/or a powder packaged in, for example, a multi-use or single-use package, including for example, a container or bottle, a blister package.

Single dosage kits and packages containing once per day, or once per treatment, amount of the pharmaceutical composition may be prepared. Single dose, unit dose, and once-daily disposable containers of the present pharmaceutical compositions are contemplated as within the scope of the present subject matter.

Combination Therapy

In another embodiment, the present pharmaceutical compositions may be used in combination with an additional pharmaceutical dosage form to enhance their effectiveness in treating a cancer, malignancy, or proliferative disorder. In this regard, the present preferred compositions may be administered as part of a regimen additionally including any other pharmaceutical and/or pharmaceutical dosage form known in the art as effective for the treatment of a cancer, malignancy, or proliferative disorder. Similarly, a pharmaceutically active ingredient other than those specified herein can be added to the present preferred compositions to enhance their effectiveness in treating a cancer, malignancy, or proliferative disorder. Accordingly, this additional pharmaceutically active ingredient or additional pharmaceutical dosage form can be administered to a patient either directly or indirectly, and concomitantly or sequentially, with the preferred compositions described herein.

In this regard, anti-cancer, anti-malignancy, or anti-proliferative disorder agents other than compounds discussed above are additionally contemplated as useful for combination therapy discussed herein. Combinations of any of the foregoing agents or their pharmaceutically acceptable salts or derivatives are contemplated herein.

In one embodiment in this regard, the present compositions and the additional pharmaceutical dosage form can be administered to a patient at the same time. In an alternative embodiment, one of the present preferred compositions and the additional pharmaceutical dosage form can be administered in the morning and the other can be administered in the evening.

In another embodiment, the presently described compounds can be administered to a patient in need thereof in multiple pharmaceutical dosage forms. This combination therapy may maximize the effectiveness of the present composition in treating a cancer, malignancy, or proliferative disorder.

EXAMPLES

The following examples are illustrative of the present pharmaceutical compositions and are not intended to be limitations thereon. Compounds were named by using the "Convert Structure to Name" function in ChemBioDraw Ultra V.11.0.1 (Cambridge Soft; Cambridge, Mass.)

Example 1: Chemical Synthesis and Purification

General.

NMR spectra were recorded on a Bruker AV-III-500 MHz NMR spectrometer. Chemical shifts are reported in δ values in ppm downfield from TMS as the internal standard. $^{1}$H data are reported as follows: chemical shift, multiplicity (s=singlet, d=doublet, t=triplet, q=quartet, br=broad, m=multiplet), coupling constant (Hz), integration. $^{13}$C chemical shifts are reported in δ values in ppm downfield from TMS as the internal standard. High resolution mass spectra were recorded on a Waters LCT Premier system. Low resolution mass spectra were obtained on Waters Acquity Ultra Performance LC with electrospray ionization and SQ detector. Analytical HPLC was performed on a Waters Autopurification system with PDA, MicroMass ZQ and ELSD detector. Analytical thin layer chromatography was performed on 250 μM silica gel F254 plates. Preparative thin layer chromatography was performed on 1000 μM silica gel F254 plates. Flash column chromatography was performed employing 230-400 mesh silica gel. Solvents were HPLC grade. All reagents were purchased from either Aldrich or Acros Organics and used without purification. All reactions were performed under argon protection.

(2)—PU24FC1

2 was synthesized according to previously published procedure. $^{1}$H NMR (500 MHz, CDCl$_3$): δ 6.46 (s, 1H), 6.17 (br s, 2H), 4.31 (s, 2H), 4.12 (t, J=7.3 Hz, 2H), 3.91 (s, 3H), 3.86 (s, 3H), 3.72 (s, 3H), 2.19 (dd, J=6.6, 2.5 Hz, 2H), 1.97 (t, J=2.5 Hz, 1H), 1.94-1.87 (m, 2H); $^{13}$C NMR (166 MHz, CDCl$_3$) δ 159.8, 157.7, 156.2, 152.8, 152.4, 150.5, 150.2, 142.6, 128.7, 119.7, 116.8, 108.5, 82.2, 69.8, 61.1, 56.2, 42.1, 31.5, 28.1, 15.7; MS (m/z): [M+H]$^+$ 434.1.

(3)—PU-H71

3 was synthesized according to previously published procedure. $^{1}$H NMR (500 MHz, CDCl$_3$): δ 8.33 (s, 1H), 7.31 (s, 1H), 6.89 (s, 1H), 5.99 (s, 2H), 5.58 (br s, 2H), 4.30 (t, J=7.0 Hz, 2H), 2.74-2.69 (m, 1H), 2.58 (t, J=7.0 Hz, 2H), 2.01-1.96 (m, 2H), 1.03 (d, J=6.2 Hz, 6H); $^{13}$C NMR (166 MHz, CDCl$_3$) δ 154.6, 152.9, 151.6, 149.2, 148.9, 146.2, 127.9, 120.1, 119.2, 112.2, 102.2, 91.1, 48.7, 43.9, 41.7, 30.3, 22.9; MS (m/z): [M+H]$^+$ 513.0.

(5)—GM-Cy3B 5 was synthesized according to previously published procedure. MS (m/z): [M+Na]$^+$ 1181.3.

Synthetic Scheme 1

Synthetic Scheme 1 provides examples of synthesizing compounds 18-26, YK5 (4), and YK20 (6).

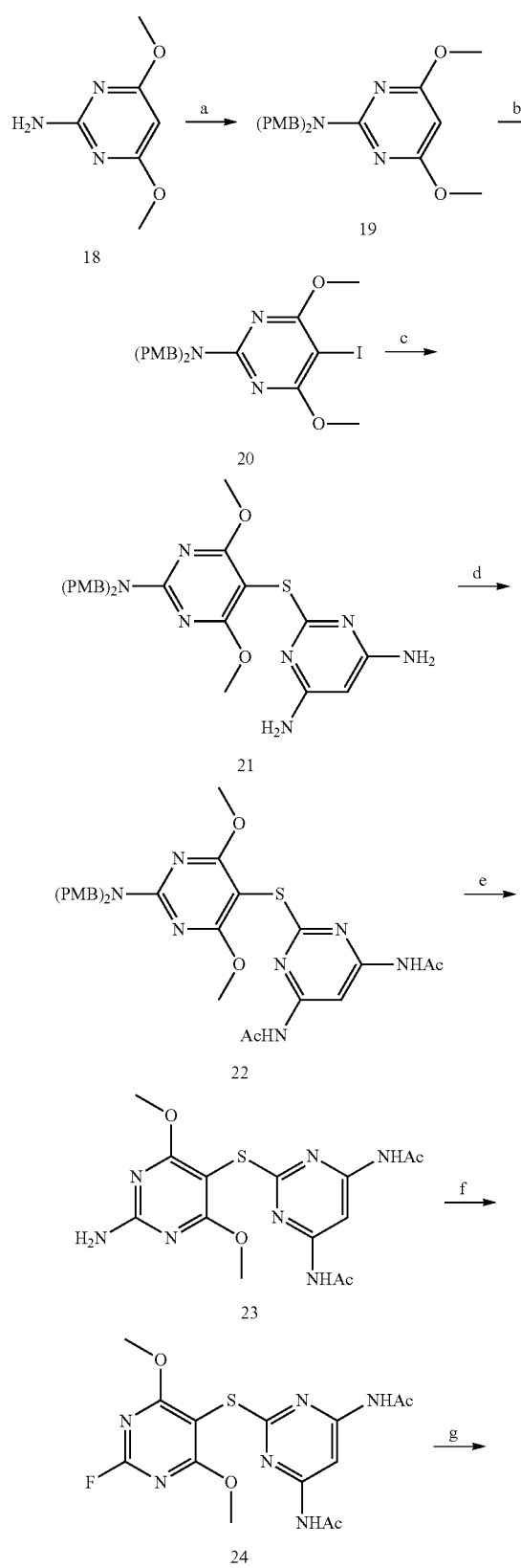

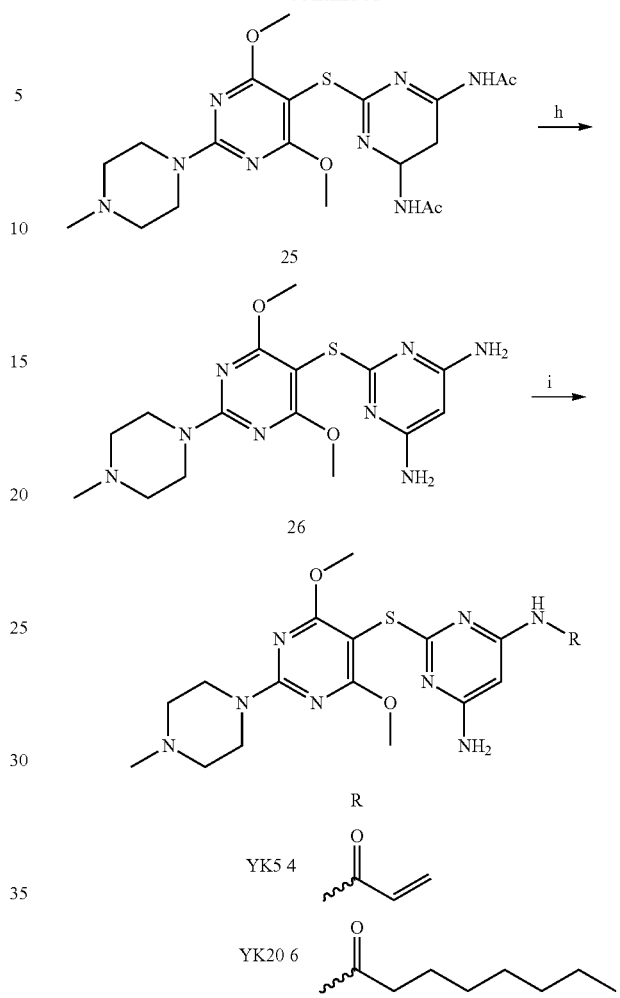

Reagents and conditions: (a) PMBCl, NaH, DMF, 0° C. to rt., 12 h, 95%; (b) NIS, MeCN, rt, 1 h, 98%; (c) 4,6-diamino-2-mercaptopyrimidine, neocuproine, CuI, $K_2CO_3$, DMSO, 120° C., 16 h, 65%; (d) $Ac_2O$, DMAP, 110° C., 2 h, 91%; (e) TFA, $CHCl_3$, 62° C., 24 h, 95%; (f) HF/pyridine, $NaNO_2$, 0° C., 1 h, 54%; (g) 1-methylpiperizine, DMF, 90 ° C., 1 h, 90%; (h) NaOH, $H_2O$, MeOH, 60° C., 1 h, 95%; (i) acryloyl chloride, $Et_3N$, dioxane, rt, 24 h, 50% or octanoyl chloride, $Et_3N$, dioxane, rt, 12 h, 71%.

(19)—4,6-dimethoxy-N,N-bis(4-methoxybenzyl) pyrimidin-2-amine

To a solution of 2-amino-4,6-dimethoxypyrimidine (2.0 g, 12.9 mmol) in 20 mL DMF at 0° C., NaH (1.24 g, 51.5 mmol) was added and the mixture stirred at rt for 10 min. 4-methoxybenzyl chloride (4.03 g, 25.7 mmol) was added and the mixture was stirred at rt overnight. The reaction was quenched with methanol and solvent removed under reduced pressure. The residue was dissolved in EtOAc, washed with brine and dried over $MgSO_4$. Solvent was evaporated under reduced pressure and the residue was purified by column chromatography (hexane:EtOAc, 4:1) to afford 4.8 g (95%) of 19. $^1$H NMR (500 MHz, $CDCl_3$): δ 7.26 (d, J=8.4 Hz, 4H), 6.89 (d, J=8.4 Hz, 4H), 5.47 (s, 1H), 4.78 (s, 4H), 3.85 (s, 6H), 3.80 (s, 6H); $^{13}$C NMR (166 MHz, $CDCl_3$): δ 171.9, 161.5, 158.7, 130.9, 129.1, 113.8, 78.7, 55.2, 53.4, 48.3; MS (m/z): $[M+H]^+$ 396.3.

(20)—5-iodo-4,6-dimethoxy-N,N-bis(4-methoxybenzyl)pyrimidin-2-amine

To a solution of 19 (4.8 g, 12.3 mmol) in 50 mL acetonitrile, N-iodosuccinimide (4.13 g, 18.4 mmol) was added and stirred at rt for 1 h. Solvent was evaporated and the residue was purified by column chromatography (hexane:EtOAc, 4:1) to afford 6.3 g (98%) of 20. $^1$H NMR (500 MHz, CDCl$_3$): δ 7.18 (d, J=8.6 Hz, 4H), 6.83 (d, J=8.6 Hz, 4H), 4.71 (s, 4H), 3.89 (s, 6H), 3.79 (s, 6H); $^{13}$C NMR (166 MHz, CDCl$_3$): δ 169.1, 160.9, 158.8, 130.5, 129.0, 113.9, 55.3, 54.7, 48.6, 43.9; MS (m/z): [M+H]$^+$ 522.4.

(21) 2-(2-(bis(4-methoxybenzyl)amino)-4,6-dimethoxypyrimidin-5-ylthio)pyrimidine-4,6-diamine A mixture of 20 (6.2 g, 11.9 mmol), 4,6-diamino-2-mercaptopyrimidine (1.7 g, 11.9 mmol), neocuproine (0.538 g, 2.38 mmol), copper iodide (0.452 g, 2.38 mmol), and potassium carbonate (3.3 g, 33.8 mmole) in 100 mL DMSO was stirred at 120° C. for 16 h. Solvent was removed under reduced pressure and the residue was purified by column chromatography (CH$_2$Cl$_2$:MeOH—NH$_3$ (7N), 20:1) to afford 4.2 g (65%) of 21. $^1$H NMR (500 MHz, DMSO-d6): δ 7.18 (d, J=8.6 Hz, 4H), 6.80 (d, J=8.6 Hz, 4H), 5.09 (s, 1H), 4.68 (s, 4H), 4.40 (s, 4H), 3.79 (s, 6H), 3.74 (s, 6H); MS (m/z): [M+H]$^+$ 536.5.

(22) N,N'-(2-(2-(bis(4-methoxybenzyl)amino)-4,6-dimethoxypyrimidin-5-ylthio) pyrimidine-4,6-diyl)diacetamide A solution of 21 (3.2 g, 6.0 mmol) and DMAP (0.037 g, 0.3 mmol) in 20 mL acetic anhydride was stirred at 110° C. for 2 h. Solvent was removed under reduced pressure and the residue was purified by column chromatography (hexane:EtOAc, 1:1) to afford 3.4 g (91%) of 22. $^1$H NMR (500 MHz, CDCl$_3$/DMSO-d6): δ 8.25 (br s, 1H), 7.70 (br s, 2H), 7.18 (d, J=10.0 Hz, 4H), 6.81 (d, J=10.0 Hz, 4H), 4.70 (s, 4H), 3.78 (s, 6H), 3.74 (s, 6H), 2.10 (s, 6H); MS (m/z): [M+H]$^+$ 620.4.

(23) N,N'-(2-(2-amino-4,6-dimethoxypyrimidin-5-ylthio)pyrimidine-4,6-diyl) diacetamide A solution of 22 (0.950 g, 1.5 mmol) in 20 mL TFA:CHCl$_3$ (1:1) was heated at 62° C. for 24 h. Excess TFA and solvent were removed under reduced pressure and the residue was purified by column chromatography (CH$_2$Cl$_2$:MeOH, 20:1) to afford 0.550 g (95%) of 23. $^1$H NMR (500 MHz, DMSO-d6): δ 10.51 (br s, 2H), 8.37 (br s, 1H), 6.98 (s, 2H), 3.78 (s, 6H), 2.06 (s, 6H); $^{13}$C NMR (166 MHz, DMSO-d6): δ 170.9, 170.1, 169.2, 162.5, 158.9, 92.8, 78.5, 53.9, 24.1; MS (m/z): [M+H]$^+$ 380.2.

(24) N,N'-(2-(2-fluoro-4,6-dimethoxypyrimidin-5-ylthio)pyrimidine-4,6-diyl) diacetamide 23 (2.0 g, 5.3 mmol) was added to a plastic tube fitted with a stir bar and cooled to 0° C. Then a solution of HF/pyridine (3.6 mL, 144 mmol) was added. NaNO$_2$ (0.545 g, 7.9 mmol) was added in portions over a period of 20 minutes with stirring. It was vigorously stirred for an additional 50 minutes at 0° C. and 2 h at rt. CaCO$_3$ (14.4 g, 144 mmol) was added to destroy excess HF. The mixture was extracted with CH$_2$Cl$_2$ and purified by column chromatography (CH$_2$Cl$_2$:MeOH—NH$_3$ (7N), 20:1) to afford 1.1 g (54%) of 24. $^1$H NMR (500 MHz, CDCl$_3$): δ 8.45 (s, 1H), 7.61 (s, 2H), 4.00 (s, 6H), 2.18 (s, 6H); MS (m/z): [M+H]$^+$ 383.2.

(25) N,N'-(2-(4,6-dimethoxy-2-(4-methylpiperazin-1-yl)pyrimidin-5-ylthio) pyrimidine-4,6-diyl)diacetamide To a solution of 24 (30 mg, 0.078 mmol) in 2 mL DMF was added 1-methylpiperazine (31 mg, 0.31 mmol) and heated at 90° C. for 1 h. Solvent and excess reagent were removed under reduced pressure and the residue was purified by column chromatography (CHCl$_3$:MeOH—NH$_3$ (7N), 10:1) to yield 32 mg (90%) of 25. $^1$H NMR (500 MHz, CDCl$_3$): δ 8.36 (br s, 1H), 8.13 (br s, 2H), 3.88 (s, 6H), 3.87 (m, 4H), 2.46 (m, 4H), 2.35 (s, 3H), 1.99 (s, 6H); $^{13}$C NMR (166 MHz, CDCl$_3$): δ 172.2, 169.4, 168.9, 160.4, 158.9, 96.1, 95.9, 54.7, 54.3, 46.1, 43.8, 24.7; MS (m/z): [M+H]$^+$ 463.2.

(26) 2-(4,6-dimethoxy-2-(4-methylpiperazin-1-yl) pyrimidin-5-ylthio)pyrimidine-4,6-diamine A mixture of 25 (50 mg, 0.108 mmol), 1 N NaOH (aq.) (2 mL) in 4 mL methanol was stirred at 60° C. for 1 h. Solvents were removed under reduced pressure and the residue was purified by preparatory TLC to afford 39 mg (95%) of 26. $^1$H NMR (500 MHz, CDCl$_3$): δ 5.19 (s, 1H), 4.48 (s, 4H), 3.88 (s, 6H), 3.87 (m, 4H), 2.48 (m, 4H), 2.35 (s, 3H); MS (m/z): [M+H]$^+$ 378.9.

YK5 (4)—N-(6-amino-2-(4,6-dimethoxy-2-(4-methylpiperazin-1-yl)pyrimidin-5-ylthio) pyrimidin-4-yl)acrylamide To a solution of 26 (0.370 g, 0.977 mmol) and Et$_3$N (0.988 g, 9.77 mmol) in 10 mL anhydrous dioxane was added acryloyl chloride (0.855 g, 9.77 mmol) dropwise under water bath. The resulting mixture was stirred at rt for 24 h. Solvent was removed under reduced pressure and the residue was purified by preparatory TLC (CHCl$_3$:MeOH—NH$_3$ (7N), 10:1) to afford 0.211 g (50%) of 4. 1H NMR (500 MHz, CDCl$_3$): δ 7.96 (br s, 1H), 7.04 (s, 1H), 6.41 (d, J=16.8 Hz, 1H), 6.17 (dd, J=16.8, 10.3 Hz, 1H), 5.78 (d, J=10.3 Hz, 1H), 4.83 (br s, 2H), 3.88 (s, 6H), 3.87 (m, 4H), 2.47 (m, 4H), 2.35 (s, 3H); $^{13}$C NMR (166 MHz, CDCl$_3$): δ 169.3, 168.8, 162.6, 162.5, 158.3, 154.9, 128.9, 127.1, 86.7, 78.2, 53.1, 52.4, 44.5, 41.9; HRMS (m/z): [M+H]$^+$ calculated for C$_{18}$H$_{25}$N$_8$O$_3$S, 433.1770; found 433.1750; HPLC: (a) H$_2$O+0.1% TFA (b) ACN+0.1% TFA (5 to 95% ACN in 10 min.) Rt=6.28 min.

YK20 (6)—N-(6-amino-2-(4,6-dimethoxy-2-(4-methylpiperazin-1-yl)pyrimidin-5-ylthio) pyrimidin-4-yl)octanamide To a solution of 26 (20 mg, 0.049 mmol) and Et$_3$N (49 mg, 0.49 mmol) in 1 mL anhydrous dioxane was added octanoyl chloride (80 mg, 0.49 mmol) dropwise. The resulting mixture was stirred at rt for 12 h. Solvent was removed under reduced pressure and the residue was purified by preparatory TLC (CHCl$_3$:MeOH—NH$_3$ (7N), 10:1) to afford 17 mg (71%) of 6. $^1$H NMR (500 MHz, CDCl$_3$): δ 8.01 (br s, 1H), 6.97 (s, 1H), 4.86 (br s, 2H), 3.89 (s, 6H), 3.86 (m, 4H), 2.46 (m, 4H), 2.35 (s, 3H), 2.30 (t, J=7.4 Hz, 2H), 1.62 (m, 2H), 1.20-1.30 (m, 8H), 0.87 (t, J=6.9 Hz, 3H); $^{13}$C NMR (166 MHz, CDCl$_3$): δ 172.7, 171.1, 170.4, 164.3, 160.0, 156.7, 87.9, 80.1, 54.9, 54.2, 46.3, 43.7, 37.7, 31.6, 29.1, 29.0, 25.2, 22.6, 14.1; HRMS (m/z): [M+H]$^+$ calculated for $C_{23}H_{37}N_8O_3S$, 505.2709; found 505.2701; HPLC: (a) H$_2$O+0.1% TFA (b) ACN+0.1% TFA (5 to 95% ACN in 10 min.) Rt=7.98 min.
Synthetic Scheme 2
Synthetic Scheme 2 provides examples of synthesizing compounds 28-36, YK30 (15), and YK31 (16).
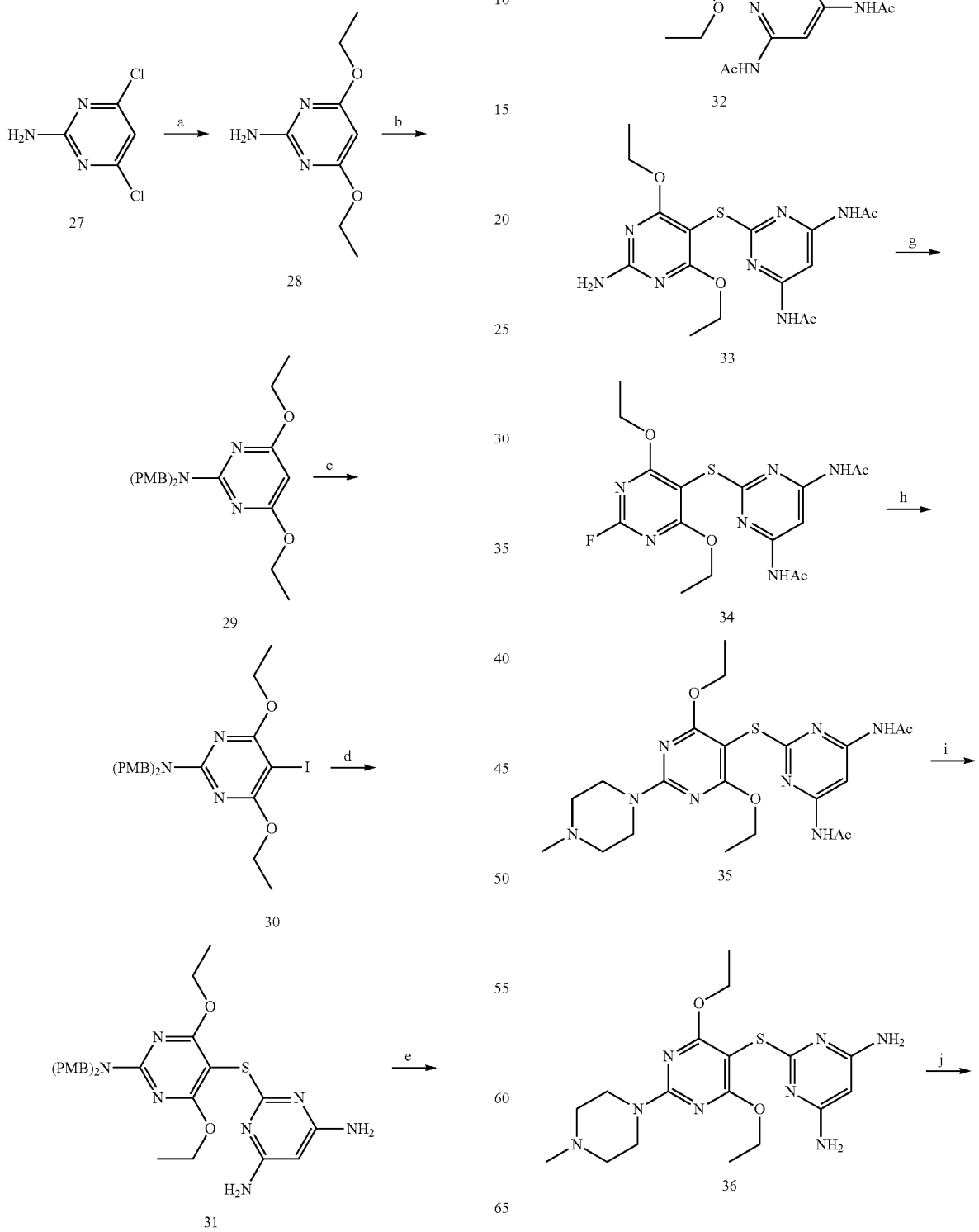

-continued

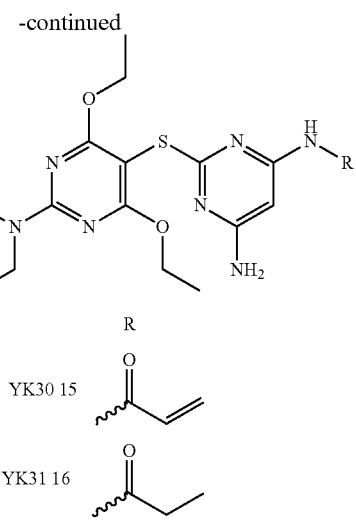

| | R |
|---|---|
| YK30 15 | ![acryloyl] |
| YK31 16 | ![propionyl] |

Reagents and conditions: (a) NaH, EtOH, reflux, 12 h, 89%; (b) PMBCl, NaH, DMF, 0° C. to rt, 12 h, 97%; (c) NIS, MeCN, rt, 1 h, 96%; (d) 4,6-diamino-2-mercaptopyrimidine, neocuproine, CuI, K$_2$CO$_3$, DMSO, 120° C., 16 h, 80%; (e) Ac$_2$O, DMAP, 110° C., 2 h, 89%; (f) TFA, CHCl$_3$, 62° C., 24 h, 92%; (g) HF/pyridine, NaNO$_2$, 0° C., 1 h, 46%; (h) 1-methylpiperizine, DMF, 90° C., 1 h, 91%; (i) NaOH, H$_2$O, MeOH, 60° C., 1 h, 93%; (j) acryloyl chloride, Et$_3$N, dioxane, rt, 12 h, 40% or propionyl chloride, Et$_3$N, dioxane, rt, 12 h, 66%.

(28)—2-amino-4,6-diethoxypyrimidine

To a solution of 2-amino-4,6-dichloropyrimidine (1.0 g, 6.09 mmol) in 20 mL absolute ethanol was added NaH (0.585 g, 24.39 mmol) at rt. The mixture was stirred under reflux for 12 h. Solvent was removed under reduced pressure and the residue was dissolved in dichloromethane and washed with brine. Solvent was evaporated and the resulting solid was purified by column chromatography (hexane: EtOAc, 4:1) to afford 1.0 g (89%) of 28. $^1$H NMR (500 MHz, CDCl$_3$): δ 5.42 (s, 1H), 4.78 (br s, 2H), 4.24 (q, J=7.1 Hz, 4H), 1.34 (t, J=7.1 Hz, 6H); MS (m/z): [M+H]$^+$ 183.9.

(29)—4,6-diethoxy-N,N-bis(4-methoxybenzyl)pyrimidin-2-amine

To a solution of 28 (1.00 g, 5.46 mmol) in 20 mL DMF at 0° C., NaH (0.524 g, 21.83 mmol) was added and stirred at rt for 10 min. 4-methoxybenzyl chloride (1.88 g, 12.0 mmol) was added and the mixture was stirred at rt overnight. The reaction was quenched with ethanol and solvent was removed under reduced pressure. The residue was dissolved in EtOAc, washed with brine, dried over MgSO$_4$ and concentrated to give a residue that was purified by column chromatography (hexane:EtOAc, 4:1) to afford 2.25 g (97%) of 29. $^1$H NMR (500 MHz, CDCl$_3$): δ 7.18 (d, J=8.1, 4H), 6.84 (d, J=8.1, 4H), 5.38 (s, 1H), 4.70 (s, 4H), 4.27 (q, J=7.1 Hz, 4H), 3.79 (s, 6H), 1.29 (t, J=7.1 Hz, 6H); $^{13}$C NMR (166 MHz, CDCl$_3$): δ 171.5, 161.4, 158.6, 130.9, 129.0, 113.7, 78.6, 61.8, 55.2, 48.1, 14.6; MS (m/z): [M+H]$^+$ 424.2.

(30)—5-iodo-4,6-diethoxy-N,N-bis(4-methoxybenzyl)pyrimidin-2-amine

To a solution of 29 (2.2 g, 5.2 mmol) in 50 mL acetonitrile, N-iodosuccinimide (1.7 g, 8 mmol) was added and stirred at rt for 1 h. Solvent was removed under reduced pressure and the residue was purified by column chromatography (hexane: EtOAc, 4:1) to afford 2.75 g (96%) of 30.

$^1$H NMR (500 MHz, CDCl$_3$): δ 7.17 (m, 4H), 6.84 (m, 4H), 4.68 (s, 4H), 4.34 (q, J=7.1 Hz, 4H), 3.80 (s, 6H), 1.32 (t, J=7.1 Hz, 6H); $^{13}$C NMR (166 MHz, CDCl$_3$/DMSO-d6): δ 168.3, 160.4, 158.2, 130.1, 128.4, 113.2, 62.6, 54.8, 48.1, 44.2, 14.1; MS (m/z): [M+H]$^+$ 550.1.

(31) 2-(2-(bis(4-methoxybenzyl)amino)-4,6-diethoxypyrimidin-5-ylthio) pyrimidine-4,6-diamine A mixture of 30 (2.75 g, 5.0 mmol), 4,6-diamino-2-mercaptopyrimidine (0.71 g, 5.0 mmol), neocuproine (0.226 g, 1.0 mmol), copper iodide (0.190 g, 1.0 mmol), and potassium carbonate (1.38 g, 10.0 mmol) in 60 mL DMSO was stirred at 120° C. for 16 h. Solvent was removed under reduced pressure and the residue was partially purified by column chromatography (CH$_2$Cl$_2$:MeOH—NH$_3$ (7N), 20:1) to afford 2.2 g (80%) of impure 31 [MS (m/z): [M+H]$^+$ 564.2], which was used without further purification in the next step.

(32) N,N'-(2-(2-(bis(4-methoxybenzyl)amino)-4,6-diethoxypyrimidin-5-ylthio) pyrimidine-4,6-diyl) diacetamide A solution of 31 (1.2 g, 2.19 mmol) and DMAP (0.013 g, 0.11 mmol) in 20 mL acetic anhydride was stirred at 110° C. for 2 h. Solvent was removed under reduced pressure and the residue was purified by column chromatography (hexane: EtOAc, 1:1) to afford 1.2 g (89%) of 32. $^1$H NMR (500 MHz, CDCl$_3$): δ 8.22 (s, 2H), 7.21 (d, J=8.5 Hz, 4H), 6.86 (d, J=8.5 Hz, 4H), 4.70 (s, 4H) 4.32 (q, J=7.1 Hz, 4H), 3.80 (s, 6H), 2.16 (s, 6H), 1.20 (t, J=7.1 Hz, 6H); MS (m/z): [M+H]$^+$ 648.1.

(33) N,N'-(2-(2-amino-4,6-diethoxypyrimidin-5-ylthio)pyrimidine-4,6-diyl) diacetamide A solution of 32 (2.00 g, 3.09 mmol) in 20 mL TFA: CHCl$_3$ (1:1) was heated at 62° C. for 24 h. Excess TFA and solvent were removed under reduced pressure and the residue was purified by column chromatography (CH$_2$Cl$_2$: MeOH, 20:1) to afford 1.15 g, (92%) of 33 [MS (m/z): [M+H]$^+$ 407.8].

(34) N,N'-(2-(2-fluoro-4,6-diethoxypyrimidin-5-ylthio)pyrimidine-4,6-diyl) diacetamide 33 (1.5 g, 3.68 mmol) was added to a plastic tube fitted with a stir bar and cooled to 0° C. Then a solution of HF/pyridine (3.0 mL, 120 mmol) was added. After several minutes NaNO$_2$ (0.380 g, 5.52 mmol) was added in portions over a period of 20 minutes with stirring. It was vigorously stirred for an additional 50 minutes at 0° C. CaCO$_3$ (12.0 g, 120 mmol) was added to destroy excess HF. The mixture was extracted with CH$_2$Cl$_2$ and purified by column chromatography (CH$_2$Cl$_2$:MeOH—NH$_3$ (7N), 20:1) to afford 0.76 g (46%) of 34. $^1$H NMR (500 MHz, CDCl$_3$): δ 8.47 (br s, 1H), 7.85 (br s, 2H), 4.44 (q, J=7.1 Hz, 4H), 2.17 (s, 6H), 1.31 (t, J=7.1 Hz, 6H); MS (m/z): [M+H]$^+$ 411.3.

(35) N,N'-(2-(4,6-diethoxy-2-(4-methylpiperazin-1-yl)pyrimidin-5-ylthio)pyrimidine-4,6-diyl)diacetamide To a solution of 34 (0.165 g, 0.402 mmol) in 3 mL DMF was added 1-methylpiperazine (400 mg, 4.4 mmol) and was heated to 90° C. for 1 h. Solvent was removed under reduced pressure and the residue was purified by column chromatography (CH$_2$Cl$_2$:MeOH—NH$_3$ (7N), 10:1) to yield 0.180 g (91%) of 35. $^1$H NMR (500 MHz, CDCl$_3$): δ 8.35 (br s, 1H), 8.06 (br s, 2H), 4.35 (q, J=7.1 Hz, 4H), 3.82 (m, 4H), 2.43 (m, 4H), 2.36 (s, 3H), 2.15 (s, 6H), 1.26 (t, J=7.1 Hz, 6H); MS (m/z): [M+H]$^+$ 491.2.

(36)—2-(4,6-diethoxy-2-(4-methylpiperazin-1-yl)pyrimidin-5-ylthio)pyrimidine-4,6-diamine A mixture of 35 (0.130 g, 0.265 mmol), 1 N NaOH (aq.) (2 mL) in 7 mL methanol was stirred at 60° C. for 1 h. Solvent was removed under reduced pressure and the residue was purified by preparatory TLC (CH$_2$Cl$_2$:MeOH, 10:1) to afford 0.100 g (93%) of 36. $^1$H NMR (500 MHz, CDCl$_3$): δ 5.17 (br s, 1H), 4.48 (s, 4H), 4.34 (q, J=7.1 Hz, 4H), 3.83 (m, 4H), 2.47 (m, 4H), 2.35 (s, 3H), 1.27 (t, J=7.1 Hz, 6H); MS (m/z): [M+H]$^+$ 407.1.

YK30 (15)—N-(6-amino-2-(4,6-diethoxy-2-(4-methylpiperazin-1-yl)pyrimidin-5-ylthio)pyrimidin-4-yl)acrylamide To a solution of 36 (20 mg, 0.049 mmol) and Et$_3$N (49 mg, 0.49 mmol) in 1 mL anhydrous dioxane was added acryloyl chloride (44 mg, 0.49 mmol) dropwise. The resulting mixture was stirred at rt for 12 h. Solvent was removed under reduced pressure and the residue was purified by preparatory TLC (CHCl$_3$:MeOH—NH$_3$ (7N), 10:1) to afford 9 mg (40%) of 15. $^1$H NMR (500 MHz, CDCl$_3$): δ 8.14 (br s, 1H), 7.04 (s, 1H), 6.40 (d, J=16.9 Hz, 1H), 6.19 (dd, J=16.9, 10.4 Hz, 1H), 5.77 (d, J=10.4 Hz, 1H), 4.83 (br s, 2H), 4.35 (q, J=7.0 Hz, 4H), 3.83 (m, 4H), 2.46 (m, 4H), 2.35 (s, 3H), 1.28 (t, J=7.0 Hz, 6H); $^{13}$C NMR (166 MHz, DMSO-d6): δ 170.1, 169.2, 164.8, 164.2, 159.4, 156.4, 131.3, 128.1, 87.5, 79.9, 62.0, 54.3, 46.6, 43.2, 14.4; HRMS (m/z): [M+H]$^+$ calculated for C$_{20}$H$_{29}$N$_8$O$_3$S, 461.2083; found 461.2096; HPLC: (a) H$_2$O+0.1% TFA (b) ACN+0.1% TFA (5 to 95% ACN in 10 min.) Rt=5.57 min.

YK31 (16)—N-(6-amino-2-(4,6-diethoxy-2-(4-methylpiperazin-1-yl)pyrimidin-5-ylthio) pyrimidin-4-yl)propionamide To a solution of 36 (20 mg, 0.049 mmol) and Et$_3$N (49 mg, 0.49 mmol) in 1 mL anhydrous dioxane was added propionyl chloride (45 mg, 0.49 mmol) dropwise. The resulting mixture was stirred at rt for 12 h. Solvent was removed under reduced pressure and the residue was purified by preparatory TLC (CHCl$_3$:MeOH—NH$_3$ (7N), 10:1) to afford 15 mg (66%) of 16. $^1$H NMR (500 MHz, CDCl$_3$): δ 8.17 (br s, 1H), 6.95 (s, 1H), 4.84 (br s, 2H), 4.35 (q, J=7.5, 4H), 3.82 (m, 4H), 2.44 (m, 4H), 2.34 (s, 3H), 2.34 (q, J=7.5 Hz, 2H), 1.28 (t, J=7.5 Hz, 6H), 1.15 (t, J=7.5 Hz, 3H); $^{13}$C NMR (166 MHz, CDCl$_3$): δ 173.3, 170.6, 170.5, 164.2, 160.0, 156.7, 87.7, 80.3, 62.4, 54.9, 46.3, 43.7, 30.6, 14.5, 9.1; HRMS (m/z): [M+H]$^+$ calculated for C$_{20}$H$_{31}$N$_8$O$_3$S, 463.2240; found 463.2253; HPLC: (a) H$_2$O+0.1% TFA (b) ACN+0.1% TFA (5 to 95% ACN in 10 min.) Rt=6.22 min.

Synthetic Scheme 3
Synthetic Scheme 3 provides examples of synthesizing compunds 38-43, YK57 (11), and YK56 (10).

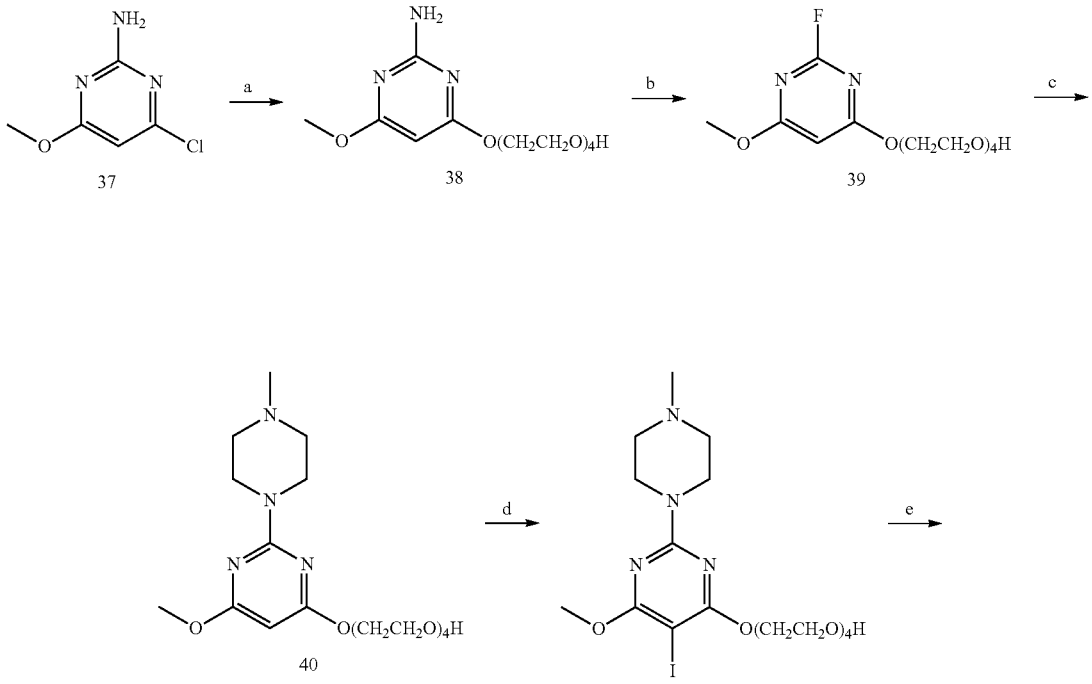

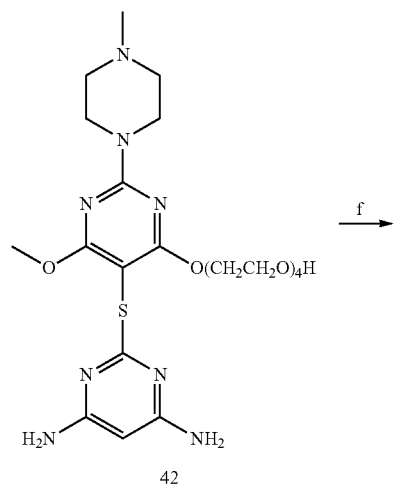
42
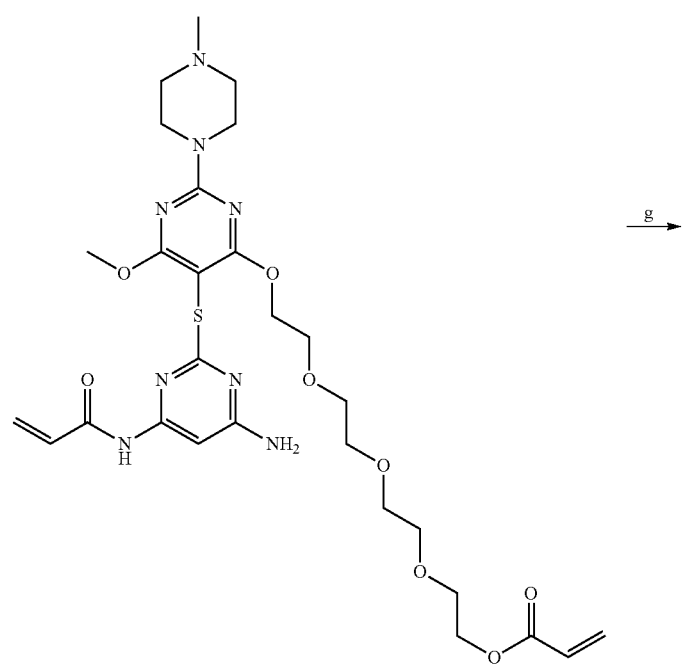
43
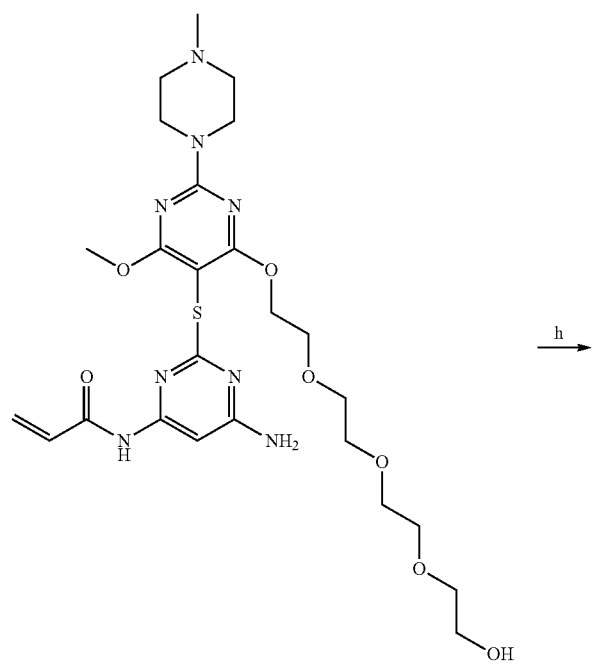
YK57_11

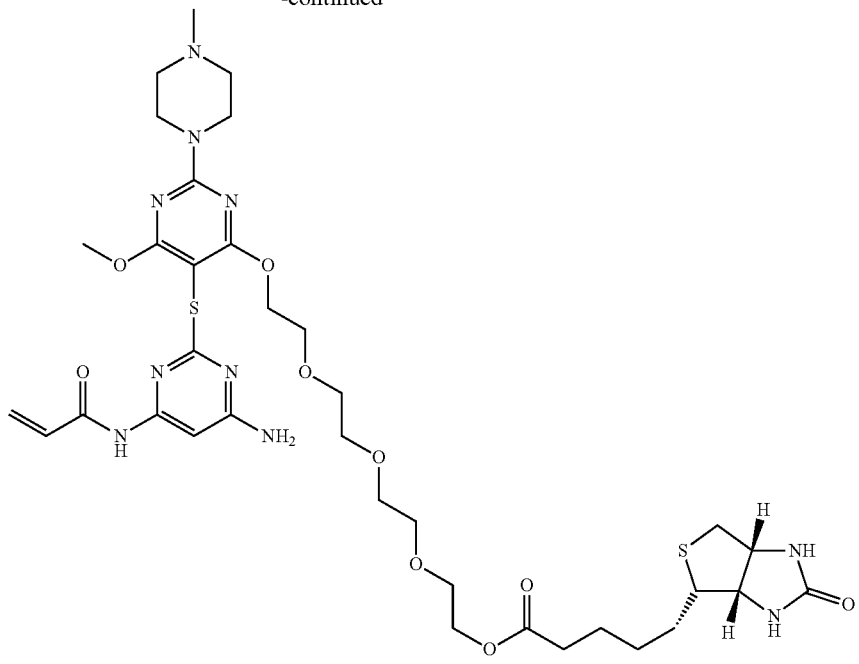

YK56 10

Reagents and conditions: (a) H(OCH₂CH₂)₄OH, DMF 80° C. 3 h, ,83%; (b) HF/pyridine, NaNO₂, 0° C., 42%; (c) 1-methylpiperazine, DMF, 90° C., 1 h, 91%; (d) NIS, CH₃CN, rt, 1.5 h, ,85%; (e) 4,6-diamino-2-mercaptopyrimidine, neocuproine, CuI, K₃PO₄, DMSO, 150° C., 2.5 h, 73%; (f) acryloyl chloride, Et₃N, CH₂Cl₂, 0° C. to rt, 8 h, 38%; (g) NaOH, H₂O, THF, rt, 6 h, 52%; (h) D-biotin, DCC, DMAP, CH₂Cl₂, sonicate, 8 h, 72%.

(38)—2-(2-(2-(2-(2-amino-6-methoxypyrimidin-4-yloxy)ethoxy)ethoxy)ethoxy) ethanol To 7.28 g (37.5 mmol) of tetraethylene glycol dissolved in 20 mL of DMF was added 0.900 g (37.5 mmol) of NaH and the resulting suspension was stirred for 10 minutes at rt. Then 2.0 g (12.5 mmol) of 2-amino-4-chloro-6-methoxypyrimidine was added and the reaction mixture heated at 80° C. for 3 h. Solvent was removed under reduced pressure and the oily residue was purified by column chromatography (EtOAc:MeOH, 100:0 to 95:5) to give 3.30 g (83%) of an oil 38. TLC (EtOAc:MeOH, 95:5 v/v): Rf=0.24; $^1$H NMR (500 MHz, CDCl₃): δ 5.48 (s, 1H), 5.08 (br s, 2H), 4.39 (t, J=4.8 Hz, 2H), 3.83 (s, 3H), 3.79 (t, J=4.8 Hz, 2H), 3.60-3.73 (m, 12H), 3.21 (br s, 1H); $^{13}$C NMR (166 MHz, CDCl₃): δ 172.6, 172.0, 162.4, 80.2, 72.8, 70.86, 70.80, 70.77, 70.57, 69.7, 65.6, 61.8, 53.9; MS (m/z): [M+H]⁺ 318.1.

(39)—2-(2-(2-(2-(2-fluoro-6-methoxypyrimidin-4-yloxy)ethoxy)ethoxy)ethoxy) ethanol 1.55 g (4.88 mmol) of 38 was added to a plastic tube fitted with a stir bar and cooled to 0° C. Then a solution of HF/pyridine (1.22 ml, 48.8 mmol) was added. After several minutes 0.505 g (7.32 mmol) of NaNO₂ was added in portions over a period of 20 minutes with stirring. It was vigorously stirred for an additional 70 minutes at 0° C. and at rt for 3 hours. Then 15 ml of CH₂Cl₂ and 4.88 g of CaCO₃ (48.8 mmol) were added and the mixture was stirred for 5 hours at rt. It was then filtered over a cintered disc funnel and the solid washed with EtOAc (4×25 ml). The combined filtrate was filtered over celite, concentrated under reduced pressure and the oily residue was purified by column chromatography (EtOAc:MeOH, 100:0 to 95:5) to give 0.65 g (42%) of an oil 39. TLC (EtOAc): Rf=0.19; $^1$H NMR (500 MHz, CDCl₃): δ 5.99 (s, 1H), 4.48-4.50 (m, 2H), 3.95 (s, 3H), 3.80-3.84 (m, 2H), 3.58-3.75 (m, 12H), 2.56 (br s, 1H); $^{13}$C NMR (166 MHz, CDCl₃): δ 173.7 (d, J=15.7 Hz), 173.0 (d, J=15.7 Hz), 161.6 (d, J=215.9 Hz), 88.0 (d, J=6.8 Hz), 72.5, 70.70, 70.68, 70.57, 70.37, 69.2, 66.6, 61.8, 54.7; MS (m/z): [M+H]⁺ 321.2.

(40) 2-(2-(2-(2-(6-methoxy-2-(4-methylpiperazin-1-yl)pyrimidin-4-yloxy)ethoxy) ethoxy) ethoxy)ethanol 0.55 g (1.72 mmol) of 39 was dissolved in 40 ml of DMF and 1.72 g (17.2 mmol) of 1-methylpiperazine was added and heated at 90° C. for 1 h. Solvent and excess reagent were removed under reduced pressure and the oily residue was purified by column chromatography (CH₂Cl₂:MeOH—NH₃ (7N), 20:1) to give 0.63 g (91%) of an oil 40. TLC (CH₂Cl₂:MeOH—NH₃ (7N), 20:1 v/v): Rf=0.24; $^1$H NMR (500 MHz, CDCl₃): δ 5.40 (s, 1H), 4.42 (t, J=5.0 Hz, 2H), 3.85 (s, 3H), 3.80 (t, J=5.1 Hz, 4H), 3.65-3.73 (m, 12H), 3.60 (t, J=4.5 Hz, 2H), 2.44 (t, J=5.1 Hz, 4H), 2.33 (s, 3H); $^{13}$C NMR (166 MHz, CDCl₃): δ 172.0, 171.3, 160.7, 78.5, 72.6, 71.8, 70.64, 70.55, 70.33, 69.5, 65.1, 61.7, 54.9, 53.5, 46.2, 43.7; MS (m/z): [M+H]⁺ 401.3.

(41) 2-(2-(2-(2-(5-iodo-6-methoxy-2-(4-methylpiperazin-1-yl)pyrimidin-4-yloxy) ethoxy) ethoxy) ethoxy)ethanol To 0.600 g (1.50 mmol) of 40 dissolved in 20 ml CH₃CN was added 0.581 g (2.58 mmol) of N-iodosuccinimide and the solution was stirred for 1.5 h at rt. Solvent was removed under reduced pressure and the oily residue was purified by column chromatography (CHCl₃:MeOH:Et₃N, 90:10:2) to give 0.670 g (85%) of an oil 41. TLC (CHCl$_3$:MeOH:Et$_3$N, 90:10:2 v/v/v): R$_f$=0.29; $^1$H NMR (500 MHz, CDCl$_3$): δ 4.46 (t, J=4.7 Hz, 2H), 3.92 (s, 3H), 3.86 (m, 4H), 3.57-3.83 (m, 14H), 2.46 (m, 4H), 2.33 (s, 3H); MS (m/z): [M+H]$^+$ 527.2.

(42)—2-(2-(2-(2-(5-(4,6-diaminopyrimidin-2-yl-thio)-6-methoxy-2-(4-methylpiperazin-1-yl)pyrimidin-4-yloxy)ethoxy)ethoxy)ethanol 0.620 g (1.18 mmol) of 41, 0.501 g (2.36 mmol) K$_3$PO$_4$, 0.053 g (0.236 mmol) neocuproine, 0.045 g (0.236 mmol) copper iodide, and 0.184 g (1.30 mmol) 4,6-diamino-2-mercaptopyrimidine in 14 ml DMSO was heated at 150° C. for 2.5 h. Solvent was removed under reduced pressure and the residue was purified by column chromatography (CHCl$_3$:MeOH:Et$_3$N, 99:1:2 to 95:5:2) to give 0.465 g (73%) of 42. TLC (CHCl$_3$:MeOH:Et$_3$N, 85:15:2 v/v/v): Rf=0.35; $^1$H NMR (500 MHz, CDCl$_3$): δ 5.18 (s, 1H), 4.94 (br s, 4H), 4.45 (t, J=4.2 Hz, 2H), 3.87 (s, 3H), 3.80-3.86 (br s, 4H), 3.74 (t, J=4.2 Hz, 2H), 3.69 (t, J=4.7 Hz, 2H), 3.51-3.63 (m, 10H), 2.46 (t, J=4.6 Hz, 4H), 2.35 (s, 3H); MS (m/z): [M+H]$^+$ 541.4.

(43)—2-(2-(2-(2-(4-acrylamido-6-aminopyrimidin-2-ylthio)-6-methoxy-2-(4-methyl piperazin-1-yl)pyrimidin-4-yloxy)ethoxy)ethyl acrylate To 0.100 g (0.185 mmol) of 42 in 2 ml of CH$_2$Cl$_2$ at 0° C. was added 0.037 g (51 μl, 0.370 mmol) of Et$_3$N. Then 0.117 g (105 μl, 1.30 mmol) of acryloyl chloride was added at 0° C. After 5 minutes the ice-bath was removed and stirring continued at rt. After 2 hrs additional 0.037 g (51 μl, 0.370 mmol) of Et$_3$N and 0.050 g (45 μl, 0.555 mmol) of acryloyl chloride were added and stirring continued for an additional 6 hours. The reaction mixture was concentrated under reduced pressure and the residue purified by preparatory TLC (CH$_2$Cl$_2$:MeOH—NH$_3$ (7N), 12:1) to yield 0.049 g (38%) of 43. $^1$H NMR (500 MHz, CDCl$_3$): δ 8.16 (br s, 1H), 7.06 (s, 1H), 6.39-6.42 (m, 2H), 6.10-6.27 (m, 2H), 5.76-5.83 (m, 2H), 4.92 (s, 2H), 4.49 (br s, 2H), 4.29 (br s, 2H), 3.89 (s, 3H), 3.86 (s, 4H), 3.51-3.74 (m, 12H), 2.48 (s, 4H), 2.37 (s, 3H); MS (m/z): [M+H]$^+$ 649.4.

YK57 (11)—N-(6-amino-2-(4-(2-(2-(2-hydroxy-ethoxy)ethoxy)ethoxy)-6-methoxy-2-(4-methylpiperazin-1-yl)pyrimidin-5-ylthio)pyrimidin-4-yl)acrylamide To 0.042 g (0.0647 mmol) of 43 dissolved in 0.8 ml of THF was added 0.2 mL of 0.5 N NaOH at rt and stirred for 6 hours. The reaction mixture was concentrated under reduced pressure and the residue purified by preparatory TLC (CHCl$_3$:MeOH—NH$_3$ (7N), 10:1) to yield 0.020 g (52%) of 11. $^1$H NMR (500 MHz, CDCl$_3$): δ 8.38 (s, 1H), 7.07 (s, 1H), 6.42 (d, J=16.7 Hz, 1H), 6.24 (dd, J=16.7, 10.3 Hz, 1H), 5.77 (d, J=10.3 Hz, 1H), 4.95 (br s, 2H), 4.49 (br a, 2H), 3.90 (s, 3H), 3.86 (br s, 4H), 3.51-3.74 (m, 14H), 2.47 (br s, 4H), 2.36 (s, 3H); HRMS (m/z): [M+H]$^+$ calculated for C$_{25}$H$_{39}$N$_8$O$_7$S, 595.2662; found, 595.2658; HPLC: (a) H$_2$O+0.1% TFA (b) ACN+0.1% TFA (5 to 95% ACN in 10 min.) Rt=5.05 min.

YK56 (10)—2-(2-(2-(2-(5-(4-acrylamido-6-aminopyrimidin-2-ylthio)-6-methoxy-2-(4-methyl piperazin-1-yl)pyrimidin-4-yloxy)ethoxy)ethoxy)ethyl 5-((3aS,4S,6aR)-2-oxohexa hydro-1H-thieno[3,4-d]imidazol-4-yl)pentanoate 5.0 mg (0.0084 mmol) of 11, 7.0 mg (0.0287 mmol) D-(+)-biotin, 1.0 mg (0.0084 mmol) DMAP, 14.0 mg (0.0679 mmol) DCC in 2 ml of CH$_2$Cl$_2$ was sonicated for 8 hours in a sealed tube. The reaction mixture was concentrated under reduced pressure and the residue purified by preparatory TLC (CHCl$_3$:MeOH—NH$_3$ (7N), 10:1) to yield 5.0 mg (72%) of 10. $^1$H NMR (500 MHz, CDCl$_3$): δ 9.58 (s, 1H), 7.15 (s, 1H), 6.41-6.43 (m, 2H), 6.19 (br s, 1H), 5.77 (br s, 1H), 5.73 (dd, J=7.3, 4.3 Hz, 1H), 5.31 (br s, 2H), 4.5-4.6 (m, 2H), 4.41-4.47 (m, 1H), 4.35-4.4 (m, 1H), 4.15-4.25 (m, 2H), 3.85-3.93 (br s, 7H), 3.5-3.75 (m, 12H), 3.14-3.19 (m, 1H), 2.93 (dd, J=12.9, 4.9 Hz, 1H), 2.84 (d, J=12.7 Hz, 1H), 2.56 (br s, 4H), 2.41 (s, 2H), 2.28 (t, J=7.5 Hz, 3H), 1.37-1.78 (m, 6H); $^{13}$C NMR (166 MHz, CDCl$_3$): δ=173.2, 170.7, 170.2, 169.4, 164.6, 164.3, 163.7, 159.5, 156.6, 130.6, 128.3, 88.3, 77.2, 70.5, 70.2, 70.1, 69.3, 68.8, 65.8, 63.1, 61.8, 59.9, 55.2, 54.2, 53.8, 45.4, 42.9, 40.1, 33.4, 29.3, 27.9, 27.8, 24.4; HRMS (m/z): [M+H]$^+$ calculated for C$_{35}$H$_{53}$N$_{10}$O$_9$S$_2$, 821.3438; found, 821.3439; HPLC: (a) H$_2$O+0.1% TFA (b) ACN+0.1% TFA (5 to 95% ACN in 10 min.) Rt=7.10 min.

Synthetic Scheme 4
Synthetic Scheme 4 provides examples of synthesizing compounds 45-50, YK54 (12), and YK55 (9).

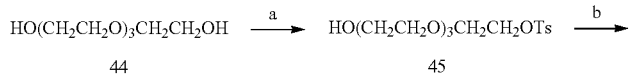

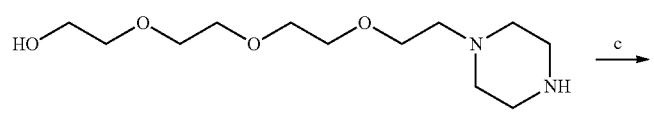

123
124
-continued
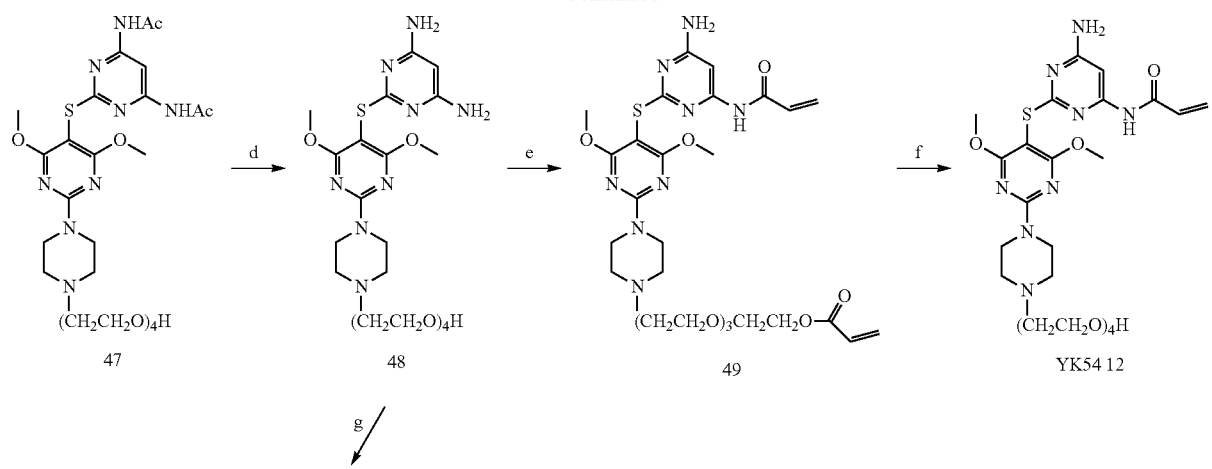
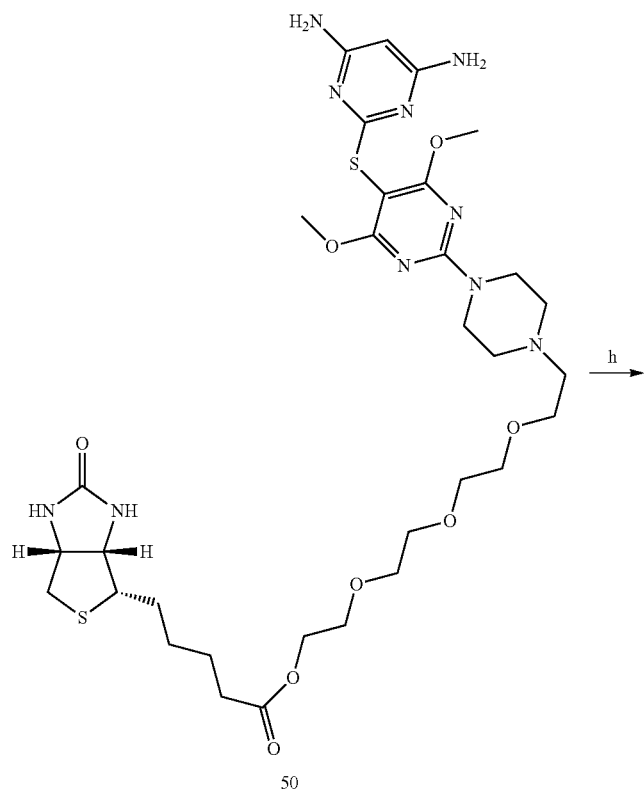

-continued

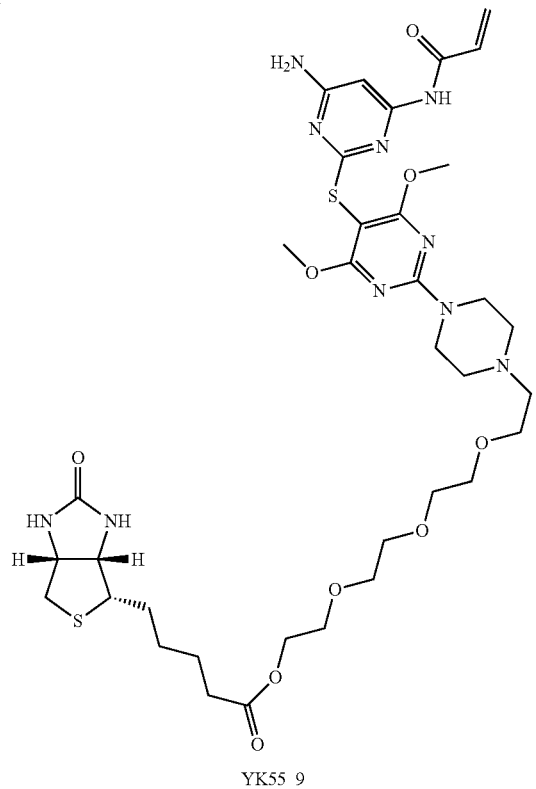

YK55_9

Reagents and conditions: (a) TsCl, NaOH, THF, H₂O, 0° C., 2 h, 78%; (b) piperazine, CH₃CN, 75° C. 12 h, 66%; (c) 24, DMF, 90° C., 2 h, 79%; (d) NaOH, MeOH, H₂O, 60° C., 2 h, 98% (e) acryloyl chloride, Et₃N, CH₂Cl₂, 0° C., 7 h, 36%; (f) NaOH, THF, H₂O, 3 h,75%; (g) D-biotin, DCC, DMAP, CH₂Cl₂, sonication, 13 h, 85%; (h) acryloyl chloride, Et₃N, CH₂Cl₂, 0° C., 6 h, 41%

(45)—2-(2-(2-(2-hydroxyethoxy)ethoxy)ethoxy) ethyl 4-methylbenzenesulfonate 2.0 g (10.3 mmol) of tetraethylene glycol in 10 ml of THF was cooled to 0° C. 0.200 g (5 mmol) of NaOH in 2 ml of distilled water was added and it was stirred for 30 minutes. Then 0.491 g (2.58 mmol) of p-toluenesulfonyl chloride was added slowly and stirring continued at 0° C. for 2 hours. Solvent was removed under reduced pressure and the residue was purified by column chromatography (hexane:EtOAc, 50:50 to 10:90) to give 0.705 g (78%) of an oil 45. TLC (hexane:EtOAc, 10:90 v/v): $R_f$=0.26; $^1$H NMR (500 MHz, CDCl₃): δ 7.80 (d, J=8.1 Hz, 2H), 7.34 (d, J=8.1 Hz, 2H), 4.16 (t, J=4.9 Hz, 2H), 3.59-3.74 (m, 14H), 2.45 (s, 3H); MS (m/z): [M+Na]⁺ 371.3.

(46)—2-(2-(2-(2-(piperazin-1-yl)ethoxy)ethoxy) ethoxy)ethanol 0.705 g (2.02 mmol) of 45 and 0.697 g (8.09 mmol) of piperazine in 45 ml of CH₃CN was heated at 75° C. for 12 h. Solvent and excess reagent were removed under reduced pressure and the oily residue was purified by column chromatography (CH₂Cl₂:MeOH:MeOH—NH₃ (7N), 90:5:5 to 90:0:10) to give 0.350 g (66%) of an oil 46. $^1$H NMR (500 MHz, CDCl₃): δ 3.72 (m, 2H), 3.58-3.70 (m, 12H), 2.91 (m, 4H), 2.59 (br m, 2H), 2.49 (m, 4H); MS (m/z): [M+H]⁺ 263.3.

(47)—N,N'-(2-(2-(4-(2-(2-(2-(2-hydroxyethoxy) ethoxy)ethoxy)ethyl)piperazin-1-yl)-4,6-dimethoxypyrimidin-5-ylthio)pyrimidine-4,6-diyl)diacetamide To 0.430 g (1.12 mmol) of 24 in 27 ml of DMF was added 0.310 g (1.18 mmol) of 46 and was heated at 90° C. for 2 h. Solvent was removed under reduced pressure and the residue was purified by column chromatography (CH₂Cl₂:MeOH, 10:1) to give 0.552 g (79%) of 47. $^1$H NMR (500 MHz, CDCl₃): δ 8.38 (br s, 2H), 8.13 (s, 1H), 3.88 (br s, 10H), 3.57-3.74 (m, 14H), 2.66 (br s, 2H), 2.58 (br s, 4H), 2.15 (s, 6H); MS (m/z): [M+H]⁺ 625.5.

(48)—2-(2-(2-(2-(4-(5-(4,6-diaminopyrimidin-2-ylthio)-4,6-dimethoxypyrimidin-2-yl) piperazin-1-yl)ethoxy)ethoxy)ethoxy)ethanol To 0.520 g (0.832 mmol) of 47 was added 25 ml of MeOH and 7 ml of 10% NaOH (aq.) and the suspension was stirred at 60° C. for 2 h. Solvent was removed under reduced pressure and the residue was purified by column chromatography (CH₂Cl₂:MeOH, 15:1) to give 0.440 g (98%) of 48. $^1$H NMR (500 MHz, CDCl₃): δ 5.17 (s, 1H), 4.60 (br s, 4H), 3.88 (br s, 10H), 3.57-3.77 (m, 14H), 2.67 (br s, 2H), 2.59 (br s, 4H); MS (m/z): [M+H]⁺ 541.4.

(49) 2-(2-(2-(2-(4-(5-(4-acrylamido-6-aminopyrimidin-2-ylthio)-4,6-dimethoxy pyrimidin-2-yl)piperazin-1-yl)ethoxy)ethoxy)ethoxy)ethyl acrylate To 22.6 mg (0.042 mmol) of 48 in 3 ml of CH₂Cl₂ at 0° C. was added 83.6 mg (116 μl, 0.836 mmol) of Et₃N. 11.4 mg (10.2 µl, 0.126 mmol) of acryloyl chloride was added at 0° C. After 1 hour an additional 11.4 mg (10.2 µl, 0.126 mmol) of acryloyl chloride was added. This was repeated five more times for a total reaction time of 7 h (total acryloyl chloride, 79.8 mg, 71.7 µl, 0.882 mmol). The reaction mixture was concentrated under reduced pressure and the residue purified by preparatory TLC (CH$_2$Cl$_2$:MeOH, 10:1) to yield 9.8 mg (36%) of 49. $^1$H NMR (500 MHz, CDCl$_3$): δ 8.10 (br s, 1H), 7.05 (s, 1H), 6.35-6.45 (m, 2H), 6.10-6.20 (m, 2H), 5.73-5.85 (m, 2H), 4.90 (br s, 2H), 4.32 (br s, 2H), 3.89 (br s, 10H), 3.60-3.70 (m, 12H), 2.69 (br s, 2H), 2.61 (br s, 4H); MS (m/z): [M+H]$^+$ 649.5.

YK54 (12) N-(6-amino-2-(2-(4-(2-(2-(2-(2-hydroxy-ethoxy)ethoxy)ethoxy)ethyl) piperazin-1-yl)-4,6-dimethoxypyrimidin-5-ylthio)pyrimidin-4-yl)acryl-amide To 8.0 mg (0.012 mmol) of 49 dissolved in 1.6 ml of THF was added 0.4 mL of 0.5 N NaOH at rt and stirred for 3 hours. The reaction mixture was concentrated under reduced pressure and the residue purified by preparatory TLC (CH$_2$Cl$_2$:MeOH, 10:1) to yield 5.5 mg (75%) of 12. $^1$H NMR (500 MHz, CDCl$_3$): δ 8.65 (s, 1H), 7.03 (s, 1H), 6.36 (d, J=16.2 Hz, 1H), 6.11 (m, 1H), 5.70 (d, J=10.1 Hz, 1H), 5.14 (br s, 2H), 3.88 (br s, 4H), 3.85 (s, 6H), 3.57-3.75 (m, 15H), 2.70 (br s, 2H), 2.62 (br s, 4H); HRMS (m/z): [M+H]$^+$ calculated for C$_{25}$H$_{39}$N$_8$O$_7$S, 595.2662; found, 595.2684. HPLC: (a) H$_2$O+0.1% TFA (b) ACN+0.1% TFA (5 to 95% ACN in 10 min.) Rt=6.05 min.

(50)—2-(2-(2-(2-(4-(5-(4,6-diaminopyrimidin-2-ylthio)-4,6-dimethoxypyrimidin-2-yl) piperazin-1-yl)ethoxy)ethoxy)ethoxy)ethyl 5-((3aS,4S,6aR)-2-oxohexahydro-1Hthieno[3,4-d]imidazol-4-yl) pentanoate 50.0 mg (0.0925 mmol) of 48, 90.0 mg (0.37 mmol) D-(+)-biotin, 11.3 mg (0.0925 mmol) DMAP, 153.0 mg (0.74 mmol) DCC in 15 ml of CH$_2$Cl$_2$ was sonicated for 13 hours in a sealed tube. The reaction mixture was evaporated to dryness and the residue column chromatographed (CH$_2$Cl$_2$:MeOH—NH$_3$ (7N), 20:1 to 10:1) to give impure 50 which was purified by preparatory TLC (CHCl$_3$: MeOH—NH$_3$ (7N), 10:1) to yield 60.0 mg (85%) of 50. $^1$H NMR (500 MHz, CDCl$_3$): δ 5.27 (br s, 1H), 5.18 (s, 1H), 4.82 (br s, 1H), 4.59 (br s, 4H), 4.49 (m, 1H), 4.32 (m, 1H), 4.22 (m, 2H), 3.88 (br s, 10H), 3.60-3.75 (m, 12H), 3.15 (m, 1H), 2.92 (m, 1H), 2.90 (m, 1H), 2.69 (m, 2H), 2.60 (m, 4H), 2.34 (t, J=5.9 Hz, 2H), 1.37-1.78 (m, 6H); HRMS (m/z): [M+H]$^+$ calculated for C$_{32}$H$_{51}$N$_{10}$O$_8$S2, 767.3333; found 767.3361.

YK55 (9)—2-(2-(2-(2-(4-(5-(4-acrylamido-6-amin-opyrimidin-2-ylthio)-4,6-dimethoxy pyrimidin-2-yl) piperazin-1-yl)ethoxy)ethoxy)ethoxy)ethyl 5-((3aS, 4S,6aR)-2-oxohexahydro-1H-thieno[3,4-d]imidazol-4-yl)pentanoate To 50.0 mg (0.065 mmol) of 50 in 10 ml of CH$_2$Cl$_2$ at 0° C. was added 195.4 mg (271 µl, 1.953 mmol) of Et$_3$N. Then 17.7 mg (15.9 µl, 0.196 mmol) of acryloyl chloride was added at 0° C. After 1 hour an additional 17.7 mg (15.9 µl, 0.196 mmol) of acryloyl chloride was added. This was repeated four more times for a total reaction time of 6 hours (total acryloyl chloride, 106.2 mg, 95.4 µl, 1.17 mmol). The reaction mixture was concentrated under reduced pressure and the residue purified by preparatory TLC (CHCl$_3$: MeOH—NH$_3$ (7N), 10:1) to yield 22.0 mg (41%) of 9. $^1$H NMR (500 MHz, CDCl$_3$): δ 8.99 (s, 1H), 7.09 (s, 1H), 6.40 (d, J=16.8 Hz, 1H), 6.31 (dd, J=16.7, 9.9 Hz, 1H), 5.79 (br s, 1H), 5.74 (d, J=10.8 Hz, 1H), 5.09 (s, 2H), 5.08 (s, 1H), 4.50 (m, 1H), 4.36 (m, 1H), 4.21 (t, J=6.8 Hz, 2H), 3.87 (s, 10H), 3.6-3.75 (m, 12H), 3.16 (m, 1H), 2.91 (dd, J=12.8, 5.0 Hz, 1H), 2.74 (d, J=12.8 Hz, 1H), 2.70 (t, J=5.4 Hz, 2H), 2.61 (t, J=4.8 Hz, 4H), 2.31 (t, J=7.6 Hz, 2H), 1.37-1.8 (m, 6H); $^{13}$C NMR (166 MHz, CDCl$_3$): δ 172.9, 170.4, 169.5, 164.1, 164.0, 163.2, 159.3, 156.3, 130.3, 127.9, 88.1, 78.9, 69.9, 69.8, 69.7, 68.5, 68.0, 62.8, 61.4, 59.6, 57.7, 57.1, 54.9, 53.5, 52.5, 42.9, 39.9, 33.1, 27.8, 27.6, 24.0; HRMS (m/z): [M+H]$^+$ calculated for C$_{35}$H$_{53}$N$_{10}$O$_9$S$_2$, 821.3438; found 821.3455; HPLC: (a) H$_2$O+0.1% TFA (b) ACN+0.1% TFA (5 to 95% ACN in 10 min.) Rt=6.98 min.

Scheme 5. Preparation of Cy3B-YK (57).

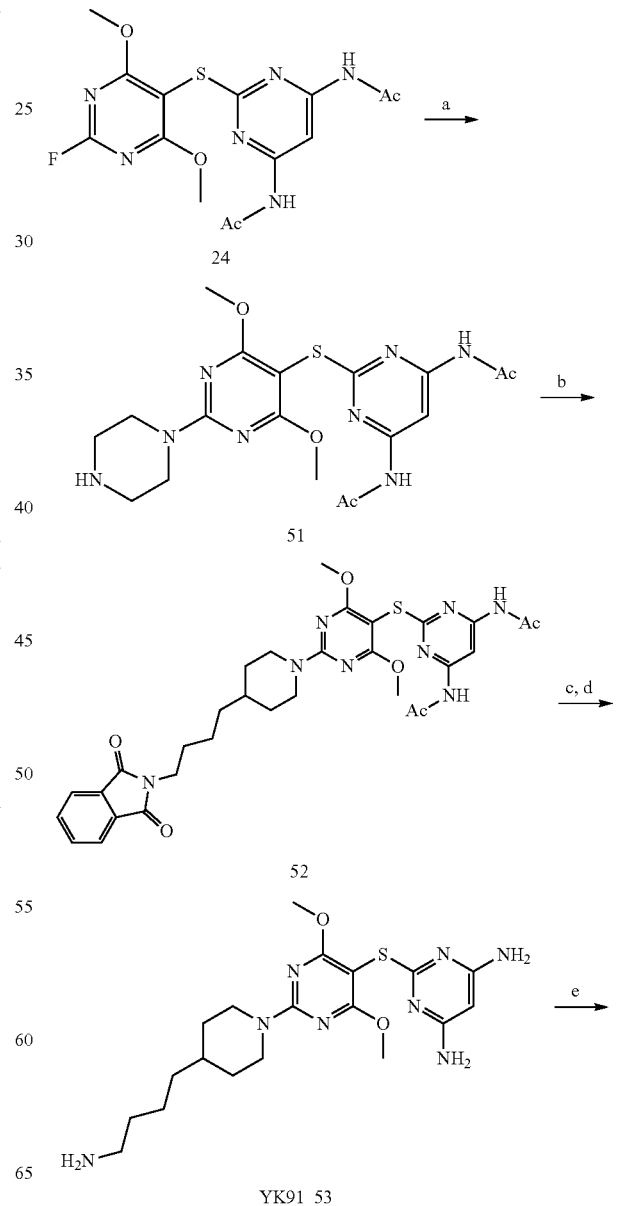

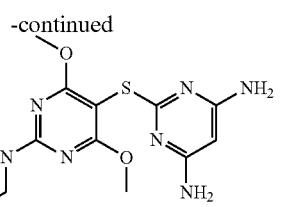

54

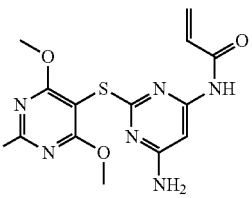

55

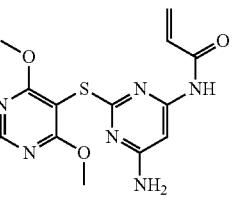

56

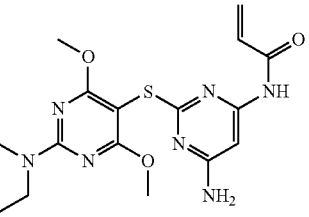

57

Reagents and conditions; a. piperazine, DMF, 90° C., 1 h; b. N-(4-bromobutyl)phthalimide, DMF, 80° C., 1 h; c. hydrazine, THF, rt, 16 h; d. NaOH, methanol, 60° C., 1 h; e. di-t-butyldicarbonate, Et₃N, CH₂Cl₂, rt, 2 h; f. acryloyl chloride, Et₃N, CH₂Cl₂; g. TFA:CH₂Cl₂ (1:4), rt, 1 h; h Cy3B—OSu, DMF, rt, 12 h.

(51) N,N'-(2-((4,6-dimethoxy-2-(piperazin-1-yl)pyrimidin-5-yl)thio)pyrimidine-4,6-diyl)diacetamide A solution of 24 (100 mg, 0.26 mmol) and piperazine (45 mg, 0.52 mmol) in 5 mL DMF was heated to 90° C. for 1 h. Solvent was removed under reduced pressure and the residue was purified by column chromatography (CH₂Cl₂:MeOH—NH₃ (7N), 10:1) to afford 84 mg (72%) of 51. ¹H NMR (500 MHz, CDCl₃) δ 8.20 (s, 1H), 8.03 (s, 2H), 3.87 (s, 6H), 3.80 (m, 4H), 3.45 (m, 4H), 2.08 (s, 6H); MS (m/z): [M+H]⁺ 449.1.

(52) N,N'-(2-((2-(4-(4-(1,3-dioxoisoindolin-2-yl)butyl)piperazin-1-yl)-4,6-dimethoxypyrimidin-5-yl)thio)pyrimidine-4,6-diyl)diacetamide A solution of 51 (50 mg, 0.111 mmol) and N-(4-bromobutyl)phthalimide (125 mg, 0.446 mmol) in 5 mL DMF was heated to 80° C. for 1 h. Solvent was removed under reduced pressure. The residue was purified by column chromatography (CH₂Cl₂:MeOH—NH₃ (7N), 10:1) to afford 61 mg (86%) of 52. MS (m/z): [M+H]⁺ 650.1.

(53) 2-((2-(4-(4-aminobutyl)piperazin-1-yl)-4,6-dimethoxypyrimidin-5-yl)thio)pyrimidine-4,6-diamine [YK91]

To a solution of 52 (61 mg, 0.095 mmol) in 3 mL THF was added hydrazine (100 μL). The resulting mixture was stirred for 16 h at rt, then the solvent was evaporated under reduced pressure. To the residue was added methanol (10 ml), sodium hydroxide (500 mg) and the mixture was heated to 60° C. for 1 h. Solvent was removed under reduced pressure and the residue was purified by column chromatography (CH₂Cl₂:MeOH—NH₃ (7N), 10:1) to afford 25 mg (60%) of 53. ¹H NMR (500 MHz, CDCl₃) δ 5.16 (s, 1H), 4.58 (s, 4H), 3.87 (s, 6H), 3.71 (m, 4H), 2.75 (m, 2H), 2.50 (m, 4H), 2.36 (m, 2H), 1.68 (m, 2H), 1.60 (m, 2H); MS (m/z): [M+H]⁺ 436.1.

(54) tert-butyl 4-(4-(5-(4,6-diaminopyrimidin-2-ylthio)-4,6-dimethoxypyrimidin-2-yl)piperazin-1-yl)butylcarbamate To a solution of 53 (80 mg, 0.18 mmol) and Et₃N (100 μL) in 3 mL CH₂Cl₂ was added di-t-butyldicarbonate (39 mg, 0.18 mmol). The mixture was stirred at rt for 2 h. Solvent was evaporated under reduced pressure, the residue was purified by column chromatography (CH₂Cl₂:MeOH—NH₃ (7N), 10:1) to afford 95 mg (95%) of 54 which was carried on to the next reaction.

(55) tert-butyl (4-(4-(5-((4,6-diaminopyrimidin-2-yl)thio)-4,6-dimethoxypyrimidin-2-yl)piperazin-1-yl)butyl)carbamate To a solution of 54 (95 mg, 0.18 mmol) and Et₃N (94 μl) in 5 mL CH₂Cl₂ was added acryloyl chloride in portions. The reaction was monitored by TLC, when the SM disappeared, the reaction was quenched by adding methanol under cooling conditions. Product was purified by preparatory TLC (CH₂Cl₂:MeOH—NH₃ (7N), 10:1) to afford 48 mg (46%) of 55. ¹H NMR (500 MHz, CDCl₃) δ 8.21 (s, 1H), 7.05 (s, 1H), 6.42 (m, 1H), 6.32 (m, 1H), 5.79 (m, 1H), 3.88 (s, 6H), 3.87 (m, 4H), 3.15 (m, 2H), 2.49 (m, 4H), 2.39 (m, 4H), 1.59 (m, 4H), 1.44 (s, 9H); MS (m/z): [M+H]⁺ 590.4.

(56) N-(6-amino-2-((2-(4-(4-aminobutyl)piperazin-1-yl)-4,6-dimethoxypyrimidin-5-yl)thio)pyrimidin-4-yl)acrylamide The solution of 55 (48 mg, 17 mmol) in 20% TFA-CH$_2$Cl$_2$ was stirred at rt for 1 h. Solvent was removed under reduced pressure and the residue was dried under high vacuum to afford 31 mg (80%) of 56 which was used without further purification. $^1$H NMR (500 MHz, CDCl$_3$) δ 7.01 (s, 1H), 6.40 (m, 1H), 6.29 (m, 1H), 5.80 (m, 1H), 3.88 (s, 6H), 3.86 (m, 4H), 2.75 (t, J=7.5, 2H), 2.54 (m, 4H), 2.45 (m, 2H), 1.59 (m, 4H); MS (m/z): [M+H]$^+$ 490.2.

(57) Cy3B-YK5

A solution of Cy3B-OSu (1 mg, 0.00178 mmole) and 56 (1.74 mg, 0.0035 mmol) in 100 μL of DMF was stirred at rt for 12 h. The product was purified by HPLC to afford 57 (0.54 mg, yield 30%). MS (m/z): [M+H]$^+$ 1312.4.

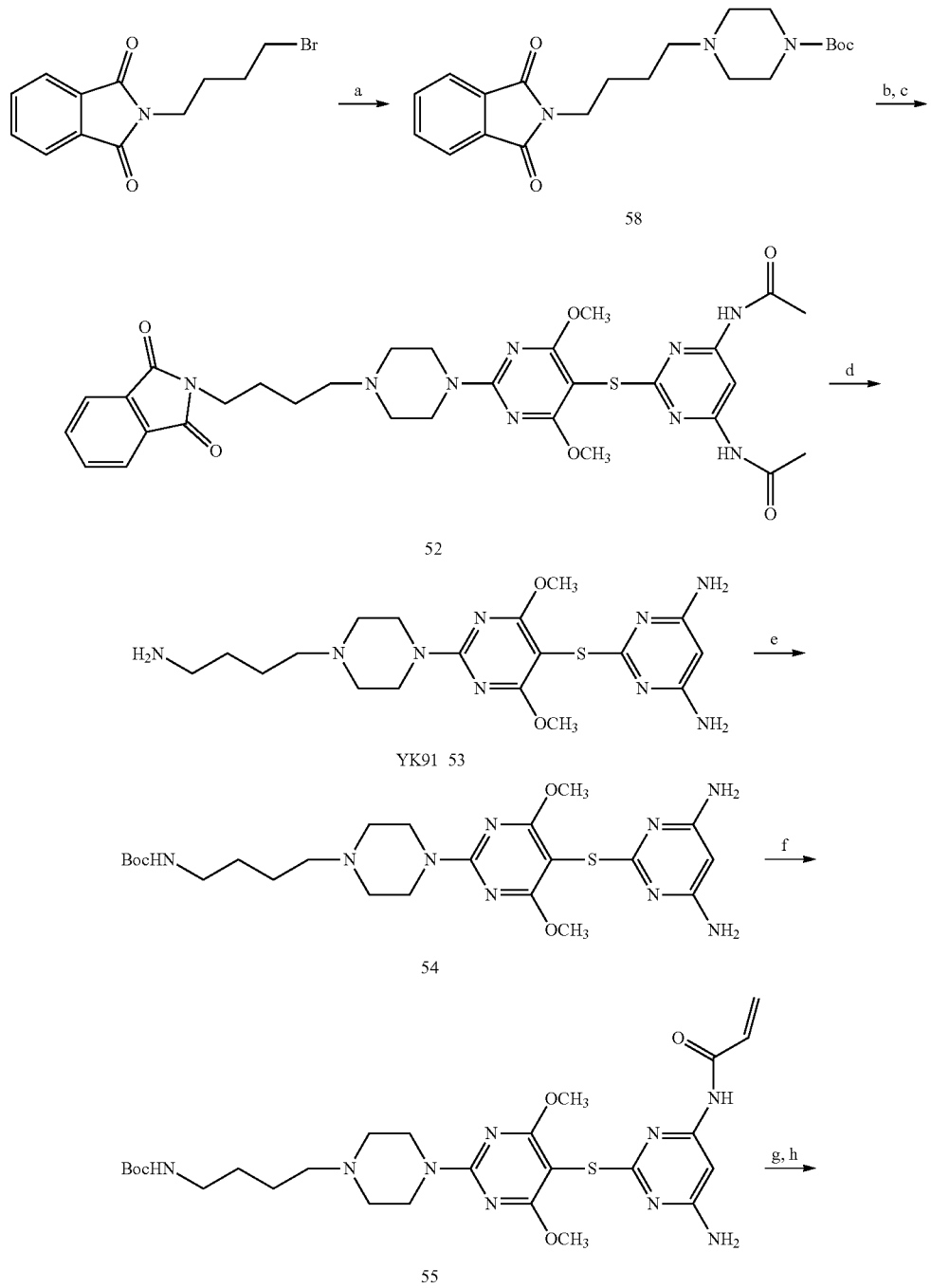

Scheme 6. Preparation of YK5 beads (59).

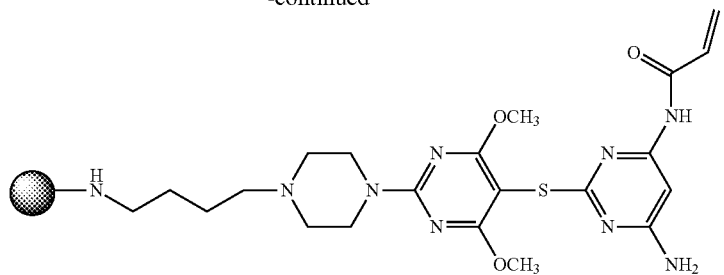

59

Reagents and conditions: a. 1-Boc-piperazine, NaI, K₂CO₃, acetone, reflux, 22 h; b. CH₂Cl₂:TFA (4:1), rt, 1 h; c. 24, K₂CO₃, 90° C., 1.5 h; d. hydrazine hydrate, MeOH, rt, 2 h, then 1M NaOH, 55° C., 2 h; e. di-t-butyldicarbonate, Et₃N, CH₂Cl₂, rt, 20 h; f. acryloyl chloride, Et₃N, CH₂Cl₂, 0° C., 2 h; g. CH₂Cl₂:TFA (4:1), rt, 45 min.; h. Affi-Gel® 10 beads, DIEA, DMAP, DMF, 3 h.

(58) tert-Butyl 4-(4-(1,3-dioxoisoindolin-2-yl)butyl) piperazine-1-carboxylate

N-(4-Bromobutyl)phthalimide (1.95 g, 6.89 mmol) and sodium iodide (81 mg, 0.537 mmol) were added to a suspension of K₂CO₃ (1.64 g, 11.88 mmol) and 1-Boc-piperazine (1.00 g, 5.37 mmol) in acetone (25 mL) and refluxed for 22 h. The reaction mixture was filtered and the solid was washed with acetone (3×50 mL). The filtrate was concentrated and the residue purified by column chromatography (hexane:EtOAc, 7:3 to 0:1) to afford 2.08 g (100%) of 58. ¹H NMR (500 MHz, CDCl₃): δ 7.84 (dd, J=3.0, 5.4 Hz, 2H), 7.71 (dd, J=3.0, 5.4 Hz, 2H), 3.71 (t, J=7.1 Hz, 2H), 3.38-3.43 (m, 4H), 2.32-2.40 (m, 6H), 1.70 (m, 2H), 1.53 (m, 2H), 1.45 (s, 9H); MS (m/z): [M+H]⁺ 388.4.

(52) N,N'-(2-(2-(4-(4-(1,3-dioxoisoindolin-2-yl) butyl)piperazin-1-yl)-4,6-dimethoxypyrimidin-5-ylthio)pyrimidine-4,6-diyl)diacetamide To 58 (429.7 mg, 1.11 mmol) in CH₂Cl₂ (12 mL) was added TFA (3 mL) dropwise and stirred at rt for 1 h. The reaction mixture was concentrated under reduced pressure and TFA removed by co-evaporating with MeOH several times and drying under high vacuum overnight. To this was added K₂CO₃ (384 mg, 2.78 mmol) and DMF (21 mL) and the resulting suspension was stirred at rt for 10 min. Then 24 (424 mg, 1.11 mmol) was added and the suspension was heated at 90° C. for 90 min. Solvent was removed under reduced pressure and the residue was purified by column chromatography (CH₂Cl₂:MeOH, 100:1 to 40:1) to give 0.355 g (49%) of 52. ¹H NMR (500 MHz, CDCl₃): δ 8.35 (br s, 1H), 7.82-7.88 (m, 4H), 7.72 (dd, J=3.1, 5.5 Hz, 2H), 3.88 (s, 6H), 3.84 (m, 4H), 3.74 (t, J=7.2 Hz, 2H), 2.48 (m, 4H), 2.43 (t, J=7.4 Hz, 2H), 2.16 (s, 6H), 1.74 (m, 2H), 1.59 (m, 2H); MS (m/z): [M+H]⁺ 650.5.

YK91 (53) 2-(2-(4-(4-aminobutyl)piperazin-1-yl)-4, 6-dimethoxypyrimidin-5-ylthio)pyrimidine-4,6-diamine 52 (0.355 g, 0.546 mmol) in MeOH (10 mL) was added hydrazine hydrate (797 μL, 0.820 g, 16.4 mmol) and stirred at rt for 2 h. Then 5 mL of 1M NaOH was added and the reaction mixture was heated at 55° C. for 2 h. The reaction mixture was concentrated under reduced pressure and the residue purified by column chromatography (CH₂Cl₂: MeOH—NH₃ (7N), 20:1 to 5:1) to give 0.228 g (96%) of 53. ¹H NMR (500 MHz, CDCl₃/MeOH-d₄): δ 5.22 (s, 1H), 3.88 (s, 10H), 2.72 (t, J=7.1 Hz, 2H), 2.53 (m, 4H), 2.42 (t, J=7.2 Hz, 2H), 1.46-1.62 (m, 4H); MS (m/z): [M+H]⁺ 436.4.

(54) tert-butyl 4-(4-(5-(4,6-diaminopyrimidin-2-ylthio)-4,6-dimethoxypyrimidin-2-yl)piperazin-1-yl) butylcarbamate 53 (0.221 g, 0.507 mmol) in CH₂Cl₂ (6 mL) was added Et₃N (107 μL, 77 mg, 0.761 mmol) and di-t-butyldicarbonate (0.133 g, 0.611 mmol) and stirred at rt for 20 h. The reaction mixture was concentrated under reduced pressure and the residue purified by column chromatography (CH₂Cl₂:MeOH—NH₃ (7N), 100:1 to 30:1) to give 0.254 g (93%) of 54. ¹H NMR (500 MHz, CDCl₃): δ 5.19 (s, 1H), 4.41 (s, 4H), 3.89 (m, 10H), 3.14 (m, 2H), 2.50 (m, 4H), 2.40 (t, J=6.8 Hz, 2H), 1.54-1.63 (m, 4H), 1.44 (s, 9H); MS (m/z): [M+H]⁺ 536.5.

(55) tert-butyl 4-(4-(5-(4-acrylamido-6-aminopyrimidin-2-ylthio)-4,6-dimethoxypyrimidin-2-yl)piperazin-1-yl)butylcarbamate To 80 mg (0.149 mmol) of 54 in 8 ml of CH₂Cl₂ at 0° C. was added 414 μl (298 mg, 2.98 mmol) of Et₃N. Then 14.5 μl (16.2 mg, 0.179 mmol) of acryloyl chloride was added. After 30 min. an additional 14.5 μl of acryloyl chloride was added at 0° C. This was repeated two more times for a total reaction time of 2 hours (total acryloyl chloride, 58 μl, 64.8 mg, 0.716 mmol). The reaction was quenched by the addition of 1 mL MeOH and then concentrated under reduced pressure. The residue was purified by preparatory TLC (CH₂Cl₂:MeOH—NH₃ (7N), 15:1) to yield 42.5 mg (48%) of 55. ¹H NMR (500 MHz, CDCl₃): δ 7.78 (s, 1H), 7.05 (s, 1H), 6.42 (d, J=16.9 Hz, 1H), 6.18 (dd, J=10.4, 16.9 Hz, 1H), 5.80 (d, J=10.2, 1H), 5.15 (br s, 1H), 4.80 (br s, 2H), 3.89 (s, 10H), 3.14 (m, 2H), 2.54 (m, 6H), 1.58 (m, 4H), 1.44 (s, 9H); MS (m/z): [M+H]⁺ 590.5.

(59) YK5 Beads

A solution of 55 (45 mg, 0.076 mmol) in 3 ml of CH₂Cl₂ was added 0.75 mL of TFA dropwise at rt. After stirring for 45 min., the reaction mixture was concentrated under reduced pressure. TFA was removed by co-evaporating with MeOH several times and drying under high vacuum overnight to yield a residue which was dissolved in DMF (2 mL) and added to 4.2 mL (0.0636 mmol) of Affi-Gel® 10 beads (prewashed, 3×6 mL DMF) in a solid phase peptide synthesis vessel. 100 μL of N,N-diisopropylethylamine and several crystals of DMAP were added and this was shaken at rt for 3 h. Then the solvent was removed and the beads washed for 10 minutes each time with CH$_2$Cl$_2$ (4×10 mL), DMF (4×10 mL), and i-PrOH (3×10 mL). The YK5 beads (59) were stored in i-PrOH at −80° C.
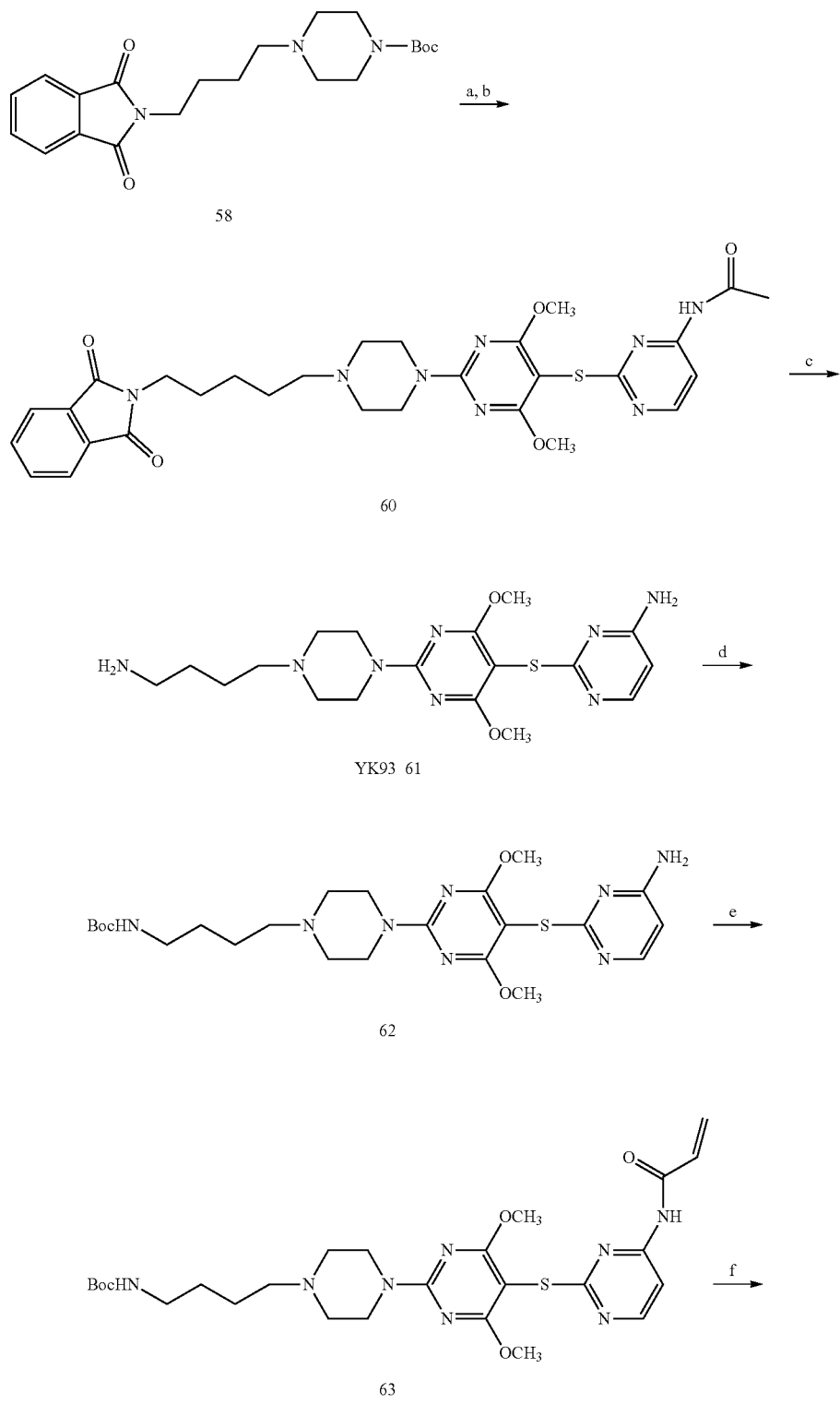

-continued

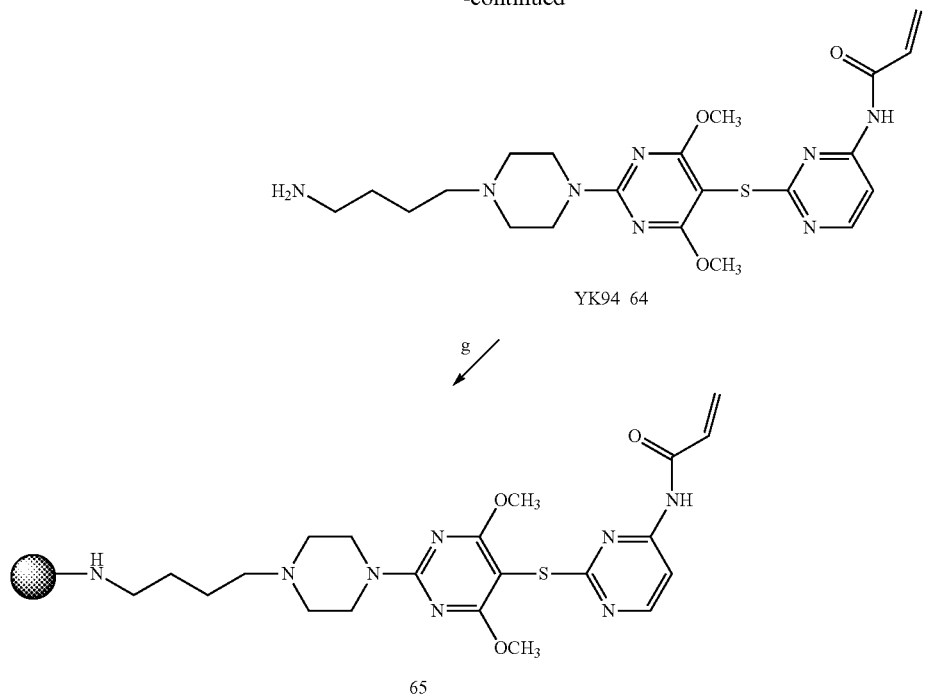

YK94 64 g

65

Reagents and conditions: a. CH₂Cl₂:TFA, (4:1), rt, 1 h; b. N-(2-(2-fluoro-4,6-dimethoxypyrimidin-5-ylthio)pyrimidin-4-yl)acetamide, K₂CO₃, 90° C., 1.5 h; c. hydrazine hydrate, MeOH, rt, 20 h, then 50° C., 3 h; d. di-t-butyldicarbonate, Et₃N, CH₃Cl₂, rt, 20 h; e. acryloyl chloride, Et₃N, CH₂Cl₂, 0° C., 1.5 h; f. CH₂Cl₂:TFA (4:1), rt, 45 min.; g. Affi-Gel® 10 beads, DIEA, DMAP, DMF, 3 h.

(60) N-(2-(2-(4-(4-(1,3-dioxoisoindolin-2-yl)butyl)piperazin-1-yl)-4,6-dimethoxypyrimidin-5-ylthio)pyrimidin-4-yl)acetamide To 58 (402.4 mg, 1.04 mmol) in CH₂Cl₂ (12 mL) is added TFA (3 mL) dropwise and is stirred at rt for 1 h. The reaction mixture was concentrated under reduced pressure and TFA removed by co-evaporating with MeOH several times and drying under high vacuum overnight. To this was added K₂CO₃ (359 mg, 2.6 mmol) and DMF (20 mL) and the resulting suspension was stirred at rt for 10 min. Then N-(2-(2-fluoro-4,6-dimethoxypyrimidin-5-ylthio)pyrimidin-4-yl)acetamide (338 mg, 1.04 mmol) was added and the suspension was heated at 90° C. for 90 min. Solvent was removed under reduced pressure and the residue was purified by column chromatography (CH₂Cl₂:MeOH, 100:1 to 40:1) to give 0.60 g (97%) of 60. ¹H NMR (500 MHz, CDCl₃): δ 8.34 (d, J=5.7 Hz, 1H), 7.85 (dd, J=3.0, 5.4 Hz, 2H), 7.81 (br s, 1H), 7.59-7.71 (m, 3H), 3.88 (s, 6H), 3.85 (m, 4H), 3.74 (t, J=7.1 Hz, 2H), 2.49 (m, 4H), 2.43 (t, J=7.5 Hz, 2H), 2.18 (s, 3H), 1.75 (m, 2H), 1.60 (m, 2H); MS (m/z): [M+H]⁺ 593.4.

YK93 (61) 2-(2-(4-(4-aminobutyl)piperazin-1-yl)-4,6-dimethoxypyrimidin-5-ylthio)pyrimidin-4-amine To 60 (0.600 g, 1.01 mmol) in MeOH (28 mL) was added hydrazine hydrate (813 μL, 0.836 g, 16.7 mmol) and stirred at rt for 20 h. Then additional hydrazine hydrate (813 μL, 0.836 g, 16.7 mmol) was added and the reaction mixture was heated at 50° C. for 3 h. The reaction mixture was concentrated under reduced pressure and the residue purified by column chromatography (CH₂Cl₂:MeOH—NH₃ (7N), 80:1 to 10:1) to give 0.370 g (87%) of 61. ¹H NMR (500 MHz, CDCl₃/MeOH-d₄): δ 7.85 (d, J=5.9 Hz, 1H), 6.11 (d, J=5.9 Hz, 1H), 3.88 (s, 10H), 2.71 (t, J=7.1 Hz, 2H), 2.53 (m, 4H), 2.42 (t, J=7.4 Hz, 2H), 1.47-1.63 (m, 4H); MS (m/z): [M+H]⁺ 421.3.

(62) tert-butyl 4-(4-(5-(4-aminopyrimidin-2-ylthio)-4,6-dimethoxypyridin-2-yl)piperazin-1-yl)butylcarbamate To 61 (0.370 g, 0.880 mmol) in CH₂Cl₂ (10 mL) was added Et₃N (186 μL, 134 mg, 1.32 mmol) and di-t-butyldicarbonate (0.230 g, 1.06 mmol) and stirred at rt for 20 h. The reaction mixture was concentrated under reduced pressure and the residue purified by column chromatography (CH₂Cl₂:MeOH:MeOH—NH₃ (7N), 100:1:0 to 50:0:1) to give 0.44 g (96%) of 62. ¹H NMR (500 MHz, CDCl₃): δ 7.97 (d, J=5.8 Hz, 1H), 6.05 (d, J=5.8 Hz, 1H), 5.21 (br s, 1H), 4.76 (br s, 2H), 3.89 (s, 6H), 3.87 (m, 4H), 3.15 (m, 2H), 2.49 (m, 4H), 2.40 (t, J=6.8 Hz, 2H), 1.54-1.63 (m, 4H), 1.44 (s, 9H); MS (m/z): [M+H]⁺ 521.3.

(63) tert-butyl 4-(4-(5-(4-acrylamidopyrimidin-2-ylthio)-4,6-dimethoxypyrimidin-2-yl)piperazin-1-yl)butylcarbamate To 100 mg (0.192 mmol) of 62 in 10 ml of CH₂Cl₂ at 0° C. was added 533 μl (384 mg, 3.84 mmol) of Et₃N. Then 19 μl (21 mg, 0.23 mmol) of acryloyl chloride was added. After 30 min. an additional 19 μl of acryloyl chloride was added at 0° C. This was repeated once more for a total reaction time of 1.5 hours (total acryloyl chloride, 57 μl, 63 mg, 0.69 mmol). The reaction was quenched by the addition of 2 mL MeOH and then concentrated under reduced pressure. The residue was purified by preparatory TLC (CH₂Cl₂:MeOH—

NH$_3$ (7N), 20:1) to yield 72 mg (65%) of 63. $^1$H NMR (500 MHz, CDCl$_3$): δ 8.83 (br s, 1H), 8.36 (d, J=5.2 Hz, 1H), 7.85 (d, J=5.2 Hz, 1H), 6.46 (d, J=16.9 Hz, 1H), 6.28 (dd, J=10.2, 16.9 Hz, 1H), 5.81 (d, J=10.2 Hz, 1H), 5.23 (br s, 1H), 3.87 (s, 6H), 3.85 (m, 4H), 3.16 (m, 2H), 2.48 (m, 4H), 2.40 (m, 2H), 1.57 (m, 4H), 1.44 (s, 9H); $^{13}$C NMR (166 MHz, CDCl$_3$): δ 171.4, 171.0, 164.4, 160.1, 158.9, 157.4, 156.1, 130.4, 129.7, 106.0, 79.1, 78.9, 58.2, 53.4, 52.9, 43.6, 40.5, 28.5, 28.0, 24.3; MS (m/z): [M+H]$^+$ 575.3.

YK94 (64) N-(2-(2-(4-(4-aminobutyl)piperazin-1-yl)-4,6-dimethoxypyrimidin-5-ylthio)pyrimidin-4-yl)acrylamide To 70 mg (0.122 mmol) of 63 in 4 ml of CH$_2$Cl$_2$ was added 1 mL of TFA dropwise at rt. After stirring for 45 min., the reaction mixture was concentrated under reduced pressure. TFA was removed by co-evaporating with MeOH several times and drying under high vacuum overnight to yield 64 as TFA salt and was used without further purification. $^1$H NMR (500 MHz, CDCl$_3$/MeOH-d$_4$): δ 8.33 (d, J=5.9 Hz, 1H), 8.19 (br s, 1H), 8.03 (d, J=6.1 Hz, 1H), 6.51 (d, J=16.9 Hz, 1H), 6.40 (dd, J=10.6, 16.9 Hz, 1H), 5.88 (d, J=10.6 Hz, 1H), 3.90 (s, 6H), 3.55-3.72 (m, 2H), 3.38-3.54 (m, 2H), 3.19 (t, J=7.7 Hz, 2H), 2.94-3.13 (m, 4H), 1.86-1.95 (m, 2H), 1.73-1.82 (m, 2H); $^{13}$C NMR (166 MHz, CDCl$_3$/MeOH-d$_4$): δ 171.4, 170.2, 165.4, 159.9, 158.9, 155.7, 130.5, 129.9, 106.2, 79.2, 56.2, 54.4, 51.5, 40.7, 38.6, 24.1, 20.6; MS (m/z): [M+H]$^+$ 475.4.

(65) YK71 Beads

A solution of 64 (~0.122 mmol) in DMF (4 mL) was added to 6.8 mL (0.102 mmol) of Affi-Gel® 10 beads (prewashed, 3×10 mL DMF) in a solid phase peptide synthesis vessel. 100 µL of N,N-diisopropylethylamine and several crystals of DMAP were added and this was shaken at rt for 3 h. Then the solvent was removed and the beads washed for 10 minutes each time with CH$_2$Cl$_2$ (4×10 mL), DMF (4×10 mL), and i-PrOH (3×10 mL). The YK71 beads (65) were stored in i-PrOH at −80° C.

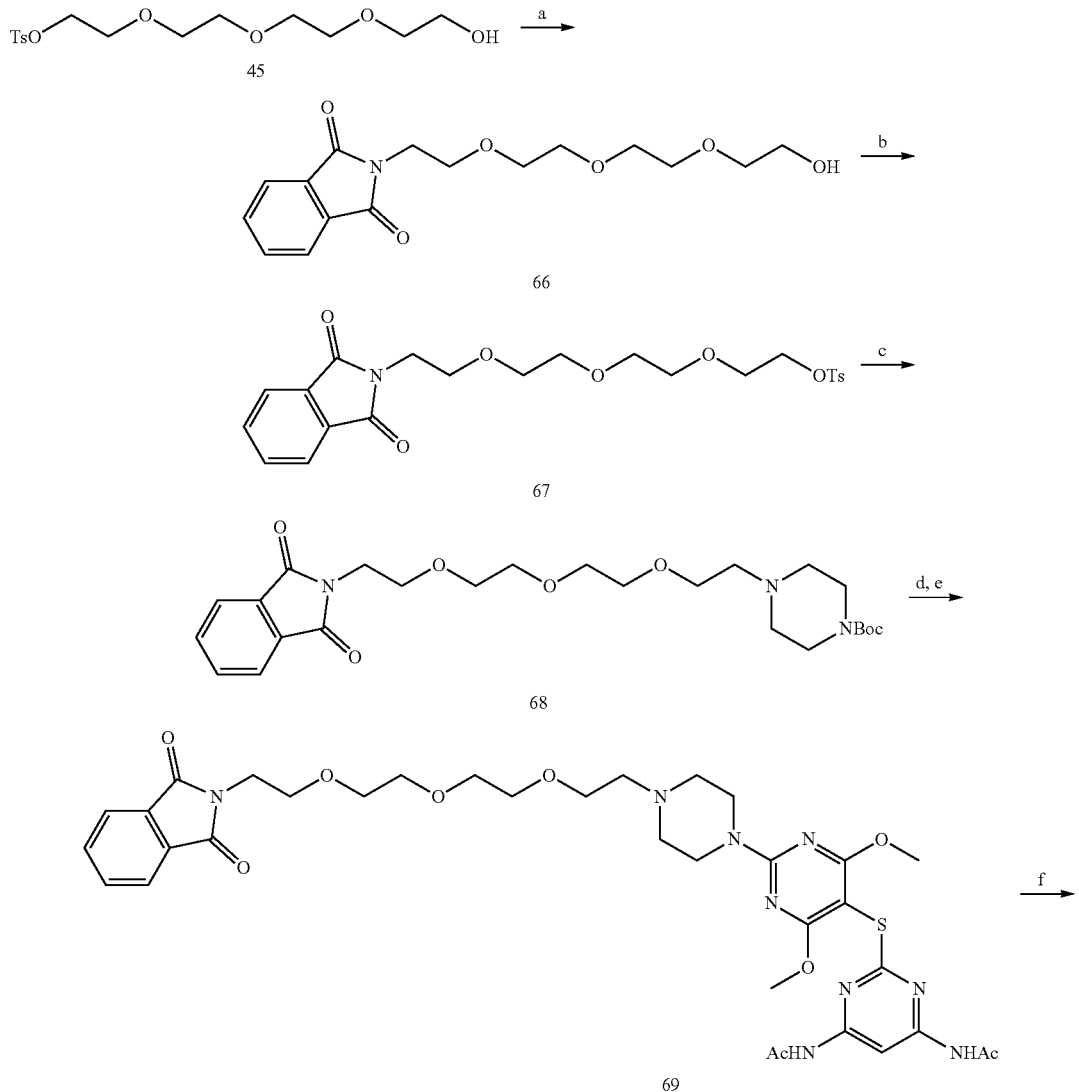

Scheme 8. Synthesis of TT-6 (72).

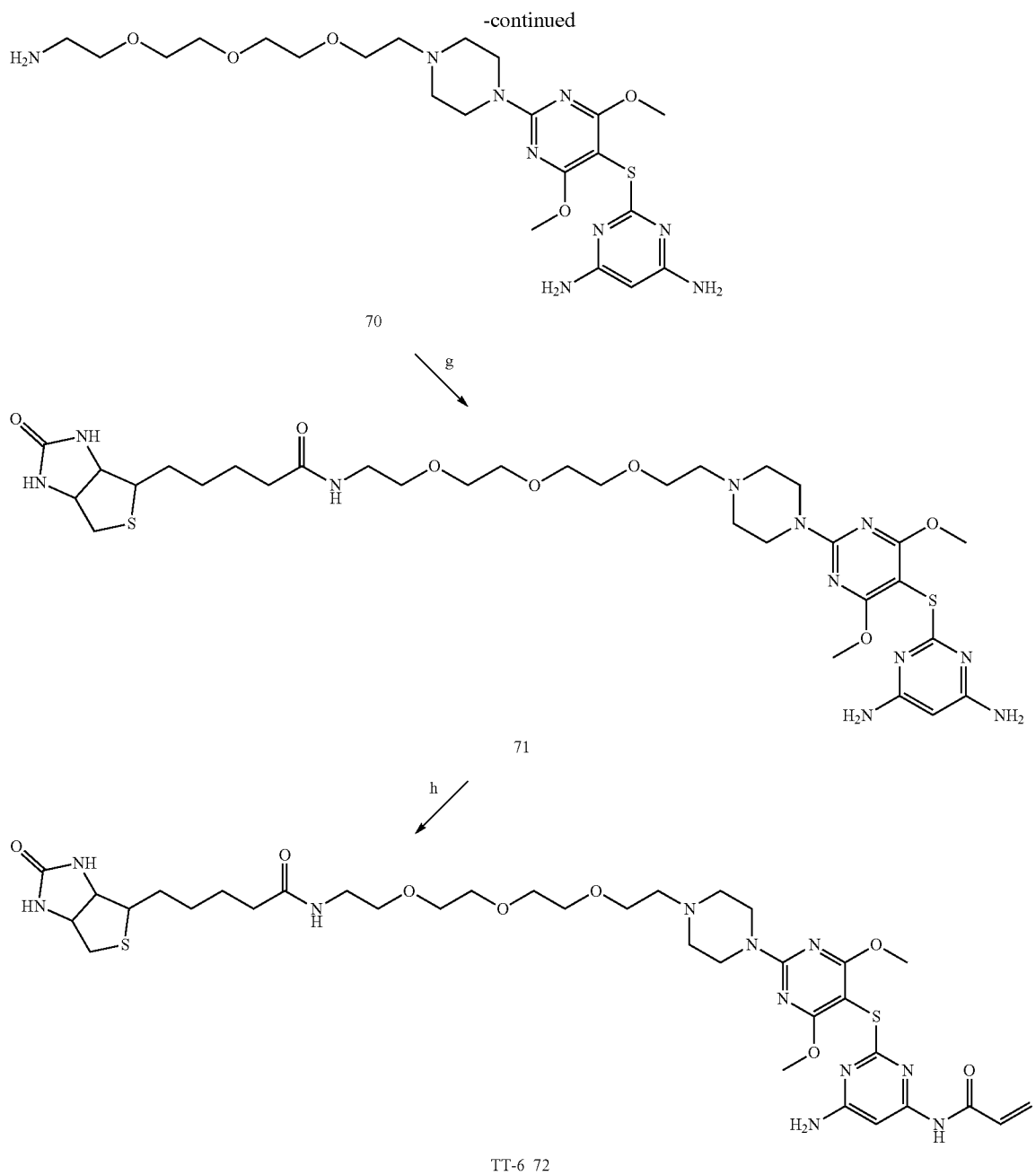

Reagents and conditions: a. potassium phthalimide, DMF, 110° C., 18 h; b. p-tosyl chloride, Et₃N, DMAP, CH₂Cl₂, 5° C. to rt, 24 h; c. 1-Boc-piperazine, K₂CO₃, dioxane, 80° C., 22 h; d. CH₂Cl₂:TFA (4:1), rt, 1 h; e. 24, K₂CO₃, DMF, 90° C., 1.5 h; f. NH₂NH₂, MeOH, rt, 2 h then 1M NaOH (aq.), 50° C., 1.5 h; g. D-biotin, EDCI, DMAP, CH₂Cl₂, sonicate, 2 h; h. acryloyl chloride, Et₃N, CH₂Cl₂ 0° C.

(66) 2-(2-(2-(2-(2-hydroxyethoxy)ethoxy)ethoxy)ethyl)isoindoline-1,3-dione 45 (1.22 &g, 3.5 mmol) and potassium phthalimide (0.713 g, 3.85 mmol) were suspended in anhydrous DMF (10 mL) and heated at 110° C. for 18 h. The reaction mixture was concentrated under reduced pressure and the residue was dissolved in CH₂Cl₂ (50 mL) and washed with 1M HCl (2×20 mL), brine (2×20 mL), dried over MgSO₄, and filtered. Solvent was removed under reduced pressure to give an oil which was purified by column chromatography (EtOAc) to afford 0.95 g (84%) of 66. $^1$H NMR (500 MHz, CDCl₃): δ 7.85 (dd, J=3.1, 5.4 Hz, 2H), 7.72 (dd, J=3.0, 5.5 Hz, 2H), 3.91 (t, J=5.9 Hz, 2H), 3.75 (t, J=5.8 Hz, 2H), 3.55-3.73 (m, 12H); MS (m/z): [M+Na]⁺ 346.1.

(67) 2-(2-(2-(2-(1,3-dioxoisoindolin-2-yl)ethoxy)ethoxy)ethoxy)ethyl 4-methylbenzenesulfonate A solution of 66 (0.95 g, 2.7 mmol), Et₃N (395 µL, 0.287 g, 2.8 mmol) and DMAP (33 mg, 0.27 mmol) in CH₂Cl₂ (30 mL) was cooled to 5° C. with ice-bath. Tosyl chloride (0.515 g, 2.7 mmol) was added in portions at 5° C. and after 30 minutes the ice-bath was removed and stirring continued at rt for 24 h. The reaction mixture was added to a seperatory funnel and washed with 1N HCl (2×25 mL), water (25 mL), and brine (2×25 mL). The organic layer was dried over $MgSO_4$, filtered and concentrated to give an oil which was purified by column chromatography (hexane:EtOAc, 6:4 to 4:6) to give 1.12 g (87%) of 67. $^1$H NMR (500 MHz, $CDCl_3$): δ 7.84 (dd, J=3.1, 5.4 Hz, 2H), 7.79 (d, J=8.3 Hz, 2H), 7.72 (dd, J=3.0, 5.5 Hz, 2H), 7.34 (d, J=8.4 Hz, 2H), 4.14 (t, J=4.8 Hz, 2H), 3.89 (t, J=5.9 Hz, 2H), 3.73 (t, J=5.8 Hz, 2H), 3.48-3.68 (m, 10H), 2.44 (s, 3H); MS (m/z): [M+Na]$^+$ 500.0.

(68) tert-butyl 4-(2-(2-(2-(2-(1,3-dioxoisoindolin-2-yl)ethoxy)ethoxy)ethyl)piperazine-1-carboxylate 67 (1.10 g, 0.0023 mol) in dioxane (25 mL) was added 1-Boc-piperazine (1.07 g, 0.0058 mol) and $K_2CO_3$ (1.37 g, 0.0099 mol) and heated at 80° C. for 22 h. Solvent was removed under reduced pressure and the residue was taken up into $CH_2Cl_2$ (100 mL) and washed with water (2×50 mL) and brine (2×50 mL). The organic layer was dried over $MgSO_4$, filtered and concentrated to an oil which was purified by column chromatography ($CH_2Cl_2$:MeOH—$NH_3$ (7N), 1:0 to 30:1) to give 0.819 (72%) of 68. $^1$H NMR (500 MHz, $CDCl_3$): δ 7.84 (dd, J=3.1, 5.4 Hz, 2H), 7.71 (dd, J=3.0, 5.5 Hz, 2H), 3.90 (t, J=5.9 Hz, 2H), 3.74 (t, J=5.9 Hz, 2H), 3.52-3.67 (m, 10H), 3.43 (m, 4H), 2.57 (t, J=6.0 Hz, 2H), 2.43 (m, 4H), 1.45 (m, 9H); MS (m/z): [M+H]$^+$ 492.1.

(69) N,N'-(2-(2-(4-(2-(2-(2-(2-(1,3-dioxoisoindolin-2-yl)ethoxy)ethoxy)ethoxy)ethyl)piperazin-1-yl)-4,6-dimethoxypyrimidin-5-ylthio)pyrimidine-4,6-diyl)diacetamide To 68 (542 mg, 1.10 mmol) in $CH_2Cl_2$ (28 mL) is added TFA (7 mL) dropwise and is stirred at rt for 1 h. The reaction mixture was concentrated under reduced pressure and TFA removed by co-evaporating with MeOH several times and drying under high vacuum overnight. To this was added $K_2CO_3$ (381 mg, 2.76 mmol) and DMF (20 mL) and the resulting suspension was stirred at rt for 10 min. Then 24 (421 mg, 1.1 mmol) was added and the suspension was heated at 90° C. for 90 min. The solvent was removed under reduced pressure and the residue was purified by column chromatography ($CH_2Cl_2$:MeOH, 100:1 to 25:1) to give 0.537 g (65%) of 69. $^1$H NMR (500 MHz, $CDCl_3$): δ 8.35 (s, 1H), 7.84 (dd, J=3.1, 5.5 Hz, 2H), 7.81 (bs, 2H), 7.71 (dd, J=3.1, 5.5 Hz, 2H), 3.83-3.92 (m, 12H), 3.74 (t, J=5.8 Hz, 2H), 3.55-3.67 (m, 10H), 2.64 (t, J=5.7 Hz, 2H), 2.56 (m, 4H), 2.15 (s, 6H); MS (m/z): [M+H]$^+$ 754.2.

(70) 2-(2-(4-(2-((2-aminoethoxy)ethoxy)ethoxyl)piperazin-1-yl-4,6-dimethoxypyrimidin-5-ylthio)pyrimidine-4,6-diamine 69 (300 mg, 0.398 mmol) in MeOH (9 mL) was added hydrazine hydrate (580 μL, 598 mg, 11.9 mmol) and stirred at rt for 2 h. Then 1M NaOH (4.5 mL) was added and the reaction mixture was heated at 50° C. for 1.5 h. The reaction mixture was concentrated to dryness and the residue purified by column chromatography ($CH_2Cl_2$:MeOH, 60:1 to 10:1) to give 0.214 g (93%) of 70. $^1$H NMR (500 MHz, $CDCl_3$): δ 5.16 (s, 1H), 4.56 (s, 4H), 3.84-3.91 (m, 10H), 3.61-3.69 (m, 10H), 3.51 (t, J=5.2 Hz, 2H), 2.86 (t, J=5.2 Hz, 2H), 2.66 (t, J=5.7 Hz, 2H), 2.57 (m, 4H); MS (m/z): [M+H]$^+$ 540.1.

(71) N-(2-(2-(2-(4-(5-(4,6-diaminopyrimidin-2-yl-thio)-4,6-dimethoxypyrimidin-2-yl)piperazin-1-yl)ethoxy)ethoxy)ethoxy)ethyl)-5-(2-oxohexahydro-1H-thieno[3,4-d]imidazol-4-yl)pentanamide 20.0 mg (0.0371 mmol) of 70, 18.1 mg (0.0741 mmol) of D-(+)-biotin, DMAP (cat.), 14.2 mg (0.0741 mmol) of EDCI in 1 ml of $CH_2Cl_2$ was sonicated for 2 hours in a sealed tube. The reaction mixture was evaporated to dryness and the residue was purified by preparatory TLC ($CH_2Cl_2$:MeOH—$NH_3$ (7N), 10:1) to give 15.6 mg (55%) of 71. $^1$H NMR (500 MHz, $CDCl_3$/MeOH-$d_4$): δ 5.23 (s, 1H), 4.49 (m, 1H), 4.30 (m, 1H), 3.86-3.91 (m, 10H), 3.60-3.72 (m, 12H), 3.40 (m, 2H), 3.12-3.18 (m, 1H), 2.91 (dd, J=5.0, 12.9 Hz, 1H), 2.72 (d, J=12.9 Hz, 1H), 2.68 (t, J=5.6 Hz, 2H), 2.60 (m, 4H), 2.19 (dd, J=2.1, 7.7 Hz, 2H), 1.38-1.76 (m, 6H); MS (m/z): [M+H]$^+$ 766.25.

TT-6 (72) N-(2-(2-(2-(2-(4-(5-(4-acrylamido-6-aminopyrimidin-2-ylthio)-4,6-dimethoxypyrimidin-2-yl)piperazin-1-yl)ethoxy)ethoxy)ethyl)-5-(2-oxohexahydro-1H-thieno[3,4-d]imidazol-4-yl)pentanamide To 15 mg (0.020 mmol) of 71 in 2 ml of $CH_2Cl_2$ at 0° C. was added 83 μl (60 mg, 0.6 mmol) of $Et_3N$. Then 3.3 μl (3.6 mg, 0.04 mmol) of acryloyl chloride in $CH_2Cl_2$ (0.5 mL) was added dropwise at 0° C. After 1 hour, an additional 3.3 μl of acryloyl chloride in $CH_2Cl_2$ (0.5 mL) was added dropwise. This was repeated four more times at 30 min. intervals for a total reaction time of 3.5 hours (total acryloyl chloride, 19.8 μl, 21.6 mg, 0.24 mmol). The reaction was quenched by the addition of 1 mL MeOH and then concentrated under reduced pressure. The residue was purified by preparatory TLC ($CH_2Cl_2$:MeOH—$NH_3$ (7N), 10:1) to yield 6.0 mg (37%) of 72. $^1$H NMR (500 MHz, $CDCl_3$): δ 9.57 (s, 1H), 7.13 (s, 1H), 6.94 (br s, 1H), 6.53 (br s, 1H), 6.32-6.45 (m, 2H), 5.72 (dd, J=2.4, 9.0 Hz, 1H), 5.58 (br s, 2H), 5.19 (br s, 1H), 4.48 (m, 1H), 4.34 (m, 1H), 3.82-3.93 (m, 10H), 3.55-3.77 (m, 12H), 3.39 (m, 2H), 3.08-3.15 (m, 1H), 2.89 (dd, J=5.1, 12.9 Hz, 1H), 2.81 (m, 2H), 2.72 (d, J=12.9 Hz, 1H), 2.70 (m, 4H), 2.19 (m, 2H), 1.38-1.76 (m, 6H); $^{13}$C NMR (166 MHz, $CDCl_3$): δ 173.6, 171.0, 170.3, 165.1, 164.8, 163.8, 159.8, 157.1, 130.9, 128.8, 88.7, 79.5, 71.0, 70.4, 70.3, 70.2, 69.5, 62.3, 59.9, 57.3, 56.0, 54.2, 53.4, 52.5, 43.6, 40.7, 39.2, 35.4, 28.5, 28.0, 25.7; MS (m/z): [M+H]$^+$ 820.3.

Scheme 9. Synthesis of YK140 (75), YK141 (77), YK142 (78).
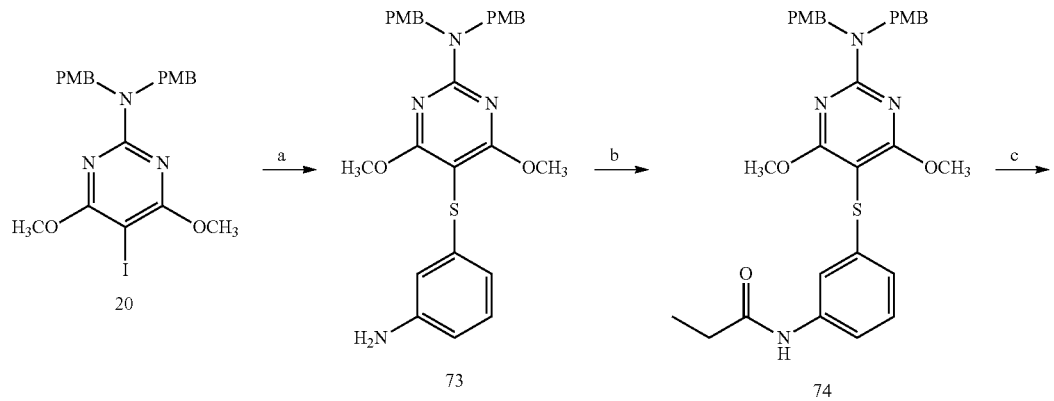
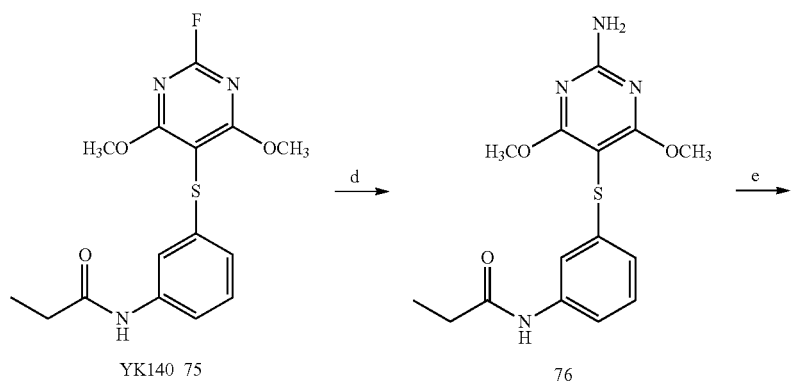
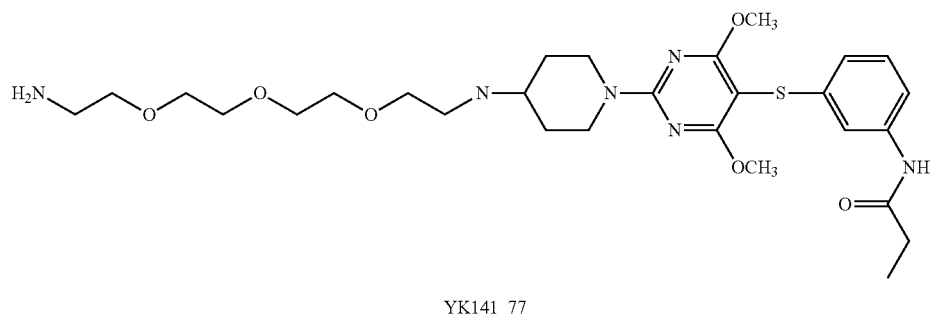

-continued

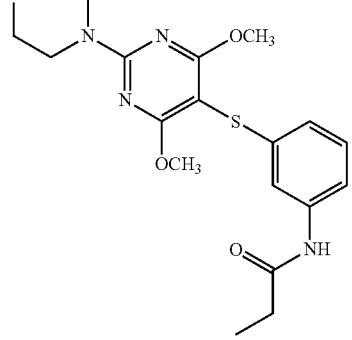

YK142 78

Reagents and conditions: a. 3-aminobenzenethiol, neocuproine, CuI, K₂CO₃, DMF, 125° C., 20 h; b. propionyl chloride, Et₃N, CH₂Cl₂, 0° C. to rt;
c. CHCl₃:TFA (1:1), 62° C., 22 h; d. HF/pyridine, NaNO₂, 0° C. to rt.; e. 46, DMF, 90° C., 75 min.; f. D-biotin, DCC, DMAP, CH₂Cl₂, sonicate, 6 h.

(73) 5-(3-aminophenylthio)-4,6-dimethoxy-N,N-bis(4-methoxybenzyl)pyrimidin-2-amine A mixture of 20 (0.521 g, 1.0 mmol), 3-aminobenzenethiol (106 μl, 0.125 g, 1.0 mmol), neocuproine (42 mg, 0.2 mmol), copper iodide (38 mg, 0.2 mmol), and potassium carbonate (0.415 g, 3.0 mmol) in DMF (10 mL) was stirred at 125° C. for 20 h. Solvent was removed under reduced pressure and the residue was purified by column chromatography (hexane:EtOAc, 75:25) to afford 0.183 g (35%) of 73. $^1$H NMR (500 MHz, CDCl₃): δ 7.23 (d, J=8.6 Hz, 4H), 7.00 (t, J=7.8 Hz, 1H), 6.87 (d, J=8.6 Hz, 4H), 6.54 (d, J=8.5 Hz, 1H), 6.44 (s, 1H), 6.41 (d, J=7.8 Hz, 1H), 4.76 (s, 4H), 3.89 (s, 6H), 3.81 (s, 6H), 3.59 (br s, 2H); MS (m/z): [M+H]⁺ 519.0.

(74) N-(3-(2-(bis(4-methoxybenzyl)amino)-4,6-dimethoxypyrimidin-5-ylthio)phenyl)propionamide To 183 mg (0.353 mmol) of 73 in 10 mL CH₂Cl₂ was added Et₃N (492 μL, 357 mg, 3.53 mmol) and cooled to 0° C. with ice-bath. A solution of propionyl chloride (168 μL, 179 mg, 1.765 mmol) in CH₂Cl₂ (5 mL) was added dropwise and the reaction mixture was stirred. After 20 min. the ice-bath was removed and stirring continued for additional 40 min. 2 mL of MeOH was added to quench the reaction and solvent was removed under reduced pressure and the residue was purified by column chromatography (hexane:EtOAc, 70:30 to 60:40) to afford 0.188 g (93%) of 74. $^1$H NMR (500 MHz, CDCl₃): δ 7.47 (d, J=7.7 Hz, 1H), 7.24 (d, J=8.5 Hz, 4H), 7.17 (t, J=7.9 Hz, 1H), 7.08 (s, 1H), 7.01 (s, 1H), 6.87 (d, J=8.6 Hz, 4H), 6.83 (d, J=7.6 Hz, 1H), 4.77 (s, 4H), 3.89 (s, 6H), 3.81 (s, 6H), 2.36 (q, J=7.5 Hz, 2H), 1.26 (t, J=7.5 Hz, 3H); MS (m/z): [M+Na]⁺ 597.1.

YK140 (75) N-(3-(2-amino-4,6-dimethoxypyrimidin-5-ylthio)phenyl)propionamide 188 mg (0.327 mmol) of 74 in 5 mL of CHCl₃:TFA (1:1) was heated at 62° C. for 22 h. Solvent was removed under reduced pressure and the residue was purified by column chromatography (hexane:EtOAc, 1:1 to 4:6) to afford 90 mg (83%) of 75. $^1$H NMR (500 MHz, CDCl₃): δ 7.43 (d, J=7.7 Hz, 1H), 7.15 (t, J=8.0 Hz, 1H), 6.95-7.06 (m, 3H), 6.74- 6.85 (m, 2H), 3.90 (s, 6H), 2.36 (q, J=7.6 Hz, 2H), 1.26 (t, J=7.6 Hz, 3H); HRMS (m/z): [M+H]⁺ calculated for C₁₅H₁₉N₄O₃S, 335.1178; found, 335.1183.

(76) N-(3-(2-fluoro-4,6-dimethoxypyrimidin-5-yl)propionamide 60 mg (0.178 mmol) of 75 and pyridine (250 μL) were added to a plastic tube fitted with a stir bar and cooled to 0° C. Then a solution of HF/pyridine (300 μL, 12 mmol) was added. After several minutes 20 mg (0.290 mmol) of NaNO₂ was added and it was vigorously stirred for an additional 90 minutes at 0° C. and at rt for 3 hours. Then 5 ml of CH₂Cl₂ and 100 mg of CaCO₃ were added and the mixture was stirred for 5 hours at rt. It was then filtered over a cintered disc funnel and the solid washed with EtOAc. The filtrate was filtered over celite, concentrated under reduced pressure and the residue was purified by preparatory TLC (hexane:EtOAc, 60:40) to give 35 mg (58%) of 76. $^1$H NMR (500 MHz, CDCl₃): δ 7.35 (d, J=7.7 Hz, 1H), 7.17 (t, J=7.9 Hz, 1H), 6.96-7.05 (m, 1H), 6.75-6.90 (m, 2H), 4.01 (s, 6H), 2.36 (q, J=7.5 Hz, 2H), 1.23 (t, J=7.5 Hz, 3H); MS (m/z): [M+H]⁺ 338.2.

YK141 (77) N-(3-(2-(4-(2-(2-(2-(2-hydroxyethoxy)ethoxy)ethyl)piperazin-1-yl)-4,6-dimethoxypyrimidin-5-ylthio)phenyl)propionamide To 35 mg (0.104 mmol) of 76 in 2 ml of DMF was added 30 mg (0.114 mmol) of 46 and was heated at 90° C. for 75 min. Solvent was removed under reduced pressure and the residue was purified by preparatory TLC (CH₂Cl₂:MeOH—NH₃ (7N), 15:1) to give 44.2 mg (74%) of 77. $^1$H NMR (500 MHz, CDCl₃): δ 7.51 (d, J=7.2 Hz, 1H), 7.22 (s, 1H), 7.14 (t, J=7.8 Hz, 1H), 6.95 (s, 1H), 6.80 (d, J=7.5 Hz, 1H), 3.94 (s, 4H), 3.89 (s, 6H), 3.60-3.80 (m, 15H), 2.60-2.82 (m, 6H), 2.35 (q, J=7.2 Hz, 2H), 1.21 (t, J=7.4 Hz, 3H); HRMS (m/z): [M+H]⁺ calculated for C₂₇H₄₂N₅O₇S, 580.2805; found, 580.2806.

YK142 (78) 2-(2-(2-(2-(4-(4,6-dimethoxy-5-(3-propionamidophenylthio)pyrimidin-2-yl)piperazin-1-yl)ethoxy)ethoxy)ethoxy)ethyl 5-(2-oxohexahydro-1H-thieno[3,4-d]imidazol-4-yl)pentanoate 29 mg (0.050 mmol) of 77, 36 mg (0.147 mmol) D-(+)-biotin, DMAP (4.5 mg, 0.037 mmol), 61 mg (0.296 mmol)

DCC in 5 ml of CH$_2$Cl$_2$ was sonicated for 6 hours in a sealed tube. The reaction mixture was evaporated to dryness and the residue was purified by preparatory TLC (CH$_2$Cl$_2$: MeOH—NH$_3$ (7N), 15:1) to give 36 mg (90%) of 78. $^1$H NMR (500 MHz, CDCl$_3$): δ 7.45-7.53 (m, 2H), 7.13 (t, J=6.6 Hz, 1H), 7.05 (s, 1H), 6.77 (d, J=6.5 Hz, 1H), 5.90 (s, 1H), 5.35 (s, 1H), 4.46-4.53 (m, 1H), 4.27-4.33 (m, 1H), 4.18-4.26 (m, 2H), 3.85-4.00 (m, 10H), 3.63-3.74 (m, 12H), 3.10-3.18 (m, 11H), 2.90 (dd, J=4.5, 10.7 Hz, 1H), 2.74 (d, J=10.7 Hz, 1H), 2.61 (m, 4H), 2.42 (t, J=7.2 Hz, 2H), 2.36 (m, 4H), 1.10-1.82 (m, 9H); HRMS (m/z): [M+H]$^+$ calculated for C$_{37}$H$_{56}$N$_7$O$_9$S$_2$, 806.3581; found, 806.3566.

Scheme 10.
Synthesis of YK129 (83), YK130 (84), YK139 (85), YK149 (86), TT-2 (87), TT-3 (88), TT-4 (89).

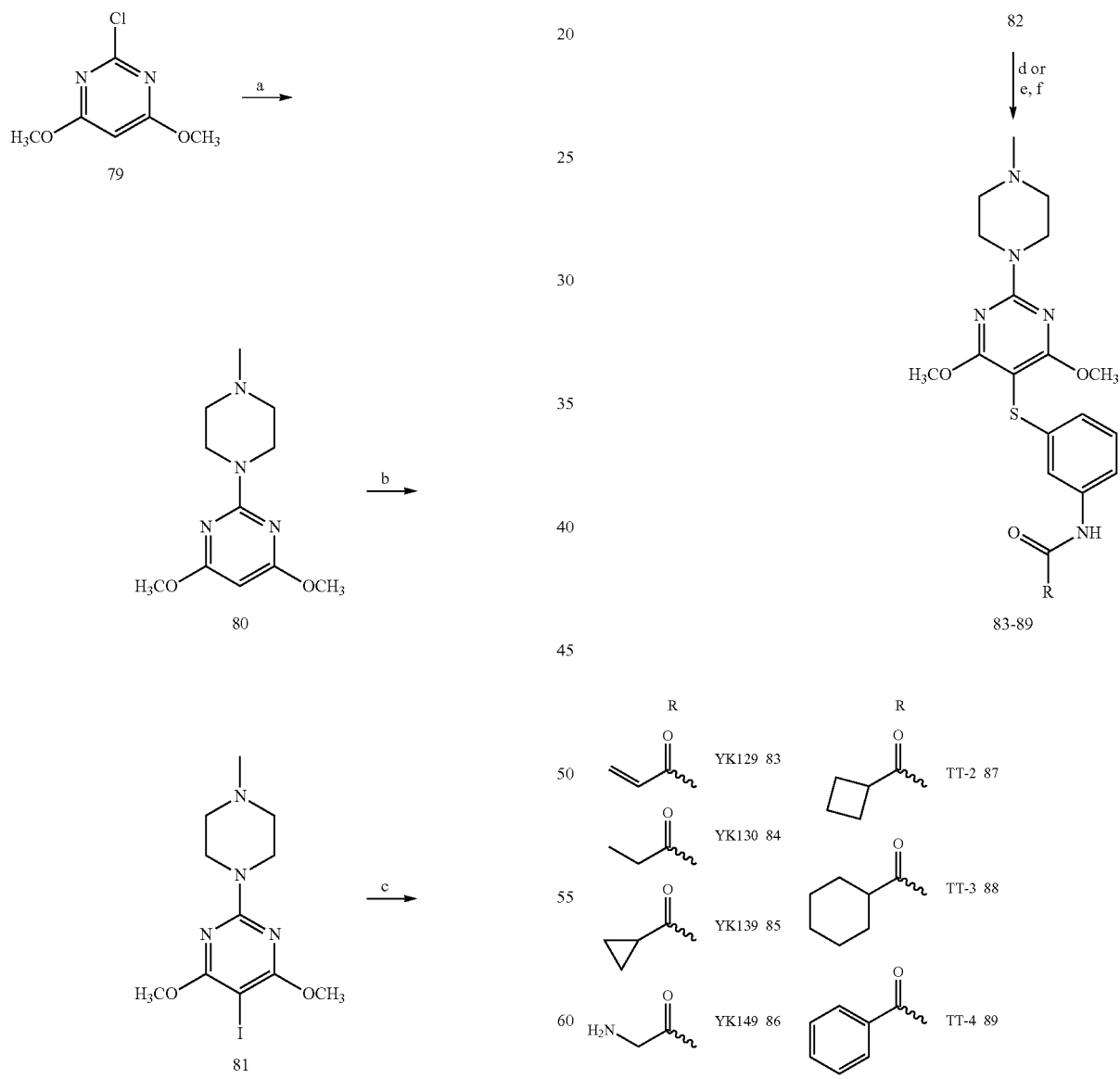

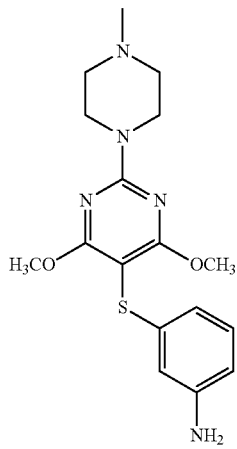

Reagents and conditions: a. N-methylpiperazine, DMF, 90° C., 2.5 h; b. NIS, TFA, CH$_3$CN, rt, 1.5 h; c. 3-aminobenzenethiol, neocuproine, CuI, K$_3$PO$_4$, DMF, 125° C., 17 h; d. RCOCl, Et$_3$N; e. RCOOH, DCC, THF, rt; f. CH$_2$Cl$_2$:TFA (4:1), rt.

(80) 4,6-dimethoxy-2-(4-methylpiperazin-1-yl)pyrimidine 5 g (0.0286 mol) of 2-chloro-4,6-dimethoxypyrimidine (79) and 7.93 mL (7.16 g, 0.0715 mol) of N-methylpiperazine in 22 mL DMF was heated at 90° C. for 2.5 h. The reaction mixture was concentrated under reduced pressure and the residue was taken up into 200 mL $CH_2Cl_2$. This was washed with brine (3×50 mL), dried over $MgSO_4$, filtered and concentrated to give 6.51 g (95%) of 80. $^1$H NMR (500 MHz, $CDCl_3$): δ 5.37 (s, 1H), 3.85 (s, 6H), 3.82 (m, 4H), 2.44 (m, 4H), 2.33 (s, 3H); $^{13}$C NMR (166 MHz, $CDCl_3$): δ 172.0, 160.8, 77.8, 55.0, 53.4, 46.3, 43.7; MS (m/z): [M+H]$^+$ 239.2.

(81) 5-iodo-4,6-dimethoxy-2-(4-methylpiperazin-1-yl)pyrimidine

To 1.59 g (6.67 mmol) of 80 in 40 mL acetonitrile was added 1.80 g (8.01 mmol) of N-iodosuccinimide, 0.771 mL (1.14 g, 10.0 mmol) of TFA and stirred at rt for 1.5 h. The reaction mixture was concentrated to dryness and the residue was taken up into 100 mL $CH_2Cl_2$ and washed with 5% $NaHCO_3$ (3×50 mL), dried over $MgSO_4$, filtered and concentrated to give a residue which was purified by column chromatography ($CH_2Cl_2$:MeOH—NH3 (7N), 1:0 to 20:1) to yield 2.06 g (86%) of 81. $^1$H NMR (500 MHz, $CDCl_3$): δ 3.93 (s, 6H), 3.82 (m, 4H), 2.47 (m, 4H), 2.36 (s, 3H); MS (m/z): [M+H]$^+$ 365.1.

YK133 (82) 3-(4,6-dimethoxy-2-(4-methylpiperazin-1-yl)pyrimidin-5-ylthio)aniline A mixture of 81 (0.500 g, 1.37 mmol), 3-aminobenzenethiol (146 μl, 0.172 g, 1.37 mmol), neocuproine (86 mg, 0.411 mmol), copper iodide (78 mg, 0.411 mmol), and potassium phosphate (0.582 g, 2.74 mmol) in DMF (15 mL) was stirred at 125° C. for 17 h. Solvent was removed under reduced pressure and the residue was purified by column chromatography ($CH_2Cl_2$:MeOH—NH$_3$ (7N), 100:1 to 30:1) to afford 0.253 g (51%) of 82. $^1$H NMR (500 MHz, $CDCl_3$): δ 6.97 (t, J=8.0 Hz, 1H), 6.46-6.51 (m, 1H), 6.36-6.40 (m, 2H), 3.88-4.03 (m, 10H), 2.52 (m, 4H), 2.38 (s, 3H); $^{13}$C NMR (166 MHz, $CDCl_3$): δ 171.8, 160.1, 146.9, 139.5, 129.6, 116.2, 112.2, 112.1, 81.1, 55.0, 54.6, 46.3, 43.8; HRMS (m/z): [M+H]$^+$ calculated for $C_{17}H_{24}N_5O_2S$, 362.1651; found, 362.1649.

YK129 (83) N-(3-(4,6-dimethoxy-2-(4-methylpiperazin-1-yl)pyrimidin-5-ylthio)phenyl)acrylamide To a solution of 82 (10 mg, 0.027 mmol) and Et$_3$N (50 μL, 36 mg, 0.36 mmol) in 1 mL $CH_2Cl_2$ was added acryloyl chloride (22 μL, 24.4 mg, 0.27 mmol). The reaction was stirred at rt for 12 h, then quenched by adding cold MeOH. Solvent was evaporated under reduced pressure and the residue was purified by preparatory TLC ($CH_2Cl_2$:MeOH—NH$_3$ (7N), 20:1) to afford 6.0 mg (54%) of 83. $^1$H NMR (500 MHz, $CDCl_3$) δ 7.49 (m, 1H), 7.36 (m, 1H), 7.14 (m, 2H), 6.84 (d, J=7.5 Hz, 1H), 6.36 (m, 1H), 6.22 (m, 1H), 5.73 (m, 1H), 4.02 (m, 4H), 3.90 (s, 6H), 2.70 (m, 4H), 2.50 (s, 3H); MS (m/z): [M+H]$^+$ 416.4.

YK130 (84) N-(3-(4,6-dimethoxy-2-(4-methylpiperazin-1-yl)pyrimidin-5-ylthio)phenyl)propionamide To a solution of 82 (10 mg, 0.027 mmol) and Et$_3$N (50 μL, 36 mg, 0.36 mmol) in 1 mL $CH_2Cl_2$ was added propionyl chloride (22 μL, 24.4 mg, 0.27 mmol). Reaction was stirred at rt for 12 h, then quenched by adding cold MeOH. Solvent was evaporated under reduced pressure and the residue was purified by preparatory TLC ($CH_2Cl_2$:MeOH—NH$_3$ (7N), 20:1) to afford 7.3 mg (65%) of 84. $^1$H NMR (500 MHz, $CDCl_3$) δ 7.44 (d, J=7.5 Hz, 1H), 7.13 (m, 2H), 7.04 (s, 1H), 6.78 (d, J=7.5 Hz, 1H), 3.93 (m, 4H), 3.90 (s, 6H), 2.55 (m, 4H), 2.36 (s, 3H), 2.33 (q, J=7.2 Hz, 2H), 1.21 (t, J=7.2 Hz, 3H); HRMS (m/z): [M+H]$^+$ calculated for $C_{20}H_{28}N_5O_3S$, 418.1913; found, 418.1910.

YK139 (85) N-(3-(4,6-dimethoxy-2-(4-methylpiperazin-1-yl)pyrimidin-5-ylthio)phenyl)cyclopropanecarboxamide To a solution of 82 (10.9 mg, 0.0302 mmol) and Et$_3$N (21 μl, 15.3 mg, 0.151 mmol) in $CH_2Cl_2$ (1 mL) was added cyclopropanecarbonyl chloride (14 μl, 15.8 mg, 0.1508 mmol) and was stirred at rt for 2 h. Solvent was removed under reduced pressure and the residue was purified by preparatory TLC ($CH_2Cl_2$:MeOH—NH$_3$ (7N), 20:1) to afford 7.9 mg (61%) of 85. $^1$H NMR (500 MHz, $CDCl_3$): δ 7.49 (m, 1H), 7.29 (s, 1H), 7.13 (t, J=7.8 Hz, 1H), 6.97 (s, 1H), 6.78 (d, J=7.6 Hz, 1H), 3.88-3.95 (m, 10H), 2.48 (m, 4H), 2.36 (s, 3H), 1.05-1.13 (m, 1H), 0.74-0.96 (m, 4H); HRMS (m/z): [M+H]$^+$ calculated for $C_{21}H_{28}N_5O_3S$, 430.1913; found, 430.1897.

YK149 (86) 2-amino-N-(3-(4,6-dimethoxy-2-(4-methylpiperazin-1-yl)pyrimidin-5-ylthio)phenyl)acetamide To a solution of 82 (20 mg, 0.0552 mmol) in THF (1 mL) was added Boc-glycine (9.7 mg, 0.0552 mmol) and DCC (12 mg, 0.058 mmol) and stirred at rt for 5 h. Reaction mixture was concentrated under reduced pressure and the residue was purified by preparatory TLC (EtOAc:MeOH—NH$_3$ (7N), 20:1) to afford a solid which was dissolved in 2 mL of $CH_2Cl_2$:TFA (4:1) and stirred at rt for 1 h. The reaction mixture was concentrated under reduced pressure and the residue was purified by preparatory TLC ($CH_2Cl_2$:MeOH—NH$_3$ (7N), 15:1) to afford 13.9 mg (60%) of 86. $^1$H NMR (500 MHz, $CDCl_3$/MeOH-d$_4$): δ 7.38 (d, J=8.2 Hz, 1H), 7.26 (s, 1H), 7.15 (t, J=7.9 Hz, 1H), 6.79 (d, J=7.6 Hz, 1H), 3.86-3.97 (m, 10H), 3.52 (s, 2H), 2.58 (m, 4H), 2.41 (s, 3H); MS (m/z): [M+H]$^+$ 419.1.

TT-2 (87) N-(3-(4,6-dimethoxy-2-(4-methylpiperazin-1-yl)pyrimidin-5-ylthio)phenyl)cyclobutanecarboxamide 82 (10 mg, 0.028 mmol), Et$_3$N (19.5 μl, 14.2 mg, 0.14 mmol) and cyclobutanecarbonyl chloride (9.6 μl, 10.0 mg, 0.084 mmol) in $CH_2Cl_2$ (1 mL) was stirred at rt for 2 h. Solvent was removed under reduced pressure and the residue was purified by preparatory TLC (EtOAc:MeOH—NH$_3$ (7N), 20:1) to afford 4.1 mg (33%) of 87. $^1$H NMR (500 MHz, $CDCl_3$): δ 7.50 (d, J=7.8 Hz, 1H), 7.14 (t, J=7.9 Hz, 1H), 7.00 (s, 1H), 6.94 (br s, 1H), 6.77 (d, J=7.9 Hz, 1H), 3.90 (br s, 10H), 3.07 (m, 1H), 2.50 (m, 14H), 2.14-2.42 (m, 7H), 1.82-2.02 (m, 2H); MS (m/z): [M+H]$^+$ 444.1.

TT-3 (88) N-(3-(4,6-dimethoxy-2-(4-methylpiperazin-1-yl)pyrimidin-5-ylthio)phenyl)cyclohexanecarboxamide 82 (10 mg, 0.028 mmol), Et$_3$N (19.5 μl, 14.2 mg, 0.14 mmol) and cyclohexanecarbonyl chloride (11.4 μl, 12.3 mg, 0.084 mmol) in CH$_2$Cl$_2$ (1 mL) was stirred at rt for 3 h. Solvent was removed under reduced pressure and the residue was purified by preparatory TLC (EtOAc:MeOH—NH$_3$ (7N), 20:1) to afford 12 mg (91%) of 88. $^1$H NMR (500 MHz, CDCl$_3$): δ 7.50 (d, J=7.9 Hz, 1H), 7.18 (s, 1H), 7.13 (t, J=7.9 Hz, 1H), 7.02 (s, 1H), 6.76 (d, J=7.7 Hz, 1H), 3.90 (br s, 10H), 2.51 (m, 4H), 2.38 (s, 3H), 2.11-2.22 (m, 1H), 1.19-1.96 (m, 10H); MS (m/z): [M+H]$^+$ 472.0.

TT-4 (89) N-(3-(4,6-dimethoxy-2-(4-methylpiperazin-1-yl)pyrimidin-5-ylthio)phenyl)benzamide 82 (10 mg, 0.028 mmol), Et$_3$N (19.5 μl, 14.2 mg, 0.14 mmol) and benzoyl chloride (9.8 μl, 11.8 mg, 0.084 mmol) in CH$_2$Cl$_2$ (1 mL) was stirred at rt for 3 h. Solvent was removed under reduced pressure and the residue was purified by preparatory TLC (EtOAc:MeOH—NH$_3$ (7N), 20:1) to afford 8.6 mg (66%) of 89. $^1$H NMR (500 MHz, CDCl$_3$): δ 7.83 (d, J=7.7 Hz, 2H), 7.74 (br s, 1H), 7.59 (d, J=7.8 Hz, 1H), 7.54 (t, J=6.4 Hz, 1H), 7.47 (t, J=7.8 Hz, 2H), 7.20 (t, J=8.0 Hz, 1H), 7.13 (s, 1H), 6.86 (d, J=7.9 Hz, 1H), 3.87-3.93 (m, 10H), 2.50 (m, 4H), 2.37 (s, 3H); MS (m/z): [M+H]$^+$ 466.1.

Scheme 11. Synthesis of TT-5 (95).

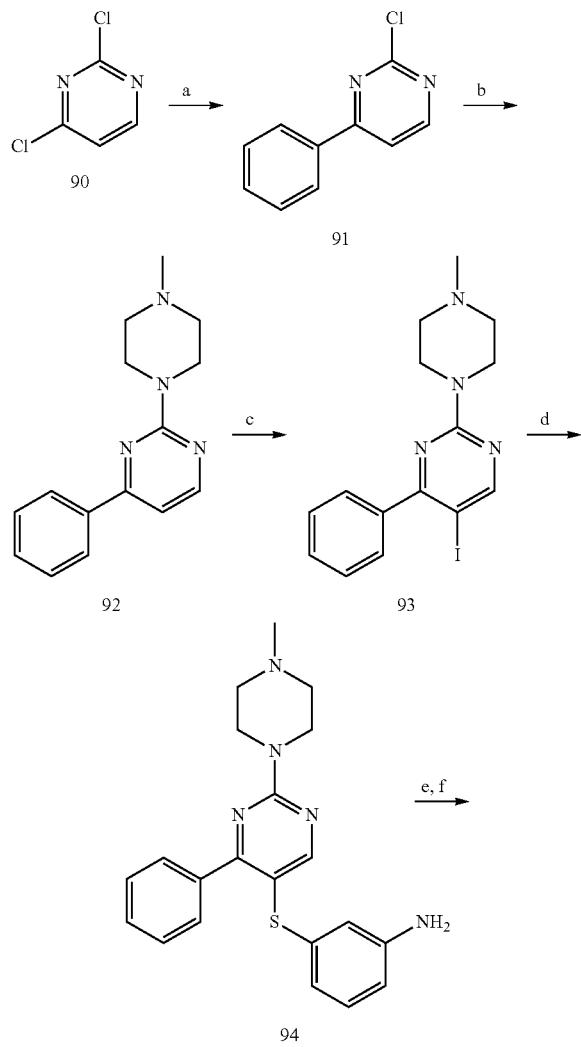

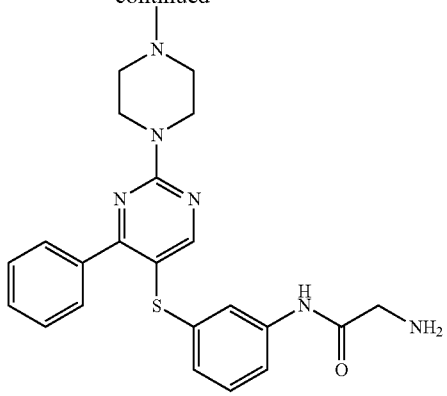

TT-5 95

Reagents and conditions: a. PhB(OH)$_2$, Na$_2$CO$_3$, Pd(OAc)$_2$, PPh$_3$, DME, 95° C., 15-20 h; b. N-methylpiperazine, DMF, 90° C., 1.5 h; c. NIS, TFA, CH$_3$CN; d. 3-aminobenzenethiol, neocuproine, CuI, K$_3$PO$_4$, DMF, 120° C., 12 h; e. Boc-glycine, DCC, THF, rt, 12 h; f. CH$_2$Cl$_2$:TFA (4:1), rt.

(91) 2-chloro-4-phenylpyrimidine

To a mixture of 2,4-dichloropyrimidine (90) (50 mg, 0.336 mmol), phenylboronic acid (41 mg, 0.336 mmol), sodium carbonate (110 mg in 0.5 mL water) and DME (2.5 mL) was added palladium acetate (3.8 mg, 0.0168 mmol) and triphenylphosphine (8.8 mg, 0.0336 mmol). The reaction mixture was heated at 95° C. for 20 h. Solvent was removed under reduced pressure and the residue taken up into dichloromethane (20 mL), washed with water (3×5 mL), dried over MgSO$_4$, and concentrated to give a residue which was purified by preparatory TLC (hexane:EtOAc, 8:2) to yield 41 mg (64%) of 91. $^1$H NMR (500 MHz, CDCl$_3$): δ 8.63 (d, J=5.2 Hz, 1H), 8.06-8.11 (m, 2H), 7.64 (d, J=5.3 Hz, 1H), 7.47-7.57 (m, 3H); $^{13}$C NMR (166 MHz, CDCl$_3$): δ 167.2, 161.9, 159.8, 135.1, 131.9, 129.1, 127.4, 115.2.

(92) 2-(4-methylpiperazin-1-yl)-4-phenylpyrimidine

To a solution of 91 (38 mg, 0.201 mmol) in 0.5 mL DMF was added 1-methylpiperazine (56 μl, 50 mg, 0.31 mmol) and heated at 90° C. for 1.5 h. Solvent was removed under reduced pressure and the residue was purified by preparatory TLC (CH$_2$Cl$_2$:MeOH—NH$_3$ (7N), 20:1) to yield 49 mg (95%) of 92. $^1$H NMR (500 MHz, CDCl$_3$): δ 8.36 (d, J=5.2 Hz, 1H), 8.01-8.09 (m, 2H), 7.43-7.50 (m, 3H), 6.92 (d, J=5.2 Hz, 1H), 3.96 (m, 4H), 2.50 (m, 4H), 2.34 (s, 3H); $^{13}$C NMR (166 MHz, CDCl$_3$): δ 164.4, 162.1, 158.4, 137.8, 130.6, 128.8, 127.1, 105.8, 55.2, 46.4, 43.9; MS (m/z): [M+H]$^+$ 255.1.

(93) 5-iodo-2-(4-methylpiperazin-1-yl)-4-phenylpyrimidine

To 92 (49 mg, 0.193 mmol) in acetonitrile (1.4 mL) was added TFA (59 μl, 88 mg, 0.772 mmol), N-iodosuccinimide (43 mg, 0.193 mmol) and stirred at rt for 1 h. Solvent was evaporated and the residue was taken up into dichloromethane (15 mL), washed with 10% Na$_2$CO$_3$ (2×5 mL), water (5 mL), dried over MgSO$_4$, and concentrated to give a residue which was purified by preparatory TLC (CH$_2$Cl$_2$:MeOH, 10:1) to yield 67 mg (92%) of 93. $^1$H NMR (500 MHz, CDCl$_3$): δ 8.60 (s, 1H), 7.65-7.73 (m, 2H), 7.42-7.49 (m, 3H), 3.86 (m, 4H), 2.45 (m, 4H), 2.33 (s, 3H); $^{13}$C NMR (166 MHz, CDCl$_3$): δ 167.5, 165.8, 160.9, 140.3, 129.7, 129.3, 128.1, 76.2, 55.0, 46.4, 43.9; MS (m/z): [M+H]$^+$ 380.9.

(94) 3-(2-(4-methylpiperazin-1-yl)-4-phenylpyrimidin-5-ylthio)aniline

A mixture of 93 (37.6 mg, 0.099 mmol), 3-aminobenzenethiol (12 μl, 13.6 mg, 0.109 mmol), neocuproine (6.2 mg, 0.0297 mmol), copper iodide (5.7 mg, 0.0297 mmol), and potassium carbonate (42 mg, 0.198 mmol) in DMF (1.4 mL) was stirred at 110° C. for 12 h. Solvent was removed under reduced pressure and the residue was purified by preparatory TLC (CH$_2$Cl$_2$:MeOH—NH$_3$ (7N), 10:1) to afford 10 mg (27%) of 94. $^1$H NMR (500 MHz, CDCl$_3$): δ 8.45 (s, 1H), 7.71 (d, J=6.6 Hz, 2H), 7.32-7.42 (m, 3H), 6.99 (t, J=7.9 Hz, 1H), 6.47 (d, J=7.8 Hz, 1H), 6.43 (dd, J=2.0, 6.4 Hz, 1H), 6.36 (d, J=1.8 Hz, 1H), 3.97 (m, 4H), 3.60 (br s, 2H), 2.52 (m, 4H), 2.37 (s, 3H); MS (m/z): [M+H]$^+$ 378.1.

TT-5 (95) 2-amino-N-(3-(2-(4-methylpiperazin-1-yl)-4-phenylpyrimidin-5-ylthio)phenyl)acetamide To a solution of 94 (5 mg, 0.0133 mmol) in THF (0.5 mL) was added Boc-glycine (2.3 mg, 0.0133 mmol) and DCC (3 mg, 0.0146 mmol). After stirring for 2 h at rt, THF was evaporated and 0.5 mL of CH$_2$Cl$_2$:TFA (4:1) was added. The solution was stirred for 45 min., then concentrated to dryness under reduced pressure to give a residue which was purified by preparatory TLC (CH$_2$Cl$_2$:MeOH—NH$_3$ (7N), 10:1) to afford 2 mg (35%) of 95. $^1$H NMR (500 MHz, CDCl$_3$/MeOH-d$_4$): δ 8.45 (s, 1H), 7.69 (d, J=8.2 Hz, 2H), 7.35-7.45 (m, 4H), 7.31 (m, 1H), 7.17 (t, J=8.0 Hz, 1H), 6.76 (d, J=7.8 Hz, 1H), 3.96 (m, 4H), 3.36 (s, 2H), 2.56 (m, 4H), 2.38 (s, 3H); MS (m/z): [M+H]$^+$ 435.0.

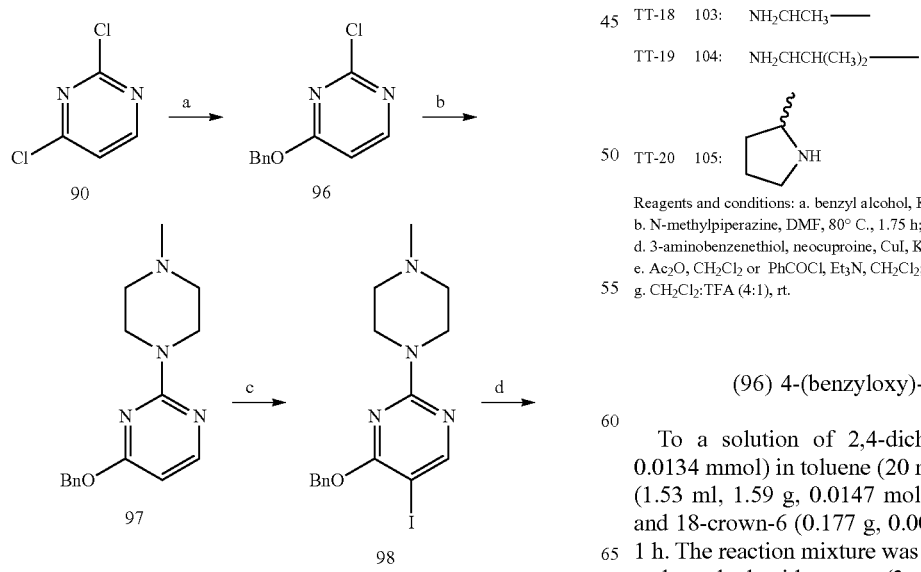

Scheme 12. Synthesis of TT-7 (100), TT-8 (101), TT-9 (102), TT-18 (103), TT-19 (104), TT-20 (105).

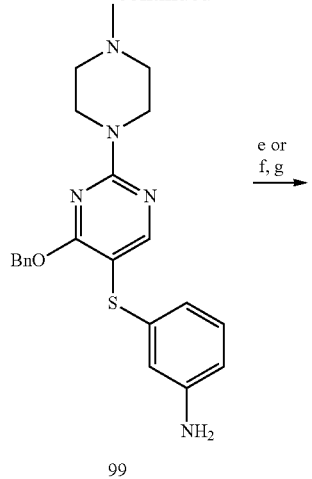

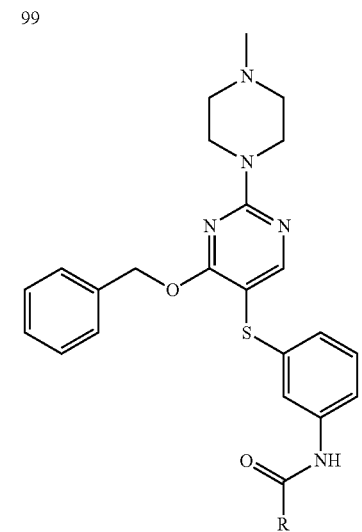

| | | |
|---|---|---|
| TT-7 | 100: | CH$_3$— |
| TT-8 | 101: | Ph— |
| TT-9 | 102: | NH$_2$CH$_2$— |
| TT-18 | 103: | NH$_2$CHCH$_3$— |
| TT-19 | 104: | NH$_2$CHCH(CH$_3$)$_2$— |
| TT-20 | 105: | 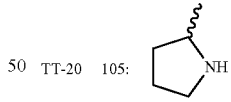 |

Reagents and conditions: a. benzyl alcohol, KOH, 18-crown-6, toluene, rt, 1 h; b. N-methylpiperazine, DMF, 80° C., 1.75 h; c. NIS, TFA, CH$_3$CN, rt, 1 h; d. 3-aminobenzenethiol, neocuproine, CuI, K$_2$CO$_3$, DMF, 120° C., 18 h; e. Ac$_2$O, CH$_2$Cl$_2$ or PhCOCl, Et$_3$N, CH$_2$Cl$_2$; f. RCOOH, DCC, THF, rt, 12 h; g. CH$_2$Cl$_2$:TFA (4:1), rt.

(96) 4-(benzyloxy)-2-chloropyrimidine

To a solution of 2,4-dichloropyrimidine (90) (2.0 g, 0.0134 mmol) in toluene (20 mL) was added benzyl alcohol (1.53 ml, 1.59 g, 0.0147 mol), KOH (0.82 g, 0.0147 mol) and 18-crown-6 (0.177 g, 0.00067 mol) and stirred at rt for 1 h. The reaction mixture was diluted with EtOAc (400 mL) and washed with water (3×50 mL), dried over MgSO$_4$, filtered and concentrated to give a white solid that was chromatographed (hexane:CH$_2$Cl$_2$, 1:1 to 3:7) to afford 2.09 g (71%) of a mixture of 96 with regioisomeric 2-(benzyloxy)-4-chloropyrimidine (relative ratio 75:25 by $^1$H-NMR, respectively); MS (m/z): [M+Na]$^+$ 243.1.

(97) 4-(benzyloxy)-2-(4-methylpiperazin-1-yl)pyrimidine

To a solution of 96 (2.09, 0.00947 mol; contains regioisomer) in DMF (34 mL) was added 1-methylpiperazine (3.15 mL, 2.85 g, 0.0284 mol) and heated at 80° C. for 1.75 h. Solvent was removed under reduced pressure and the residue was taken up into EtOAc (350 mL) and washed with brine (3×50 mL). The aqueous layer was extracted with EtOAc (2×50 mL) and the combined organic layers were was dried over MgSO$_4$, filtered and concentrated to give an oil that was purified by column chromatography (EtOAc:MeOH—NH$_3$ (7N), 1:0 to 25:1) to afford 1.88 g (70%) of 97. $^1$H NMR (500 MHz, CDCl$_3$): δ 8.06 (d, J=5.6 Hz, 1H), 7.41 (d, J=7.0 Hz, 2H), 7.35 (t, J=7.0 Hz, 2H), 7.32 (d, J=7.0 Hz, 1H), 6.03 (d, J=5.6 Hz, 1H), 5.35 (s, 2H), 3.83 (m, 4H), 2.45 (m, 4H), 2.33 (s, 3H); MS (m/z): [M+H]$^+$ 284.9.

(98) 4-(benzyloxy)-5-iodo-2-(4-methylpiperazin-1-yl)pyrimidine

To 97 (0.937 g, 0.0033 mol) in acetonitrile (16 mL) was added TFA (1.02 mL, 1.51 g, 0.0132 mol) and N-iodosuccinimide (0.965 g, 0.0043 mol) and stirred at rt for 1 h. Then 7 mL of 10% Na$_2$CO$_3$ (0.70 g, 0.066 mol) was added and stirred for 2 minutes. The reaction mixture was concentrated to dryness and the residue was taken up into CH$_2$Cl$_2$ (200 ml) and washed with 10% Na$_2$CO$_3$ (2×50 mL), 10% sodium thiosulfate (50 mL) and brine (50 mL). The organic layer was dried over MgSO$_4$, filtered and concentrated to give an oil which was purified by column chromatography (CH$_2$Cl$_2$:MeOH—NH$_3$ (7N), 50:1) to yield 1.31 g (97%) of 98. $^1$H NMR (500 MHz, CDCl$_3$): δ 8.27 (s, 1H), 7.44 (d, J=7.4 Hz, 2H), 7.37 (t, J=7.2 Hz, 2H), 7.32 (d, J=7.3 Hz, 1H), 5.40 (s, 2H), 3.79 (m, 4H), 2.42 (m, 4H), 2.32 (s, 3H); MS (m/z): [M+H]$^+$ 411.0.

(99) 3-(4-(benzyloxy)-2-(4-methylpiperazin-1-yl)pyrimidin-5-ylthio)aniline

A mixture of 98 (0.985 g, 2.40 mmol), 3-aminobenzenethiol (255 µl, 300.5 mg, 2.40 mmol), neocuproine (150 mg, 0.72 mmol), copper iodide (137 mg, 0.72 mmol), and potassium carbonate (0.663 g, 4.80 mmol) in DMF (25 mL) was stirred at 120° C. for 18 h. Solvent was removed under reduced pressure and the residue was purified by column chromatography (CH$_2$Cl$_2$:MeOH—NH$_3$ (7N), 50:1 to 20:1) to afford 0.75 g (77%) of 99. $^1$H NMR (500 MHz, CDCl$_3$): δ 8.24 (s, 1H), 7.16-7.30 (m, 5H), 6.99 (t, J=7.3 Hz, 1H), 6.56 (d, J=7.6 Hz, 1H), 6.38-6.46 (m, 2H), 5.38 (s, 2H), 3.84 (m, 4H), 3.56 (br s, 2H), 2.45 (br s, 4H), 2.33 (s, 3H); $^{13}$C NMR (166 MHz, CDCl$_3$): δ 169.3, 164.5, 161.4, 158.1, 146.9, 138.5, 136.8, 129.6, 128.3, 127.7, 127.4, 117.6, 113.6, 112.6, 67.6, 54.8, 46.2, 43.9; MS (m/z): [M+H]$^+$ 408.1.

TT-7 (100) N-(3-(4-(benzyloxy)-2-(4-methylpiperazin-1-yl)pyrimidin-5-ylthio)phenyl)acetamide To 99 (5.2 mg, 0.013 mmol) in CH$_2$Cl$_2$ (0.2 mL) was added acetic anhydride (1.5 µL, 1.6 mg, 0.0156 mmol) and stirred at rt for 4 h. It was then concentrated to dryness under reduced pressure to give a residue which was purified by preparatory TLC (CH$_2$Cl$_2$:MeOH—NH$_3$ (7N), 20:1) to afford 4.5 mg (79%) of 100. $^1$H NMR (500 MHz, CDCl$_3$/MeOH-d$_4$): δ 8.24 (s, 1H), 7.54 (d, J=7.7 Hz, 1H), 7.22-7.27 (m, 3H), 7.13-7.20 (m, 3H), 7.09 (s, 1H), 6.87 (d, J=7.7 Hz, 1H), 5.36 (s, 2H), 3.85 (m, 4H), 2.49 (m, 4H), 2.35 (s, 3H), 2.10 (s, 3H); MS (m/z): [M+H]$^+$ 450.1.

TT-8 (101) N-(3-(4-(benzyloxy)-2-(4-methylpiperazin-1-yl)pyrimidin-5-ylthio)phenyl)benzamide 99 (14 mg, 0.034 mmol), Et$_3$N (24 µl, 17.2 mg, 0.17 mmol) and benzoyl chloride (12 µl, 14.3 mg, 0.102 mmol) in CH$_2$Cl$_2$ (1 mL) was stirred at rt for 2 h. Solvent was removed under reduced pressure and the residue was purified by preparatory TLC (CH$_2$Cl$_2$:MeOH—NH$_3$ (7N), 25:1) to afford 13.6 mg (78%) of 101. $^1$H NMR (500 MHz, CDCl$_3$/MeOH-d$_4$): δ 8.26 (s, 1H), 7.84 (d, J=7.4 Hz, 2H), 7.69 (dd, J=1.4, 8.2 Hz, 1H), 7.54 (t, J=7.3 Hz, 1H), 7.47 (t, J=7.9 Hz, 2H), 7.14-7.27 (m, 7H), 6.93 (dd, J=0.9, 7.9 Hz, 1H), 5.37 (s, 2H), 3.85 (m, 4H), 2.48 (m, 4H), 2.35 (s, 3H); $^{13}$C NMR (166 MHz, CDCl$_3$/MeOH-d$_4$): δ 168.6, 166.3, 164.2, 161.3, 138.6, 138.3, 136.4, 134.8, 131.8, 129.3, 128.6, 128.3, 127.7, 127.5, 127.2, 123.4, 118.8, 117.9, 100.1, 67.8, 54.6, 45.9, 43.6; MS (m/z): [M+H]$^+$ 512.1.

TT-9 (102) 2-amino-N-(3-(4-(benzyloxy)-2-(4-methylpiperazin-1-yl)pyrimidin-5-ylthio)phenyl)acetamide 99 (30 mg, 0.0736 mmol) in THF (3 mL) was added Boc-glycine (14.2 mg, 0.081 mmol), DCC (16.7 mg, 0.081 mmol) and stirred at rt overnight. Reaction mixture was concentrated under reduced pressure and the residue was purified by preparatory TLC (CH$_2$Cl$_2$:MeOH—NH$_3$ (7N), 25:1) to afford an oil which was dissolved in 2.5 mL of CH$_2$Cl$_2$:TFA (4:1) and stirred at rt for 45 minutes. The reaction mixture was concentrated under reduced pressure and the residue was purified by preparatory TLC (CH$_2$Cl$_2$:MeOH—NH$_3$ (7N), 15:1) to afford 24.6 mg (72%) of 102. $^1$H NMR (500 MHz, CDCl$_3$/MeOH-d$_4$): δ 8.24 (s, 1H), 7.50 (dd, J=1.2, 8.1 Hz, 1H), 7.31 (m, 1H), 7.22-7.27 (m, 3H), 7.13-7.20 (m, 3H), 6.86 (d, J=7.9 Hz, 1H), 5.37 (s, 2H), 3.85 (m, 4H), 3.39 (s, 2H), 2.49 (m, 4H), 2.35 (s, 3H); $^{13}$C NMR (166 MHz, CDCl$_3$/MeOH-d$_4$): δ 171.4, 168.5, 164.1, 161.2, 138.2, 138.1, 136.4, 129.2, 128.2, 127.6, 127.2, 123.0, 118.2, 117.0, 67.7, 54.5, 45.8, 44.6, 43.5; MS (m/z): [M+H]$^+$ 465.3.

TT-20 (105) N-(3-(4-(benzyloxy)-2-(4-methylpiperazin-1-yl)pyrimidin-5-ylthio)phenyl)pyrrolidine-2-carboxamide 99 (8.6 mg, 0.0211 mmol) in THF (0.5 mL) was added Boc-L-proline (5 mg, 0.0232 mmol), DCC (5 mg, 0.0232 mmol) and stirred at rt overnight. Reaction mixture was concentrated under reduced pressure and the residue was dissolved in 0.35 mL of CH$_2$Cl$_2$:TFA (4:1) and stirred at rt for 45 minutes. The reaction mixture was concentrated under reduced pressure and the residue was purified by preparatory TLC (CH$_2$Cl$_2$:MeOH—NH$_3$ (7N), 15:1) to afford 6.0 mg (57%) of 105. $^1$H NMR (500 MHz, CDCl$_3$): δ 9.63 (s, 1H), 8.26 (s, 1H), 7.58 (dd, J=1.2, 8.1 Hz, 1H), 7.31 (t, J=1.9 Hz, 1H), 7.12-7.17 (m, 3H), 7.22-7.26 (m, 3H), 6.83 (d, J=7.9 Hz, 1H), 5.36 (s, 2H), 3.80-3.91 (m, 5H), 3.04-3.11 (m, 1H), 2.94-3.00 (m, 1H), 2.47 (m, 4H), 2.35 (s, 3H), 2.15-2.25 (m, 1H), 1.98-2.06 (m, 1H), 1.70-1.81 (m, 1H); MS (m/z): [M+H]+ 505.2.
Scheme 13. Synthesis of TT-12 (115), TT-13 (116), TT-14 (117), TT-15 (118), TT-16 (119), TT-17 (120).
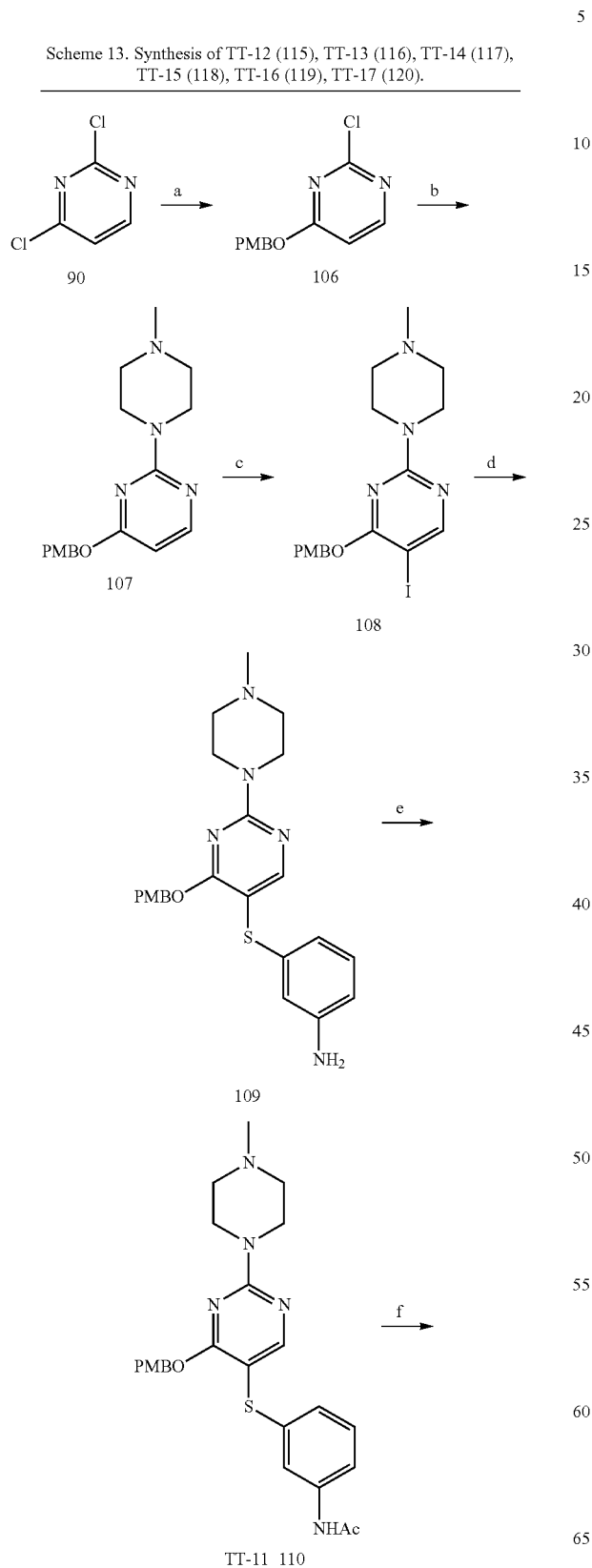
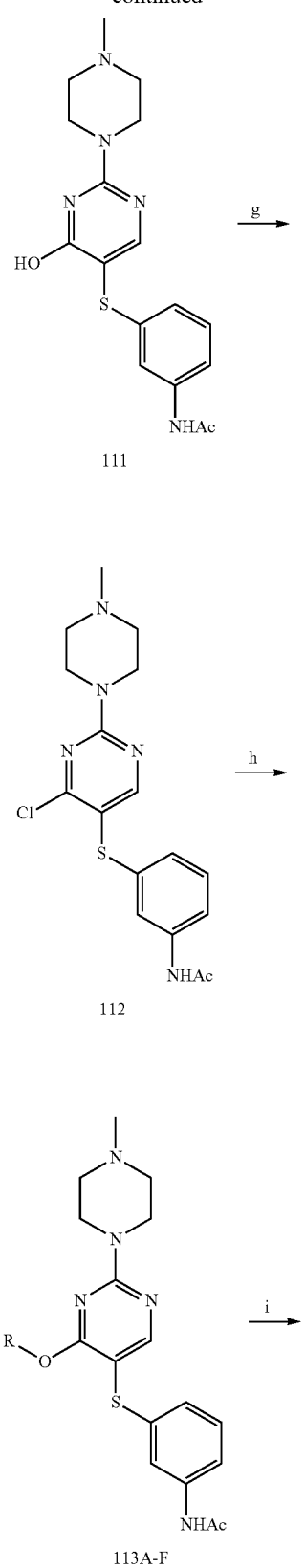

-continued

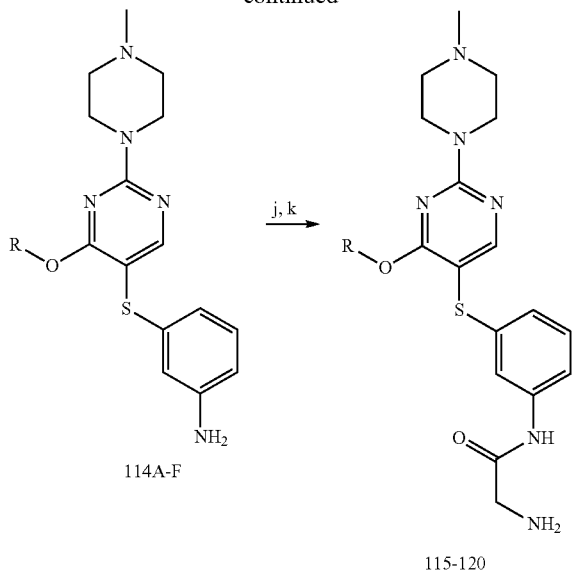

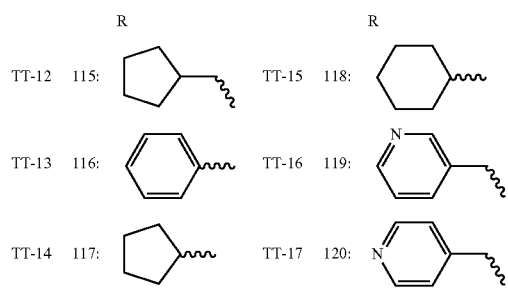

Reagents and conditions: a. p-methoxybenzyl alcohol, KOH, 18-crown-6, toluene, rt, 1 h; b. N-methylpiperazine, DMF, 80° C., 1.5 h; c. NIS, TFA, CH₃CN, rt, 1 h; d. 3-aminobenzenethiol, copper(I)thiophene-2-carboxylate, K₂CO₃, DMF, 120° C., 25 h; e. Ac₂O, CH₂Cl₂, rt, 3 h; f. CH₂Cl₂:TFA (1:1), rt, 4 h; g. POCl₃, 60° C., 2 h; h. ROH, NaH, DMF, 80° C., 1.5 h; i. BF₃—MeOH, reflux, 5 h; j. RCOOH, DCC, THF, rt, 12 h; k. CH₂Cl₂:TFA (4:1), rt or CH₂Cl₂:piperidine (9:1), rt.

(106) 2-chloro-4-(4-methoxybenzyloxy)pyrimidine 2,4-dichloropyrimidine (90) (2.0 g, 0.0134 mmol) in toluene (20 mL) was added p-methoxybenzyl alcohol (1.84 ml, 2.04 g, 0.0147 mol), KOH (0.825 g, 0.0147 mol) and 18-crown-6 (0.177 g, 0.00067 mol) and is stirred at rt for 1 h. The reaction mixture was diluted with EtOAc (350 mL), washed with water (2×50 mL), dried over MgSO₄, filtered and concentrated to give an oil that was purified by column chromatography (hexane:CH₂Cl₂, 1:1 to 3:7) to afford 2.39 g (71%) of a mixture of 106 with the regioisomeric 4-chloro-2-(4-methoxybenzyloxy)pyrimidine (relative ratio 78:22 by ¹H-NMR, respectively).

(107) 4-(4-methoxybenzyloxy)-2-(4-methylpiper-azin-1-yl)pyrimidine

To a solution of 106 (2.39, 0.0095 mol; contains regioisomer) in DMF (34 mL) was added 1-methylpiperazine (3.16 mL, 2.85 g, 0.0285 mol) and heated at 80° C. for 1.5 h. Solvent was removed under reduced pressure and the residue was taken up into EtOAc (350 mL) and washed with brine (3×50 mL). The aqueous layer was extracted with EtOAc (2×50 mL) and the combined organic layers were was dried over MgSO₄, filtered and concentrated to give an oil that was purified by column chromatography (EtOAc:i-PrOH:Et₃N, 40:1:1% to 20:1:1%) to afford 2.10 g (70%) of 107. ¹H NMR (500 MHz, CDCl₃): δ 8.05 (d, J=5.6 Hz, 1H), 7.35 (d, J=8.5 Hz, 2H), 6.90 (d, J=8.5 Hz, 2H), 6.00 (d, J=5.6 Hz, 1H), 5.27 (s, 2H), 3.84 (m, 4H), 3.81 (s, 3H), 2.46 (m, 4H), 2.34 (s, 3H); MS (m/z): [M+H]⁺ 315.2.

(108) 5-iodo-4-(4-methoxybenzyloxy)-2-(4-methyl-piperazin-1-yl)pyrimidine

To 107 (1.16 g, 3.69 mmol) in acetonitrile (18 mL) was added N-iodosuccinimide (1.08 g, 4.80 mmol), TFA (1.14 mL, 1.68 g, 14.76 mmol), and stirred at rt for 1 h. Then 15.6 mL of 10% Na₂CO₃ (1.56 g, 14.76 mmol) was added and stirred for 2 minutes. The reaction mixture was concentrated to dryness and the residue was taken up into CH₂Cl₂ (200 ml) and washed with 10% Na₂CO₃ (2×50 mL), 10% sodium thiosulfate (50 mL) and brine (50 mL). The organic layer was dried over MgSO₄, filtered and concentrated to give an oil which was purified by column chromatography (CH₂Cl₂:MeOH—NH₃ (7N), 50:1) to yield 1.44 g (85%) of 108. ¹H NMR (500 MHz, CDCl₃): δ 8.26 (s, 1H), 7.37 (d, J=8.5 Hz, 2H), 6.90 (d, J=8.5 Hz, 2H), 5.33 (s, 2H), 3.81 (s, 3H), 3.80 (m, 4H), 2.44 (m, 4H), 2.33 (s, 3H); MS (m/z): [M+H]⁺ 441.0.

(109) 3-(4-(4-methoxybenzyloxy)-2-(4-methylpiper-azin-1-yl)pyrimidin-5-ylthio)aniline A mixture of 108 (1.14 g, 2.59 mmol) and potassium carbonate (0.716 g, 5.18 mmol) in DMF (37 mL) was evacuated and backfilled with argon three times. Copper(I) thiophene-2-carboxylate (0.198 g, 1.04 mmol) was added and evacuated and backfilled with argon two times. 3-Aminothiophenol (330 μl, 0.389 g, 3.11 mmol) was added and the reaction mixture was heated at 120° C. for 25 h. Solvent was removed under reduced pressure and the residue was purified by column chromatography (CH₂Cl₂:MeOH—NH₃ (7N), 200:1 to 40:1) to afford 0.933 g (82%) of 109. ¹H NMR (500 MHz, CDCl₃): δ 8.23 (s, 1H), 7.14 (d, J=8.7 Hz, 2H), 6.98 (t, J=7.8 Hz, 1H), 6.80 (d, J=8.7 Hz, 2H), 6.54 (d, J=7.8 Hz, 1H), 6.44 (d, J=7.9 Hz, 1H), 6.40 (t, J=1.9 Hz, 1H), 5.30 (s, 2H), 3.86 (m, 4H), 3.79 (s, 3H), 3.55 (br s, 2H), 2.47 (m, 4H), 2.35 (s, 3H); ¹³C NMR (166 MHz, CDCl₃): δ 168.6, 164.4, 161.4, 159.2, 146.8, 138.6, 129.5, 129.3, 128.8, 117.6, 113.7, 113.6, 112.5, 100.1, 67.4, 55.3, 54.8, 46.2, 43.9; MS (m/z): [M+H]⁺ 438.3.

TT-11 (110) N-(3-(4-(4-methoxybenzyloxy)-2-(4-methylpiperazin-1-yl)pyrimidin-5-ylthio)phenyl) acetamide To a solution of 109 (0.933 g, 2.13 mmol) in CH₂Cl₂ (6 mL) was added acetic anhydride (242 μL, 261 mg, 2.56 mmol) and stirred at rt for 3 h. The reaction mixture was diluted with CH₂Cl₂ (90 mL) and washed with 10% Na₂CO₃ (2×25 mL), dried over MgSO₄, filtered, and concentrated under reduced pressure to give a residue which was purified by column chromatography (CH₂Cl₂:MeOH—NH₃ (7N), 200:1 to 50:1) to afford 0.895 g (88%) of 110. ¹H NMR (500 MHz, CDCl₃): δ 8.24 (s, 1H), 7.55 (d, J=7.8 Hz, 1H), 7.16 (t, J=7.9 Hz, 1H), 7.11 (d, J=8.6 Hz, 2H), 6.85-6.93 (m, 3H), 6.78 (d, J=8.6 Hz, 2H), 5.31 (s, 2H), 3.88 (m, 4H), 3.78 (s, 3H), 2.48 (m, 4H), 2.35 (s, 3H), 2.12 (s, 3H); MS (m/z): [M+H]$^+$ 480.1.

(111) N-(3-(4-hydroxy-2-(4-methylpiperazin-1-yl)pyrimidin-5-ylthio)phenyl)acetamide To a solution of 110 (0.872 g, 1.82 mmol) in CH$_2$Cl$_2$ (4 mL) was added TFA (4 mL) dropwise over 5 minutes and stirred at rt for 4 h. The reaction mixture was concentrated under reduced pressure and dried under high vacuum overnight to afford 111 which was used without further purification. MS (m/z): [M+H]$^+$ 360.2.

(112) N-(3-(4-chloro-2-(4-methylpiperazin-1-yl)pyrimidin-5-ylthio)phenyl)acetamide 111 (~1.82 mmol) and POCl$_3$ (5 mL) were heated at 65° C. for 2 h. After cooling to rt, the reaction mixture was added to a beaker containing ice chips. Following complete quenching of POCl$_3$, solid Na$_2$CO$_3$ was carefully added until pH ~9. This was transferred to a seperatory funnel and extracted with CH$_2$Cl$_2$ (4×60 mL), dried over MgSO$_4$, filtered and concentrated to a solid which was purified by column chromatography (CH$_2$Cl$_2$:MeOH—NH$_3$ (7N), 200:1 to 50:1) to afford 0.215 g (31%) of 112. $^1$H NMR (500 MHz, CDCl$_3$): δ 8.37 (s, 1H), 7.40 (d, J=8.0 Hz, 1H), 7.16-7.25 (m, 2H), 6.89 (d, J=7.7 Hz, 1H), 3.88 (m, 4H), 2.47 (m, 4H), 2.34 (s, 3H), 2.14 (s, 3H); MS (m/z): [M+H]$^+$ 378.2.

(113A) N-(3-(4-(cyclopentylmethoxy)-2-(4-methylpiperazin-1-yl)pyrimidin-5-ylthio)phenyl)acetamide To cylcopentanemethanol (21.3 g L, 19.9 mg, 0.198 mmol) dissolved in DMF (250 μL) was added NaH (4.3 mg, 0.179 mmol) and the resulting suspension was stirred for 10 min. at rt. Then 112 (15 mg, 0.0397 mmol) was added and the reaction mixture was heated at 80° C. for 1.5 h. MeOH (1 mL) was added and stirred for 5 minutes then the reaction mixture was concentrated under reduced pressure to give a residue which was purified by preparatory TLC (CH$_2$Cl$_2$:MeOH—NH$_3$ (7N), 20:1) to afford 13.9 mg (79%) of 113A. $^1$H NMR (500 MHz, CDCl$_3$): δ 8.23 (s, 1H), 7.42 (d, J=8.0 Hz, 1H), 7.10-7.22 (m, 3H), 6.86 (d, J=7.7 Hz, 1H), 4.16 (d, J=6.7 Hz, 2H), 3.86 (m, 4H), 2.48 (m, 4H), 2.35 (s, 3H), 2.19 (m, 1H), 2.09 (s, 3H), 1.56-1.67 (m, 2H), 1.40-1.55 (m, 4H), 1.10-1.20 (m, 2H); MS (m/z): [M+H]$^+$ 442.1.

(114A) 3-(4-(cyclopentylmethoxy)-2-(4-methylpiperazin-1-yl)pyrimidin-5-ylthio)aniline 113A (13.9 mg, 0.0315 mmol) in methanol (1 mL) was added BF$_3$-MeOH (47 μL, 53.6 mg, 0.378 mmol) and refluxed for 5 h. Et$_3$N was added then the reaction mixture was concentrated to give a residue which was purified by preparatory TLC (CH$_2$Cl$_2$:MeOH—NH$_3$ (7N), 20:1) to afford 11 mg (87%) of 114A. $^1$H NMR (500 MHz, CDCl$_3$): δ 8.22 (s, 1H), 6.98 (t, J=7.8 Hz, 1H), 6.55 (d, J=7.7 Hz, 1H), 6.45 (s, 1H), 6.43 (d, J=7.9 Hz, 1H), 4.17 (d, J=6.7 Hz, 2H), 3.86 (m, 4H), 3.58 (br s, 2H), 2.48 (m, 4H), 2.35 (s, 3H), 2.23 (m, 1H), 1.59-1.68 (m, 2H), 1.43-1.58 (m, 4H), 1.13-1.23 (m, 2H); MS (m/z): [M+H]$^+$ 400.3.

TT-12 (115) 2-amino-N-(3-(4-(cyclopentylmethoxy)-2-(4-methylpiperazin-1-yl)pyrimidin-5-ylthio)phenyl)acetamide 114A (11 mg, 0.0275 mmol) in THF (1 mL) was added Boc-glycine (5.3 mg, 0.030 mmol), DCC (6.2 mg, 0.030 mmol) and stirred at rt overnight. The reaction mixture was concentrated under reduced pressure and the residue was purified by preparatory TLC (CH$_2$Cl$_2$:MeOH—NH$_3$ (7N), 20:1) to afford a residue which was dissolved in 1.25 mL of CH$_2$Cl$_2$:TFA (4:1) and stirred at rt for 45 minutes. The reaction mixture was concentrated under reduced pressure and the residue was purified by preparatory TLC (CH$_2$Cl$_2$: MeOH—NH$_3$ (7N), 10:1) to afford 10.3 mg (82%) of 115. $^1$H NMR (500 MHz, CDCl$_3$/MeOH-d$_4$): δ 8.21 (s, 1H), 7.44 (d, J=8.0 Hz, 1H), 7.34 (s, 1H), 7.17 (t, J=8.0 Hz, 1H), 6.86 (d, J=7.1 Hz, 1H), 4.17 (d, J=6.8 Hz, 2H), 3.84 (m, 4H), 3.41 (s, 2H), 2.51 (m, 4H), 2.36 (s, 3H), 2.21 (m, 1H), 1.57-1.67 (m, 2H), 1.42-1.57 (m, 4H), 1.10-1.22 (m, 2H); MS (m/z): [M+H]$^+$ 457.4.

(113B) N-(3-(2-(4-methylpiperazin-1-yl)-4-phenoxypyrimidin-5-ylthio)phenyl)acetamide To phenol (19 mg, 0.198 mmol) dissolved in DMF (250 μL) was added NaH (4.3 mg, 0.179 mmol) and the resulting solution was stirred for 10 min. at rt. Then 112 (15 mg, 0.0397 mmol) was added and the reaction mixture was heated at 80° C. for 1.5 h. MeOH (1 mL) was added and stirred for 5 minutes, then the reaction mixture was concentrated under reduced pressure to give a residue which was purified by preparatory TLC (CH$_2$Cl$_2$:MeOH—NH$_3$ (7N), 20:1) to afford 16.2 mg (94%) of 113B. $^1$H NMR (500 MHz, CDCl$_3$): δ 8.35 (s, 1H), 7.40 (d, J=7.7 Hz, 1H), 7.30-7.36 (m, 3H), 7.28 (br s, 1H), 7.15-7.23 (m, 2H), 7.02 (d, J=8.0 Hz, 2H), 6.96 (d, J=7.6 Hz, 1H), 3.65 (m, 4H), 2.36 (m, 4H), 2.28 (s, 3H), 2.13 (s, 3H); MS (m/z): [M+H]$^+$ 436.2.

(114B) 3-(2-(4-methylpiperazin-1-yl)-4-phenoxypyrimidin-5-ylthio)aniline 113B (16.2 mg, 0.037 mmol) in methanol (1 mL) was added BF$_3$-MeOH (55 μL, 63.3 mg, 0.446 mmol) and refluxed for 5 h. Et$_3$N was added then the reaction mixture was concentrated to give a residue which was purified by preparatory TLC (hexane:CH$_2$Cl$_2$:EtOAc:MeOH—NH$_3$ (7N), 2:2:1:0.5) to afford 6.5 mg (45%) of 114B. $^1$H NMR (500 MHz, CDCl$_3$): δ 8.34 (s, 1H), 7.33 (t, J=7.7 Hz, 2H), 7.18 (t, J=7.4 Hz, 1H), 7.01-7.07 (m, 3H), 6.63 (d, J=7.8 Hz, 1H), 6.56 (t, J=2.0 Hz, 1H), 6.47 (dd, J=2.2, 8.0 Hz, 1H), 3.63 (m, 6H), 2.37 (m, 4H), 2.30 (s, 3H); MS (m/z): [M+H]$^+$ 394.3.

TT-13 (116) 2-amino-N-(3-(2-(4-methylpiperazin-1-yl)-4-phenoxypyrimidin-5-ylthio)phenyl) acetamide 114B (6.5 mg, 0.0165 mmol) in THF (0.65 mL) was added Fmoc-glycine (5.4 mg, 0.018 mmol), DCC (3.8 mg, 0.018 mmol) and stirred at rt overnight. Reaction mixture was concentrated under reduced pressure and the residue was purified by preparatory TLC (hexane:CH$_2$Cl$_2$:EtOAc: MeOH—NH$_3$ (7N), 2:2:1:0.5) to afford a residue which was dissolved in CH$_2$Cl$_2$ (0.9 mL) and piperidine (0.1 mL) and stirred at rt for 5 h. The reaction mixture was concentrated under reduced pressure and the residue was purified by preparatory TLC (CH$_2$Cl$_2$:MeOH—NH$_3$ (7N), 15:1) to afford 3.5 mg (47%) of 116. $^1$H NMR (500 MHz, CDCl$_3$): δ 9.34 (br s, 1H), 8.36 (s, 1H), 7.50 (d, J=8.0 Hz, 1H), 7.47 (s, 1H), 7.33 (t, J=8.2 Hz, 2H), 7.22 (t, J=8.0 Hz, 1H), 7.18 (t, J=7.4 Hz, 1H), 7.03 (d, J=7.7 Hz, 2H), 6.96 (d, J=7.9 Hz, 1H), 3.68 (m, 4H), 3.46 (s, 2H), 2.40 (m, 4H), 2.31 (s, 3H); MS (m/z): [M+H]$^+$ 451.1.

(113C) N-(3-(4-(cyclopentyloxy)-2-(4-methylpiperazin-1-yl)pyrimidin-5-ylthio)phenyl)acetamide To cyclopentanol (11.8 µL, 11.2 mg, 0.13 mmol) dissolved in DMF (200 µL) was added NaH (2.8 mg, 0.117 mmol) and the resulting suspension was stirred for 10 min. at rt. Then 112 (10 mg, 0.026 mmol) was added and the reaction mixture was heated at 80° C. for 2 h. MeOH (1 mL) was added and stirred for 5 minutes then the reaction mixture was concentrated under reduced pressure to give a residue which was purified by preparatory TLC (CH$_2$Cl$_2$:MeOH—NH$_3$ (7N), 15:1) to afford 8.5 mg (77%) of 113C. $^1$H NMR (500 MHz, CDCl$_3$): δ 8.21 (s, 1H), 7.41 (d, J=7.9 Hz, 1H), 7.10-7.19 (m, 3H), 6.86 (d, J=7.8 Hz, 1H), 5.39 (m, 1H), 3.86 (m, 4H), 2.48 (m, 4H), 2.35 (s, 3H), 2.14 (s, 3H), 1.63-1.86 (m, 4H), 1.45-1.56 (m, 4H); MS (m/z): [M+H]$^+$ 428.2.

(114C) 3-(4-(cyclopentyloxy)-2-(4-methylpiperazin-1-yl)pyrimidin-5-ylthio)aniline 113C (8.5 mg, 0.020 mmol) in methanol (0.75 mL) was added BF$_3$-MeOH (30 µL, 34.1 mg, 0.24 mmol) and refluxed for 5 h. Et$_3$N was added then the reaction mixture was concentrated to give a residue which was purified by preparatory TLC (CH$_2$Cl$_2$:MeOH—NH$_3$ (7N), 15:1) to afford 7.2 mg (94%) of 114C. $^1$H NMR (500 MHz, CDCl$_3$): δ 8.20 (s, 1H), 6.98 (t, J=7.8 Hz, 1H), 6.55 (d, J=7.0 Hz, 1H), 6.46 (t, J=2.0 Hz, 1H), 6.43 (dd, J=2.0, 7.9 Hz, 1H), 5.40 (m, 1H), 3.86 (m, 4H), 3.58 (br s, 2H), 2.48 (m, 4H), 2.35 (s, 3H), 1.67-1.87 (m, 4H), 1.51-1.62 (m, 4H); MS (m/z): [M+H]$^+$ 386.2.

TT-14 (117) 2-amino-N-(3-(4-(cyclopentyloxy)-2-(4-methylpiperazin-1-yl)pyrimidin-5-ylthio)phenyl)acetamide To a solution of 114C (7.2 mg, 0.0187 mmol) in THF (0.5 mL) was added Boc-glycine (3.6 mg, 0.0206 mmol) and DCC (4.3 mg, 0.0206 mmol). After stirring overnight at rt, THF was evaporated and 0.5 mL of CH$_2$Cl$_2$:TFA (4:1) was added. The solution was stirred for 45 min., then concentrated to dryness under reduced pressure to give a residue which was purified by preparatory TLC (CH$_2$Cl$_2$:MeOH—NH$_3$ (7N), 15:1) to afford 7.4 mg (89%) of 117. $^1$H NMR (500 MHz, CDCl$_3$): δ 9.29 (br s, 1H), 8.22 (s, 1H), 7.52 (d, J=7.7 Hz, 1H), 7.30 (s, 1H), 7.16 (t, J=8.0 Hz, 1H), 6.86 (d, J=7.9 Hz, 1H), 5.40 (m, 1H), 3.86 (m, 4H), 3.45 (s, 2H), 2.48 (m, 4H), 2.35 (s, 3H), 1.61-1.86 (m, 4H), 1.44-1.57 (m, 4H); MS (m/z): [M+H]$^+$ 443.2.

(113D) N-(3-(4-(cyclohexyloxy)-2-(4-methylpiperazin-1-yl)pyrimidin-5-ylthio)phenyl)acetamide To cyclohexanol (14 µL, 13.0 mg, 0.13 mmol) dissolved in DMF (200 µL) was added NaH (2.8 mg, 0.117 mmol) and the resulting suspension was stirred for 10 min. at rt. Then 112 (10 mg, 0.026 mmol) was added and the reaction mixture was heated at 80° C. for 2 h. MeOH (1 mL) was added and stirred for 5 minutes then the reaction mixture was concentrated under reduced pressure to give a residue which was purified by preparatory TLC (hexane:CH$_2$Cl$_2$:EtOAc:MeOH—NH$_3$ (7N), 2:2:1:0.5) to afford 2.9 mg (25%) of 113D. $^1$H NMR (500 MHz, CDCl$_3$): δ 8.23 (s, 1H), 7.43 (d, J=7.9 Hz, 1H), 7.12-7.19 (m, 2H), 7.06 (br s, 1H), 6.88 (d, J=7.6 Hz, 1H), 5.05 (m, 1H), 3.85 (m, 4H), 2.50 (m, 4H), 2.36 (m, 3H), 2.14 (s, 3H), 1.22-1.80 (m, 10H); MS (m/z): [M+H]$^+$ 442.2.

(114D) 3-(4-(cyclohexyloxy)-2-(4-methylpiperazin-1-yl)pyrimidin-5-ylthio)aniline 113D (2.9 mg, 0.0066 mmol) in methanol (0.5 mL) was added BF$_3$-MeOH (10 µL, 11.2 mg, 0.079 mmol) and refluxed for 5 h. Et$_3$N was added then the reaction mixture was concentrated to give a residue which was purified by preparatory TLC (CH$_2$Cl$_2$:MeOH—NH$_3$ (7N), 15:1) to afford 2.4 mg (92%) of 114D. $^1$H NMR (500 MHz, CDCl$_3$): δ 8.22 (s, 1H), 6.98 (t, J=7.9 Hz, 1H), 6.57 (d, J=7.8 Hz, 1H), 6.48 (t, J=2.0 Hz, 1H), 6.43 (dd, J=2.0, 8.0 Hz, 1H), 5.05 (m, 1H), 3.86 (m, 4H), 3.58 (br s, 2H), 2.51 (m, 4H), 2.37 (s, 3H), 1.22-1.80 (m, 10H); MS (m/z): [M+H]$^+$ 400.2.

TT-15 (118) 2-amino-N-(3-(4-(cyclohexyloxy)-2-(4-methylpiperazin-1-yl)pyrimidin-5-ylthio) phenyl)acetamide To a solution of 114D (2.4 mg, 0.006 mmol) in THF (0.25 mL) was added Boc-glycine (1.2 mg, 0.0066 mmol) and DCC (1.4 mg, 0.0066 mmol). After stirring overnight at rt, THF was evaporated and 0.25 mL of CH$_2$Cl$_2$:TFA (4:1) was added. The solution was stirred for 45 min., then concentrated to dryness under reduced pressure to give a residue which was purified by preparatory TLC (CH$_2$Cl$_2$:MeOH—NH$_3$ (7N), 15:1) to afford 2.5 mg (93%) of 118. $^1$H NMR (500 MHz, CDCl$_3$): δ 9.28 (br s, 1H), 8.24 (s, 1H), 7.54 (d, J=7.9 Hz, 1H), 7.30 (s, 1H), 7.17 (t, J=7.9 Hz, 1H), 6.88 (d, J=7.8 Hz, 1H), 5.06 (m, 1H), 3.84 (m, 4H), 3.45 (s, 2H), 2.48 (m, 4H), 2.35 (s, 3H), 1.22-1.80 (m, 10H); MS (m/z): [M+H]$^+$ 457.1.

(113E) N-(3-(2-(4-methylpiperazin-1-yl)-4-(pyridin-3-ylmethoxy)pyrimidin-5-ylthio) phenyl)acetamide To 3-pyridylcarbinol (15.5 µL, 17.4 mg, 0.159 mmol) dissolved in DMF (200 µL) was added NaH (3.4 mg, 0.143 mmol) and the resulting suspension was stirred for 10 min. at rt. Then 112 (12 mg, 0.0318 mmol) was added and the reaction mixture was heated at 80° C. for 1.5 h. MeOH (1 mL) was added and stirred for 5 minutes, then the reaction mixture was concentrated under reduced pressure to give a residue which was purified by preparatory TLC (hexane:CH$_2$Cl$_2$:EtOAc:MeOH—NH$_3$ (7N), 2:2:1:0.5) to afford 11.8 mg (83%) of 113E. MS (m/z): [M+H]$^+$ 451.3.

(114E) 3-(2-(4-methylpiperazin-1-yl)-4-(pyridin-3-ylmethoxy)pyrimidin-5-ylthio)aniline 113E (11.8 mg, 0.026 mmol) in methanol (1 mL) was added BF$_3$-MeOH (39 µL, 44.3 mg, 0.312 mmol) and refluxed for 5 h. Et$_3$N was added, then the reaction mixture was concentrated to give a residue which was purified by preparatory TLC (CH$_2$Cl$_2$:MeOH—NH$_3$ (7N), 15:1) to afford 7 mg (66%) of 114E. $^1$H NMR (500 MHz, CDCl$_3$/MeOH-d$_4$): δ 8.45 (d, J=4.9 Hz, 1H), 8.43 (s, 1H), 8.25 (s, 1H), 7.50 (d, J=7.9 Hz, 1H), 7.27 (dd, J=5.0, 7.8 Hz, 1H), 7.01 (t, J=7.8 Hz, 1H), 6.47-6.55 (m, 3H), 5.39 (s, 2H), 3.88 (m, 4H), 2.52 (m, 4H), 2.37 (s, 3H); MS (m/z): [M+H]$^+$ 409.3.

TT-16 (119) 2-amino-N-(3-(2-(4-methylpiperazin-1-yl)-4-(pyridin-3-ylmethoxy)pyrimidin-5-ylthio) phenyl)acetamide To a solution of 114E (6 mg, 0.015 mmol) in THF (0.5 mL) was added Boc-glycine (3 mg, 0.016 mmol) and DCC (3.3 mg, 0.016 mmol). After stirring overnight at rt, THF was evaporated and 0.35 mL of CH$_2$Cl$_2$:TFA (4:1) was added. The solution was stirred for 45 min., then concentrated to dryness under reduced pressure to give a residue which was purified by preparatory TLC (CH$_2$Cl$_2$:MeOH—NH$_3$ (7N), 15:1) to afford 6.1 mg (88%) of 119. $^1$H NMR (500 MHz, CDCl$_3$/MeOH-d$_4$): δ 9.31 (br s, 1H), 8.50 (m, 2H), 8.28 (s, 1H), 7.50 (d, J=7.8 Hz, 1H), 7.42 (m, 1H), 7.33 (s, 1H), 7.11-7.25 (m, 2H), 6.86 (d, J=7.9 Hz, 1H), 5.40 (s, 2H), 3.87 (m, 4H), 3.46 (s, 2H), 2.48 (m, 4H), 2.36 (s, 3H); MS (m/z): [M+H]$^+$ 466.2.

Scheme 14. Synthesis of TT-10 (121).

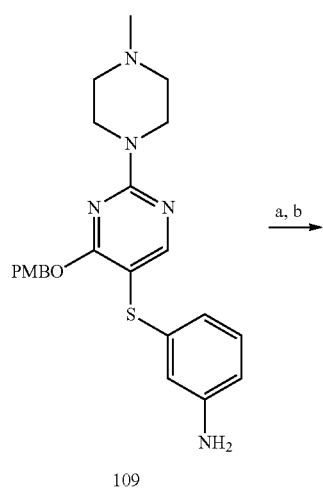

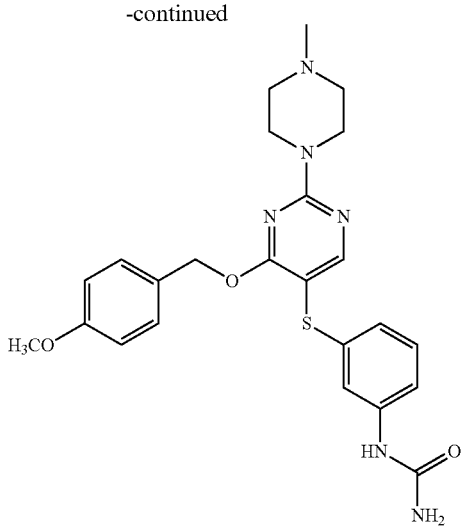

TT-10 121

Reagents and conditions: a. Fmoc-glycine, DCC, THF, rt, 12 h; b. CH$_2$Cl$_2$:piperidine (9:1), rt, 2 h.

TT-10 (121) 2-amino-N-(3-(4-(4-methoxybenzyloxy)-2-(4-methylpiperazin-1-yl)pyrimidin-5-ylthio) phenyl)acetamide 109 (10 mg, 0.0228 mmol) in THF (1 mL) was added Fmoc-glycine (7.5 mg, 0.0251 mmol), DCC (5.2 mg, 0.0251 mmol) and stirred at rt overnight. The reaction mixture was concentrated under reduced pressure and the residue was dissolved in CH$_2$Cl$_2$ (0.9 mL) and piperidine (0.1 mL) and stirred at rt for 2 h. The reaction mixture was concentrated under reduced pressure and the residue was purified by preparatory TLC (CH$_2$Cl$_2$:MeOH—NH$_3$ (7N), 15:1) to afford 8.2 mg (73%) of 121. $^1$H NMR (500 MHz, CDCl$_3$): δ 9.20 (br s, 1H), 8.25 (s, 1H), 7.60 (d, J=7.8 Hz, 1H), 7.17-7.20 (m, 2H), 7.09 (d, J=8.5 Hz, 2H), 6.85 (d, J=7.1 Hz, 1H), 6.77 (d, J=8.6 Hz, 2H), 5.30 (s, 2H), 3.88 (m, 4H), 3.78 (s, 3H), 3.44 (s, 2H), 2.48 (m, 4H), 2.35 (s, 3H); MS (m/z): [M+H]$^+$ 495.2.

Scheme 15.
Synthesis of YK171 (126), YK172 (127), YK173 (129), YK174 (130), YK175 (131).

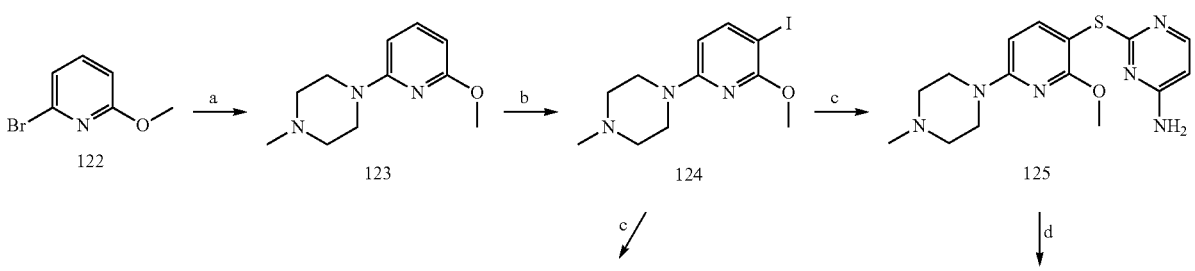

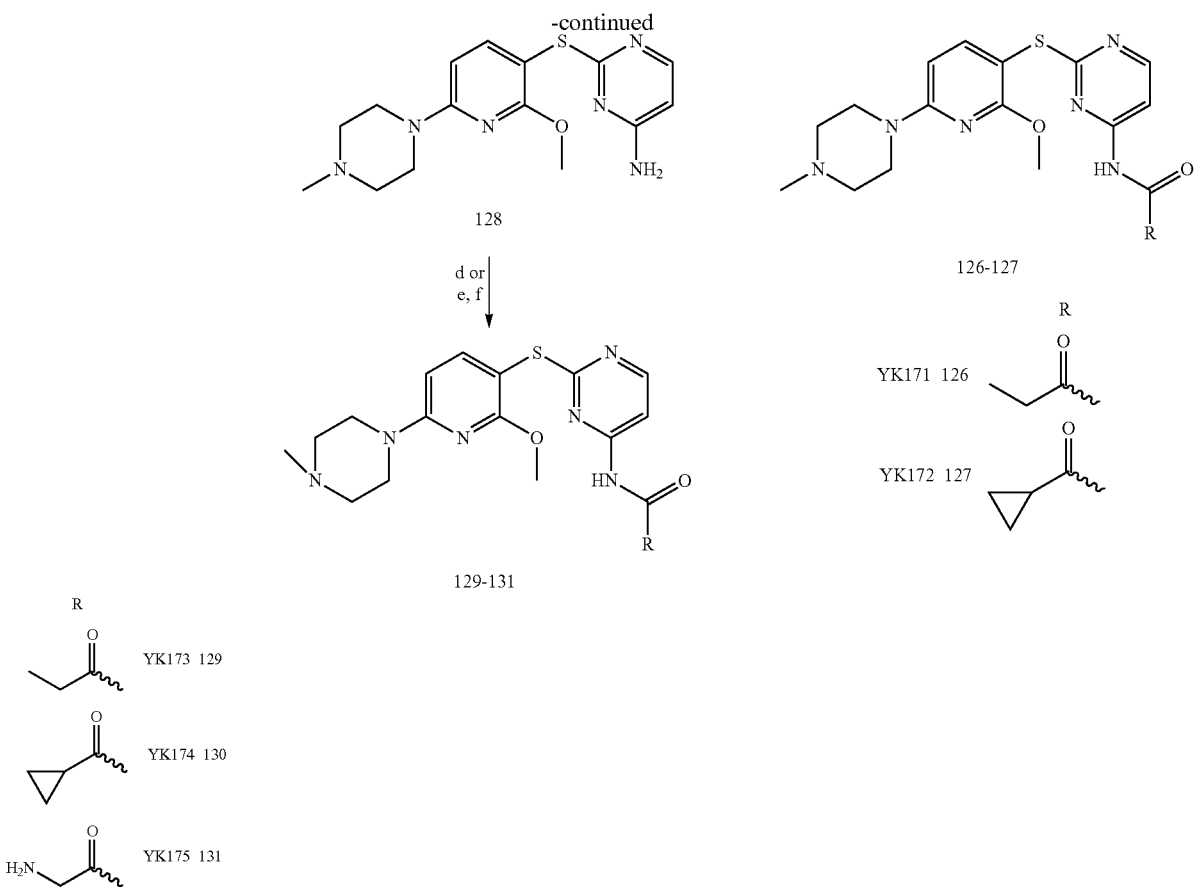

Reagents and conditions: a. N-methylpiperazine, K₂CO₃, DMF, 130° C., 16 h; b. NIS, CH₃CN,. rt, 2 h; c. 3-aminobenzenethiol, neocuproine, CuI, K₂CO₃, DMF, 130° C., 16 h; d. RCOCl, Et₃N; e. RCOOH, EDCl, THF, rt; f. CH₂Cl₂:TFA (4:1), rt.

(123) 1-(6-methoxypyridin-2-yl)-4-methylpiperazine

To a solution of 2-bromo-6-methoxypyridine (122) (150 mg, 0.8 mmol) and 1-methyl piperazine (240 mg, 2.4 mmol) in 2 ml DMF was added of K₂CO₃ (220 mg, 1.6 mmol) and the resulting mixture was heated to 130° C. for 16 h. Solvent was evaporated under reduced pressure and the residue was purified by column chromatography with (5-10% MeOH in CH₂Cl₂) to afford 145 mg (88%) of 123. $^1$H NMR (500 MHz, CDCl₃): δ 7.41 (t, J=8.0 Hz, 1H), 6.16 (d, J=8.0 Hz, 1H), 6.08 (d, J=8.0 Hz, 1H), 3.87 (s, 3H), 3.54 (m, 4H), 2.51 (m, 4H), 2.54 (s, 3H); $^{13}$C NMR (125 MHz, CDCl₃): δ 163.1, 158.3, 140.1, 98.2, 98.1, 54.8, 52.9, 46.2, 45.1; MS (m/z): [M+H]⁺ 208.4.

(124) 1-(5-iodo-6-methoxypyridin-2-yl)-4-methyl-piperazine

To a solution of 123 (124 mg, 0.6 mmol) in 5 mL of acetonitrile was added N-iodosuccinimide (203 mg, 0.9 mmol) and the resulting mixture was stirred at rt for 2 h. The solvent was evaporated under reduced pressure and the residue was purified by column chromatography with (CH₂Cl₂:MeOH—NH₃ (7N), 1:0 to 85:15) to afford 190 mg (95%) of 124. $^1$H NMR (500 MHz, CDCl₃): δ 7.70 (d, J=8.0 Hz, 1H), 6.02 (d, J=8.0 Hz, 1H), 3.90 (s, 3H), 3.60 (m, 4H), 2.62 (m, 4H), 2.39 (s, 3H); $^{13}$C NMR (125 MHz, CDCl₃): δ 177.7, 160.5, 157.8, 148.6, 100.7, 61.7, 54.2, 45.5, 44.5; MS (m/z): [M+H]⁺ 334.1.

(125) 2-((2-methoxy-6-(4-methylpiperazin-1-yl) pyridin-3-yl)thio)pyrimidin-4-amine The mixture of 124 (100 mg, 0.3 mmol), 4-aminopyrimi-dine-2-thiol (39 mg, 0.3 mmol), K₂CO₃ (83 mg, 0.6 mmol), neocuproine (11 mg, 0.05 mmol), and CuI (10 mg, 0.05 mmol) in DMF (3 ml) was heated to 130° C. for 16 h. Solvent was removed under reduced pressure and the residue was purified by column chromatography (CH₂Cl₂: MeOH—NH₃ (7N), 1:0 to 85:15) to afford 60 mg (60%) of 125. $^1$H NMR (500 MHz, CDCl₃): δ 7.95 (d, J=8.0 Hz, 1H), 7.59 (d, J=8.5 Hz, 1H), 6.20 (d, J=8.5 Hz, 1H), 6.05 (d, J=8.0 Hz, 1H), 5.01 (s, 2H), 3.87 (s, 3H), 3.62 (m, 4H), 2.54 (m, 4H), 2.36 (s, 3H); $^{13}$C NMR (125 MHz, CDCl₃): δ 171.9, 162.9, 162.5, 158.6, 156.2, 147.8, 101.1, 98.6, 97.6, 54.6, 53.6, 46.0, 44.6; MS (m/z): [M+H]⁺ 333.5.

YK171 (126) N-(2-((2-meth oxy-6-(4-methylpiper-azin-1-yl)pyridin-3-yl)thio)pyrimidin-4-yl) propio-namide To a solution of 125 (20 mg, 0.06 mmol) in 1.5 mL CH₂Cl₂ and Et₃N (100 μL) was added propionyl chloride in CH₂Cl₂ dropwise. Upon completion (by TLC), reaction was quenched by adding cold MeOH. Solvent was removed under reduced pressure and the residue was purified by column chromatography with (MeOH—NH$_3$ (7N) 2-10% in CH$_2$Cl$_2$ to afford 18 mg (80%) of 126. $^1$H NMR (500 MHz, CDCl$_3$): δ 8.53 (bs, 1H), 8.34 (d, J=8.0 Hz, 1H), 7.79 (d, J=8.0 Hz, 1H), 7.58 (d, J=8.0 Hz, 1H), 6.21 (d, J=8.0 Hz, 1H), 3.86 (s, 3H), 3.63 (m, 4H), 2.52 (m, 4H), 2.41 (q, J=7.2 Hz, 2H), 2.36 (s, 3H), 1.08 (t, J=7.2 Hz, 3H); $^{13}$C NMR (125 MHz, CDCl$_3$): δ 173.4, 172.2, 171.7, 162.9, 158.8, 157.3, 147.6, 105.6, 98.7, 96.7, 54.6, 53.7, 46.0, 44.6, 30.6, 8.96; MS (m/z): [M+H]$^+$ 389.3.

YK172 (127) N-(2-((2-methoxy-6-(4-methylpiperazin-1-yl)pyridin-3-yl)thio)pyrimidin-4-yl) cyclopropanecarboxamide To a solution of 125 (20 mg, 0.06 mmol) in 1.5 mL CH$_2$Cl$_2$ and Et$_3$N (100 μL) was added cyclopropanecarbonyl chloride in CH$_2$Cl$_2$ dropwise. Upon completion (by TLC), reaction was quenched by adding cold MeOH. Solvent was removed under reduced pressure and the residue was purified by column chromatography with (MeOH—NH$_3$ (7N) 2-10% in CH$_2$Cl$_2$) to afford (21 mg (90%) of 127. $^1$H NMR (500 MHz, CDCl$_3$): δ 8.87 (br s, 1H), 8.31 (d, J=8.0 Hz, 1H), 7.75 (d, J=8.0 Hz, 1H), 7.57 (d, J=8.0 Hz, 1H), 6.20 (d, J=8.0 Hz, 1H), 3.87 (s, 3H), 3.62 (m, 4H), 2.52 (m, 4H), 2.36 (s, 3H), 1.61 (m, 1H), 1.08 (m, 2H), 0.88 (m, 2H); $^{13}$C NMR (125 MHz, CDCl$_3$): δ 176.4, 173.5, 171.7, 162.9, 158.8, 157.2, 147.6, 105.7, 98.6, 96.7, 54.7, 53.6, 46.1, 44.6, 14.0, 7.7; MS (m/z): [M+H]$^+$ 401.3.

(128) 3-((2-methoxy-6-(4-methylpiperazin-1-yl)pyridin-3-yl)thio)aniline

A mixture of 124 (100 mg, 0.3 mmol), 3-aminobenzenethiol (37 mg, 0.3 mmol), K$_2$CO$_3$ (83 mg, 0.6 mmol), neocuproine (11 mg, 0.05 mmol) and CuI (10 mg, 0.05 mmol) in DMF (3 ml) was heated to 130° C. for 16 h. Solvent was removed under reduced pressure and the residue was purified by column chromatography (CH$_2$Cl$_2$:MeOH—NH$_3$ (7N), 1:0 to 85:15) to afford 60 mg (60%) of 128. $^1$H NMR (500 MHz, CDCl$_3$): δ 7.54 (d, J=8.0 Hz, 1H), 6.96 (m, 1H), 6.51 (d, J=8.0 Hz, 1H), 6.41 (m, 2H), 6.19 (d, J=8.0 Hz, 1H), 3.88 (s, 3H), 3.62 (m, 4H), 2.54 (m, 4H), 2.36 (s, 3H); $^{13}$C NMR (125 MHz, CDCl$_3$): δ 162.7, 158.4, 147.5, 146.8, 139.5, 129.5, 117.1, 113.0, 112.2, 99.8, 98.9, 54.6, 53.7, 46.1, 44.8; MS (m/z): [M+H]$^+$ 331.2.

YK173 (129) N-(3-((2-methoxy-6-(4-methylpiperazin-1-yl)pyridin-3-yl)thio)phenyl)propionamide To a solution of 128 (20 mg, 0.06 mmol) and Et$_3$N (100 μL) in 1.5 mL CH$_2$Cl$_2$ was added propionyl chloride in CH$_2$Cl$_2$ dropwise. Upon completion (by TLC), the reaction was quenched by adding cold MeOH. Solvent was removed under reduced pressure and the residue was purified by column chromatography with (MeOH—NH$_3$ (7N) 2-10% in CH$_2$Cl$_2$) to afford 15 mg (70%) of 129. $^1$H NMR (500 MHz, CDCl$_3$): δ 7.55 (d, J=8.0 Hz, 1H), 7.45 (d, J=8.0 Hz, 1H), 7.22 (br s, 1H), 7.14 (t, J=8.0 Hz, 1H), 7.08 (s, 1H), 6.81 (d, J=8.0 Hz, 1H), 6.20 (d, J=8.0 Hz, 1H), 3.88 (s, 3H), 3.47 (m, 4H), 2.57 (m, 4H), 2.36 (s, 3H), 2.33 (q, J=7.2 Hz, 2H), 1.19 (t, J=7.2 Hz, 3H); MS (m/z): [M+H]$^+$ 387.2.

YK174 N-(3-((2-methoxy-6-(4-methylpiperazin-1-yl)pyridin-3-yl)thio)phenyl) cyclopropanecarboxamide To a solution of 128 (20 mg, 0.06 mmol) and Et$_3$N (100 μL) in 1.5 mL CH$_2$Cl$_2$ was added cyclopropanecarbonyl chloride in CH$_2$Cl$_2$ dropwise. Upon completion (by TLC), the reaction was quenched by adding cold MeOH. Solvent was removed under reduced pressure and the residue was purified by column chromatography with (MeOH—NH$_3$ (7N) 2-10% in CH$_2$Cl$_2$) to afford 16 mg (70%) of 130. $^1$H NMR (500 MHz, CDCl$_3$) δ 7.61 (s, 1H), 7.31 (d, J=8.0 Hz, 1H), 7.20 (br s, 1H), 6.88 (m, 2H), 6.55 (m, 1H), 5.95 (d, J=8.0 Hz, 1H), 3.63 (s, 3H), 3.37 (m, 4H), 2.29 (m, 4H), 2.09 (s, 3H), 1.25 (m, 1H), 0.78 (m, 2H), 0.57 (m, 2H); $^{13}$C NMR (125 MHz, CDCl$_3$) δ 176.4, 172.1, 162.7, 158.4, 147.5, 139.3, 138.7, 129.2, 122.2, 117.5, 116.8, 99.0, 54.6, 53.6, 46.1, 44.7, 13.9, 7.9; MS (m/z): [M+H]$^+$ 398.3.

YK175 (131) 2-amino-N-(3-((2-methoxy-6-(4-methylpiperazin-1-yl)pyridin-3-yl)thio)phenyl)acetamide To a solution of 128 (20 mg, 0.06 mmol) in CH$_2$Cl$_2$ (1 ml) was added Boc-glycine (10.6 mg, 0.06 mmol), DMAP (1.0 mg), Et$_3$N (10 μL) and EDCI (11 mg, 0.06 mmol). The resulting solution was stirred at rt for 2 h. Solvent was evaporated under reduced pressure and the residue was purified by column chromatography (CH$_2$Cl$_2$:MeOH—NH$_3$ (7N), 1:0 to 85:15) to afford 26 mg (90%) of residue. To this was added 5 ml of 10% TFA-CH$_2$Cl$_2$ and stirred at rt for 1 h. Solvent was evaporated under reduced pressure and the residue was purified by column chromatography (CH$_2$Cl$_2$:MeOH—NH$_3$ (7N), 1:0 to 85:15) to afford 16 mg (85%) of 131. $^1$H NMR (500 MHz, CDCl$_3$): δ 9.26 (br s, 1H), 7.55 (d, J=8.0 Hz, 1H), 7.47 (d, J=8.0 Hz, 1H), 7.28 (s, 1H), 7.15 (t, J=8.0 Hz, 1H), 6.82 (d, J=8.0, 1H), 6.21 (d, J=8.0 Hz, 1H), 3.89 (s, 3H), 3.62 (m, 4H), 3.42 (s, 2H), 2.54 (m, 4H), 2.36 (s, 3H); $^{13}$C NMR (125 MHz, CDCl$_3$): δ 170.6, 162.7, 158.4, 147.5, 139.4, 138.0, 129.3, 122.5, 117.5, 116.5, 99.4, 98.9, 54.6, 53.6, 46.0, 45.1, 44.7; MS (m/z): [M+H]$^+$ 388.3.

Example 2: Human Hsp70 (hHsp70) Homology Model Construction and Design of YK5

To design inhibitors/modulators of Hsp70, different computational approaches were employed such as homology modeling, SiteMap and docking to determine the 3D model of the human Hsp70 (hHsp70), identify probable binding sites and evaluate the protein/ligand interactions, respectively. No information is available on the full length crystal structure of the hHsp70 protein, and a theoretical 3D structure (homology model) of hHsp70 was planned for construction. As described by Wallner et al., the most important factor in homology model construction is correctness of alignment and the choice of the best template structures. Three template crystal structures which share high sequence identity (more than 50%) with the receptor of interest were selected for building the homology model of the hHsp70 protein. The N-terminal crystal structure of the hHsp70 protein (PDB ID: 1S3X) was the best available template for the N-terminus amino acids (Met1-Gly382, hHsp70). There was no crystal structure for the SBD of hHsp70, so the *E. coli* Hsp70 (DNAK) structure (PDB ID: 2KHO), which shares a 62% similarity with hHsp70, was selected as the template for modeling a segment of the SBD (Asp385-Gln538, *E. coli*.; Asp383-Ala541, hHsp70). Finally, the crystal structure of *C. elegans* Hsp70 (PDB ID: 2P32) was used as a template for the C-terminus amino acids (Leu543-Ser614, *C. elegans*; Leu542-Gly613, hHsp70). The C-terminal amino acids (614-641) of hHsp70 did not have a template structure, hence were not modeled. As suggested by Chothia and Lesk, after template selection, alignment of the template and the ability to detect the structural similarities based on the amino acid sequence determine the overall quality of the model. The hHsp70 residues were aligned. It has been reported by Wallner et al., that for closely related protein sequences with high similarity the alignment is most often optimal. In our study, 606 out of 613 residues were identical to the three implemented templates (PDB ID: 1S3X, PDB ID: 2KHO, PDB ID: 2P32), indicating optimal alignment. Following alignment of the residue side chains, amino acids missing in the template structure (PDB ID: 2KHO), such as Lys384, Ser385, Glu386, Asn387 and Arg509 (hHsp70), were successfully inserted using an automated or semi-automated procedure in Prime. The homology model thus obtained contained intracellular and extracellular loops based on the template structure (excluding termini). All the loop regions (33 loops) were optimized using the loop refinement tool in Prime to generate firm conformations for loops. Finally, the obtained protein model was subjected to a protein preparation wizard utility, followed by rigorous energy minimization to relax unfavorable contacts.

It has been previously shown by Wallner et al., that the rms deviation between the template and the modeled protein is a good method of validation. Superimposition of the backbone atoms in the NBD of the homology model and the template structure (PDB ID: 1S3X) gave a rms deviation of 1.01 Å and a good alignment score of 0.05, validating our model.

The homology model thus created contains 613 amino acid residues and has two major domains, a NBD and a SBD, joined together by a flexible linker (FIG. 2a). The N-terminal ATPase domain displays an actin like hexokinase fold and has two globular lobes, I (subdomains IA and IB) and II (subdomains IIA and IIB). Twelve α helices and sixteen β sheets compile the NBD, which corroborates with the crystal structures of the NBD. The C-terminal SBD can be further divided into two functionally relevant subdomains; a sandwich of two four stranded β-sheets containing the peptide binding subdomain (SBD-β) and a four α-helices subdomain (SBD-α), also called the lid domain. In the absence of a full length crystal structure of this therapeutically important chaperone, this homology model is useful to determine binding sites for the design of Hsp70 inhibitors, by methods such as but not limited to structure based design and virtual screening.

Site Prediction:

For a structure-based design strategy, the potential binding sites on hHsp70 amenable for small molecule inhibitor targeting were identified by SiteMap. SiteMap considers several physical descriptors such as size, degree of enclosure/exposure, tightness, van der Waals forces, hydrophobic/hydrophilic character, and hydrogen-bonding possibilities, to determine a potential site. It does so by linking together site points that are most likely to contribute to protein/ligand or protein/protein interaction.

SiteMap examines the entire structure and ranks the sites. The size of the site (measured by the number of found site points), the relative openness of the site (measured by the exposure and enclosure properties) and tightness of the site (measured by the contact term, and the hydrophobic and hydrophilic character of the site) contribute significantly towards ranking. To extensively explore the available binding sites on Hsp70, SiteMap was configured to return up to ten sites. We noticed that poorly scored sites, such as sites 6-10, were on the surfaces (not shown in FIG. 2). These are artifacts of the computational model, which finds sites corresponding to outer surfaces and have lower S-score. Hence, SiteMap was configured to return up to top five ranked probable binding sites in the homology modeled hHsp70 protein. These five sites had an S-score of 0.80 or higher, which is recommended by T. A Halgreen to define a plausible binding site.

Another important criterion for binding site determination is druggability of the site, as described by the D-score in SiteMap. This includes terms that promote ligand binding, such as adequate size and isolation from solvents, but offsets them with a term that penalizes increasing hydrophilicity. According to T. A. Halgreen, sites are classified into undruggable, difficult to drug and druggable. Undruggable sites are strongly hydrophilic, relatively smaller in size, with little or no hydrophobic character, and are characterized by a D-score value lower than 0.83. Difficult sites are sufficiently hydrophilic to require administration as a prodrug, but they are less hydrophobic than a typical binding site, and are defined by a D-score value between 0.83 and 0.98. Druggable sites are of reasonable size, enclosure and hydrophobicity, of unexceptional hydrophilicity and hold a D-score value higher than 0.98.

Among the five sites (Sites 1-5) predicted by SiteMap (FIG. 2), Sites 3, 4 and 5 have very few site points, the cavity is small and the site is shallow. As a result, it is difficult to generate sufficient binding affinity for these sites. Site 2, including the groove occupied by the endogenous ligands ATP and ADP, has a reasonable size (site points: 178), and a reasonably high S-score. On visual inspection, Site 2 has a relatively smaller groove, and it mainly consists of hydrophilic amino acids. In the absence of suitable regions for hydrophobic interactions, it is potentially more difficult to target, as depicted by a relatively lower D-score (0.91). Site 1, located in a cleft region outside the ATP/ADP binding domain, and flanked by sub-regions Ib and IIb, is larger in size (site points: 385), has a larger groove and consists of hydrophilic and hydrophobic amino acids, making it a more druggable site (D-score: 1.00). Taking together the S- and D-scores, its size, its balanced hydrophobic and hydrophilic character, exposure and enclosure properties, Site 1 is predicted to be the most druggable cavity, and thus focus was placed on this novel allosteric Site 1 for further design of Hsp70 inhibitors.

To recognize the properties of the entire site, hydrophobic/hydrophilic maps were generated on Sites 1 and 2. These maps take into account the site as a whole, in contrast to the surface model where only the closest receptor atoms are considered. These maps explicitly show the shape of the site, and suggest the extent of the hydrophobic and hydrophilic regions. Site 2 is mainly of a hydrophilic character, with little hydrophobic character. In contrast, Site 1 has a balanced character, with both hydrophobic and hydrophilic regions present. These results further support the higher druggability of Site 1.

Protein/Ligand Interactions and Design of Inhibitors:

To date, few molecules are known to modulate the activity of Hsp70. A number of molecules targeting the SBD have been identified, including 15-deoxyspergualin and fatty acid acyl benzamides. A small molecular weight peptide designed to bind to the SBD of bacterial Hsp70, stimulated its ATPase activity. Among agents that target the NBD are the dihydropyrimidines and the nucleotide mimetics. The dihydropyrimidines were discovered in a screen measuring the ATPase activity of yeast Hsp70. Identification of ATP competitive inhibitors has proven difficult. Williamson et al., described adenosine-based analogs designed to bind within the ATPase pocket. Hsp70 belongs to the actin-like family of ATPases, and a high structural homology, especially within their ATPase domain, exists between these proteins. As a result, taken together with the poorer drug like character of this site as determined above, it is unclear if development of direct ATP-competitors is the most favorable approach for Hsp70. We therefore chose Site 1 for targeting.

FIG. 21:

Alignment of protein sequence of full length hHsp70 (Accession number: P08107), N-terminal hHsp70 protein (PDB ID: 1S3X), *E. coli* Hsp70 (DNAK) structure (PDB ID: 2KHO) and *C. elegans* (PDB ID: 2P32). Residue annotations are underlined and conserved residues are displayed in similar color. Sequences defining the allosteric pocket Site 1 are shown in boxes. Important amino acids in these sequences interact with the herein designed ligands.

Figure 1:
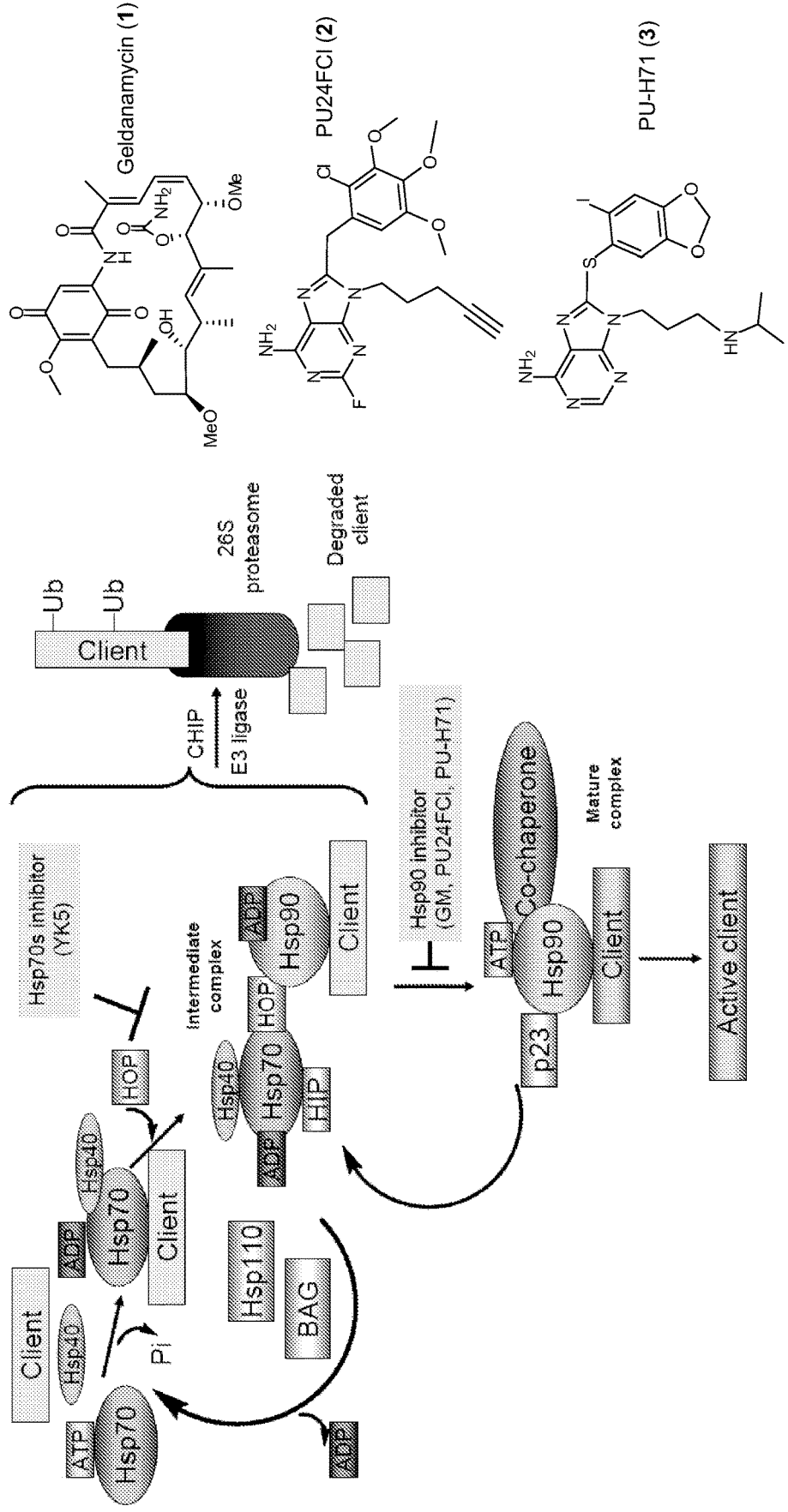
FIG. 1. Various aspects of the Hsp90 machinery chaperoning cycle, a) The Hsp90 chaperoning cycle is a dynamic process in which client proteins are presented to Hsp90 in an intermediate complex containing Hsp70s, Hsp40, HIP and HOP. Upon ATP binding and hydrolysis, Hsp90 forms a mature complex, containing p23, p50/cdc37 and immunophilins (IP), which catalyzes the conformational maturation of Hsp90 client proteins. Hsp90-inhibitor drugs, such as geldanamycin (GM) and the purine-scaffold derivatives PU-H71 and PU24FC1, bind to the N-terminal ATP-binding pocket of Hsp90 and inhibit ATP binding and hydrolysis, thereby locking Hsp90 in the intermediate complex. The client protein is subsequently ubiquitinated (possibly by an E3 ubiquitin ligase such as CHIP) and targeted to the proteasome for degradation. This is a schematic representation based on one current understanding of the process. b) Structures of representative Hsp90 inhibitors.
Figure 2:
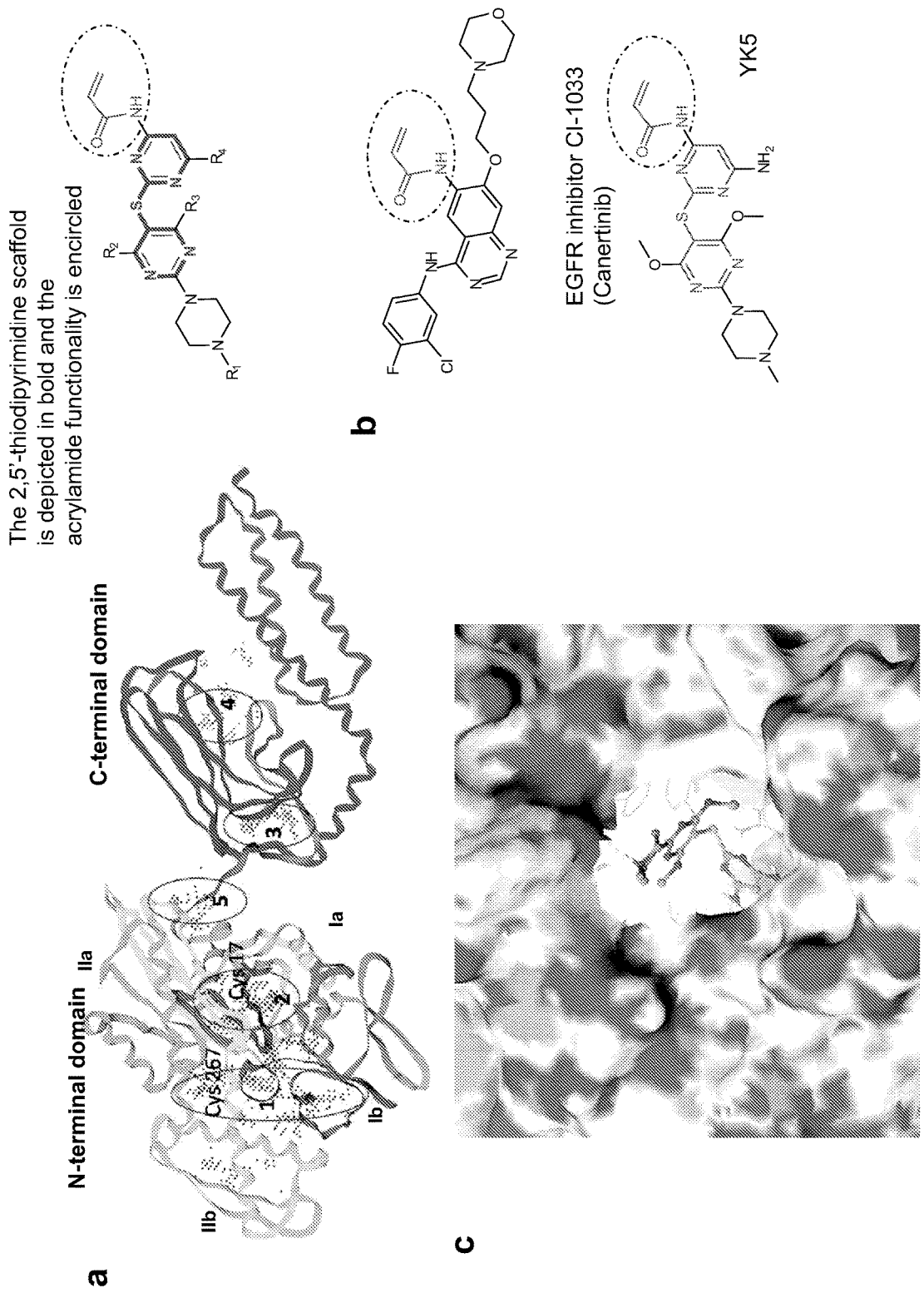
FIG. 2. Design of the YK-class Hsp70s interactors and the computational model of the YK5-Hsp70 complex. a) Putative binding sites of Hsp70 were predicted by SiteMap v2.2 program of Maestro 8.5 (Schrodinger L.L.C., NY). SiteMap was configured to return up to 5 probable sites ranked according to Site score and Druggability score. In this study all other parameters of SiteMap were set to default values. The presented structure is a homology model constructed using the human Hsp70 N-terminal domain (PDB ID: 1S3X), the *E. coli* DnaK (PDB ID: 2kho) and the human Hsp70 protein sequence. Several compounds based on the 2,5'-thiodipyrimidine scaffold (right) were rationally designed to interact with Hsp70. The 2,5'-thiodipyrimidine scaffold is presented with bold bonds for ease of recognition. b) Structures of cysteine-modifying small molecule protein interactors. The acrylamide-functionality is circled for ease of recognition. c) Proposed interaction of YK5 with homology model of human Hsp70 as revealed by molecular modeling using Maestro 8.5 and Glide 4.0 (Schrödinger).

To identify Hsp70 inhibitors specifically targeting Site 1, several chemical libraries of unexplored chemical space suitable to interact with its structural grooves were designed and synthesized. Site 1 also contains a potentially reactive cysteine, Cys267, and to take advantage of a potential covalent interaction, an acrylamide functionality (NH—C (=O)—CH=CH$_2$) was incorporated within the designed chemical library. Successful feedback design and testing, as exemplified in FIG. 3, resulted in the identification of YK5 (FIG. 2). In order to confirm the binding of YK5 to Site 1 and to study potential ligand/protein interactions, compound YK5 was docked onto each of the five predicted sites by SiteMap. Investigation of binding interactions, orientation of compound and Glidescore values concluded that YK5 binds most favorably to Site 1. Best binding mode derived by docking of YK5 onto Site 1 is shown in FIG. 2c.

TABLE 13

SiteMap predicted binding sites for inhibitors/modulators on hHsp70 protein

| Binding Site | Position | S-score | D-score | Size |
| --- | --- | --- | --- | --- |
| Site 1 | IB and IIB | 1.05 | 1.00 | 365 |
| Site 2 | IA and IIA | 1.12 | 0.91 | 178 |
| Site 3 | SBD-β | 1.06 | 0.98 | 95 |
| Site 4 | SBD-β and SBD-α | 0.94 | 0.97 | 83 |
| Site 5 | Linker domain | 0.78 | 0.71 | 51 |

In order to further validate the proposed binding interactions, YK20, predicted to be of lower affinity for Hsp70, was docked on to the allosteric binding Site 1. Unlike YK5, all the docked poses of YK20 oriented outside the binding pocket and had a poorer G-Score. In order to determine potential reason for such orientation, YK20 was overlaid with YK5 bound to homology-modeled hHsp70, to show that YK20 has potential steric clash accounting for its poorer inhibitory activity.

Example 3: Characterization of Novel Modulators

To identify Hsp70 inhibitors, several chemical libraries of unexplored chemical space designed to interact with structural grooves of the N-terminal region (FIG. 2, panel a) were synthesized. This domain accommodates two potentially druggable regions. One is the nucleotide binding site (depicted as Site 2 in FIG. 2, panel a), which has a mainly hydrophilic character, and is therefore potentially more difficult to target. The second is a larger and potentially more drug-like binding groove, located in a cleft region outside the nucleotide binding domain, and flanked by subregions Ib and IIb (depicted as Site 1 in FIG. 2, panel a). Hsp70s also contain several potentially reactive cysteines, two of which are located in the vicinity of the two potential druggable sites (FIG. 2, panel a). To take advantage of these residues, an acrylamide functionality was incorporated into some of the designed derivatives, probing possible covalent bond formation between the inhibitor and cysteine residues upon protein binding (FIG. 2, panel a). There is precedent for the use of an acrylamide "warhead" in the development of irreversible EGFR and HER2 inhibitors, such as CI-1033 (Canertinib) (FIG. 2, panel b) and EKB-569 (Pelitinib), compounds in clinical trials for cancer. EGFR and HER2, like Hsp70s, contain a reactive cysteine in their regulatory site.

In accord with one working hypothesis that in cancer cells, Hsp70 inhibitors will have the phenotypic outcome of Hsp90 inhibitors while lacking a feed-back Hsp70 induction, these agents were screened in phenotypic assays previously developed by the Chiosis lab for tumor Hsp90. These assays were designed to read cellular fingerprints of Hsp90 inhibition, such as degradation of an Hsp90 onco-client in the relevant genetic background and associated inhibition of tumor cell growth. Induction of Hsp70 was analyzed to exclude those that activated HSF-1. To assure that at the pharmacologically relevant concentrations compounds are likely to selectively act through an Hsp70-mediated mechanism, only those active at similar concentrations in all assays were selected. Binding to Hsp90 was further probed to exclude direct Hsp90 inhibitors.

Several entities of a novel scaffold, the 2,5'-thiodipyrimidines which are part of a larger genus that is termed herein as YK, were active by these criteria (FIG. 2, panel a). The synthetic methodology to assemble the YK-scaffold is presented in Example 1 Schemes.

One derivative identified from our design and screening strategy was YK5 (FIG. 2, panel b) of whose synthesis is described herein.

Figure 3:
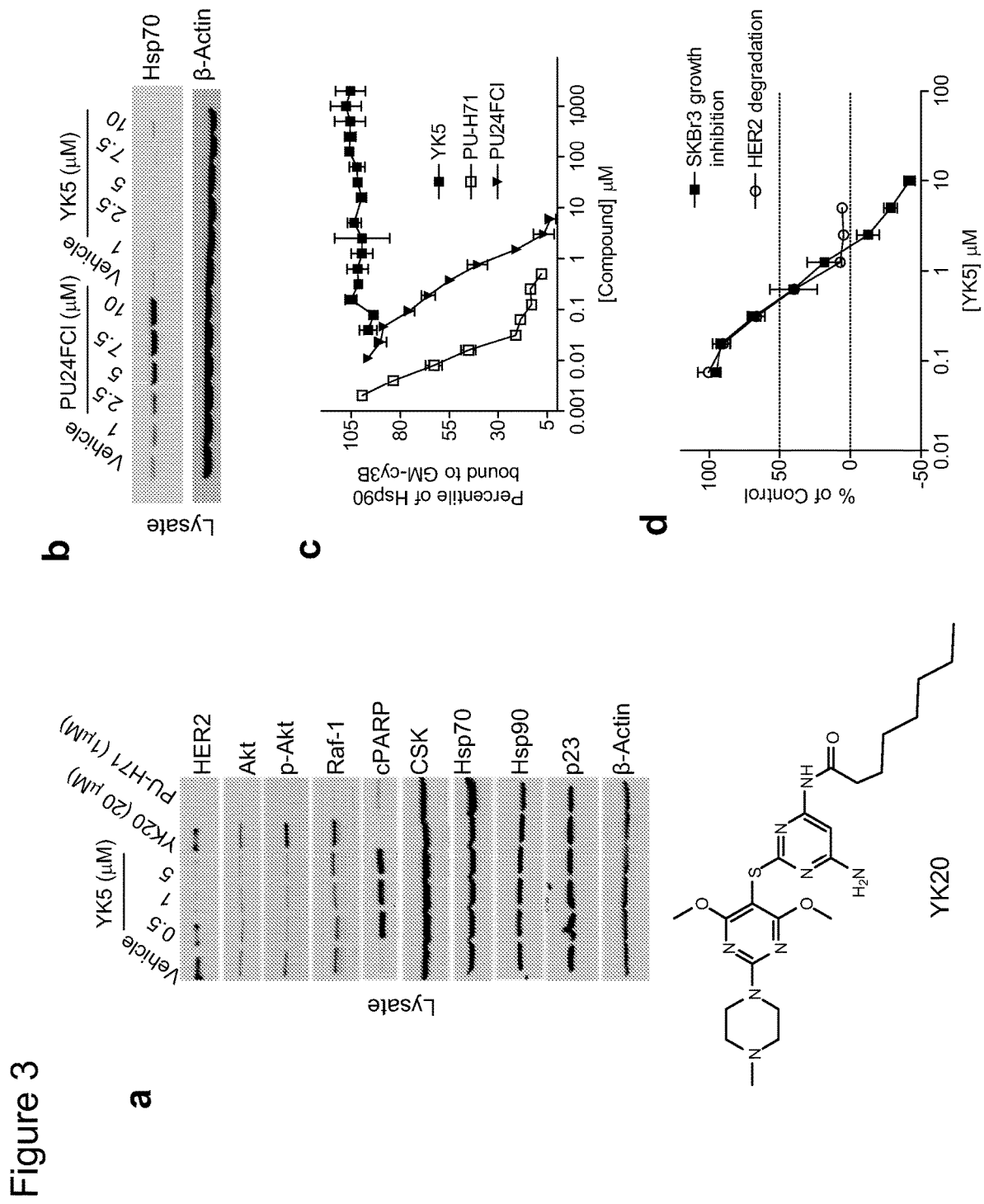
FIG. 3. Testing strategy for the discovery of YK5. a, b) SKBr3 cells were treated for 24 h with the indicated concentrations of inhibitors and cells were lysed for western blot (WB) analysis. β-actin was used as loading control. The data are consistent with those obtained from multiple repeat experiments (n≥3). c) The ability of the indicated inhibitors to compete with GM-Cy3B for Hsp90 binding in SKBr3 cell extracts was examined by fluorescence polarization. Values recorded in wells with added inhibitor were normalized to values read in control wells and plotted against the concentration of tested inhibitor. Drugs were assayed in triplicate. All compounds were used as DMSO stocks. Points, mean; bars, s.d. d) Growth inhibition: SKBr3 cells were incubated in triplicate with increasing concentrations of compound and growth over 72 h was assessed. Y-axis values below 0% represent cell death of the starting population. HER2 degradation was analyzed as in panel a), and gels were quantified by densitometry. Recorded values were normalized to control (vehicle only treated cells) and data graphed against YK5 concentration. Error bars represent the s.d. of the mean (n=3).

As evidenced in the SKBr3 breast cancer cells, YK5, but not the control derivative YK20 (20 μM), which binds to the target with less affinity, induced the degradation of HER2, Raf-1 and Akt kinases, all three of which are known Hsp90 onco-client proteins in this cellular context (FIG. 3, panel a). Furthermore, the non-oncogenic tyrosine-protein kinase CSK, a c-Src related tyrosine kinase, remained unaffected by the YK-agents and the direct Hsp90 inhibitor PU-H71 (FIG. 3, panel a). YK5 also induced apoptosis in these cells as evidenced by PARP cleavage (FIG. 3, panel a). In agreement with previous reports on direct Hsp90 inhibitors, and as observed here with PU-H71 (FIG. 3, panel a), 3-actin and the Hsp90 co-chaperone p23, proteins whose levels are insensitive to Hsp90 inhibition, remained unchanged upon cellular addition of YKs (FIG. 3, panel a).

Feed-back induction of Hsp70 was undetected with YK5 at concentrations where it degraded Hsp90 machinery onco-clients (FIG. 3, panels a and b). Meanwhile, in these cells, direct Hsp90 inhibitors potently activated a heat shock response, as evidenced by Hsp70 induction (FIG. 3, PU-H71 in panel a, and PU24FC1 in panel b). Unlike the direct Hsp90 inhibitors PU-H71 and PU24FC1, YK-derivatives failed to compete with a fluorescently labeled geldanamycin derivative, GM-Cy3B, for Hsp90 binding (FIG. 3, panel c).

In the SKBr3 breast cancer cells, degradation of Hsp90-onco-client proteins by YK5 occurred at the increasing low micromolar concentrations (FIG. 3, panel a) that also led to inhibition of cell proliferation (FIG. 3, panel d), suggesting that, in this concentration range, the biological activity of YK5 is likely channeled through inhibition of a functional Hsp90 machinery, potentially by an Hsp70-binding mechanism.

YK5 is a Selective Hsp70 Binder in Cancer Cells.

To confirm that Hsp70 is responsible for the activity of YK5, a biotinylated YK5 derivative, YK55 (FIG. 4, panel a) was designed. Synthesis of YK55 is described herein. In another embodiments, other compounds of the present subject matter may be biotinylated and used according to the methods described herein.

Figure 4:
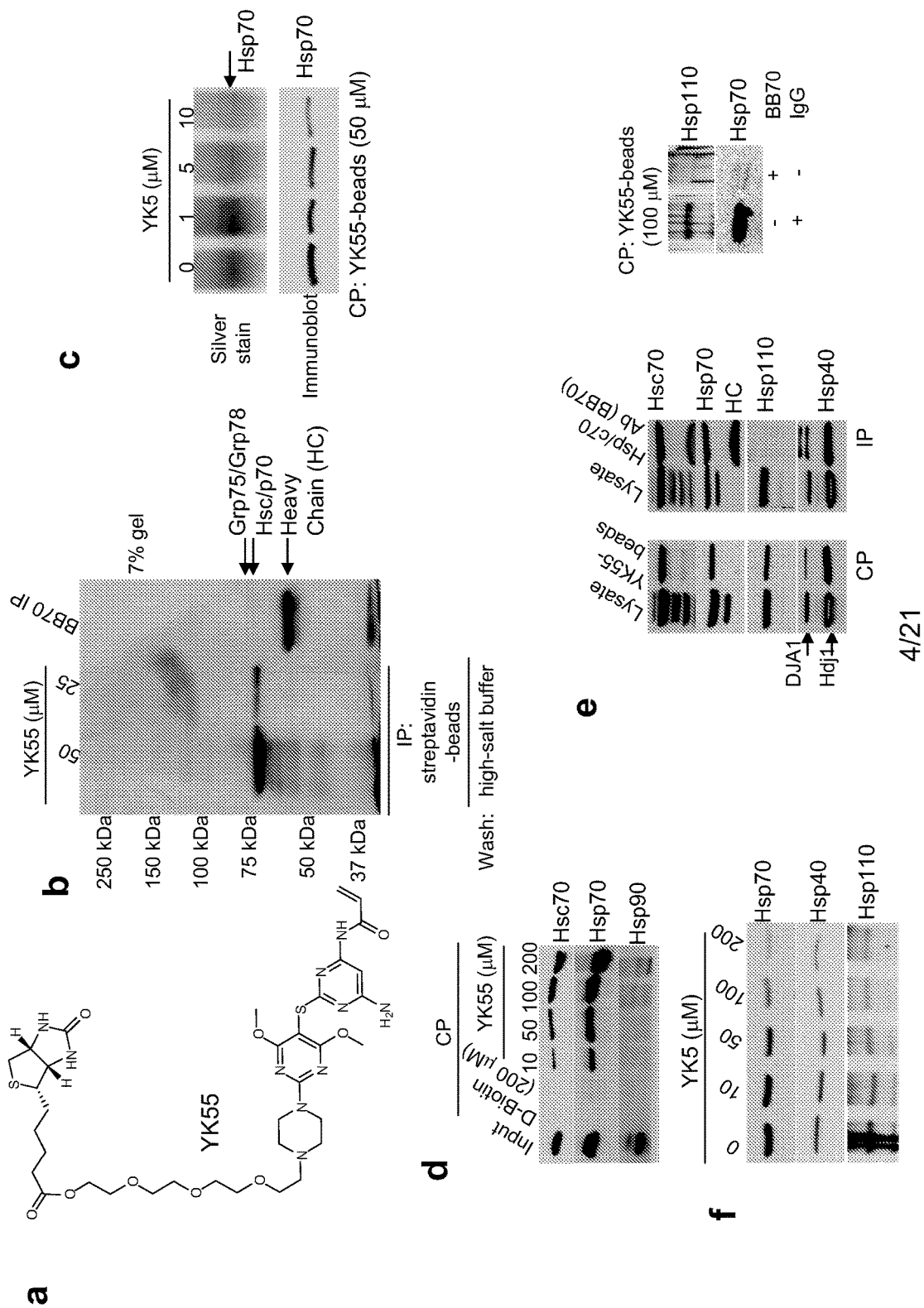
FIG. 4. YK5 interacts selectively with Hsp70 and Hsc70. a) Structure of biotinylated YK5. b) K562 cells were treated with the indicated concentrations of YK55 for 6 h prior to lysing and precipitation of protein complexes on streptavidin beads (50 µl) for 1 h at 4° C. Beads were washed with high-salt (1 M NaCl) buffer, proteins eluted by boiling in 2% SDS, separated on a denaturing gel and silver stained. BB70 Ab pull-downs were used to indicate the position of Hsp70s (BB70 IP; 2 µl). This antibody recognizes several Hsp70 isoforms, such as Hsp70, Hsc70, Grp75 and Grp78. HC=heavy chain. c) SKBr3 cells were treated for 24 h with the indicated concentrations of YK5 and cells were lysed. Protein complexes were isolated through chemical precipitation by incubating the cell extract (500 µg) with YK55-beads (50 µl), eluted with 2% SDS, separated on a denaturing gel and visualized as indicated. YK55 beads were made by incubating YK55 (50 µM) with streptavidin beads (50 µl). d) Protein complexes from SKBr3 cell extracts (500 µg) were isolated through chemical precipitation with YK55- beads or an inert molecule, D-biotin. Beads were made by incubating indicated concentrations of YK55 or D-biotin with streptavidin beads (50 µl). Proteins were then separated on a denaturing gel and analyzed by Western blot. e) Hsp70 complexes precipitated from SKBr3 extracts (500 µg) with YK55-beads (100 µM YK55 added to 50 µl streptavidin beads) or an Hsp70 Ab (5 µl Ab added to 30 µl protein G beads) were analyzed by WB. HC=heavy chain (left). Binding of protein complexes to YK55 beads was probed in SKBr3 cell extracts in which Hsp/c70 levels were reduced by BB70 Ab or IgG immunoprecipitation, respectively. Proteins were analyzed by WB (right). f) SKBr3 extracts were incubated for 3 h at 4° C. with the indicated concentrations of YK5, followed by precipitation of Hsp70s complexes on YK55-beads (100 µM YK55 added to 50 µl streptavidin beads). Proteins were analyzed by WB. The data are consistent with those obtained from multiple repeat experiments (n≥3).

Addition of YK55, but not of D-biotin, to cells followed by isolation on streptavidin beads, identified a major band around 70 kDa (FIG. 4, panel b), which was competed off in a dose-dependent manner by soluble YK5 (FIG. 4, panel c). Tandem liquid chromatography-mass spectrum (LC/MS/MS) analysis of peptide digests obtained from this band confirmed the presence of the two inducible Hsp70 isoforms (Hsp70-1 and Hsp70-6), and of Hsc70, the constitutive Hsp70 member. Their identity was further investigated by Western blot, to demonstrate Hsp70s but not Hsp90, in the YK55-pulldowns (FIG. 4, panel d).

To investigate the Hsp70 cycling stage most sensitive to YK5, co-chaperone complexes isolated by YK55-beads were analyzed and compared to those identified by an anti-Hsp70s antibody (FIG. 4, panel e, left). YK55-beads preferentially trapped Hsp70 in complex with its activating co-chaperones, Hsp40 and Hsp110, whereas the Ab isolates lacked the nucleotide exchange factor, Hsp110. Because the anti-Hsp70s Ab BB70 can deplete the cellular levels of Hsp70 and Hsc70, but is weak at trapping Hsp70s in a co-chaperone (i.e. Hsp110)-bound conformation, it was possible to further probe the specificity of YK55-beads for Hsp70s (FIG. 4, panel e, right). Namely, when incubated with BB70 but not irrelevant IgG Hsp70s-depleted extracts, YK55-beads failed to significantly interact with Hsp110, confirming that interaction of YK55 with Hsp110 occurred through an Hsp70s-mediated complex. Soluble YK5 dose-dependently competed with YK55-beads for binding to the Hsp70 complexes (FIG. 4, panel f).

Upon incubation of cells with YK55, a strong and selective interaction, not disrupted by high-salt washes (1M NaCl), was formed between the agent and Hsp70s (FIG. 4, panel b). YK5 contains an acrylamide functionality which may create a covalent bond upon protein binding. For compounds where irreversible binding plays a role, the half inhibitory binding (IC50) value for binding consists of two components, one reflecting reversible binding and another reflecting the subsequent covalent binding, and depends on the extent to which the covalent interaction has occurred. Indeed, incubation of cells for one to four hours with YK55, led to a progressive increase in the amount of immobilized 70 kDa band (FIG. 5, panel a), which by anti-biotin and Hsp70 immunoblots, was suggested to be an YK55-Hsp70-containing species (FIG. 5, panel b). Weak to no interaction of YK55 with Grp75 and Grp78, the mitochondrial and the endoplasmic reticulum Hsp70 family members, respectively, was detected under these conditions (FIG. 5, panel b).

Elution of protein complexes from the YK55-streptavidin beads in conditions sufficiently harsh to disrupt the tightest known non-covalent binding, the streptavidin-biotin complex, confirmed that indeed a covalently bound YK55-Hsp70 species was formed when cells were incubated with YK55 (FIG. 5, panel c). Trypsin digestion of the YK55-bound Hsp70s species, but not of BB70 pulldowns, an anti-Hsp70s antibody, identified two m/z peaks at 1867.915 and 1372.649 atomic mass units (FIG. 5, panel d). These peaks correspond to YK55 (820.34 Da) attached to LRTAC$^{267}$ERAK and YK55 lacking the biotin (YK55-Biotin) (594.26 Da) attached to TAC$^{267}$ERAK, respectively. No labeling of these peptides was observed when YK55Hsp70s isolates were reduced and alkylated using beta-mercaptoethanol and acrylamide, respectively. Mass spectrometric sequencing of LRTAC$^{267}$(YK55)ERAK was performed to further confirm the sequence identity (not shown).

The TACERAK sequence is conserved in human cytosolic Hsp70s, but divergent in Grp75 and Grp78, consistent with their lack of interaction with YK55 under similar conditions (FIG. 5, panel b). Collectively, these data suggest specific derivatization of cytosolic Hsp70s by YK55.

YK5 Inhibits Main Biochemical Hsp70s Functions.

Next, the binding of YK5 to Hsp70s was investigated to see if it interferes with its main biochemical activities, specifically refolding of a de-natured client protein and its ATPase activity. Hsp70 activities are stimulated by Hsp40 proteins and nucleotide exchange factors, such as Hsp110. Humans have several cytosolic Hsp40s, among which Hdj1, DJA1, DJA2 and DJA4, and it was recently reported that DJA1 provides the strongest stimulation of Hsc70 ATPase activity, whereas DJA2 is most efficient in promoting the refolding of an Hsc70 polypeptide substrate, firefly luciferase. YK5 dose-dependently inhibited the refolding of luciferase by purified Hsc70 and DJA2 (FIG. 6, panel a) and partially inhibited the stimulated ATPase rate of Hsc70 (FIG. 6, panel b). Because YK5 binding to the Hsp70 N-terminal domain does not occlude the ATPase site, its effect most probably results from disruption of the essential coordination of the N- and C-terminal domains. The core biochemical functions of Hsp70 were inhibited by YK5 in assay conditions that do not favor covalent bond formation, suggesting in addition to covalent reactivity, an appropriate fit for YK5 in the active site of the target.

YK5 Inhibits the Formation of Active Hsp70/Hsp90/Oncoprotein Complexes.

It is suggested that Hsp70 facilitates the function of the Hsp90 multi-chaperone complex and acts at the initial step of complex formation by loading client proteins onto the Hsp90 complex through the intermediary protein HOP. Clients of Hsp90 are several malignancy driving and supporting client proteins with important roles in the development and progression of pathogenic cellular transformation. In addition to oncoproteins, Hsp90 regulates the transcription factor heat-shock factor-1 (HSF-1), the master regulator of a heat shock response in response to cellular insults. Hsp90 binds to HSF-1 and maintains the transcription factor in a monomeric state. Upon exposure of cells to an Hsp90 inhibitor or to elements inducing cellular stress, the chaperone dissociates from HSF-1, permitting it to trimerize, enter the nucleus, and bind to heat shock response elements found in the promoters of heat shock proteins, including Hsp70 and its activator, Hsp40.

YK5 interfered dose-dependently with the formation of the Hsp90-complexes (FIG. 6, panel c, left and middle) without affecting the cellular expression of complex-component chaperones (FIG. 6, panel c, right). Inhibition of Hsp90 complex formation by YK5 led to onco-protein release and destabilization (FIG. 6, panel d), but had no effect on HSF-1 activation (FIG. 6, panel e). In agreement with lack of Hsp90/HSF-1 complex destabilization by YK5, only heat shock and direct Hsp90 inhibitors, but not YK5, led to the formation of HSF-1 trimers (FIG. 6, panel e). These results bring supporting evidence to the hypothesis that transcription competence of HSF-1 is repressed by association with an Hsp90 and not Hsp70s containing complex. They also show that the onco-protein regulatory action of the Hsp90 machinery can be differentiated from its effects on HSF-1, by upstream Hsp70s inhibition. In this regard YK5 becomes a chemical tool to study the biological effect of Hsp90 machinery inhibition in a chemical-HSF-1 knockdown environment. The advantages of this intervention are evident over the genetic manipulations of HSF-1, allowing for temporal and spatial analysis of the cellular environment. Alteration of Hsp90 complexes by YK5 took place at the increasing low micromolar concentrations (FIG. 6c, middle) at which the degradation of Hsp90-onco-client proteins also occurred (FIG. 3a). Collectively, YK5 inhibited the growth of SKBr3 cells and degraded the Hsp70/Hsp90 onco-protein client HER2 at concentrations it disrupted the formation of Hsp70/Hsp90 complexes, suggesting that, in this concentration range, the biological activity of YK5 was partly channeled through disruption of a functional Hsp90 machinery. Disruption of the Hsp90 machinery/onco-protein complex by YK5, was associated with onco-protein destabilization and its cell clearance acceleration, as demonstrated by reduced protein half-life (FIG. 7b), and consequent reduction in the cellular steady-state levels of the onco-protein (FIG. 7a). Further confirmatory of an Hsp90 machinery-mediated effect, and consistent with degradation of Hsp90-machinery client proteins via the proteasome pathway upon chaperone inhibition, proteasome inhibitors but not inhibitors of other proteolytic enzymes, efficiently rescued degradation of onco-proteins by YK5 (FIG. 7c).

Collectively, these embodiments demonstrate that the biological activity of YK5 and other related compounds of the present subject matter with regard to regulation of onco-client proteins, is, at least partly, a consequence of its ability to interfere with the formation of the active intermediate Hsp90 machinery complex, leading to improper cellular processing of Hsp90 onco-client proteins and resulting in their subsequent degradation, mainly by the proteasome.

Example 4: Structure-Activity Relationship in the YK-Series

To further confirm that an absolute dependence of the IC50 value with reactivity of the YK5-inhibitor cannot be accounted for by the component of the IC50 that reflects reversible (noncovalent) binding, relevant structure-activity relations studies were conducted. Indeed, reduction of the acrylamide, as in YK30, to ethylamide, as in YK31 (FIG. 8a), retained an Hsp70-driven mechanism of action, and lowered biological activity by only 30-fold (FIG. 8a and not shown). In addition, maintaining the acrylamide but switching the ethylene glycol chain from position R1, as in YK54 and its biotinylated version YK55, to R2 as in YK57 and its biotinylated version YK56, lowered biological activity by approximately 20-25 fold (FIGS. 8b and c). In some embodiments, compounds of the present subject matter with lowered biological activity, as compared to other compounds of the present subject matter, may still have sufficient activity to attain inhibition or binding of selected enzymes or proteins at useful IC50 concentrations or binding constants.

Collectively, these data indicate that the interaction of YK5, and other related compounds of the present subject matter, with Hsp70s consists of two elements, one reflecting reversible binding and another subsequent covalent cysteine modification.

While there is a concern that an acrylamide entity could indiscriminately react with non-target related proteins resulting in pleiotropic effects, incubation of cells with YK55 resulted selectively in the formation of YK55-Hsp70 adducts (FIGS. 4 and 5). In addition, agents that result in unspecific oxidation of cysteines are known to increase cellular protein misfolding and to lead to consequent protective activation of a heat shock response, phenomenon not observed with YK5. At the physiologically relevant concentration of 10 μM, YK5 was also inert when tested against 359 kinases (FIG. 6f). These findings confirm that at the tested concentrations, YK5 is a specific Hsp70s modulator, and thus, an appropriate tool to dissect the significance of pharmacologic Hsp70s inhibition in in vitro biological systems.

Drug discovery efforts tend to avoid molecules that exhibit noncompetitive kinetics, an understandable caution considering the potential toxicology events associated with irreversible inhibition. Nonetheless, at least 25 agents in clinical use as anti-cancer and anti-microbial agents are covalent protein modifiers. One may reason that for irreversible binders, there is a lower need to keep high drug concentrations in the systemic circulation, and thus once target inhibition is achieved the effects remain until new target protein is synthesized. In addition, for proteins with relatively high affinity for ATP, such as Hsp70s, one can argue that in the presence of high cellular ATP levels, irreversible target inhibition offers a therapeutic advantage. Collectively, these observations suggest that if a balance between first-passage metabolism and sufficient target delivery and inhibition is achieved at the cost of limited toxicity, irreversible inhibitors could have a significant role in anti-cancer therapies.

For YK5, our data demonstrate that reversible inhibitors retain an Hsp70-mediated mechanism, suggesting that the acrylamide group could be eliminated altogether and potent reversible inhibitors could be identified by improving the enthalpy of the binding. Indeed, other embodiments herein show compounds of the present subject matter with reversible Hsp70 interaction mode (FIG. 9, FIG. 10 and FIG. 11). Addition of these compounds of the present subject matter to several cancer cells resulted in degradation of relevant onco-client proteins and induced apoptosis in a manner similar to YK5. These embodiments therefore demonstrate that important activity as described herein, may be achieved by compounds of the present subject matter that interact with Hsp70 by either a irreversible or reversible binding mode. In a particular embodiment, these compounds interact with the above described Site 1.

Efforts to investigate the biological relevance of Hsp70 inhibition by small molecules have also been reported. These suggest that Hsp70s are not as easily targetable as Hsp90. Several Hsp70 modulators have been recently disclosed, nevertheless these compounds are of low potency and their potential pleiotropic effects on cellular physiology are completely unclear. Little is also known on their mode of interaction with the Hsp70 isoforms. Moreover, these compounds are based on scaffolds of limited drug-like characteristics. Further, surprisingly low to no apoptotic response was observed in cancer cells with several of these Hsp70 inhibitors, an apparent paradox considering the reported potent anti-apoptotic functions of Hsp70.

In addition, genetic manipulation of Hsp70 led to conflicting findings. Havik et al reported that single or mixed reduction in Hsp70 and Hsc70 expression in two breast cancer cells, SKBr3 and MCF-7, while reducing cell viability, displayed no ability to reduce the activity of the Hsp90/Hsp70 chaperone complex. On the other hand, simultaneous transfection targeting of both hsc70 and hsp70 inhibited Hsp90 functions in HCT116 colon cancer cells. Nylansted et al found that Hsp70 depletion alone led to eradication of glioblastoma, and breast and colon carcinoma xenografts, whereas in prostate cancer cells, others reported only sensitization to anticancer agents.

In contrast to the above mentioned strategies, our work identifies YK5, a dual and selective modulator of Hsp70 and Hsc70, designed on a potentially druggable scaffold amenable to extensive medicinal chemistry. Also in contrast to the above strategies, YK5 and related compounds of the present subject matter have shown to have potent antiproliferative properties, by the many measures described herein, without being toxic to normal cells.

Example 5: Pharmacologic Hsp70 Modulation Interferes with Major Hallmarks of Malignancy Transformation of normal cells into malignant cells is a multistep process, requiring the accumulation of a number of genetic alterations influencing key regulatory processes in the cell. Hanahan and Weinberg described six essential phenotypic traits that are required for development of the full malignant phenotype, referred to as the "six hallmarks" of cancer. For each hallmark trait, at least one Hsp90-machinery client protein has been identified which has the capacity to regulate this process, and direct Hsp90 inhibitors have the capacity to influence all six of these features. Having developed a pharmacologic Hsp70 regulator, the role of Hsp70 in the Hsp90-machinery in respect to the cancer hallmarks was then investigated.

Cancer cells are characterized by aberrant proliferation. Certain Hsp90-machinery clients, such as Akt and Raf-1, are major players in pathways necessary for the growth and survival of tumors, and are regulated by Hsp90 in a majority of tumors. Consistent with participation of Hsp70s in these Hsp90 functions, a dose-dependent degradation and inactivation of these ubiquitous tumor driving molecules was observed upon addition of YK5 and related compounds of the present subject matter to a range of cancer cells, including the breast cancer cells SKBr3 and MDA-MB-468, the small cell lung carcinoma NCI-H526 and the acute myeloid leukemia MOLM-13 (FIGS. 3, 7-10 and Table 1). Other Hsp90 onco-clients, specific to a particular malignant phenotype, were also sensitive to YK5. In the case of the breast cancer cell line SKBr3, transformation is driven by overexpression of HER2 tyrosine kinase, which activates signaling pathways promoting cell growth and survival. HER2 stability in this cell is regulated by Hsp90, and chaperone inhibition by direct Hsp90 inhibitors results in HER2 degradation (FIG. 3). Mutant androgen receptor (AR) expressed in LNCaP prostate cancer cells and mutant FLT-3 kinase characteristic of acute myeloid leukemia and expressed in the MOLM-13 cells, both Hsp90 machinery clients, were also sensitive to YK5 and related compounds of the present subject matter described herein (FIGS. 10a and 15d). STAT3 and PDK1, activated in triple-negative breast cancer and STAT5, activated in leukemias, were also sensitive to YK5 and related compounds of the present subject matter described herein (FIG. 9-11, 15d).

Concordant with a common mechanism of action through pathogenic Hsp70/Hsp90 complex inhibition, the direct Hsp90 inhibitors PU-H71 and PU24FC1, as well as YK5 inhibited the growth of all tested cancer cells, regardless of their origin and genetic background (FIG. 12a and Table 1). Tested were MDA-MB-468 triple-negative breast cancer cells, SKBr3 HER2+ breast cancer cells, LNCaP mAR+ prostate cancer cells, MOLM-13 and Kasumi-1 acute myeloid leukemia cells, OCI-Ly7 diffuse large B-cell lymphoma cells and HuH7 hepatocellular carcinoma cells. YK5 also inhibited the growth of MDA-MB-468 xenografted tumors (FIG. 12b). In cancer cells, half growth inhibitory concentrations ($GI_{50}$s) recorded for YK5 were in high agreement with its potency to degrade Hsp90 onco-clients. Collectively, these results further suggest that, at the pharmacologically relevant dose, the biological activity of YK5 is a reflection of its target, Hsp70, inhibition.

Aberrant proliferation in cancer cells is associated with deregulation of the cell cycle, and several molecular components of the transition through the cell cycle are controlled by the Hsp90 machinery. Direct Hsp90 inhibitors lead to cell-dependent cycle arrest—certain cells, such as SKBr3, are blocked at a $G_0/G_1$ stage, whereas others such as MDA-MB-468, in $G_2/M$. In accord with its Hsp90-machinery targeting mechanism, YK5 had a similar effect on the cell cycle in these cells (FIG. 12c, left). Its effects were associated with depletion of Hsp90 machinery-dependent cell cycle proteins, such as the $G_2/M$ regulatory protein CDK1 in MDA-MB-468, and the $G_1$-regulatory protein Cyclin D1 in SKBr3 (FIG. 12c, right). Moreover, these proteins were found in complex with YK5-isolated Hsp70 (FIG. 12d).

Invasion into adjacent tissues and metastasis to distant sites are major features of malignant cancer cells and are the cause of 90% of human cancer deaths. Invasion and metastasis are complex processes and require coordinated actions of a large assortment of genes, including many kinases. Several proteins involved in increasing the metastatic potential of cancer cells are regulated by Hsp90, including the PI3K/Akt pathway, a key signaling pathway that drives tumor cell invasion. In the highly metastatic MDA-MB-231 breast cancer cells, inhibition of this pathway is sufficient to reduce their invasive potential. Concordantly, YK5, which lowered the cellular levels of activated Akt, as evidenced by reduction in Akt phosphorylated at Ser473 (FIG. 12e, upper), inhibited the ability of MDA-MB-231 cells to invade through Matrigel (FIG. 12e, lower). Collectively, these findings demonstrate that pharmacologic Hsp70 modulation through an YK5-mediated mechanism, partly mimics the effects of direct Hsp90 inhibitors with respect to oncoprotein degradation, inhibition of aberrant cell proliferation and cycling, and reduction of invasive potential. Similarly, other compounds of the present subject matter may also be expected to also have these same activities.

Evasion of apoptosis is another important hallmark of cancer. Cancer cells undergo significant cell death when challenged with YK5, and for certain cancer cell lines this effect was consistently higher than upon direct Hsp90 inhibition (FIGS. 3a and 13). While in certain cells, such as MDA-MB-468, OCI-Ly7 and MOLM-13, considerable and equal killing is observed upon Hsp90 inhibition by PU24FC1 and Hsp70 inhibition by YK5, others, such as LNCaP, SKBr3 and HuH7, appear more sensitive towards Hsp70 inhibition (FIG. 12a). Reduced cell killing effect in these cells was reported for other Hsp90 inhibitors of distinct chemotypes, suggesting it a specific target related consequence, and not an unspecific event, such as potential Hsp90 inhibitor metabolism.

To determine whether cell death by YK5 was attributable to apoptosis, cells were treated with YK5 and effects on morphology, as well as on several effectors and mediators of apoptosis were analyzed (FIG. 13). To quantify the number of cells undergoing apoptosis, cells were stained with acridine orange/ethidium bromide (AO/EB) and analyzed under a fluorescence microscope for the percentage of viable, apoptotic (early and late) and necrotic cells. YK5 treated cell cultures demonstrated a significant and preferential dose-dependent increase in cells showing the morphological features of apoptosis, such as nuclear shrinkage and fragmentation (FIG. 13a, left and FIG. 13b). Quantification of these experiments after 24 h of treatment, showed that approximately 5% of cells were undergoing apoptosis in vehicle treated acute myeloid leukemia (AML) Kasumi-1 cells, and their number increased to 70% when challenged with 10 µM YK5 (FIG. 13a, right). Only 9% apoptotic cell death was observed in identical conditions with PU24FC1 (FIG. 13a, right). Increased apoptotic effect of YK5 when compared to direct Hsp90 inhibitors was observed in other cancer cells, such as in breast and prostate cancer cells (not shown). Most sensitive to YK5 were pancreatic cancer cells. When tested in a panel consisting of Mia-PaCa2, AsPC-1, BxPC3 and PL45 cells, YK5 (10 µM) induced significant apoptosis after only 24-48 h of treatment (FIG. 13b and not shown), a remarkable finding considering the high anti-apoptotic threshold of pancreatic cancer, and its resistance to therapies.

At molecular level, apoptosis by YK5 and related compounds of the present subject matter in cancer cells was demonstrated by an increase in PARP (FIG. 13c) and caspase-3 cleavage and activation (FIGS. 9,10,14). These effects on apoptotic markers occurred at concentrations of YK5 in agreement with its anti-proliferative activity and its ability to degrade Hsp90-machinery dependent onco-proteins, suggestive of a common Hsp70-mediated mechanism of action of YK5 on the cancer hallmarks.

Example 6: YK5 Induces Apoptosis Through Hsp70 and Hsp90-Mediated Pathways

Both Hsp70 and Hsp90 have been documented to inhibit apoptosis. Hsp70 protects cells from a wide range of apoptotic and necrotic stimuli, and it is believed that elevated levels of Hsp70 augment tumor cell survival. Succinctly, Hsp70 has been reported to inhibit the loss of mitochondrial membrane potential that precedes release of both cytochrome c and AIF from mitochondria. A direct effect of Hsp70 on cytochrome c, Apaf-1 and AIF has been also noted. Involvement of Hsp70 at an early step in apoptotic signal transduction was also documented via suppression of stress-activated JNK kinase. Moreover, Hsp70 was found to mediate protection from TNF cytotoxicity, to bind and modulate the activity and localization of anti-apoptotic factors such as Bcl2, and to promote the degradation and inactivation of pro-apoptotic factors such as p53 and c-myc. Thus, Hsp70 inhibits apoptosis by regulating a number of key elements of the intrinsic and extrinsic apoptotic pathways. In contrast, regulation of apoptosis by Hsp90 is more limited, and the main anti-apoptotic molecules regulated by Hsp90 are Akt and Bcl-xL. While regulating several anti-apoptotic molecules, the two chaperones, Hsp90 and Hsp70, are not ubiquitous inhibitors of apoptosis in cancer. Their effect manifests in a transformation-specific manner that is dependent on the cell's wiring and functionality of apoptotic pathways.

Along these lines, it was recently reported that in SKBr3 cells Hsp90 inactivation arrests their growth and leads to Akt degradation but fails to induce appreciable apoptosis. In contrast these agents induce massive apoptosis in the small cell lung carcinoma cells NCI-H526. Quite the reverse, treatment of cells with MAL3-101, an agent that interferes with Hsp70 activation by J-proteins, or with quercetin and KNK437, both inducible Hsp70 expression inhibitors, resulted in substantial cell death by apoptosis in SKBr3 but not in NCI-H526. Reduction of Hsp70 expression by anti-sense sequences also induced substantial death in SKBr3 cells. Collectively these studies proposed Hsp70 an important regulator of apoptotic pathways in SKBr3 but not NCI-H526, and conversely, indicated Hsp90 as a major regulator of apoptosis in NCI-H526 but not SKBr3. Acting simultaneously on the Hsp90 and the Hsp70-pathways, YK5 and related compounds of the present subject matter induce significant apoptosis in both SKBr3 (FIG. 13c) and NCI-H526 cells (FIG. 14 and not shown).

In addition to inhibiting the autonomous cell survival, induction of Hsp70 expression is reported to render cells highly resistant to cell death induced by tumor necrosis factor (TNF), oxidative stress, UV radiation, caspase-3 over-expression, and several chemotherapeutic drugs. In accord with its effect on Hsp70, YK5 increased the apoptotic effect of TNFα in MDA-MB-468, triple-negative breast cancer cells (FIG. 13e).

Collectively, these findings suggest that dual inhibition of Hsp70 and Hsc70 induces apoptosis in a spectrum of tumors larger than Hsp90 or Hsp70 inhibition alone, indicating a potential increased therapeutic potency of these inhibitors in cancers. They also show that compounds of the present subject matter described herein may potentiate the therapeutic effect of other interventions.

The increased apoptosis observed with YK5 when compared to direct Hsp90 inhibitors could be also partly explained by its inability to induce a feed-back heat shock response. Whereas it has been shown that certain tumors are susceptible to apoptosis following direct Hsp90 inhibition, a feed back induction of Hsp70 upon direct Hsp90 inhibition limits the cytotoxicity of these agents in many tumor types. At the protein level, induction of Hsp70 protein synthesis had been demonstrated for all known Hsp90 inhibitors, and has been observed both pre-clinically and clinically. Direct Hsp90 inhibitors are preferentially cytotoxic to cells in which HSF-1 was knocked-out, and even a short-term downregulation of Hsp70 in certain cancer cells by siRNA and antisense approaches makes them more sensitive to inhibitors of Hsp90. Along these lines, small molecules which impair HSF-1 activation also sensitize cells to Hsp90 inhibition. Further, certain tumor cells that fail to upregulate Hsp70 levels seem to be particularly sensitive to Hsp90 inhibition. Induction of Hsp70 by other interventions is documented to result in cytoprotection, and experimental evidence suggests that the cellular level of Hsp70 is a critical parameter for susceptibility to apoptosis. Considering these major anti-apoptotic capabilities, the inability of YK5 to induce Hsp70 and activate HSF-1 (FIG. 3), at least in part, accounts for its higher cytotoxicity (FIG. 12a) and apoptotic response (FIG. 13) when compared to direct Hsp90 inhibitors. In further accord with this observation, Hsp90 inhibitors were more toxic to cancer cells pre-treated with YK5, or when the Hsp90 and Hsp70 inhibitory agents were added together.

Collectively, these findings suggest that dual pharmacologic inhibition of Hsp70 and Hsc70 has the capacity to influence a multitude of oncogenic hallmarks, leading to a comprehensive attack on the malignant phenotype and resulting in cancer cell lethality.

In addition, our data demonstrate that inhibition of Hsp70 has a more profound effect on apoptosis when compared to Hsp90 inactivation, suggesting a potential increased therapeutic potency of these inhibitors in cancers.

Example 7: Pharmacologic Hsp70 Inhibition is Selectively Toxic to Cancer Cells

Because Hsp70 assists in house-keeping functions of normal cells, such as folding of newly synthesized polypeptides, refolding of misfolded proteins, and translocation of proteins through biological membranes, it remains unclear whether pharmacologic interventions which target both Hsp70 and Hsc70 isoforms, such as YK5, are non-toxic to these cells. To address this matter, the cytotoxic effect of YK5 in a panel of normal cells was evaluated, namely peripheral blood leukocytes (PBLs) obtained from healthy blood donors, and cultured normal fibroblasts, such as the colon cells CCD18Co and the lung MRC-5 (FIG. 14*a-c*). Cell death was minimal in normal cells after Hsp70 pharmacologic inactivation by YK5 by measure of metabolic activity (FIG. 14*a*, upper), apoptosis activation (FIG. 14*b,c*) and visual inspection of cell morphology (FIG. 14*c*, lower). Meanwhile, in similar conditions, cancer cells underwent significant death when challenged with YK5 (FIG. 14*a-c*). In primary AML specimens YK5 induced potent cell death in blast populations, while non-tumor cells found within the same patient sample were significantly less affected by treatment. In addition, when fresh tissue obtained at surgery from a patient with a poorly differentiated infiltrating ductal carcinoma of ER,PR,HER2− status was treated ex vive with YK5 (5 µM), no treatment related changes were observed in stroma and normal blood vessels, but massive apoptosis in tumor cells (60% of tumor cells were dead or dying at 24 h post-YK5 addition) (not shown). Collectively, these findings indicate that YK5 and related compounds of the present subject matter are selectively toxic to cancer cells.

Together with findings from genetic Hsp70 manipulations, where silencing of Hsp70 isoforms was less toxic in nontumorigenic cell lines than in cancer cells, the higher sensitivity of cancer cells towards Hsp70 expression and function inactivation may be justified by a model akin to the "oncogene addiction" model proposed by Weinstein. In this model, degradation of a specific Hsp70 client in the appropriate genetic context (for example HER2 in cells with overexpression of the tyrosine kinase) by YK5 will result in apoptosis and/or differentiation, whereas its degradation in normal cells will have little or no effect. This model has been used to justify the clinical development of direct Hsp90 inhibitors in a broad range of tumor types.

One cannot however, exclude a more sophisticated use of Hsp70s in cancer cells, which can be selectively targeted by the YK5 small molecule, in a manner certain Hsp90 inhibitors select for tumor Hsp90 species. To investigate such possibility, the interaction of YK55-beads with normal and cancer cells extracts was measured. In a first experiment, chemical precipitation experiments from a normal cell, MRC-5, and a cancer cell, SKBr3, were conducted with increasing concentrations of YK55-beads (FIG. 14*d*, top panel). YK55-beads interacted strongly with an Hsp40 bound Hsc/p70 species in SKBr3. In MRC-5, interaction was weaker, and Hsp40 species undetectable in the YK55-pulldown. To augment the Hsp levels in MRC-5 cells, these cells were exposed to heat shock treatment before the chemical precipitation step. Heat shock elevated the expression of Hsp70s and Hsp40s, but unaltered YK55's selectivity and affinity (FIG. 14*d*, middle panel). Similar findings were determined in brain extracts. Although this tissue has high Hsc70 expression, comparable to cancer cells, the Hsp70 species in brain extracts interacted weakly with YK55 (FIG. 14*d*, lower panel).

In a second experiment, the ability of soluble YK5 to compete YK55-binding to normal and cancer cell Hsp70 species were tested (FIG. 14*e*). Interestingly, binding of YK55-beads to Hsp70 species from SKBr3 cancer cell extracts was competed by low micromolar concentrations of YK5, whereas a concentration of YK5 that exceeded 200 it M was necessary to observe displacement of Hsp70s expressed in the MRC-5 cells (FIG. 14*e*). Interaction of YK5 was even weaker with recombinant human Hsp70 (FIG. 14*e*).

Hsp70 in cancer cells exists in heterogeneous complexes, with onco-client protein and co-chaperone bound Hsp70-species likely to coexist at any time with free Hsp70 and co-chaperone bound Hsp70. Analysis in this context of findings from FIG. 15, indicate that Hsp70 species that are onco-protein bound are most sensitive to competition with soluble YK5, suggesting a higher affinity of YK5 for these Hsp70 species.

Collectively, these results suggest that compounds of the present subject matter, such as YK5, may have a higher affinity for Hsp70s species expressed in malignant cells, and moreover they may prefer those Hsp70 species that are onco-protein and co-chaperone bound, providing a potential explanation for the observed selective sensitivity of cancer cells to compounds of the present subject matter, such as YK5, and for the increased sensitivity of onco-proteins to inhibition induced by compounds of the present subject matter.

Example 8: Hsp70 Cy3B-K5 Competition Fluorescence Polarization Assay

Because YK5 and related compounds of the present subject matter bind with higher affinity to Hsp/c70 complexes found in cancer cells than to recombinant protein (FIG. 14*d,e*), a fluorescence polarization (FP) assay was designed that measured the competitive binding of cy3B-labelled YK5 or related compounds of the present subject matter to cancer lysate Hsp/c70 complexes. In principle, cellular lysates are pre-incubated with a compound of the present subject matter described herein, and upon YK5-cy3B addition and equilibration, the signal is read in an Analyst GT plate reader. The assay was developed for 96-well format and allows a quick evaluation of the compounds (FIG. 16).

Human Cancer Cell lysate preparation: The human breast cancer cell line MDA-MB-468 was obtained from the American Type Culture Collection (Manassas, Va.) and cultured as indicated by the vendor. Cells were collected and frozen to rupture the membranes and then dissolved in binding buffer with added protease and phosphotase inhibitors to form the lysate. Lysates were stored at −80° C. before use. Total protein content was determined using the bicinchoninic acid assay kit (Pierce Biotechnology, Rockford, Ill.) according to the manufacturer's instructions.

Hsp70 Cy3B-K5 competition FP assay: FP measurements were performed using black 96-well microtiter plates (Corning #3650), where both the excitation and the emission occurred from the top of the well. The Hsp70 FP binding buffer contained the following: 25 mM HEPES-K, pH=7.2, 20 mM NaCl, 200 µM $CaCl_2$, 110 mM KOAc, 2 mM $Mg(OAc)_2$, 0.01% NP40. Each assay well contained 20 µg cell lysate and the YK-inhibitor in 75 µL buffer. The mixture was kept on a shaker for 10 min, then incubated at 37° C. for 2 h. The tracer was added to each well resulting in a final concentration of 3 nM Cy3B-YK5 and a final volume of 100

µL. Measurement was then performed on an Analyst GT plate reader (Molecular Devices, Sunnyvale, Calif.). An integration time of 100 ms was used, and Z height was set at 3 mm (middle). The excitation polarization was set at static, and the emission polarization was set at dynamic. For cy3B-YK5, an excitation filter at 530 nm and an emission filter at 580 nm were used with a dichroic mirror of 561 nm. All FP values were expressed in millipolarization (mP) units. The mP values were calculated using the equation mP=1000×[(IS−ISB)−(IP−IPB)]/[(IS−ISB)+(IP−IPB)], where IS is the parallel emission intensity measurement, IP is the perpendicular emission intensity sample measurement, and ISB and SP are the corresponding measurements for background (buffer). Total fluorescence was determined as 2×IP+IS.

As can be seen in FIG. 16, increasing concentrations of indicated inhibitors were added in triplicate to the assay plate and the FP assay was performed as indicated above. The competitive effect was expressed as percentage of control and was calculated by dividing the millipolarization (mP; subtracting free cy3B-YK5) value from inhibitor wells by the average mP (subtracting free cy3B-YK5) from controls (cy3B-YK5 and cell lysate with vehicle DMSO) in each plate. Ligand binding was plotted against the $\log_{10}$ inhibitor concentration, and $EC_{50}$ values were calculated using a nonlinear least-square curve-fitting program in Prism 4.0. Points, mean; bars, s.d. FIG. 16 indicates that addition of indicated compounds of the present subject matter dose-dependently competed the binding of YK5-cy3B to Hsp70 in the cell lysate.

Example 9: YK5 Traps Hsp70 in a Client-Protein Bound Conformation. Use of Solid Support Immobilized YK5 to Identify Cancer-Specific Onco-Proteins: STAT1 in Breast Cancer YK55-beads preferentially isolate Hsp70 in complex with several tumor-specific onco-proteins (FIG. 15a-d). Pre-incubation of cell lysates with YK5, diminished in a dose-dependent manner, the ability of YK55-beads to interact with Hsp70s, and resulted in displacement of bound onco-proteins (FIG. 15c). Because the anti-Hsp70s Ab BB70 can deplete the cellular levels of Hsp70 and Hsc70, but is weak at trapping Hsp70s in a co-chaperone (i.e. Hsp110) and onco-protein client-bound conformation, the specificity of YK55-beads for Hsp70s was probed. Namely, when incubated with BB70 but not irrelevant IgG Hsp70s-depleted extracts, YK55-beads failed to significantly interact with Hsp110 and Raf-1, confirming that interaction of YK55 with Hsp110 and Raf-1 occurred through an Hsp70s-mediated complex (FIG. 15a, right).

Collectively, these findings indicate that YK5 isolates Hsp70 in an onco-client conformation, suggesting the use of YK55-beads or related compounds of the present subject matter in the discovery of tumor-type dependent Hsp70 clients, which confers the unprecedented possibility to investigate the cancer Hsp70s interactome in an endogenous cellular environment. These efforts are critical for the discovery of mechanisms associated with sensitivity of tumors to Hsp70 inhibition, for designing rational combinatorial therapies including the compounds of the present subject matter described herein and inhibitors of YK-beads isolated activated onco-proteins and pathways, and for a rational translation of compounds of the present subject matter described herein and of other Hsp70 inhibitors to cancer treatment.

To validate the utility of YK55-beads, the Hsp70s pool isolated by YK55, but not biotin, was first shown to contain an established Hsp70s client such as serine/threonine kinase Raf-1 (FIG. 15a, left). YK55-beads failed to significantly interact with the oncogenic Raf-1 kinase in Hsp70-depleted cells, confirming that interaction of YK55 with the oncogene product occurred through an Hsp70s-mediated complex (FIG. 15a, right).

Next, whether Hsp70s, like Hsp90, have the ability to interact with onco-proteins specific to a genetic background was probed. Several oncoproteins were found, involved either in increased signaling through a pathogenic pathway or in aberrant cell cycling, in complex with Hsp70s. These, also known Hsp90 interactors, include Cyclin D1 and the HER2 kinase in the HER2 overexpressing SKBr3 breast cancer cells, cyclin dependent kinase 1 (CDK1) and phosphoinositide-dependent kinase-1 (PDK1) in the MDA-MB-468 breast cancer cells and mutant androgen receptor (AR) in LNCaP prostate cancer cells (FIG. 15b,c). Pre-incubation of cell lysates with YK5, diminished in a dose-dependent manner the ability of YK55-beads to interact with Hsp70s, and resulted in displacement of bound onco-proteins (FIG. 15c).

Collectively, these data demonstrate that YK5-beads isolate several Hsp70 regulated oncogene products that are involved in effecting cell-specific aberrant signaling. Inhibition of these oncogene products in the right genetic context leads to tumor inhibition and apoptosis, and thus their degradation can be used as a functional assay (i.e. biomarkers of response) to evaluate clinically response to herein described compounds of the present subject matter. Inhibitors of these oncogene products can be also used in combination with compounds of the present subject matter described herein to design personalized therapies with improved outcome. To identify the relevant oncoge products sensitive to inhibition of Hsp70 by the herein described and related compositions of matter, use of YK55-beads is described here.

Investigation of the Hsp70s Interactome in Breast Tumors

HSPs are ubiquitously expressed proteins with wide-ranging functions in the folding and cellular translocation of a variety of proteins. Whereas these house-keeping functions are well recognized and have been the subject of intense investigation, it is now becoming clearer that chaperones are co-opted in pathogenic cells to carry out distinct and specialized disease-specific roles.

For the Hsp90 chaperone, these functions in malignancy have been mainly deciphered through the discovery of a small molecule inhibitor, geldanamycin. In contrast, the lack of small molecules that modulate selectively Hsp70s in this context and the somewhat contradictory findings by means of Hsp70 and Hsc70 genetic manipulations, has curbed our ability to fully understand the involvement of Hsp70 and Hsc70 in malignant transformation Because YK5 and related compounds of the present subject matter are Hsp70s modulators with a novel mechanism of action, locking Hsp70s in complex with onco-client proteins and apoptosis-regulatory molecules, this allows for the unique opportunity to unbiasedly investigate the Hsp70s interactome in the cancer cell.

| Sequence | SEQ ID NO | MDA-MD-468 Control beads Intensity | MDA-MB-468 YK55-beads Intensity | SKBr3 Control beads Intensity | SKBr3 YK55-beads Intensity |
|---|---|---|---|---|---|
| (R)FHDLLSQLDDQYSR(F) | SEQ ID NO: 5 | | 9.51E+07 | | 5.32E+07 |
| (R)FNQAQSGNIQSTVMLDK(Q) | SEQ ID NO: 6 | | | | 5.44E+07 |
| (R)FNQAQSGNIQSTVmLDK(Q) | SEQ ID NO: 7 | | | | 5.50E+07 |
| (R)GLNYDQLNMLGEK(L) | SEQ ID NO: 8 | | 2.58E+08 | | 1.60E+08 |
| (K)LLGPNASPDGLIPWTR(F) | SEQ ID NO: 9 | | 1.34E+08 | | |
| (K)SLEDLQDEYDEK(C) | SEQ ID NO: 10 | | | | 8.30E+07 |
| (K)TELISVSEVHPSR(L) | SEQ ID NO: 11 | | | | 3.97E+08 |
| (K)VMAAENIPENPLK(Y) | SEQ ID NO: 12 | | | | 6.39E+07 |

Table 14. A solid-support immobilized YK5 identifies STAT1 as an Hsp70 interactor in breast cancer cells. Protein complexes isolated by control beads, having D-biotin attached, and by YK55-beads in human MDA-MB-468 and human SKBr3 breast cancer lysates, were separated on SDA-PAGE, a 90 kDa band was excised, and extracted proteins were digested and analyzed by LC/MS/MS as described in Methods. Amino acids in parentheses were cleaved off from the rest of the sequence during extraction. Sequence analysis identified the band to be STAT1.

To conduct an unbiased analysis of the cancer Hsp70s interactome, proteomic analyses was performed on control- and YK55-beads-pulldowns from SKBr3 and MDA-MB-468 breast cancer cells. Among the identified (Table 14) and validated (FIG. 17, FIG. 18) cargo proteins were signal transducer and activator of transcription 1 and 3 (STAT1 and STAT3). YK55 failed to interact with STATs in Hsp70s immunodepleted cells (FIG. 18b), indicating that binding of YK55 to STATs was Hsp70-mediated and Hsp70-specific. Intriguingly, contrarily to Raf-1 and to other oncoproteins, addition of YK5 to cells failed to reduce the steady-state levels of STAT1 (FIG. 17a, right). On the other hand, a reduction in active STAT3 but not STAT1, as evidenced by largely diminished levels of p-STAT3, was observed upon YK5 treatment (FIG. 17a, right).

STATs are a family of transcription factors with critical roles in the integration of a variety of extracellular stimuli. Whereas most STAT family members, such as STAT3 and STAT5 have been shown to promote oncogenesis, STAT1 suppresses oncogenesis, suggesting that to survive, cancer cells need to develop opposing mechanisms for concomitantly keeping an increased expression of p-STAT3 and p-STAT5 while suppressing p-STAT1 levels. Indeed, in breast cancer cells abundant p-STAT3 was found (FIGS. 8-11, FIG. 17), but barely detectable levels of activated STAT1 (FIGS. 17,18, see p-STAT1 levels in endogenous versus IFNγ stimulated cells). We therefore asked whether in cancer cells, fine-tuning in the levels of p-STAT1 and p-STAT3 species may be regulated by Hsp70s. Given that STAT1 activation can promote cell death, and because breast cancer cells express STAT1, it was hypothesized that binding of Hsp70s to STAT1 in these cells may play a role in inhibiting its pro-apoptotic function, suggesting a possible mechanism by which cancer cells protect against IFNγ and the immune system.

Along these lines, IFNγ was found to both increase the cellular levels of p-STAT1 (FIG. 18c,d) and induce apoptosis in MDA-MB-468 cells (FIG. 18c). The effects of IFNγ on p-STAT1 were augmented by YK5 (FIG. 18c). Comparison of STAT1 and p-STAT1 levels in these cells, to those sequestered by YK55-beads, indicated that the majority of activated STAT1 was in complex with YK5/Hsp70, suggesting that capture of p-STAT1 by Hsp70s is implicated in inhibition of the IFNγ-STAT1-pathway.

STAT1 is a major effector of interferon-(IFNγ) signaling. IFNγ is a cytokine produced by T-cells and natural killer cells with an essential immune-stimulating function that provides defense against pathogens and the development of tumors. IFNγ can exert antiproliferative effects on a wide variety of tumor cells, including those of the breast, and these effects are channeled through STAT1. IFNγ has extrinsic tumor surveillance effects in immunocompetent mice, and those effects require an intact JAK (Janus Kinase)-STAT signaling pathway. Specifically, IFNγ results in the phosphorylation of STAT1 on tyrosine residue 701 and serine residue 727 leading to homodimerisation, DNA binding and transcriptional activation of its target genes, several with apoptotic roles. Apoptosis and caspase activation in response to IFNγ are abolished in cells lacking functional STAT1. Similarly, STAT1 negative cells show reduced caspase expression and tumor necrosis factor α (TNFα)-induced apoptosis compared to closely matched cells expressing functional STAT1. These findings indicate that activation of STAT1 plays a key role in inducing apoptosis in response to regulatory cytokines such as IFNγ or TNFα. Furthermore, a recent study showed that mice deficient in both STAT1 and RAG2, a protein critical for V(D)J recombination, were predisposed to spontaneous mammary gland carcinomas. Evidence that STAT1 is a negative regulator for tumor angiogenesis, growth, and metastasis has also been provided.

These results indicate that the use of combination therapies incorporating compounds of the present subject matter as described herein have the potential of stimulating the effect of interferon and allow immune responses to much more potently wipe out tumors by blocking a tumor related dampening mechanism. This is an exciting finding for vaccine therapy trials, suggesting that co-administration of biologically active interferon with compounds of the present subject matter described herein can improve the vaccine efficiency and allow the use of a smaller vaccination dose.

Because other pathogenic transformations rely on cytokine/STAT1 signaling, such as microbial and viral infections and late complications of type-II diabetes, our work suggests that therapies incorporating Hsp70s inhibitors, in addition to cancers, may also have a potentiating effect in the treatment of these diseases.

Hsp70s Binding is a Novel Mechanism of Inhibition of Tumor Suppressor Activity.

To detail the mechanism of STAT1 inhibition by Hsp70s, IFNγ-treated MDA-MB-468 cells were analyzed at different time points in the presence and absence of YK5, and of inhibitors of protein phosphorylation and dephosphorylation, with the goal of measuring time-dependent tyrosine phosphorylation of STAT1 at residue Tyr701 (FIG. 18e,f). While in the presence of YK5, STAT1-phosphorylation rapidly reached maximal levels, in the absence of the Hsp70s inhibitor, its activation was delayed and failed to reach similar magnitude.

Since the overall level of p-STAT1 is determined by the balance of phosphorylation and dephosphorylation events, prolonged tyrosine phosphorylation of STAT1 Hsp70-inhibited cells may result from either an increase in JAK kinase activity or a decrease in protein tyrosine phosphatase (PTPase) activity toward STAT1.

To monitor the rate of STAT1 dephosphorylation, a pulse-chase strategy was employed in which staurosporine, a protein kinase inhibitor, was added to cells pretreated with IFNγ for 30 min, abruptly blocking the continuous phosphorylation of STAT1 by JAKs (FIG. 18f, upper). The residual level of tyrosine-phosphorylated STAT1 was then determined at several later time points. In the absence of YK5, tyrosine phosphorylation of STAT1 declined immediately, whereas in its presence, cellular p-STAT1 levels were prolonged. These results indicate that Hsp70s can attenuate IFNγ induction of STAT1 phosphorylation in breast cancer cells, and Hsp70s inhibitors facilitate accumulation of p-STAT1 due to a potential delay in dephosphorylation. Accordingly, in the presence of orthovanadate ($Na_3VO_4$), a nonspecific PTPase inhibitor, STAT1 phosphorylation occurred almost as efficiently in YK5-untreated and treated cells (FIG. 18f, lower). Blockage of STAT1 dephosphorylation by orthovanadate led to nuclear accumulation of the tyrosine phosphorylated STAT1 and its subsequent persistence. Concordantly, pre-treatment of MDA-MB-468 cells with YK5 before IFNγ stimulation, enhanced the nuclear translocation of activated STAT1 (FIG. 19a) and increased its DNA-binding efficacy ((FIG. 19b). These results are consistent with a mechanism whereby Hsp70s hold p-STAT1 in a conformation that alters the rate of dephosphorylation by PTPases.

Example 10: Use of Solid Support Immobilized YK5 to Identify Cancer-Specific Onco-Proteins: STAT3 in Breast Cancer As indicated in Example 9, STAT3 was also identified in the YK55-beads isolates (FIG. 17c). Contrary to STAT1, STAT3 is frequently found to be constitutively active in breast cancer and tumors can become addicted to STAT3. STAT3 tyrosine phosphorylation and DNA-binding has been found to be elevated in a large number of breast cancer tumors and cell lines. Evidence suggests that STAT3 can activate the transcription of several genes associated with cell cycle progression, cell survival and transformation. Conversely, pharmacologic and dominant-negative inhibition of STAT3 activity blocked proliferation and survival of breast cancer cells, collectively suggesting that STAT3 activity is required for the transformed phenotype in breast cancer.

Using the experimental strategy designed for STAT1, Hsp70s play on STAT3 an effect opposite to that on STAT1. Our results indicate that Hsp70s facilitate accumulation of cellular p-STAT3 by easing phosphorylation by kinases and/or delaying STAT3 dephosphorylation by PTPses. STAT3 activation is contingent on the phosphorylation of a conserved tyrosine residue (Y705) by upstream kinases such as Janus kinase 2 (JAK2). Collectively, it was concluded that binding to Hsp70s retains p-STAT3 in a conformation little accessible to PTPases but favorable for JAK phosphorylation, and is a major mechanism of maintaining an elevated reservoir of p-STAT3 levels in the cell. Along with a mechanism of STAT3-activity regulation by Hsp70, compounds of the present subject matter described herein potently inactivate STAT3 as indicated by reduction of tyrosine residue (Y705) phosphorylation in the presence of described compounds (FIGS. 9b, 10a, 11b). Thus the p-STAT3 promoting effects of Hsp70s are reverted by YK5 and related compounds of the present subject matter. Persistent activation of the STAT3 signaling pathway has been documented in a wide range of human solid and blood cancers and is commonly associated with a worse prognosis. Among the cancer-promoting activities ascribed to persistent STAT3 signaling are those involved with cell proliferation, metastasis, angiogenesis, host immune evasion, and resistance to apoptosis. We show here that interference with the STAT signaling pathway by compounds of the present subject matter described herein is a new strategy to inhibit aberrantly activated STAT signaling in cancerous cells.

In conclusion, embodiments included herein show the use of YK5 and its biotinylated derivative, YK55, to investigate the interactome of cytosolic Hsp70s. Several oncogene products activated in a wide-range of cancer types were identified by these beads. These include but are not limited to HER2, Cyclin D1, Raf-1, STAT1 and STAT3 in HER2 overexpressing breast cancer, PDK1, STAT1, STAT3 and CDK1 in triple-negative breast cancer and mutant AR in prostate cancer. These provide evidence that compounds of the present subject matter described herein combinatorially acts on several activated oncogenic pathways and will have activity in a large spectrum of cancers. Binding of these proteins by Hsp70 is required to maintain their functional stability, and inhibition of Hsp70 by YK5 and related compounds of the present subject matter leads to oncoprotein destabilization and subsequent elimination by a proteasomal pathway, or alternatively to its inactivation.

There is a need to better understand the molecular aberrations that result in the transformed phenotype. Such understanding may lead to the development of less toxic anti-cancer treatments, based on inhibitors of tumor-promoting molecules. Because most cancers are characterized by several molecular alterations, it is difficult in clinical settings to determine the exact combination of molecularly-targeted agents that will result in a best outcome. One can imagine using the YK-beads to "fish out" a subset of proteins that become aberrant in every cancer cell type/patient tumor tissue. The information gained from these "fish out" experiments may be compiled in creating a molecular map of cell- and cancer-specific transformation pathways. The generation of a map of "tumor specific molecular aberrations" will ultimately allow the physician to design a personalized therapy for patients. Such proteomic map has obvious advantages over the more common genetic signature maps because most anti-cancer agents are small molecules that target proteins not genes, and many small molecules targeting specific molecular alterations are currently in development. These efforts may set the basis for designing combination therapies with better efficacy and less toxicity in the treatment of patients with cancers, and moreover, define the specific molecular alterations in a particular tumor, facilitating the development of novel molecularly targeted therapies.

One embodiment of the present subject matter provides a method of monitoring the treatment status of a patient being treating for a tumor or proliferative disorder, comprising covalently linking a compound of claims 1 to 20 to a solid substrate to form a substrate-compound complex; obtaining a first biological sample from the patient at a time before or during the treatment period; contacting the sample with the substrate-compound complex to allow the substrate-compound complex to contact HSP70 complex; measuring and recording the type and amount of oncoprotein displaced from the HSP70 complex; obtaining a second biological sample from the patient at a time later during the treatment period and repeat the step of measuring t and recording the type and amount of oncoprotein displaced from the HSP70 complex; comparing the results with the previous measurement and identifying whether oncoprotein metabolic pathways have been inhibited or shifted to other oncoprotein pathways; and identifying whether the patient therapy has had a beneficial effect.

These embodiments also show that the use of YK5 and related compounds of the present subject matter identify a novel mechanism of regulation of protein phosphorylation in the cell. Specifically, it shows that Hsp70s act as a cellular buffer for STAT1 and STAT3 activity in breast cancer cells. Our data are indicative of a mechanism by which Hsp70s bind to STAT1 and STAT3, and hold the proteins in a conformation that facilitates and accelerates (for STAT1) or that decelerates (for STAT3) their dephosphorylation by phosphatases. By this mechanism Hsp70s lower endogenous p-STAT1 and decrease its pro-apoptotic capabilities and conversely, increase endogenous p-STAT3 and augment its proliferation inducing capabilities Not lastly, our findings suggest that pharmacologic inhibition of Hsp70s though an YK5-mechanism has a multimodal effect in a wide-range of cancer cells and results in a comprehensive attack on the major cancer hallmarks. This effect is highly connected to the ability of compounds of the present subject matter described herein to impair multiple oncoprotein stability and function, and to restore tumor suppressor activity. Together with its lack of feed-back heat shock response, little cytotoxic effect on normal cells and potent activity in a wide range of cancer cells of distinct genetic background, our results position dual Hsp70 and Hsc70 pharmacologic inhibition as a potential novel anticancer intervention.

Example 11: Use of Compounds of the Present Subject Matter to Ablate Stem Cells

YK5 Potently Kills Cancer Stem Cells.

Increasing evidence suggests that acute myelogenous leukemia (AML) is generated and maintained by a relatively rare, chemotherapy-resistant subpopulation of cells known as leukemia stem cells (LSCs) that can self-renew, proliferate, and differentiate into leukemic blasts. Patients who present with a higher proportion of phenotypically defined LSCs demonstrate significantly poorer relapse-free survival than patients with low proportions of LSCs. Also, a higher proportion of LSCs at diagnosis is highly predictive of minimal residual disease (MRD), suggesting that LSCs are significant contributors to MRD. Finally, it has been demonstrated that, while many drugs can kill leukemia blasts, very few ablate the LSCs.

In primary AML specimens, YK5 induced potent cell death in blast, stem and progenitor populations (FIG. 20). Strikingly, a high sensitivity of phenotypically described leukemia stem cells and of total leukemic blasts was observed (FIG. 20b; red vs. gray bars). Finally, non-tumor cells found within the same patient sample were significantly less affected by treatment by YK5 (FIG. 20, white bars). Thus, a compound with cancer stem cell toxicity, such as YKs, is of significant value to improving cancer therapy.

Example 12: Methods of Analysis

Reagents.

PU24FC1 and PU-H71 were synthesized and characterized as previously described. The ansamycin Hsp90 inhibitor based fluorescent probe GM-cy3B, was synthesized as reported. The synthesis and characterization of compounds of the present subject matter described herein. Leupeptin, MG 132, MG 101, PMSF, propidium iodine and tumor necrosis factor-α were obtained from Sigma-Aldrich; AEBSF—from A.G. Scientific; Z-VAD-FMK, BOC-D-FMK, cathepsin inhibitor 1, calpeptin and IFNγ—from Calbiochem. Recombinant human Hsp70 protein was purchased from Stressgen.

Cell Lines.

Human cancer cells MDA-MB-468, MDA-MB-231, LNCaP and normal human lung fibroblasts MRC5 and normal human colon cells CCD18Co were purchased from the American Type Culture Collection (Manassas, Va.). SKBr-3 cells were a gift from Dr. Neal Rosen, MSKCC, HuH7 cells were a gift from Dr. Massague, MSKCC, OCI-Ly7, MOLM-13 and Kasumi-1 from Dr. S. Nimer, MSKCC and Mia-PaCa2, AsPC-1, BxPC3 and PL45 were a gift from Dr. D. Bar-Sagi, NYU. Cells were cultured routinely in DME/F12 (MDA-MB-468, MDA-MB-231 and SKBr3) or in RPMI (LNCaP, MOLM-13, BxPC3, and AsPC-1 and Kasumi-1) or in MEM (MRC5 and CCD18Co) or in IMDM (OCI-Ly7) or in DMEM (HuH7, Mia-Paca2, and PL45) supplemented with 10% fetal bovine serum, 1% L-glutamine, 1% penicillin and streptomycin. PBL (human peripheral blood leukocytes) were isolated from patient blood purchased from the New York Blood Center. Thirty five ml of the cell suspension was layered over 15 ml of Ficoll-Paque plus (GE Healthcare). Samples were centrifuged at 2,000 rpm for 40 min at 4° C., and the leukocyte interface was collected. Cells were plated in RPMI medium with 10% FBS and treated next day with appropriate concentrations of YK5 for the indicated times.

Primary Cell Isolation and Culture.

Primary human AML cells were obtained with informed consent. All manipulation and analysis of specimens was approved by the Weill Cornell Medical College Institutional Review Board. Mononuclear cells were isolated using Ficoll-Plaque (Pharmacia Biotech, Piscataway, N.Y.) density gradient separation. In some cases, cells were cryopreserved in freezing medium consisting of of Iscove's modified Dulbecco medium (IMDM), 40% fetal bovine serum (FBS), and 10% dimethylsulfoxide (DMSO) or in CryoStor™ CS-10 (Biolife).

Buffers:

To wash protein complexes isolated on YK55-beads or BB70-Ab either high-salt buffer (20 mM Tris pH 7.4, 1M NaCl, 0.1% NP-40) or low-salt buffer (20 mM Tris pH 7.4, 25 mM NaCl, 0.1% NP-40 buffer), was used as indicated. To elute protein complexes from YK55-beads, as indicated, either elution buffer A (62.5 mM TrisHCl pH 6.8, 2% SDS, 10% Glycerol, 15.5 mg/ml DTT, Bromophenol Blue 0.02 mg/ml) was used and boiled the sample at 100° C. for 3 min or elution buffer B (2% SDS, 50 mM phosphate, 100 mM NaCl, 6 M urea and 2 mM thiourea) and incubated the sample for 15 min at room temperature, followed by 15 min at 100° C.

Computational Methods: Protein Sequence and Crystal Structures were downloaded from NCBI and RCSB database, respectively. Homology model was constructed by Prime v2.0 and the crude homology model was further refined by minimization using Macromodel v9.6. SiteMap v2.2 analysis was performed on the ensuing homology model, followed by design and docking of YK5 onto the predicted allosteric site. All computations were carried out on a HP workstation xw8200 with the Ubuntu 8.10 operating system using Maestro v8.5.

Residue Numbering Scheme:

The position of each amino acid residue in the Hsp70 protein was according to the sequence numbering of hHsp70 (Accession number: P08107) proposed by Milner, et al., unless otherwise specified.

Homology Model Building:

The homology model was generated using Prime v2.0. The protein structures of the hHsp70 N-terminal domain in complex with ATP (PDB ID: 1S3X), the *E. coli* Hsp70 (DnaK) complexed with both ADP and substrate (peptide—NRLLLTG) (PDB ID: 2KHO), the C-terminal domain of *C. elegans* Hsp70 (PDB ID: 2P32) and the amino acid sequence of full length hHsp70 protein (Accession number: P08107) were used for model building. To create the model, the protein sequence of hHsp70 (Accession number: P08107) was entered as an input sequence in Prime's Structure Preparation wizard. A sequence homology search was conducted to identify templates that exhibit more than 50% sequence homology. This search led to the identification of three template crystal structures (PDB ID's: 1S3X, 2KHO and 2P32). The full length hHsp70 sequence and the templates were aligned using default parameters of Prime. In the build structure option of Prime, amino acids Met1-Gly382 (hHsp70) were selected from PDB ID: 1S3X, amino acids Asp385-Gln538 (*E. coli.*) i.e., Asp383-Ala541 (hHsp70) from PDB ID: 2KHO and finally, amino acids Leu543-Ser614 (*C. elegans*) i.e., Leu542-Gly613 (hHsp70) from PDB ID: 2P32. Amino acid residues (614-641, hHsp70) were not modeled because there was no template structure for these C-terminal amino acids. The structure was then built using atom positions from the aligned portions of the template(s), taking solvent, ligand (ADP), force field, and other contributions into account via a series of algorithms implemented in Prime. Structural discontinuities were optimized by inserting template gaps for more than twenty residues. All loops were refined with the default parameter settings of Prime.

Structure Preparation:

The homology modeled hHsp70 protein structure was refined for SiteMap and docking calculations using the protein preparation wizard available in Maestro 8.5. Partial atomic charges were assigned according to the OLPS-AA force field. To obtain a more reliable 3D structure of hHsp70, the homology model was further subjected to a series of energy minimization steps that consisted of 5000 iterations of steepest descent (SD) and conjugate gradient (CG), until the root mean-square (rms) gradient energy was lower than 0.001 kcal mol$^{-1}$ Å$^{-1}$.

Binding Site Prediction:

The refined homology model of hHsp70 was subjected to computational investigation aiming to determine the probable druggable sites using default parameters implemented in SiteMap v2.2 of Maestro v8.5. A SiteMap calculation is divided into three stages as described by T. Halgren. In the first stage, relevant site points are selected based on geometric and energetic properties, and the points are grouped into sets to define the sites. Next, hydrophobic, hydrophilic, and other key properties are computed at grid points and contour maps are prepared. Finally, site properties like Site score (S-score), Druggability score (D-score), size, enclosure, hydrophilic and hydrophobic are computed. Potential receptor binding sites are ranked based on S-scores and D-scores.

In order to determine an appropriate drug binding site, SiteMap recognizes a site which can bind ligands strongly (higher S-score), but does not rate it as druggable if active ligands of highest activity contain charged structures, such as those of the natural phosphate substrate, and thus are of unlikely druglike character (lower D-score).

Ligand Structure Preparation:

hHsp70 modulator (YK5) and newly designed modulators were constructed using the fragment dictionary of Maestro v8.5. The geometry of modulators was optimized by the Macromodel program v9.6 using the OLPS-AA force field.

Ligand Docking.

Docking calculations were run in the Standard Precision (SP) mode of Glide v4.0. Grids were prepared using the Receptor Grid Generation tool in Glide by selecting individual entry sites obtained by SiteMap (Sites 1-5) as input ligand. The binding site, for which the various energy grids were calculated and stored, is defined in terms of two concentric cubes: the bounding box, which must contain the center of any acceptable ligand pose, and the enclosing box, which must contain all ligand atoms of an acceptable pose. The bounding and the enclosing boxes are defined by cubes with an edge length of 12 Å and 30 Å, respectively that are centered at the midpoint of the longest atom-atom distance of the ligand. Poses with rms deviation of less than 0.5 Å and a maximum atomic displacement of less than 1.3 Å were eliminated to exclude redundancy. The scale factor for van der Waals radii was applied to those atoms with absolute partial charges less than or equal to 0.15 (scale factor of 0.8) and 0.25 (scale factor of 1.0) electrons for ligand and protein, respectively. The maxkeep variable which sets the maximum number of poses generated during the initial phase of the docking calculation was set to 5000, and the keep best variable which sets the number of poses per ligand that enters the energy minimization was set to 1000. The energy minimization protocol includes a dielectric constant of 4.0 and 1000 steps of conjugate gradient. Upon completion of each docking calculation, at most 100 poses per ligand were allowed to generate. The best docked conformation was chosen considering orientation and Glidescore (G-score).

Western Blotting.

Cells were grown to 60-70% confluence and treated with inhibitor or DMSO vehicle for the indicated times. Protein lysates were prepared in 50 mM Tris pH 7.4, 150 mM NaCl and 1% NP-40 lysis buffer. Protein concentrations were measured using the BCA kit (Pierce) according to the manufacturer's instructions. Protein lysates (10-50 g) were resolved by SDS-PAGE, transferred onto nitrocellulose membrane and incubated with the indicated primary antibodies: anti-erbB2 from rabbit (1:250, 28-0004, Zymed), anti-Hsp90 from mouse (1:500, SPA-830, Stressgen), anti- Hsp40 from rabbit (1:1000, SPA-400, Stressgen), anti-HOP from mouse (1:1000, SRA-1500 Stressgen), anti-Hsc70 from rabbit (1:500, SPA-816, Stressgen), anti-androgen receptor from mouse (1:500, 554225, Biosciences), anti-Flt-3 from rabbit (1:500, sc-480, Santa Cruz), antibiotin from mouse (1:250, B7653, Sigma-Aldrich), anti-Hsp90 from mouse (1:1000, SMC-107, Stressmarq), anti-HSF1 from rabbit (1:500, SPA-901, Stressgen), anti-CDK1 from mouse (1:1000, 905-777-100, Assay Designs), anti-cyclin D1 from mouse (1:125, 2926, Cell Signaling), anti-caspase 3 from rabbit (1:500, 9665, Cell Signaling), antiphospho-STAT1 (Tyr 701) from rabbit (1:250, 9171, Cell Signaling), anti-STAT1 from mouse (1:1000, 610186, BD Biosciences), anti-Hsp70 from mouse (1:500, SPA-810, Stressgen), anti-Akt from rabbit (1:500, 9272, Cell Signaling), anti-phospho-Akt (Ser 473) from rabbit (1:500, 9271, Cell Signaling), anti-Raf-1 from rabbit (1:500, sc-133, Santa Cruz), anti-PARP (p85 fragment) from rabbit (1:500, G7341, Promega), anti-CSK from rabbit (1:1000, sc-13074, Santa Cruz), anti-β-actin from mouse (1:2500, A1978, Sigma-Aldrich) and anti-PI3K (p85) from rabbit (1:4000, 06-195, Upstate). Membranes were then incubated with a corresponding peroxidase-conjugated secondary antibody (1:3,000 dilution). The anti-p23 (JJ3) was a gift of Dr. D. Toft. The anti-HIP, anti-Hsp90 (H9010) and anti-Hsp/c70 (BB70) antibodies were produced as previously described.

Hsp90 Binding Assay.

Measurements were performed in black 96-well microtiter plates (Corning #3650) as previously described[7]. In short, each 96-well plate contained 3 nM Cy3B-GM, 10 nM Hsp90 (Stressgen # SPP-770) and tested inhibitor (initial stock in DMSO) in a final volume of 100 μl. The plate was left on a shaker at 4° C. for 24 h and the fluorescence polarization (FP) values in mP were recorded. $EC_{50}$ values were determined as the competitor concentrations at which 50% of the Cy3B-GM was displaced. FP measurements were performed on an Analyst GT instrument (Molecular Devices).

Hsc70 ATPase Activity and Luciferase Refolding.

Human Hsc70, DJA1/DNAJA1, DJA2/DNAJA2 and Hsp110/Hsp105/HSPH1 were purified and analyzed. To measure Hsc70 ATPase activities, 4 μM Hsc70 was preincubated in assay buffer (100 mM KOAc, 20 mM Hepes-KOH pH 7.5, 5 mM $MgOAc_2$) at 37° C. for 2 h with different concentrations of YK5 or 1% DMSO as a vehicle control. 4 μM DJA1 or DJA2, 1 μM Hsp110, 2 mM ATP and 5 μCi/ml μ[$^{32}$P]-ATP (Perkin Elmer) were added and reactions incubated at 30° C. Samples at time points were terminated with 37.5 mM EDTA and analyzed by thin layer chromatography on polyethylene-imine cellulose (Mallinckrodt Baker) developed in 0.5 M LiCl and 0.5 M formic acid. The ADP produced was determined by image phosphor quantitation and the linear enzymatic rates ($V_{max}$) were calculated by regression analysis. To analyze luciferase refolding, firefly luciferase (Sigma) was denatured in 6 M guanidinium-HCl and 1 mM dithiothreitol for 10 min. 4 μM Hsc70 was preincubated with drug or vehicle control as above. 4 μM DJA2 and 2 mM ATP were added, and luciferase was quickly diluted 1:100 to 5.4 nM in the reactions, which were incubated at 30° C. At the 60 min or indicated time point, samples were diluted 2:25 into luciferase assay reagent (Promega) and activity measured in a Berthold Lumat LB9507 luminometer.

Hsp70 Competition Assay Using the YK55 Beads.

Protein lysates were prepared using 20 mM Tris pH 7.4, 25 mM NaCl, 0.1% NP-40 lysis buffer. Cell extracts were incubated for 3 h at 4° C. with the indicated concentrations of soluble competitor in 20 mM Tris pH 7.4, 25 mM NaCl, 0.1% NP-40 buffer. Meanwhile, YK55-beads were prepared by incubating streptavidin agarose beads (50 μl) (Thermo Scientific) with YK55 (50 or 100 μM, as indicated) at 4° C. for 1 h. Upon a three-time wash of beads with buffer, the above soluble competitor containing lysates, were incubated with the YK55-beads. Samples were incubated at 4° C. overnight, washed five times with the lysis buffer and applied to SDS-PAGE.

Hsp70 Cy3B-K5 Competition Fluorescence Polarization Assay:

FP measurements were performed using black 96-well microtiter plates (Corning #3650), where both the excitation and the emission occurred from the top of the well. The Hsp70 FP binding buffer contained the following: 25 mM HEPES-K, pH=7.2, 20 mM NaCl, 200 M $CaCl_2$, 110 mM KOAc, 2 mM $Mg(OAc)_2$, 0.01% NP40. Each assay well contained 20 μg cell lysate and the YK-inhibitor in 75 μL buffer. The mixture was kept on a shaker for 10 min, then incubated at 37° C. for 2 h. The tracer was added to each well resulting in a final concentration of 3 nM Cy3B-YK5 and a final volume of 100 μL. Measurement was then performed on an Analyst GT plate reader (Molecular Devices, Sunnyvale, Calif.). An integration time of 100 ms was used, and Z height was set at 3 mm (middle). The excitation polarization was set at static, and the emission polarization was set at dynamic. For cy3B-GA, an excitation filter at 530 nm and an emission filter at 580 nm were used with a dichroic mirror of 561 nm. All FP values were expressed in millipolarization (mP) units. The mP values were calculated using the equation mP=1000×[(IS−ISB)−(IP−IPB)]/[(IS−ISB)+(IP−IPB)], where IS is the parallel emission intensity measurement, IP is the perpendicular emission intensity sample measurement, and ISB and ISP are the corresponding measurements for background (buffer). Total fluorescence was determined as 2×IP+IS.

Native Gel Electrophoresis.

Cells were heat shocked for 45 min at 42° C. or treated with indicated inhibitor or vehicle for 3 h, and consequently lysed in 20 mM Hepes pH 7.9, 0.42 M NaCl, 1.5 mM $MgCl_2$, 0.2 mM EDTA, 25% glycerol buffer. Seventy five μg protein samples were loaded onto a prerun, nondenaturing gradient polyacrylamide gel (4% stacking gel, 5 to 20% separation gel) and separated in 50 mM Tris pH 8.0, 0.38 M glycine electrophoresis buffer at 4° C. overnight. The gel was pre-equilibrated in SDS-PAGE running buffer for 15 min at room temperature. Proteins were then transferred electrophoretically in 50 mM Tris, 380 mM glycine, 0.1% SDS, 20% methanol buffer at 4° C. onto nitrocellulose membrane and blotted for HSF-1.

Immunoprecipitation.

Cells were collected and lysed in 20 mM Tris pH 7.4, 25 mM NaCl, 0.1% NP-40 buffer. Each sample contained 500 kg of a total protein. Appropriate antibody (BB70 for Hsp70 and H9010 for Hsp90) (5 μl) or normal IgG (5 μl) (as a negative control) was added to each sample together with protein G agarose beads (30 μl) (Upstate) and incubated at 4° C. overnight. Samples were washed five times with lysis buffer, and applied on SDS-PAGE followed by a standard western blotting procedure.

Chemical Precipitation.

Protein lysates were prepared using 20 mM Tris pH 7.4, 25 mM NaCl, 0.1% NP-40 lysis buffer. Streptavidin agarose beads (50 μl) (Thermo Scientific) were washed three times with lysis buffer, YK55 was added at the indicated concentrations and the complexes incubated at 4° C. for 1 h. Upon a three-time wash with buffer, beads were added to indicated total cellular protein in buffer. Samples were incubated at 4° C. overnight, washed five times with the lysis buffer and applied to SDS-PAGE.

Hsp70 Depletion.

Four μl of BB70 anti-Hsp70 antibody or normal mouse IgG and 30 μl of protein G agarose suspension were added to 200 μg of MDA-MB-468 protein cell lysate in 20 mM Tris pH 7.4, 25 mM NaCl, 0.1% NP-40 buffer. Following incubation at 4° C. for 3 h, samples were centrifuged, the supernatant collected and the bead pellet discarded. The procedure was repeated twice. YK55-beads (100 μM of YK55 added to 50 μl streptavidin beads) were prepared as described above, added to the supernatants and incubated at 4° C. overnight. Beads were washed five times with 20 mM Tris pH 7.4, 25 mM NaCl, 0.1% NP-40 buffer and applied to SDS-PAGE.

Covalent Binding.

K562 cells were treated with the indicated amount of YK55 for the indicated time. Cells were collected and lysed in 20 mM Tris pH 7.4, 25 mM NaCl, 0.1% NP-40 buffer. Cell extract (500 μg) in 100 μl of the lysis buffer was incubated with streptavidin agarose beads for 1 h at 4° C. Samples were washed five times with the lysis buffer or high salt (20 mM Tris pH 7.4, 1M NaCl, 0.1% NP-40) buffer and subjected to SDS-PAGE. Gels were silver stained according to the manufacturer's procedure (Invitrogen) or proteins were transferred onto nitrocellulose membrane followed by immunoblotting.

Irreversibility Test Protocol.

MDA-MB-468 cells were grown in 6-well plates to about 80% confluency. Sets of cells were treated with YK5 (10 μM) or vehicle (DMSO) for 2 h. One set of YK5 treated cells was then stimulated with 100 ng/mL IFNγ for 30 min and extracts made for Western blotting. The other set of cells was washed free of the compound with warmed media, incubated for 2 h, washed again, incubated another 2 h, washed again, and then incubated a further 4 h. This set of cells was then stimulated with IFNγ and extracts were made similar to the first set of cells.

Cycloheximide Treatments.

Cells were treated with cycloheximide (at a final concentration of 100 g/ml) with added vehicle or a compound of the present subject matter for the indicated times. Cells were lysed as indicated above and resulting samples were analyzed by Western blotting.

Cells were lysed in 50 mM Tris pH 7.4, 150 mM NaCl and 1% NP-40 lysis buffer. NP-40 insoluble fractions were lysed in 50 mM Tris pH 7.4 and 2% SDS and boiled for 15 min. Proteins were separated by SDS-PAGE followed by a standard western blotting procedure. Blots were visualized by autoradiography using enhanced chemiluminescence detection system (GE Healthcare).

Densitometry.

Gels were scanned in Adobe Photoshop 7.0.1 and quantitative densitometric analysis was performed using UnScan-It 5.1 software (Silk Scientific, Orem, Utah).

Kinase Screen.

For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 min). The lysates were centrifuged (6,000×g) and filtered (0.2 μm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1x PBS, 0.05% Tween 20, 0.5 μm non-biotinylated affinity ligand) and incubated at room temperature with shaking for 30 minutes. The kinase concentration in the eluates was measured by qPCR. KINOMEscan's selectivity score (S) is a quantitative measure of compound selectivity. It is calculated by dividing the number of kinases that bind to the compound by the total number of distinct kinases tested, excluding mutant variants. TREEspot™ is a proprietary data visualization software tool developed by KINOMEscan. Kinases found to bind are marked with red circles, where larger circles indicate higher-affinity binding. The kinase dendrogram was adapted and is reproduced with permission from Science and Cell Signaling Technology, Inc.

Growth Inhibition Assay.

Antiproliferative effects of inhibitors were evaluated using the dye Alamar blue. This reagent offers a rapid objective measure of cell viability in cell culture, and it uses the indicator dye resazurin to measure the metabolic capacity of cells, an indicator of cell viability. Briefly, cells were plated on Costar 96-well plates. For attached cells (such as SKBr3, MDA-MB-468, LNCaP, MRC5), 8,000 cells/well were used. For suspension cells (such as MOLM-13, Kasumi-1, OCI-Ly7, PBL), 20,000 cells/well were plated. Cells were allowed to incubate for 24 h at 37° C. before drug treatment. Drugs were added in triplicates at the indicated concentrations, and the plate was incubated for 72 h. Alamar Blue (440 μM) was added, and the plate read 6 h later using the Analyst GT (Fluorescence intensity mode, excitation 530 nm, emission 580 nm, with 560 nm dichroic mirror). Results were analyzed using the Softmax Pro software. The percentage cell growth inhibition was calculated by comparing fluorescence readings obtained from treated versus control cells, accounting for initial cell population (time zero). The IC50 was calculated as the drug concentration that inhibits cell growth by 50%.

Apoptosis-Acridine Orange/Ethidium Bromide.

Apoptosis was determined using acridine orange/ethidium bromide (AO/EB) double staining. Acridine orange is taken up by both viable and nonviable cells and emits green fluorescence if intercalated into double stranded nucleic acid (DNA) or red fluorescence if bound to single stranded nucleic acid (RNA). Ethidium bromide is taken up only by nonviable cells and emits red fluorescence by intercalation into DNA. (1) Viable cells have uniform green nuclei with organized structure. (2) Early apoptotic cells (which still have intact membranes but have started to undergo DNA cleavage) have green nuclei, but perinuclear chromatin condensation is visible as bright green patches or fragments. (3) Late apoptotic cells have orange to red nuclei with condensed or fragmented chromatin. (4) Necrotic cells have a uniformly orange to red nuclei with organized structure. In brief; cells were platted on 20 mm Falcon plates and incubated for an additional 24 h. Drugs were added at the indicated concentrations for 24 or 48 h, cells were washed with PBS and trypsinized. Following staining with Acridine Orange and Ethidium Bromide cells were visualized with a fluorescent microscope (Zeiss Axiovert 40 CFL) and counted. Percentage of apoptotic cells was determined from 200-300 cells counted in each group.

Propidium Iodide Cell Staining and Flow Cytometry Analysis.

Presence of cells with fragmented DNA (indication of apoptosis) can also be detected as cells with less than 2N DNA content (sub-$G_1$). For DNA content analysis, cells were washed in ice-cold PBS and fixed in 70% ethanol for 1 h at 4° C. Fixed cells were centrifuged at 1,200 rpm for 5 minutes and stained by incubation in PBS containing 50 µg/mL propidium iodide (Sigma-Aldrich) and 50 µg/mL DNase-free ribonuclease A (Sigma-Aldrich) for 1 h at room temperature. DNA content was analyzed by flow cytometry in FACScan (BD Biosciences). Data were collected with Cell Quest Pro software (Becton Dickinson) from no fewer than 10,000 cells, and analyzed with FlowJo (Ashland, Oreg.).

Pulse-Chase.

MDA-MB-468 cells were pre-treated with 100 ng/ml IFNγ for 30 min, then 10 µM YK5 was added for 30 min, followed by 500 nM staurosporine or 1 mM $Na_3VO_4$ treatment. Cells were collected at indicated times and lysed in 50 mM Tris pH 7.4, 150 mM NaCl and 1% NP-40 lysis buffer and subjected to western blotting procedure.

Activated STAT1 DNA Binding Assay.

The DNA-binding capacity of STAT1 was assayed by an ELISA-based assay (TransAM, Active Motif, Carlsbad, Calif.) following the manufacturer instructions. Briefly, $5 \times 10^6$ MDA-MB-468 cells were treated with IFNγ (100 ng/ml), YK5 (10 µM) or the combination of IFNγ (100 ng/ml) plus YK5 (1, 5 and 10 µM). Ten micrograms of cell lysates were added to wells containing pre-adsorbed STAT consensus oligonucleotides (5'-TTCCCGGAA-3'). For IFNγ-treated cells the assay was performed in the absence or presence of 20 pmol of competitor oligonucleotides that contains either a wild-type or mutated STAT consensus binding site. Interferon-treated HeLa cells (5 µg per well) were used as positive controls for the assay. After incubation and washing, rabbit polyclonal anti-STAT1a antibody (1:1000, Active Motif) was added to each well, followed by HPR-anti-rabbit secondary antibody (1:1000, Active Motif). After HRP substrate addition, absorbance was read at 450 nm with a reference wavelength of 655 nm (Synergy4, Biotek, Winooski, Vt.). In this assay the absorbance is directly proportional to the quantity of DNA-bound transcription factor present in the sample. Experiments were carried out in four replicates. Results were expressed as mean absorbance values with SEM. P-values were obtained by two-tailed T-test.

Immunofluorescent Microscopy.

MDA-MB-468 cells were treated with 100 ng/ml IFNγ for 30 min, then a compound of the present subject matter was added for another 30 min. Cells were fixed in paraformaldehyde (4%) at room temperature for 15 min followed by washes with 1×TBS (3-5 min). Cells were then quenched for 5 minutes with 0.1% sodium borohydride in 1×TBS, rinsed as previously described, followed by incubation with block solution containing 5.5% normal calf serum and 0.1% Triton X-100 at room temperature to reduce nonspecific binding. Cells were then incubated with primary antibody (anti-phospho-STAT1 (Y701); Cell Signaling) for 1 h at room temperature followed by rinses and additional incubation with FITC-labeled goat anti-rabbit secondary antibody (Invitrogen, Camarillo, Calif.). Slides were mounted in Vectashield with 4',6-diamidino-2-phenylindole (DAPI) for nuclear staining (Vector Laboratories, Inc., Burlingame, Calif.). Fluorescence was monitored with a Zeiss Axiovert 200M inverted microscope, with DAPI and fluorescein isothiocyanate (FITC) filter sets, and an objective setting of 40×.

Cell Invasion Assay.

The invasion capacity of MDA-MB-231 cells was examined using a Boyden chamber Matrigel invasion assay. MDA-MB-231 cells platted at $5 \times 10^5$ cells/well in a 6-well plate (Becton Dickinson, Franklin Lakes, N.J.), were pretreated for 24 h with DMSO and YK5 (1 µM). Cell viability was estimated by trypan blue exclusion. In summary, cells were stained with tryptan blue and counted manually with a hemacytometer. Viable cells, which are cells that exclude tryptan blue, were washed three times with serum free DMEM and re-suspended in 0.3 ml of serum-free DMEM. Equal numbers of viable cells ($2 \times 10^5$) were added to the upper compartment of the Boyden chamber and treatment medium containing 10% FBS in DMEM was added to the lower chamber. Boyden chambers contained an 8 µm PET track-etched membrane, coated with Matrigel transwells (BD Biosciences, San Jose, Calif.). After cells were incubated for 20 h at 37° C., cells invading to the lower side of the membrane were fixed with were fixed in 100% methanol for 2 min, stained in 0.5% crystal violet for 2 min, rinsed in water, and examined under a bright-field microscope. Cells in ten fields per membrane were counted at ×100 objective.

Caspase 3/7 Activation Apoptosis Assay.

On a black 96-well plate (Corning 3603), cells were plated except background column (no cells) with 50 ul of media, and left in the incubator (37° C., 5% $CO_2$) to allow cells to attach and equilibrate. Compounds in 50 ul of media were added in the indicated concentration range for the indicated times. 100 uL of the assay buffer (10 mM HEPES (pH. 7.5), 2 mM EDTA, 0.1% CHAPS, 0.1 mg/ml PMSF, Complete Protease Inhibitor Mix (Roche 1 697 498)) containing Z-DEVD-R110 (Molecular Probes R22120) were added to each well. Following incubation, fluorescence intensity was read with Analyst (Emission 485 Excitation at 530).

Chemical Precipitation and Proteomies.

Protein lysates were prepared using 20 mM Tris pH 7.4, 25 mM NaCl, 0.1% NP-40 lysis buffer. Streptavidin agarose (Thermo Scientific) were washed three times with lysis buffer, YK55 (100 µM) was added and the complexes incubated at 4° C. for 1 h. Upon a three-time wash with buffer, beads were added to 500 µg of cellular protein in buffer. Samples were incubated at 4° C. overnight, washed five times with the lysis buffer and applied to SDS-PAGE. Gels were stained by SilverQuest Silver Staining kit (Invitrogen) according to manufacturer's instructions. Protein bands were cut out and, after washing with water, gel slices were cut into 1 $mm^3$ pieces, reduced with 10 mM DTT in 100 mM $NH_4HCO_3$ at 56° C. for 30 min, alkylated with a 55 mM iodacetamide solution in 100 mM $NH_4HCO_3$ at room temperature in the dark for 20 min, and then digested with trypsin (13 ng/µl) at 37° C. overnight. Peptides were extracted with 100-200 µl 66.6% acetonitrile/5% formic acid, and the volume of combined peptide extract was reduced to −10 µl in a SpeedVac prior to MS analysis. Liquid chromatography-tandem mass spectrometry analysis (LC-MS/MS) at the Proteomics facility of Weill Cornell Medical College (WCMC) was performed using an 1100 series LC coupled to an XCT plus ion trap mass spectrometer (Agilent Technologies, Palo Alto, Calif.). The system is equipped with an Agilent Chip Cube interface and a silicon wafer "chip-column" that integrates a C18 enrichment column, C18 resolving column, and nanospray emitter. In-gel protein digests were loaded and desalted on the enrichment column at a flow rate of 4 µL/min and then resolved at a flow rate of 0.35 l/min on a 40 mm×75 µM ZORBAX 300 C18 column (Agilent). The LC gradient was 3 to 45% Solvent B for 25 min, followed by 45 to 90% Solvent B for 5 min. Mobile phase solvent A was 0.1% formic acid in 3% ACN and Solvent B is 0.1% formic acid in 90% ACN. Mass spectra were acquired in positive-ion mode with automated data-dependent MS/MS on the four most intense ions from precursor MS scans. SPECTRUM MILL software (Agilent) was used to process LC-MS/MS raw data and to search protein database for protein identification.

Chemical Precipitation and MS Analyses: 1: Nano-LC-MS/MS.

K562 cells were treated for 4 h with 100 µM YK55 or D-biotin. Cells were collected and lysed in 20 mM Tris pH 7.4, 25 mM NaCl, 0.1% NP-40 buffer. YK55 treated cell extract (500 µl) in 100 µl of the lysis buffer was incubated with streptavidin agarose beads for 1 h at 4° C. D-biotin treated cell extract (500 µg) was incubated for 1 h at 4° C. with the BB70 antibody (4 µl) attached on protein G agarose beads (30 µl) (Upstate). Beads were washed with high-salt buffer (1 M NaCl), proteins eluted by boiling in 2% SDS, separated on a denaturing gel and Coumassie stained according to manufacturer's procedure (Biorad). Gel-resolved proteins from YK55-drug treated and BB70 pulldowns were digested with trypsin, cysteine containing peptides reduced and alkylated using beta-mercaptoethanol and acrylamide, as described (10). In-gel tryptic digests were subjected to a micro-clean-up procedure on 2 µL bed-volume of Poros 50 R2 (Applied Biosystems—'AB') reversed-phase beads, packed in an Eppendorf gel-loading tip, and the eluant diluted with 0.1% formic acid. Analyses of the batch purified pools were done using an OrbiTrap (Thermo Scientific LTQ XL Linear Ion Trap) Mass spectrometer, equipped with a nano spray ion source. Peptide mixtures (in 20 microL) are loaded onto a trapping guard column (0.3×5-mm PepMap C18 100 cartridge from LC Packings) using an Eksigent nano MDLC system (Eksigent Technologies, Inc) at a flow rate of 20 microL/min. After washing, the flow was reversed through the guard column and the peptides eluted with a 5-45% MeCN gradient (in 0.1% FA) over 85 min at a flow rate of 200 nL/min, onto and over a 75-micron×15-cm fused silica capillary PepMap C18 column (LC Packings); the eluant is directed to a 75-micron (with 10-micron orifice) fused silica nano-electrospray needle (New Objective). Electrospray ionization (ESI) needle voltage was set at about 1800 V. The mass analyzer was operated in automatic, data-dependent MS/MS acquisition mode; the collision energy was automatically adjusted in accordance with the m/z value of the precursor ions selected for MS/MS. Initial protein identifications from LC-MS/MS data was done using the Mascot search engine (Matrix Science, version 2.2.04; www.matrixscience.com) and the NCBI (National Library of Medicine, NIH) and IPI (International Protein Index, EBI, Hinxton, UK) databases. Two missed tryptic cleavage site was allowed, precursor ion mass tolerance=10 ppm, fragment ion mass tolerance=0.8 Da, protein modifications were allowed for Met-oxide, Cys-acrylamide and N-terminal acetylation. MudPit scoring was typically applied with 'require bold red' activated, and using significance threshold score p<0.01. Unique peptide counts (or 'spectral counts') and percent sequence coverages for all identified proteins were exported to Excel for further analysis.

MALDI-reTOF-MS/MS:

Resulting peptide pools from in-gel digests were analyzed by matrix-assisted laser-desorption/ionization reflectron time-of-flight (MALDI-reTOF) MS using a BRUKER UltraFlex TOF/TOF instrument (Bruker Daltonics; Bremen, Germany). Selected experimental masses (m/z) were taken to search the human segment of a non-redundant protein database ('NR'; ~223,695 entries; National Center for Biotechnology Information; Bethesda, Md.), utilizing the Mascot Peptide Mass Fingerprint (PMF) program, version 2.2.04 for Windows (www.matrixscience.com), with a mass accuracy restriction better than 35 ppm, and maximum two missed cleavage site allowed per peptide. This served to confirm the identity of the proteins and to locate differences between the tryptic peptide maps of the modified (cysteine acrylamide derivatized) peptides. Differential peak m/z values were matched to the identified proteins, allowing for the presence of drug derivatizing groups at 820.34 (plus YK55-drug) and 594.26 Daltons (plus YK55-drug without the biotin group). To confirm observed peptides with calculated mono-isotopic fragments matching to the experimental values, mass spectrometric sequencing of selected peptides were done by MALDI-TOF/TOF (MS/MS) analysis on the same prepared samples, using the UltraFlex instrument in 'LIFT' mode. Fragment ion spectra were taken to search NR using the MASCOT MS/MS Ion Search program (Matrix Science) and the on-line proteomics toolkit available at http://db.systemsbiology.net:8080/proteomicsToolkit/FragIonServlet.html. Results were confirmed manually. Any tentative result thus obtained was verified by comparing the computer-generated fragment ion series of the predicted tryptic peptide with the experimental MS/MS data.

Tumor Xenografts.

Four to six-week old nu/nu athymic female mice were obtained from Taconic (Farms INC). Experiments were carried out under an Institutional Animal Care and Use Committee-approved protocol, and institutional guidelines for the proper and humane use of animals in research were followed. MDA-MB-468 ($1\times10^7$ cells) were subcutaneously implanted in the right flank of mice using a 20-gauge needle and allowed to grow. Before administration, a solution of YK5.HCl was formulated in sterile water. Mice were injected intratumorally (i.t.) 20 µl of the YK5 solution on an alternate day schedule. The concentration of the injected YK5 was estimated in rapport to the tumor volume, and was kept at 10 µM throughout the experimental period. All mice received Augmentin (Amoxicillin/Clavulanate potassium; SmithKline Beecham) in their drinking water while on therapy. Mice were sacrificed by $CO_2$ euthanasia. Mice (n=5) bearing MDA-MB-468 tumors reaching a volume of 100-150 mm$^3$ were treated intratumorally (i.t.) on alternate days. Tumor volume was determined by measurement with Vernier calipers, and tumor volume was calculated as the product of its length×width$^2$×0.4. Tumor volume was expressed on indicated days as the median tumor volume±s.d. indicated for groups of mice. Percent (%) tumor growth inhibition values were measured on the final day of study for drug-treated compared with vehicle-treated mice and are calculated as $100\times\{1-[(\text{Treated}_{Final\ day}-\text{Treated}_{Day\ 1})/(\text{Control}_{Final\ day}-\text{Control}_{Day\ 1})]\}$.

Statistics.

W Data were analyzed by unpaired 2-tailed t tests as implemented in GraphPad Prism (version 4; GraphPad Software). A P value of less than 0.05 was considered significant. Unless otherwise noted, data are presented as the mean±SD

Example 13: Treatment of a Patient

A patient is suffering from breast cancer. A pharmaceutical composition comprising a pharmaceutically effective amount of compound YK5 or a related compound of the present subject matter is administered to the patient. It is expected that the patient would improve or recover from breast cancer, and/or the proliferation of the breast cancer would slow and/or be inhibited.

Example 14: Treatment of a Patient

A patient is suffering from Leukemia. A pharmaceutical composition comprising a pharmaceutically effective amount of a compound of the present subject matter is administered to the patient. It is expected that the patient would improve or recover from leukemia, and/or the proliferation of the leukemia would slow and/or be inhibited.

It is appreciated that certain features of the presently described subject matter, which are, for clarity, described in the context of separate embodiments, may also be provided in combination in a single embodiment. Conversely, various features of the presently described subject matter, which are, for brevity, described in the context of a single embodiment, may also be provided separately or in any suitable subcombination.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following described subject matter.

We claim:

1. A method of treating a cancer or proliferative disorder in a subject comprising administering to the subject a pharmaceutical composition comprising a compound of Formula 2a:

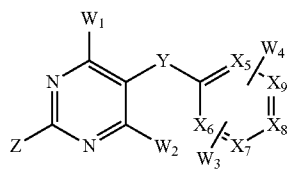

Formula 2a or a pharmaceutically acceptable salt thereof, and a pharmaceutically acceptable carrier,
wherein:
$X_5$-$X_9$ are independently selected from CH, C substituted with $W_3$ or $W_4$, and N;
Y is S, SO, $SO_2$, $CH_2$, CHR, CRR, or CO, wherein R is a $C_1$-$C_6$ alkyl or alkoxy chain;
Z is selected from the group consisting of alkenyl, alkynyl, saturated or unsaturated cycloalkyl, saturated or unsaturated heterocycle, halogen, hydroxyl, nitro, aryloxy, alkoxy, halogenated alkoxy, alkenyloxy, hydroxyalkyl, dialkylamino, cycloalkylamino, arylamino, diarylamino, acylamino, carbamyl, amido, alkylamido, alkylsulfonamido, sulfonamido, —$NHSO_2$alkenyl, —NHCOalkenyl, —NHCOalkynyl, —COalkenyl, —COalkynyl, trihalocarbon, thioalkyl, —$SO_2$-alkyl, —COO-alkyl, —COalkyl, and alkyl-CN;
$W_1$ and $W_2$ are independently selected from the group consisting of hydrogen, alkyl, alkenyl, alkynyl, aryl, saturated or unsaturated cycloalkyl, unsaturated heterocycle, halogen, nitro, cyano, aryloxy, alkoxy, halogenated alkoxy, alkenyloxy, hydroxyalkyl, amino, alkylamino, cycloalkylamino, arylamino, diarylamino, acylamino, carbamyl, amido, alkylamido, alkylsulfonamido, sulfonamido, —$NHSO_2$alkenyl, —NHCOalkenyl, —NHCOalkynyl, —COalkenyl, —COalkynyl, trihalocarbon, thioalkyl, —$SO_2$-alkyl, —COO-alkyl, —COalkyl, and alkyl-CN, and
$W_3$ and $W_4$ independently at each occurrence are selected from the group consisting of hydrogen, alkyl, alkenyl, alkynyl, aryl, saturated or unsaturated cycloalkyl, saturated or unsaturated heterocycle, halogen, hydroxyl, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, amido, alkylamido, alkylsulfonamido, sulfonamido, —$NHSO_2$alkenyl, —NHCOalkenyl, —NHCOalkynyl, —COalkenyl, —COalkynyl, trihalocarbon, thioalkyl, —$SO_2$-alkyl, —COO-alkyl, —COalkyl, and alkyl-CN.

2. The method of claim 1, wherein the cancer or proliferative disorder is selected from the group consisting of breast cancer, prostate cancer, lung cancer, colon cancer, stomach cancer, pancreatic cancer, ovarian cancer, brain cancer, hematopoietic cancer, esophageal carcinoma, renal cell carcinoma, bladder cancer, head and neck cancer, leukemia, cholangiosarcoma, esophageal sarcoma, hepatocellular carcinoma, non-small- and small-cell lung cancer (NSCLC and SCLC), and lymphoma.

3. The method of claim 1, wherein:
Y is S, SO, or $SO_2$;
Z is alkenyl, alkynyl, saturated or unsaturated cycloalkyl, saturated or unsaturated heterocycle, halogen, hydroxyl, alkoxy, dialkylamino, cycloalkylamino, arylamino, or diarylamino;
$W_1$ and $W_2$ are independently hydrogen, alkyl, alkenyl, alkynyl, aryl, alkoxy, amino, alkylamino, cycloalkylamino, arylamino, or diarylamino; and
$W_3$ and $W_4$ are independently hydrogen, halogen, hydroxyl, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, amido, alkylamido, alkylsulfonamido, sulfonamido, —$NHSO_2$alkenyl, —NHCOalkenyl, —NHCOalkynyl, —COalkenyl, —COalkynyl, trihalocarbon, thioalkyl, —$SO_2$-alkyl, —COO-alkyl, —COalkyl, or alkyl-CN.

4. The method of claim 1, wherein $X_5$-$X_9$ are selected from:

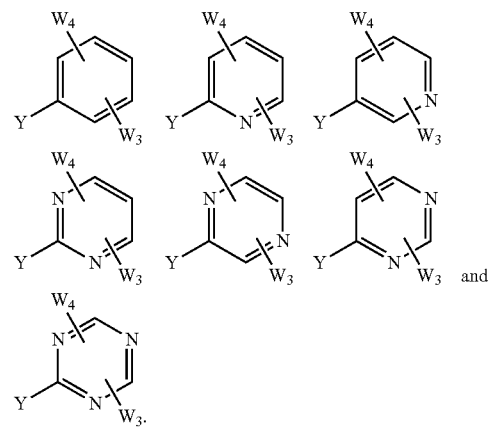

5. The method of claim 1, wherein Y is S, SO, or $SO_2$.

6. The method of claim 1, wherein Z is alkenyl, alkynyl, saturated or unsaturated cycloalkyl, saturated or unsaturated heterocycle, halogen, hydroxyl, alkoxy, dialkylamino, cycloalkylamino, arylamino, or diarylamino.

7. The method of claim 1, wherein $W_1$ and $W_2$ are independently hydrogen, alkyl, alkenyl, alkynyl, aryl, alkoxy, amino, alkylamino, cycloalkylamino, arylamino, or diarylamino.

8. The method of claim 1, wherein $W_3$ and $W_4$ are independently hydrogen, halogen, hydroxyl, cyano, aryloxy, alkoxy, halogenated alkoxy, alkenyloxy, hydroxyalkyl, amino, alkylamino, dialkylamino, cycloalkylamino, arylamino, diarylamino, acylamino, carbamyl, amido, alkylamido, alkylsulfonamido, sulfonamido, —NHSO$_2$alkenyl, —NHCOalkenyl, —NHCOalkynyl, —COalkenyl, —COalkynyl, trihalocarbon, thioalkyl, —SO$_2$-alkyl, —COO-alkyl, —COalkyl, or alkyl-CN.

9. The method of claim 1, wherein when $W_1$ or $W_2$ are alkoxy, the alkoxy is a substituted alkoxy group.

10. A method of treating a cancer or proliferative disorder in a subject comprising administering to the subject a pharmaceutical composition comprising a compound of Formula 2a'':

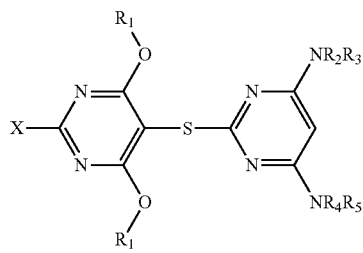

Formula 2a'' or a pharmaceutically acceptable salt thereof, and a pharmaceutically acceptable carrier, wherein:
each $R_1$ is independently selected from the group consisting of H; optionally substituted straight or branched alkyl, alkenyl, or alkynyl; an optionally substituted carbocyclic, heterocyclic, aryl, or heteroaryl group; halogen; an optionally substituted $C_{2-22}$ acyl group; a $C(O)R_6$ group; and an -(ethoxy)$_n$-$R_6$ group, wherein n is 1-12;
$R_2$, $R_3$, $R_4$, and $R_5$ are each independently selected from the group consisting of H; optionally substituted straight or branched alkyl, alkenyl, or alkynyl; an optionally substituted carbocyclic, heterocyclic, aryl, or heteroaryl group; an optionally substituted $C_{2-22}$ acyl group; a $C(O)R_6$ group; and an optionally substituted alkoxycarbonyl group; and
X is selected from the group consisting of optionally substituted straight or branched alkyl, alkenyl, or alkynyl; an optionally substituted carbocyclic, heterocyclic, aryl, or heteroaryl group; halogen; an optionally substituted $C_{2-22}$ acyl group; a —NR$_4$R$_5$ group; a —C(O)R$_6$ group; an -(ethoxy)$_n$-$R_6$ group, wherein n is 1-12; an optionally substituted alkoxycarbonyl group; an optionally substituted alkyloxy group; an optionally substituted amino group; a nitro group; and a carboxyl group; and
each $R_6$ is independently selected from the group consisting of an optionally substituted straight or branched alkyl, alkenyl, or alkynyl; an optionally substituted carbocyclic, heterocyclic, aryl, or heteroaryl group; an optionally substituted alkyloxy group; and an alkylacrylate group;
provided that X does not comprise a bridged ring structure.

11. The method of claim 10, wherein the cancer or proliferative disorder is selected from the group consisting of breast cancer, prostate cancer, lung cancer, colon cancer, stomach cancer, pancreatic cancer, ovarian cancer, brain cancer, hematopoietic cancer, esophageal carcinoma, renal cell carcinoma, bladder cancer, head and neck cancer, leukemia, cholangiosarcoma, esophageal sarcoma, hepatocellular carcinoma, non-small- and small-cell lung cancer (NSCLC and SCLC), and lymphoma.

12. The method of claim 10, wherein:
each $R_1$ is independently selected from the group consisting of H; and optionally substituted straight or branched alkyl, alkenyl, or alkynyl;
$R_2$, $R_3$, $R_4$, and $R_5$ are each independently selected from the group consisting of H; optionally substituted straight or branched $C_1$-$C_6$ alkyl; and —C(O)$R_6$ wherein $R_6$ is an optionally substituted straight or branched $C_1$-$C_6$ alkyl, alkenyl, or alkynyl; and
X is selected from the group consisting of an optionally substituted straight or branched alkyl, alkenyl, or alkynyl group; an optionally substituted carbocyclic, heterocyclic, aryl, or heteroaryl group; and halogen.

13. The method of claim 12, wherein:
each $R_1$ is independently selected from the group consisting of unsubstituted straight or branched $C_1$-$C_6$ alkyl and substituted straight or branched $C_1$-$C_6$ alkyl.

14. The method of claim 12, wherein:
each $R_1$ is independently selected from methyl and ethyl;
$NR_2R_3$ is $NH_2$;
$NR_4R_5$ is NHC(O)—$C_1$-$C_6$ alkyl or NHC(O)—$C_2$-$C_6$ alkenyl; and
X is a piperazine ring linked at a nitrogen atom, and the piperazine ring is optionally substituted with halogen, haloalkyl, or straight or branched $C_1$-$C_6$ alkyl.

15. The method of claim 10, wherein:
each $R_1$ is the same or different and is methyl or ethyl;
$R_2$, $R_3$, and $R_4$ are each H;
$R_5$ is —C(O)-methyl, —C(O)-ethyl, or —C(O)-ethenyl; and
X is piperazine, 4-methylpiperazin-1-yl, or 4-(2-(2-(2-(2-hydroxyethoxy)ethoxy) ethoxy)ethyl)piperazin-1-yl.

16. A method of treating a cancer or proliferative disorder in a subject comprising administering to the subject a pharmaceutical composition comprising a compound selected from the group consisting of:
N-(6-amino-2-(4,6-dimethoxy-2-(4-methylpiperazin-1-yl)pyrimidin-5-ylthio)pyrimidin-4-yl)acrylamide,
N-(6-amino-2-(4,6-diethoxy-2-(4-methylpiperazin-1-yl)pyrimidin-5-ylthio)pyrimidin-4-yl)acrylamide,
N-(2-(4,6-dimethoxy-2-(4-methylpiperazin-1-yl)pyrimidin-5-ylthio)pyrimidin-4-yl)acrylamide,
N-(3-(4-(benzyloxy)-2-(4-methylpiperazin-1-yl)pyrimidin-5-ylthio)phenyl)acetamide,
N-(3-(4-(benzyloxy)-2-(4-methylpiperazin-1-yl)pyrimidin-5-ylthio)phenyl)benzamide,
2-amino-N-(3-(4-(benzyloxy)-2-(4-methylpiperazin-1-yl)pyrimidin-5-ylthio)phenyl)acetamide,
2-amino-N-(3-(2-(4-methylpiperazin-1-yl)-4-(pyridin-3-ylmethoxy)pyrimidin-5-ylthio)phenyl)acetamide,
2-amino-N-(3-(2-(4-methylpiperazin-1-yl)-4-(pyridin-4-ylmethoxy)pyrimidin-5-ylthio)phenyl)acetamide,
2-amino-N-(3-(4-(4-chlorobenzyloxy)-2-(4-methylpiperazin-1-yl)pyrimidin-5-ylthio)phenyl)acetamide,
2-amino-N-(3-(4-(3-aminobenzyloxy)-2-(4-methylpiperazin-1-yl)pyrimidin-5-ylthio)phenyl)acetamide,
2-amino-N-(3-(4-(2-aminobenzyloxy)-2-(4-methylpiperazin-1-yl)pyrimidin-5-ylthio)phenyl)acetamide, 2-amino-N-(3-(4-(difluoro(phenyl)methoxy)-2-(4-methylpiperazin-1-yl)pyrimidin-5-ylthio)phenyl)acetamide, 2-amino-N-(3-(4-(3,5-difluorobenzyloxy)-2-(4-methylpiperazin-1-yl)pyrimidin-5-ylthio)phenyl)acetamide, N-(3-(4-(benzyloxy)-2-(4-methylpiperazin-1-yl)pyrimidin-5-ylthio)phenyl)acrylamide, N-(2-(4-(benzyloxy)-2-(4-methylpiperazin-1-yl)pyrimidin-5-ylthio)pyrimidin-4-yl)acrylamide, and N-(6-amino-2-(4-(benzyloxy)-2-(4-methylpiperazin-1-yl)pyrimidin-5-ylthio)pyrimidin-4-yl)acrylamide, or a pharmaceutically acceptable salt thereof, and a pharmaceutically acceptable carrier.

17. The method of claim 16, wherein the cancer or proliferative disorder is selected from the group consisting of breast cancer, prostate cancer, lung cancer, colon cancer, stomach cancer, pancreatic cancer, ovarian cancer, brain cancer, hematopoietic cancer, esophageal carcinoma, renal cell carcinoma, bladder cancer, head and neck cancer, leukemia, cholangiosarcoma, esophageal sarcoma, hepatocellular carcinoma, non-small- and small-cell lung cancer (NSCLC and SCLC), and lymphoma.

18. The method of claim 16, wherein the compound is N-(6-amino-2-(4,6-dimethoxy-2-(4-methylpiperazin-1-yl)pyrimidin-5-ylthio)pyrimidin-4-yl)acrylamide, or a pharmaceutically acceptable salt thereof.

* * * * *